(12) United States Patent
Moriya et al.

(10) Patent No.: US 8,796,272 B2
(45) Date of Patent: Aug. 5, 2014

(54) GLYCINE TRANSPORTER-INHIBITING SUBSTANCES

(75) Inventors: Minoru Moriya, Toshima-ku (JP); Hiroshi Ohta, Toshima-ku (JP); Shuji Yamamoto, Toshima-ku (JP); Kumi Abe, Toshima-ku (JP); Yuko Araki, Toshima-ku (JP); Xiang-Min Sun, Toshima-ku (JP); Daisuke Wakasugi, Toshima-ku (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 0 days.

(21) Appl. No.: 14/000,261

(22) PCT Filed: Feb. 21, 2012

(86) PCT No.: PCT/JP2012/054110
§ 371 (c)(1),
(2), (4) Date: Aug. 19, 2013

(87) PCT Pub. No.: WO2012/115097
PCT Pub. Date: Aug. 30, 2012

(65) Prior Publication Data
US 2013/0331571 A1    Dec. 12, 2013

(30) Foreign Application Priority Data
Feb. 21, 2011    (JP) .................................. 2011-035169

(51) Int. Cl.
*A61K 31/50* (2006.01)
*A61K 31/501* (2006.01)

(52) U.S. Cl.
USPC ................. 514/252.02; 514/255.05; 514/275; 544/238; 544/295; 544/357; 546/272.7

(58) Field of Classification Search
USPC ..................... 544/238, 295, 357; 546/272.7; 514/252.02, 255.05, 275
See application file for complete search history.

(56) References Cited

U.S. PATENT DOCUMENTS

2009/0270412 A1 * 10/2009 Hung et al. ............. 514/253.04

FOREIGN PATENT DOCUMENTS

| WO | WO 9603386 A1 * | 2/1996 |
| WO | 2008/092878 A1 | 8/2008 |
| WO | 2009/034062 A1 | 3/2009 |

OTHER PUBLICATIONS

H. Girouard et al., 100 Journal of Applied Physiology, 328-335, 332 (2006).*
R. S. Shah et al., 52 Biomedicine & Pharmacotherapy, 199-207 (2008).*
I. Collins, 1 Current Signal Transduction Therapy, 13-23 (2006).*
J.T. O'Brien et al., 2 The Lancet Neurology, 89-98 (2003).*
T. Bruna et al., Drug Treatments in: Handbook of Eating Disorders (J. Treasure et al., Eds., 2nd Ed., 2003).*
E. Szabadi, 61 British Journal of Clinical Pharmacology, 761-766 (2006).*
R. Depoortère et al., 30 Neuropsychopharmacology, 1963-1985, 1982 (2005).*
B. Ellenbroek, 62 Neuropharmacology, 1371-1383, 1375 (2012).*
C. Sur et al., 13 Expert Opinion Investigational Drugs, 515-521 (2004).*
A. Slassi et al., 14 Expert Opinion Therapeutic Patents, 201-214 (2004).*
G.E. Tsai et al., 16 Current Pharmaceutical Design, 522-537 (2010).*
DC Javitt "Glutamate as a therapeutic target in psychiatric disorders", Molecular Psychiatry, 2004, pp. 984-997, vol. 9.
L.G. Harsing Jr., et al., "Glycine Transporter Type-1 and its Inhibitors", Current Medicinal Chemistry, 2006, pp. 1017-1044, vol. 13.
Ronan Depoortere, et al., "Neurochemical, Electrophysiological and Pharmacological Profiles of the Selective Inhibitor of the Glycine Transporter-I SSR504734, a Potential New Type of Antipsychotic", Neuropsychopharmacology, 2005, pp. 1963-1985, vol. 30.
Abdelmalik Slassi, et al., "Recent progress in the use of glycine transporter-1 inhibitors for the treatment of central and peripheral nervous system diseases", Expert Opinion on Therapeutic Patents, 2004, pp. 201-214, vol. 14, No. 2.

* cited by examiner

*Primary Examiner* — Deepak Rao
*Assistant Examiner* — Alexander R Pagano
(74) *Attorney, Agent, or Firm* — Sughrue Mion, PLLC

(57) ABSTRACT

The present invention relates to novel compounds of formula [I] or pharmaceutically acceptable salts thereof:

[Formula 1]

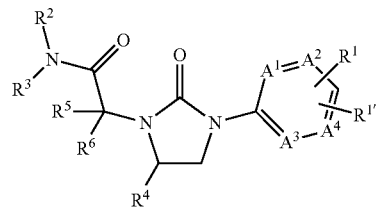

The compounds of the present invention are useful in the prevention or treatment of diseases such as schizophrenia, Alzheimer's disease, cognitive impairment, dementia, anxiety disorders (e.g., generalized anxiety disorder, panic disorder, obsessive-compulsive disorder, social anxiety disorder, post-traumatic stress disorder, specific phobias, acute stress disorder), depression, drug dependence, spasm, tremor, pain, Parkinson's disease, attention deficit hyperactivity disorder, bipolar disorder, eating disorder, or sleep disorders, which is based on the glycine uptake-inhibiting action.

16 Claims, No Drawings

GLYCINE TRANSPORTER-INHIBITING SUBSTANCES

CROSS REFERENCE TO RELATED APPLICATIONS

This is a National Stage of International Application No. PCT/JP2012/054110, filed Feb. 21, 2012, claiming priority from Japanese Patent Application No. 2011-035169, filed Feb. 21, 2011, the contents of all of which are incorporated herein by reference in their entirety.

TECHNICAL FIELD

The present invention relates to compounds having a glycine transporter-inhibiting action.

BACKGROUND ART

The NMDA receptor, which is one of glutamate receptors, is located on the nerve cell membranes in the brain and involved in various neurophysiologic events such as neuronal plasticity, cognition, attention, and memory. The NMDA receptor has a plurality of allosteric binding sites, one of which is the glycine binding site (glycine binding site on NMDA receptor complex). It has been reported that the glycine binding site on NMDA receptor complex is involved in the activation of NMDA receptors (Non-Patent Document 1).

Action potential arriving at the presynaptic terminals of glycinergic nerves triggers the release of glycine into synaptic clefts. The released glycine binds to the postsynaptic receptors or the like and is then removed from the synaptic clefts by transporters. Based on this fact, glycine transporters are believed to regulate the functions of NMDA receptors through regulation of the amount of glycine in the extracellular fluid.

Glycine transporters (GlyTs) are proteins involved in the reuptake of extracellular glycine into cells, and two subtypes, GlyT1 and GlyT2, have so far been identified. GlyT1, which is expressed primarily in the cerebral cortex, hippocampus, thalamus and the like, has been reported to be associated with diseases such as schizophrenia, Alzheimer's disease, cognitive impairment, dementia, anxiety disorders (e.g., generalized anxiety disorder, panic disorder, obsessive-compulsive disorder, social anxiety disorder, specific phobias, acute stress disorder), depression, drug dependence, spasm, tremor, pain, Parkinson's disease, attention deficit hyperactivity disorder, bipolar disorder, eating disorder, and sleep disorders (Non-Patent Documents 2-4).

Compounds having a GlyT1-inhibiting action and having an imidazolidin-2-one structure have been reported in the documents shown below (Patent Documents 1 and 2). These compounds described in Patent Documents 1 and 2 are characterized in that a phenyl group is attached via amide or carbonyl to one of the endocyclic nitrogen atoms of the imidazolidine, while another phenyl group is attached to the other endocyclic nitrogen atom of the imidazolidine, and that an endocyclic carbon atom of the imidazolidinone is a spiro carbon atom.

CITATION LIST

Patent Documents

Patent Document 1: WO2008092878
Patent Document 2: WO2009034062

Non-Patent Documents

Non-Patent Document 1: Molecular Psychiatry (2004) 9, 984-997
Non-Patent Document 2: Current Medicinal Chemistry, 2006, 13, 1017-1044
Non-Patent Document 3: Neuropsychopharmacology (2005), 30, 1963-1985
Non-Patent Document 4: Expert Opinion on Therapeutic Patents (2004) 14 (2) 201-214

SUMMARY OF INVENTION

Technical Problem

The present invention aims to provide novel compounds or pharmaceutically acceptable salts thereof which are useful in the prevention or treatment of diseases such as schizophrenia, Alzheimer's disease, cognitive impairment, dementia, anxiety disorders (e.g., generalized anxiety disorder, panic disorder, obsessive-compulsive disorder, social anxiety disorder, post-traumatic stress disorder, specific phobias, acute stress disorder), depression, drug dependence, spasm, tremor, pain, Parkinson's disease, attention deficit hyperactivity disorder, bipolar disorder, eating disorder, or sleep disorders, which is based on the glycine uptake-inhibiting action.

Solution to Problem

As a result of extensive and intensive studies on structurally novel compounds with an inhibitory action against GlyT1, the present inventors found that the compounds represented by the following formula, in which a nitrogen-containing aromatic ring group is attached to one of the endocyclic nitrogen atoms of the imidazolidine and the endocyclic carbon atoms of the imidazolidinone are not spiro carbon atoms, are superior GlyT1-inhibiting substances. This finding has led to the completion of the present invention.

The present invention will be described below in detail. Embodiments of the present invention (hereinafter each referred to as "the inventive compound") are as shown below.
(1) A compound of formula [I] or a pharmaceutically acceptable salt thereof:

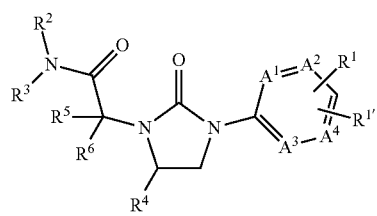

[Formula 1]

wherein
$R^1$ and $R^{1'}$ are the same or different, and each represent a hydrogen atom, a halogen atom, a $C_{1-6}$ alkoxy group, a halo$C_{1-6}$ alkyl group, a cyano group, a heteroaryl group (which may be substituted by a $C_{1-6}$ alkyl group), a $C_{1-6}$ alkyl group, a $C_{3-6}$ cycloalkyl group, a $C_{1-6}$ alkylamino group, or the formula $CONR^7R^8$ ($R^7$ and $R^8$ are the same or different, and each represent a hydrogen atom or a $C_{1-6}$ alkyl group),
$R^2$ represents a hydrogen atom or a $C_{1-6}$ alkyl group,
$R^3$ represents a phenyl group (which may be substituted by 1 to 3 substituents selected from halogen atoms, cyano groups, $C_{1-6}$ alkyl groups, $C_{1-6}$ alkoxy groups, $C_{1-6}$ alkylamino groups, $C_{1-6}$ alkylsulfonyl groups, halo$C_{1-6}$ alkyl groups, halo$C_{1-6}$ alkoxy groups, halo$C_{1-6}$ alkylsulfanyl groups, phenyl groups, phenoxy groups, heteroaryl groups (which may be substituted by a $C_{1-6}$ alkyl group), and the formula —SO$_2$NR$^9$R$^{10}$ (R$^9$ and R$^{10}$ are the same or different, and each represent a hydrogen atom or a $C_{1-6}$ alkyl group)) or a heteroaryl group or a bicyclic heteroaryl group (the each heteroaryl group may be substituted by 1 to 3 substituents selected from halogen atoms, $C_{1-6}$ alkyl groups, $C_{3-6}$ cycloalkyl groups, $C_{1-6}$ alkoxy groups, cyano groups, $C_{1-6}$ alkanoyl groups, and halo$C_{1-6}$ alkyl groups), R$^4$ represents a $C_{1-6}$ alkyl group (which may be substituted by 1 to 3 halogen atoms, a $C_{1-6}$ alkoxy group, a $C_{3-6}$ cycloalkyl group, or a phenyl group), a $C_{3-6}$ cycloalkyl group, or a phenyl group, R$^5$ and R$^6$ are the same or different, and each represent a hydrogen atom or a $C_{1-6}$ alkyl group, and A$^1$, A$^2$, A$^3$, and A$^4$ are the same or different, and each represent the formula CH or a nitrogen atom, provided that one or two of A$^1$, A$^2$, A$^3$, and A$^4$ represent a nitrogen atom.

(2) The compound or pharmaceutically acceptable salt thereof according to (1), wherein R$^1$ is a hydrogen atom, a halogen atom, a $C_{1-6}$ alkoxy group, a halo$C_{1-6}$ alkyl group, a cyano group, a heteroaryl group (which may be substituted by a $C_{1-6}$ alkyl group), a $C_{1-6}$ alkyl group, a $C_{1-6}$ alkylamino group, or the formula CONR$^7$R$^8$ (R$^7$ and R$^8$ are the same or different, and each represent a hydrogen atom or a $C_{1-6}$ alkyl group), R$^{1'}$ is a hydrogen atom, R$^3$ is a phenyl group (which may be substituted by 1 to 3 substituents selected from halogen atoms, cyano groups, $C_{1-6}$ alkyl groups, $C_{1-6}$ alkoxy groups, $C_{1-6}$ alkylamino groups, $C_{1-6}$ alkylsulfonyl groups, halo$C_{1-6}$ alkyl groups, halo$C_{1-6}$ alkoxy groups, halo$C_{1-6}$ alkylsulfanyl groups, phenyl groups, phenoxy groups, heteroaryl groups (which may be substituted by a $C_{1-6}$ alkyl group), and the formula —SO$_2$NR$^9$R$^{10}$ (R$^9$ and R$^{10}$ are the same or different, and each represent a hydrogen atom or a $C_{1-6}$ alkyl group)) or a heteroaryl group (which may be substituted by 1 to 3 substituents selected from halogen atoms, $C_{1-6}$ alkyl groups, $C_{1-6}$ alkoxy groups, cyano groups, and halo$C_{1-6}$ alkyl groups), and R$^4$ is a $C_{1-6}$ alkyl group (which may be substituted by a $C_{3-6}$ cycloalkyl group or a phenyl group) or a phenyl group.

(3) The compound or pharmaceutically acceptable salt thereof according to (1), wherein R$^4$ is a $C_{1-6}$ alkyl group which may be substituted by 1 to 3 halogen atoms.

(4) The compound or pharmaceutically acceptable salt thereof according to (1) or (2), wherein R$^4$ is a $C_{1-6}$ alkyl group.

(5) The compound or pharmaceutically acceptable salt thereof according to any one of (1) to (4), wherein R$^2$ is a hydrogen atom, and R$^5$ and R$^6$ are both a hydrogen atom.

(6) The compound or pharmaceutically acceptable salt thereof according to (5), wherein R$^1$ is a halogen atom, a $C_{1-6}$ alkoxy group, a halo$C_{1-6}$ alkyl group, a cyano group, a heteroaryl group (which may be substituted by a $C_{1-6}$ alkyl group), a $C_{1-6}$ alkyl group, a $C_{1-6}$ alkylamino group, or the formula CONR$^7$R$^8$ (R$^7$ and R$^8$ are the same or different, and each represent a hydrogen atom or a $C_{1-6}$ alkyl group), and R$^{1'}$ is a hydrogen atom.

(7) The compound or pharmaceutically acceptable salt thereof according to any one of (1) and (3) to (5), wherein R$^1$ is a halogen atom, a $C_{1-6}$ alkoxy group, a halo$C_{1-6}$ alkyl group, a $C_{1-6}$ alkyl group, or a $C_{3-6}$ cycloalkyl group, and R$^{1'}$ is a hydrogen atom, a halogen atom, a $C_{1-6}$ alkoxy group, a halo$C_{1-6}$ alkyl group, a $C_{1-6}$ alkyl group, or a $C_{3-6}$ cycloalkyl group.

(8) The compound or pharmaceutically acceptable salt thereof according to any one of (1) to (7), wherein R$^1$ is attached in the para position.

(9) The compound or pharmaceutically acceptable salt thereof according to any one of (1) to (8), wherein any one of A$^1$, A$^2$, A$^3$ and A$^4$ is a nitrogen atom or A$^1$ and A$^3$ are both a nitrogen atom.

(10) The compound or pharmaceutically acceptable salt thereof according to any one of (1) to (8), wherein A$^1$ is a nitrogen atom, A$^2$ and A$^4$ are both the formula CH, and A$^3$ is the formula CH or a nitrogen atom.

(11) The compound or pharmaceutically acceptable salt thereof according to any one of (1) and (3) to (10), wherein R$^3$ is a heteroaryl group (which may be substituted by 1 to 3 substituents selected from halogen atoms, $C_{1-6}$ alkyl groups, $C_{3-6}$ cycloalkyl groups, $C_{1-6}$ alkoxy groups, cyano groups, $C_{1-6}$ alkanoyl groups, and halo$C_{1-6}$ alkyl groups). (12) The compound or pharmaceutically acceptable salt thereof according to any one of (1) and (3) to (10), wherein R$^3$ is a pyridyl group (which may be substituted by 1 to 3 substituents selected from halogen atoms, $C_{1-6}$ alkyl groups, $C_{3-6}$ cycloalkyl groups, $C_{1-6}$ alkoxy groups, cyano groups, $C_{1-6}$ alkanoyl groups, and halo$C_{1-6}$ alkyl groups). (13) The compound or pharmaceutically acceptable salt thereof according to any one of (1) and (3) to (10), wherein R$^3$ is a pyridyl group (which may be substituted by 1 to 3 substituents selected from halogen atoms, $C_{1-6}$ alkyl groups, $C_{3-6}$ cycloalkyl groups, and halo$C_{1-6}$ alkyl groups).

(14) The compound or pharmaceutically acceptable salt thereof according to (1), wherein the compound is selected from the group consisting of:

2-[(5S)-3-(5-methoxypyrimidin-2-yl)-2-oxo-5-(propan-2-yl)imidazolidin-1-yl]-N-[4-(trifluoromethyl)pyridin-2-yl]acetamide, 2-[(5S)-3-(5-ethylpyrimidin-2-yl)-2-oxo-5-(propan-2-yl)imidazolidin-1-yl]-N-[4-(trifluoromethyl)pyridin-2-yl]acetamide, 2-[(5S)-3-(5-chloropyrimidin-2-yl)-2-oxo-5-propylimidazolidin-1-yl]-N-[4-(trifluoromethyl)pyridin-2-yl]acetamide, N-(4-chloropyridin-2-yl)-2-[(5S)-3-(5-chloropyrimidin-2-yl)-2-oxo-5-propylimidazolidin-1-yl]acetamide, 2-[(5S)-3-(5-chloropyrimidin-2-yl)-2-oxo-5-propylimidazolidin-1-A-N-(4-ethylpyridin-2-yl]acetamide, 2-[(5S)-3-(5-fluoropyrimidin-2-yl)-2-oxo-5-propylimidazolidin-1-yl]-N-[4-(trifluoromethyl)pyridin-2-yl]acetamide, 2-[(5S)-3-(5-fluoropyrimidin-2-yl)-2-oxo-5-(propan-2-yl)imidazolidin-1-yl]-N-[4-(trifluoromethyl)pyridin-2-yl]acetamide, N-(4-cyclopropylpyridin-2-yl)-2-[(5S)-2-oxo-5-(propan-2-yl)-3-[5-(trifluoromethyl)pyrimidin-2-yl]imidazolidin-1-yl]acetamide, 2-[(5S)-5-[(2S)-butan-2-yl]-3-(5-chloropyrimidin-2-yl)-2-oxoimidazolidin-1-yl]-N-[4-(trifluoromethyl)pyridin-2-yl]acetamide, N-(4-chloropyridin-2-yl)-2-[(5S)-3-(5-chloropyrimidin-2-yl)-2-oxo-5-(propan-2-yl)imidazolidin-1-yl]acetamide, N-(4-chloropyridin-2-yl)-2-{(5S)-2-oxo-5-(propan-2-yl)-3-[5-(trifluoromethyl)pyrimidin-2-yl]imidazolidin-1-yl}acetamide, 2-[(5S)-3-(5-cyclopropylpyrimidin-2-yl)-2-oxo-5-(propan-2-yl)imidazolidin-1-yl]-N-[4-(trifluoromethyl)pyridin-2-yl]acetamide, N-(4-chloropyridin-2-yl)-2-[(5S)-3-(5-cyclopropylpyrimidin-2-yl)-2-oxo-5-(propan-2-yl)imidazolidin-1-yl]acetamide,
2-[(5S)-5-[(2S)-butan-2-yl]-3-(5-chloropyrimidin-2-yl)-2-oxoimidazolidin-1-yl]-N-(4-cyclopropylpyridin-2-yeacetamide,
2-[(5S)-5-[(2S)-butan-2-yl]-3-(5-chloropyrimidin-2-yl)-2-oxoimidazolidin-1-yl]-N-(4-chloropyridin-2-yOacetamide,
2-[(5S)-5-[(2S)-butan-2-yl]-3-(5-chloropyrimidin-2-yl)-2-oxoimidazolidin-1-yl]-N-(4-ethylpyridin-2-yl)acetamide,
N-(4-chloropyridin-2-yl)-2-{(5R)-5-[(1S)-1-fluoropropyl]-2-oxo-3-[5-(trifluoromethyl)pyrimidin-2-yl]imidazolidin-1-yl}acetamide,
N-(4-chloropyridin-2-yl)-2-{(5R)-3-(5-chloropyrimidin-2-yl)-5-[(1S)-1-fluoropropyl]-2-oxoimidazolidin-1-yl}acetamide,
N-(4-cyclopropylpyridin-2-yl)-2-{(5R)-5-[(1S)-1-fluoropropyl]-2-oxo-3-[5-(trifluoromethyl)pyrimidin-2-yl]imidazolidin-1-yl}acetamide,
2-{(5R)-5-[(1S)-1-fluoropropyl]-2-oxo-3-[5-(trifluoromethyl)pyrimidin-2-yl]imidazolidin-1-yl}-N-[4-(trifluoromethyl)pyrimidin-2-yl]acetamide,
2-{(5R)-3-(5-chloropyrimidin-2-yl)-5-[(1S)-1-fluoropropyl]-2-oxoimidazolidin-1-yl}-N-[4-(trifluoromethyl)pyridin-2-yl]acetamide,
2-[(5R)-5-[(1S)-1-fluoropropyl]-3-(5-fluoropyrimidin-2-yl)-2-oxoimidazolidin-1-yl]-N-[4-(trifluoromethyl)pyridin-2-yl]acetamide,
2-{(5R)-3-(5-cyclopropylpyrimidin-2-yl)-5-[(1S)-1-fluoropropyl]-2-oxoimidazolidin-1-yl}-N-[4-(trifluoromethyl)pyridin-2-yl]acetamide,
2-{(5R)-3-(5-ethoxypyrimidin-2-yl)-5-[(1S)-1-fluoropropyl]-2-oxoimidazolidin-1-yl}-N-[4-(trifluoromethyl)pyridin-2-yl]acetamide,
N-(4-cyclopropylpyridin-2-yl)-2-{(5R)-3-(5-ethoxypyrimidin-2-yl)-5-[(1S)-1-fluoropropyl]-2-oxoimidazolidin-1-yl}acetamide,
N-(4-chloropyridin-2-yl)-2-{(5R)-3-(5-ethoxypyrimidin-2-yl)-5-[(1S)-1-fluoropropyl]-2-oxoimidazolidin-1-yl}acetamide,
2-[(5S)-5-[(2S)-butan-2-yl]-3-(5-fluoropyrimidin-2-yl)-2-oxoimidazolidin-1-yl]-N-[4-(trifluoromethyl)pyridin-2-yl]acetamide,
2-{(5S)-5-[(2S)-butan-2-yl]-2-oxo-3-[5-(trifluoromethyl)pyrimidin-2-yl]imidazolidin-1-yl}-N-(4-cyclopropylpyridin-2-yl)acetamide,
2-{(5S)-5-[(2S)-butan-2-yl]-2-oxo-3-[5-(trifluoromethyl)pyrimidin-2-yl]imidazolidin-1-yl}-N-(4-chloropyridin-2-yl)acetamide,
2-[(5S)-3-(5-ethoxypyrimidin-2-yl)-2-oxo-5-(propan-2-ypimidazolidin-1-yl]-N-[4-(trifluoromethyl)pyridin-2-yl]acetamide,
N-(4-chloropyridin-2-yl)-2-[(5S)-3-(5-ethoxypyrimidin-2-yl)-2-oxo-5-(propan-2-ypimidazolidin-1-yl]acetamide,
N-(4-cyclopropylpyridin-2-yl)-2-[(5S)-3-(5-ethoxypyrimidin-2-yl)-2-oxo-5-(propan-2-ypimidazolidin-1-yl]acetamide,
2-[(5S)-5-[(2S)-butan-2-yl]-3-(5-ethoxypyrimidin-2-yl)-2-oxoimidazolidin-1-yl]-N-[4-(trifluoromethyl)pyridin-2-yl]acetamide,
2-[(5S)-5-[(2S)-butan-2-yl]-3-(5-cyclopropylpyrimidin-2-yl)-2-oxoimidazolidin-1-yl]-N-[4-(trifluoromethyl)pyridin-2-yl]acetamide,
N-(5-chloropyridin-2-yl)-2-{(5S)-2-oxo-5-propyl-3-[5-(trifluoromethyl)pyrimidin-2-yl]imidazolidin-1-yl}acetamide,
N-(5-chloro-6-methylpyridin-2-yl)-2-{(5S)-2-oxo-5-propyl-3-[5-(trifluoromethyl)pyrimidin-2-yl]imidazolidin-1-yl}acetamide,
N-(5-chloro-6-methylpyridin-2-yl)-2-[(5S)-3-(5-chloropyrimidin-2-yl)-2-oxo-5-propylimidazolidin-1-yl]acetamide,
2-{(5S)-2-oxo-5-(propan-2-yl)-3-[5-(propan-2-yloxy)pyrimidin-2-yl]imidazolidin-1-yl}-N-[4-(trifluoromethyl)pyridin-2-yl]acetamide,
2-[(5S)-5-[(2S)-butan-2-yl]-3-(5-ethoxypyrimidin-2-yl)-2-oxoimidazolidin-1-yl]-N-(4-chloropyridin-2-yl)acetamide,
2-[(5S)-5-[(2S)-butan-2-yl]-3-(5-cyclopropylpyrimidin-2-yl)-2-oxoimidazolidin-1-yl]-N-(4-chloropyridin-2-yl)acetamide,
2-[(5S)-5-[(2S)-butan-2-yl]-3-(5-ethoxypyrimidin-2-yl)-2-oxoimidazolidin-1-yl]-N-(4-cyclopropylpyridin-2-yl)acetamide, and
2-[(5S)-5-[(2S)-butan-2-yl]-3-(5-cyclopropylpyrimidin-2-yl)-2-oxoimidazolidin-1-yl]-N-(4-cyclopropylpyridin-2-yDacetamide.

(15) A pharmaceutical composition comprising, as an active ingredient, the compound or pharmaceutically acceptable salt thereof according to any one of (1) to (14).

(16) An agent for preventing or treating diseases of schizophrenia, Alzheimer's disease, cognitive impairment, dementia, anxiety disorders, depression, drug dependence, spasm, tremor, pain, Parkinson's disease, attention deficit hyperactivity disorder, bipolar disorder, eating disorder, or sleep disorders, which comprises, as an active ingredient, the compound or pharmaceutically acceptable salt thereof according to any one of (1) to (14).

Advantageous Effects of Invention

The inventive compounds have glycine transporter (GlyT1)-inhibiting activity.

DESCRIPTION OF EMBODIMENTS

The term "$C_{x-y}$ (x and y each denote a natural number)" as used herein means that the number of carbon atoms is x to y.

The term "$C_{1-6}$ alkyl group" as used herein refers to a straight-chain or branched-chain alkyl group having 1 to 6 carbon atoms, and includes, for example, a methyl group, an ethyl group, a propyl group, an isopropyl group, a butyl group, an isobutyl group, a tert-butyl group, a pentyl group, an isopentyl group, and a hexyl group.

The term "$C_{3-6}$ cycloalkyl group" as used herein refers to a cycloalkyl group having 3 to 6 carbon atoms, which is a cyclopropyl group, a cyclobutyl group, a cyclopentyl group, or a cyclohexyl group.

The term "$C_{1-6}$ alkoxy group" as used herein refers to a straight-chain or branched-chain alkoxy group having 1 to 6 carbon atoms, and includes, for example, a methoxy group, an ethoxy group, a propoxy group, an isopropoxy group, a butoxy group, an isobutoxy group, a pentyloxy group, an isopentyloxy group, and a hexyloxy group.

The term "$C_{1-6}$ alkanoyl group" as used herein refers to a straight-chain or branched-chain alkanoyl group having 1 to 6 carbon atoms, and includes, for example, a formyl group, an acetyl group, a propanoyl group, a butanoyl group, and a pivaloyl group.

The term "halogen (halo)" as used herein refers to fluorine, chlorine, bromine, or iodine.

The term "halo$C_{1-6}$ alkyl group" as used herein refers to a straight-chain or branched-chain alkyl group which has 1 to 6 carbon atoms and which has been substituted by a halogen atom or halogen atoms. The preferred number of the substituting halogen atom(s) is 1 to 3. Examples of the haloC$_{1-6}$ alkyl group include a fluoromethyl group, a difluoromethyl group, a trifluoromethyl group, and a trichloromethyl group. Among these groups, a trifluoromethyl group is preferred.

The term "C$_{1-6}$ alkylamino group" as used herein refers to a group characterized in that 1 or 2 straight-chain or branched-chain alkyl groups each having 1 to 6 carbon atoms are attached to an amino group. Examples of the C$_{1-6}$ alkylamino group include a methylamino group, a dimethylamino group, a diethylamino group, an N-ethyl-N-methylamino group, and the like.

The term "C$_{1-6}$ alkylamine" as used herein refers to an amine which has one or two straight-chain or branched-chain alkyl groups having 1 to 6 carbon atoms. Examples of the C$_{1-6}$ alkylamine include methylamine, dimethylamine, diethylamine, N-ethyl-N-methylamine, and the like.

The term "C$_{1-6}$ alkylsulfonyl group" as used herein refers to a straight-chain or branched-chain alkylsulfonyl group having 1 to 6 carbon atoms, and includes, for example, a methylsulfonyl group, an ethylsulfonyl group, a propylsulfonyl group, an isopropylsulfonyl group, a butylsulfonyl group, an isobutylsulfonyl group, a tert-butylsulfonyl group, a pentylsulfonyl group, an isopentylsulfonyl group, and a hexylsulfonyl group.

The term "haloC$_{1-6}$ alkylsulfanyl group" as used herein refers to a straight-chain or branched-chain alkylsulfanyl group which has 1 to 6 carbon atoms and which has been substituted by a halogen atom or halogen atoms. The preferred number of the substituting halogen atom(s) is 1 to 3. Examples of the haloC$_{1-6}$ alkylsulfanyl group include a fluoromethylsulfanyl group, a difluoromethylsulfanyl group, a trifluoromethylsulfanyl group, and a trichloromethylsulfanyl group.

The term "haloC$_{1-6}$ alkoxy group" as used herein refers to a straight-chain or branched-chain alkoxy group which has 1 to 6 carbon atoms and which has been substituted by a halogen atom or halogen atoms. The preferred number of the substituting halogen atom(s) is 1 to 3. Examples of the haloC$_{1-6}$ alkoxy group include a fluoromethoxy group, a difluoromethoxy group, and a trifluoromethoxy group.

The term "heteroaryl group" as used herein refers to a monocyclic heteroaryl group having in the ring at least one atom selected from the group consisting of a nitrogen atom, an oxygen atom, and a sulfur atom. When the monocyclic heteroaryl group has a nitrogen atom or nitrogen atoms in the ring, the each nitrogen atom may be an N-oxide.

The heteroaryl group is preferably a 5- or 6-membered heteroaryl group, and includes, for example, a pyridyl group, a pyridazyl group, a pyrimidyl group, a pyrazyl group, a pyrazolyl group, a thiazolyl group, an imidazolyl group, an oxazolyl group, an isoxazolyl group, a thienyl group, a triazolyl group, an oxadiazolyl group, and a thiadiazolyl group.

The term "bicyclic heteroaryl group" as used herein refers to a bicyclic heteroaryl group having in the ring at least one atom selected from the group consisting of a nitrogen atom, an oxygen atom, and a sulfur atom. When the bicyclic heteroaryl group has a nitrogen atom or nitrogen atoms in the ring, the each nitrogen atom may be an N-oxide.

The bicyclic heteroaryl group is preferably a 9- or 10-membered heteroaryl group, and includes, for example, a quinolyl group, an isoquinolyl group, and an indolyl group.

The term "pharmaceutically acceptable salt" as used herein refers to an acid addition salt that may be accepted in pharmaceutical terms. Examples of the acid that may be used include inorganic acids such as sulfuric acid, hydrochloric acid, hydrobromic acid, nitric acid and phosphoric acid, and organic acids such as acetic acid, oxalic acid, lactic acid, citric acid, malic acid, gluconic acid, tartaric acid, fumaric acid, maleic acid, methanesulfonic acid, ethanesulfonic acid, benzenesulfonic acid and p-toluenesulfonic acid. The free forms may be converted to these salts in a conventional manner.

In connection with the inventive compounds, preferred embodiments will be shown below.

Preferred compounds are those wherein $R^1$ is a halogen atom, a C$_{1-6}$ alkoxy group, a haloC$_{1-6}$ alkyl group, a cyano group, a heteroaryl group (which may be substituted by a C$_{1-6}$ alkyl group), a C$_{1-6}$ alkyl group, a C$_{3-6}$ cycloalkyl group, a C$_{1-6}$ alkylamino group, or the formula CONR$^7$R$^8$ (R$^7$ and R$^8$ are the same or different, and each represent a hydrogen atom or a C$_{1-6}$ alkyl group). More preferred compounds are those wherein R$^1$ is a halogen atom, a C$_{1-6}$ alkoxy group, a haloC$_{1-6}$ alkyl group, a C$_{1-6}$ alkyl group, or a C$_{3-6}$ cycloalkyl group. The haloC$_{1-6}$ alkyl group is more preferably a trifluoromethyl group, and the halogen atom is more preferably a chlorine atom. Compounds wherein R$^1$ is attached in the para position are preferred.

Preferred compounds are those wherein $R^{1'}$ is a hydrogen atom, a halogen atom, a C$_{1-6}$ alkoxy group, a haloC$_{1-6}$ alkyl group, a C$_{1-6}$ alkyl group, or a C$_{3-6}$ cycloalkyl group. More preferred compounds are those wherein R$^{1'}$ is a hydrogen atom or a halogen atom. When R$^1$ is an atom or group other than a hydrogen atom, R$^{1'}$ is preferably attached in the ortho position.

Preferred compounds are those wherein $R^2$ is a hydrogen atom.

Preferred compounds are those wherein $R^3$ is a phenyl group (which has been substituted by 1 to 3 substituents selected from halogen atoms, cyano groups, C$_{1-6}$ alkyl groups, C$_{1-6}$ alkoxy groups, C$_{1-6}$ alkylamino groups, C$_{1-6}$ alkylsulfonyl groups, haloC$_{1-6}$ alkyl groups, haloC$_{1-6}$ alkoxy groups, haloC$_{1-6}$ alkylsulfanyl groups, phenyl groups, phenoxy groups, heteroaryl groups (which may be substituted by a C$_{1-6}$ alkyl group), and the formula —SO$_2$NR$^9$R$^{10}$ (R$^9$ and R$^{10}$ are the same or different, and each represent a hydrogen atom or a C$_{1-6}$ alkyl group)) or a heteroaryl group (which has been substituted by 1 to 3 substituents selected from halogen atoms, C$_{1-6}$ alkyl groups, C$_{3-6}$ cycloalkyl groups, C$_{1-6}$ alkoxy groups, cyano groups, C$_{1-6}$ alkanoyl groups, and haloC$_{1-6}$ alkyl groups). More preferred compounds are those wherein R$^3$ is a pyridyl group (which has been substituted by 1 to 3 substituents selected from halogen atoms, C$_{1-6}$ alkyl groups, C$_{3-6}$ cycloalkyl groups, C$_{1-6}$ alkoxy groups, cyano groups, C$_{1-6}$ alkanoyl groups, and haloC$_{1-6}$ alkyl groups). Still more preferred compounds are those wherein R$^3$ is a pyridyl group (which has been substituted by 1 to 3 substituents selected from halogen atoms, C$_{1-6}$ alkyl groups, C$_{3-6}$ cycloalkyl groups, and haloC$_{1-6}$ alkyl groups). In the embodiments of R$^3$, the haloC$_{1-6}$ alkyl group mentioned as a substituent by which a phenyl group or a heteroaryl group (more preferably, a pyridyl group) is substituted is more preferably a trifluoromethyl group, and the halogen atom also mentioned as a substituent is more preferably a chlorine atom. The pyridyl group is preferably a pyridin-2-yl group having a substituent in the 4-position.

Preferred compounds are those wherein $R^4$ is a C$_{1-6}$ alkyl group which may be substituted by 1 to 3 halogen atoms, and more preferred compounds are those wherein R$^4$ is a branched-chain C$_{1-6}$ alkyl group or a straight-chain C$_{1-6}$ alkyl group substituted by 1 to 3 halogen atoms. The configuration of the carbon atom to which R$^4$ is attached is preferably as shown below.

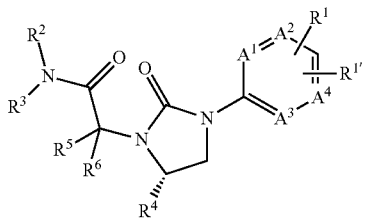

[Formula 2]

Preferred compounds are those wherein $R^5$ and $R^6$ are both a hydrogen atom.

Preferred compounds are those wherein any one of $A^1$, $A^2$, $A^3$ and $A^4$ is a nitrogen atom or $A^1$ and $A^3$ are both a nitrogen atom. More preferred compounds are those wherein $A^1$ is a nitrogen atom, $A^2$ and $A^4$ are both the formula CH, and $A^3$ is the formula CH or a nitrogen atom.

The inventive compounds may contain a plurality of asymmetric centers. Thus, the aforementioned compounds may exist not only in optically active forms but also in their racemates. Further, a plurality of diastereomers may also exist. All of these forms are included in the scope of the present invention. Individual isomers may be obtained by known methods, for example, by use of optically active starting materials or intermediates, by an optically selective reaction or a diastereoselective reaction in the preparation of intermediates or final products, or by chromatographic separation or the like in the preparation of intermediates or final products. If the inventive compounds form hydrates or solvates, these hydrates or solvates are also included in the scope of the present invention. Likewise, pharmaceutically acceptable salts of hydrates or solvates of the inventive compounds are also included in the scope of the present invention.

The compounds according to the present invention may be administered orally or parenterally. The dosage forms are tablets, capsules, granules, dispersions, powders, lozenges, ointments, creams, emulsions, suspensions, suppositories, injections and the like, all of which may be produced by conventional formulation techniques (for example, the methods set forth in the 15th revised Japanese Pharmacopoeia). These dosage forms may be selected as appropriate, according to the symptoms and age of patients and the purpose of treatment.

To produce these preparations, a composition containing the compound of the present invention may be blended with one or more pharmacologically acceptable carriers, namely, excipients (e.g., crystalline cellulose, starch, lactose, mannitol), binders (e.g., hydroxypropylcellulose, polyvinylpyrrolidone), lubricants (e.g., magnesium stearate, talc), disintegrants (e.g., carboxymethylcellulose calcium), and/or various other pharmacologically acceptable additives.

The compounds of the present invention may be used in combination with one or more other therapeutic agents, namely, various antipsychotics, antidepressants, for example, 5HT3 antagonists, 5HT2 antagonists, serotonin agonists, NK-1 antagonists, selective serotonin reuptake inhibitors (SSRIs), serotonin noradrenaline reuptake inhibitors (SNRIs), tricyclic antidepressants, dopaminergic antidepressants, H3 antagonists, 5HT1A antagonists, 5HT1B antagonists, 5HT1D antagonists, D1 agonists, M1 agonists, anticonvulsants, cognitive enhancement drugs, and other psychoactive drugs.

Examples of other therapeutic agents that may be used in combination with the compounds of the present invention include ondansetron, granisetron, metoclopramide, sumatriptan, rauwolscine, yohimbine, fluoxetine, citalopram, escitalopram, femoxetine, fluvoxamine, paroxetine, indalpine, sertraline (registered trademark), zimeldine, venlafaxine, reboxetine, Milnacipran, duloxetine, imipramine, amitriptiline, chlomipramine, nortriptiline, bupropion, amineptine, divalproex, carbamazepine, diazepam, risperidone, olanzapine, ziprasidone, aripiprazole, quetiapine, perospirone, clozapine, haloperidol, pimozide, droperidol, chlorpromazine, thioridazine, mesoridazine, trifluoperazine, perphenazine, fluphenazine, thiflupromazine, prochlorperazine, acetophenazine, thiothixene, chlorprothixene, lamotrigine, loxapine, molindone, and the like. Such combinations may be administered simultaneously (in the same pharmaceutical formulation or in different pharmaceutical formulations), separately, or sequentially.

Particular advantages associated with the use of, and methods for treatment with, combinations of the compounds of the present invention include comparable or improved effects achieved by using individual ingredients at lower doses than their usual doses. Such use and treatment methods are also expected to further enhance the therapeutic effects on positive and/or negative symptoms of psychiatric disorders and/or cognitive impairment. The use of and methods for treatment with combinations of the compounds of the present invention also may provide benefits in the treatment of patients who do not sufficiently respond to, or who are resistant to, treatment with some type of neuroleptic.

The compounds according to the present invention may be administered in doses which, in the case of treating adults, range from 1 to 2000 mg per day, either once daily or in divided portions. The dose may be increased or decreased as appropriate, depending on the age, body weight and symptom of a patient.

The compounds of formula [I] may be produced by various methods of synthesis. The methods described below are only illustrative of the process for producing the inventive compounds and should not be taken as limiting.

In the general production processes, the term "inert solvent" refers to, for example, an alcohol such as methanol, ethanol, isopropanol, n-butanol, or ethylene glycol; an ether such as diethyl ether, t-butyl methyl ether, diisopropyl ether, tetrahydrofuran, 1,4-dioxane, or 1,2-dimethoxyethane; a hydrocarbon such as pentane, hexane, heptane, toluene, benzene, or xylene; an ester such as ethyl acetate or ethyl formate; a ketone such as acetone or methyl ethyl ketone; a halogenated carbon-based solvent such as chloroform or dichloromethane; an amide such as dimethylformamide or N-methylpyrrolidone; acetonitrile; dimethyl sulfoxide; water; or a mixed solvent thereof.

The term "base" refers to, for example, an alkali metal or alkaline earth metal hydride such as lithium hydride, sodium hydride, potassium hydride, or calcium hydride; an alkali metal or alkaline earth metal amide such as lithium amide, sodium amide, lithium diisopropylamide, lithium dicyclohexylamide, lithium hexamethyldisilazide, sodium hexamethyldisilazide, or potassium hexamethyldisilazide; an alkali metal or alkaline earth metal lower alkoxide such as sodium methoxide, sodium ethoxide, or potassium tert-butoxide; an alkyl lithium such as butyl lithium, sec-butyl lithium, tert-butyl lithium, or methyl lithium; an alkali metal or alkaline earth metal hydroxide such as sodium hydroxide, potassium hydroxide, lithium hydroxide, or barium hydroxide; an alkali metal or alkaline earth metal carbonate such as sodium carbonate, potassium carbonate, or cesium carbonate; an alkali metal or alkaline earth metal hydrogencarbonate such as sodium hydrogen carbonate or potassium hydrogen carbonate; an amine such as triethylamine, N-methylmorpholine, N,N-diisopropylethylamine, 1,8-diazabicyclo[5.4.0]undec-7-ene (DBU), 1,5-diazabicyclo[4.3.0]non-5-ene (DBN), or N,N-dimethylaniline; or a basic heterocyclic compound such as pyridine, imidazole, or 2,6-lutidine. These bases are selected as appropriate, according to various reaction conditions known to skilled artisans.

The tell "acid" refers to, for example, an inorganic acid such as hydrochloric acid, hydrobromic acid, sulfuric acid, nitric acid, or phosphoric acid; or an organic acid such as p-toluenesulfonic acid, methanesulfonic acid, trifluoroacetic acid, founic acid, acetic acid, citric acid, or oxalic acid. These acids are selected as appropriate, according to various reaction conditions known to skilled artisans.

In the general production processes, $X^1$ represents a halogen atom or a hydroxyl group; $X^2$ represents a chlorine atom, a bromine atom, an iodine atom, or a trifluoromethanesulfonyloxy group; $P^1$ represents an ester-protective group such as a methyl group or a benzyl group (refer to Theodora W. Green, Peter G. M. Wuts, "Green's Protective Groups in Organic Synthesis, Fourth Edition", Wiley Interscience); $P^2$ represents a nitrogen atom-protective group such as a tert-butoxycarbonyl group or a benzyloxycarbonyl group (refer to the same reference as mentioned above); $R^{1'}$ represents a $C_{1-6}$ alkyl group, a $C_{3-6}$ cycloalkyl group, a halo$C_{1-6}$ alkyl group, or a heteroaryl group; $R^{1b}$ represents a $C_{1-6}$ alkylamino group or a heteroaryl group; and the other symbols are as defined above.

General Production Process 1

Step 1: Compound (1) and compound (2) where $X^1$ is a halogen atom may be reacted in an inert solvent in the presence or absence of a base, to obtain compound (3). Alternatively, a Mitsunobu reaction between compound (1) and compound (2) where $X^1$ is a hydroxyl group may be performed using either an organophosphorus compound and an azo compound or a phosphorus ylide reagent, in an inert solvent in the presence or absence of a base, to obtain compound (3). Examples of the organophosphorus compound include triphenylphosphine, tributylphosphine, and the like. Examples of the azo compound include azodicarboxylic acid diethyl, azodicarboxylic acid diisopropyl, azodicarboxylic acid di-tert-butyl, and the like. Examples of the phosphorus ylide reagent include cyanomethylene tributylphosphorane and the like.

Step 2: A deprotection reaction described in Theodora W. Green, Peter G. M. Wuts, "Green's Protective Groups in Organic Synthesis, Fourth Edition" may be performed to obtain compound (4).

Step 3: An amidation reaction of compound (4) with compound (5) may be performed in an inert solvent in the presence or absence of a base, to obtain the inventive compound [I]. Such an amidation reaction may be performed in accordance with many standard procedures known to skilled artisans, and includes, for example, amidation via a mixed acid anhydride using ethyl chlorocarbonate, isobutyl chlorocarbonate, pivaloyl chloride or the like; amidation via an acid chloride using oxalyl chloride, thionyl chloride or the like; and amidation using a condensing agent such as 1-ethyl-3-(3-dimethylaminopropyl)carbodiimide hydrochloride (EDC.HCl), 1,3-dicyclohexylcarbodiimide (DCC), diphenylphosphoryl azide (DPPA), diethyl phosphorocyanidate, carbonyldiimidazole (CDI), O-(7-azabenzotriazol-1-yl)-N,N,N',N'-tetramethyluronium hexafluorophosphate (HATU), or benzotriazol-1-yloxytris(dimethylamino)phosphonium hexafluorophosphate (BOP reagent). To perform the amidation reaction using a condensing agent, an additive such as 1-hydroxybenzotriazole (HOBt) or hydroxysuccinimide (HOSu) may be used as needed. General production process 2

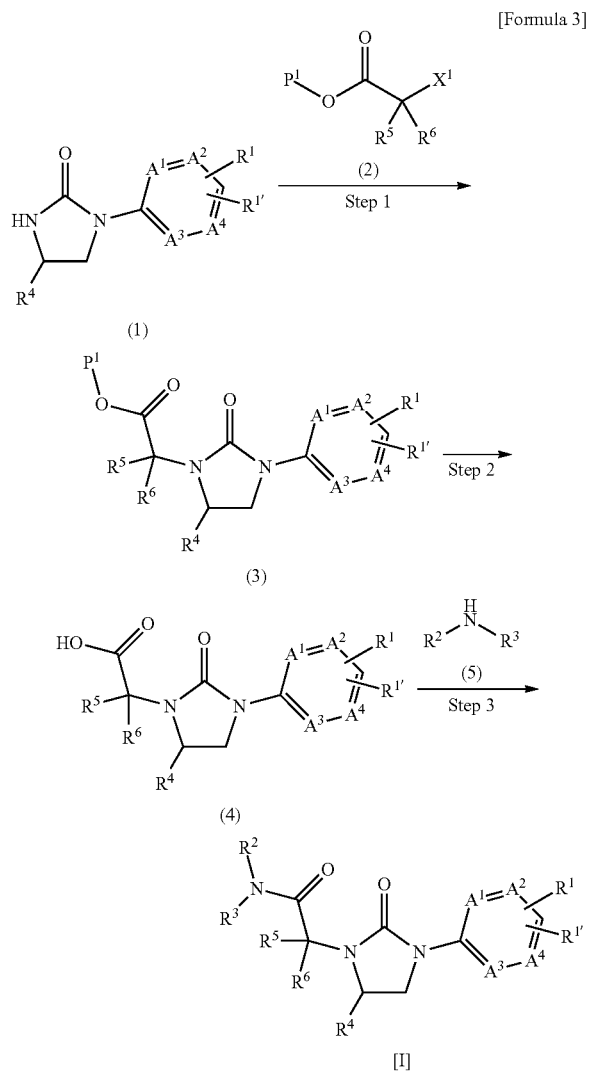

Step 4: Compound (1) and compound (6) may be reacted in the same manner as shown in Step 1 of General production process 1, to obtain the inventive compound [I].

Compound (1) mentioned above may be produced in accordance with the process described below.

General Production Process 3

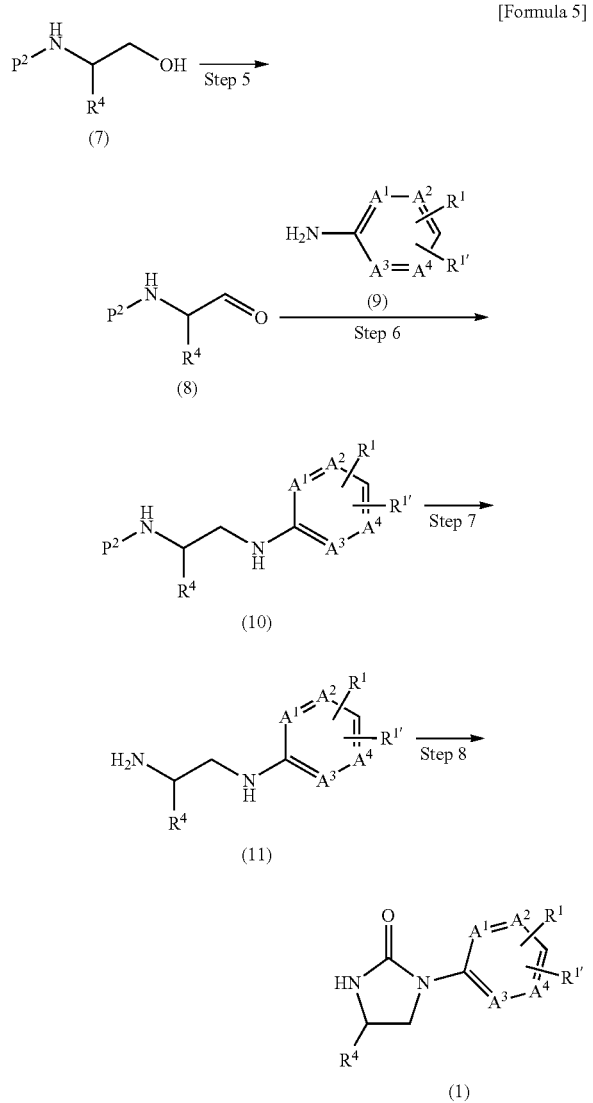

Step 5: A general oxidation reaction of an alcohol into an aldehyde may be performed using an oxidizing agent in an inert solvent to obtain compound (8). Examples of the oxidation reaction include processes using an oxidizing agent such as IBX, TEMPO, PCC, or PDC; Swern oxidation; and the like.

Step 6: Compound (8) and compound (9) may be subjected to a reductive amination reaction using a reducing agent in an inert solvent in the presence or absence of an acid, to obtain compound (10). Examples of the reducing agent include sodium triacetoxyborohydride, sodium cyanoborohydride, sodium borohydride, and the like.

Step 7: A deprotection reaction described in Theodora W. Green, Peter G. M. Wuts, "Green's Protective Groups in Organic Synthesis, Fourth Edition" may be performed to obtain compound (11).

Step 8: Compound (11) may be cyclized using a reagent such as triphosgene, phosgene, or carbonyldiimidazole, in an inert solvent in the presence or absence of a base, to obtain compound (1).

Compound (1) mentioned above may also be produced in accordance with the process described below.

General Production Process 4

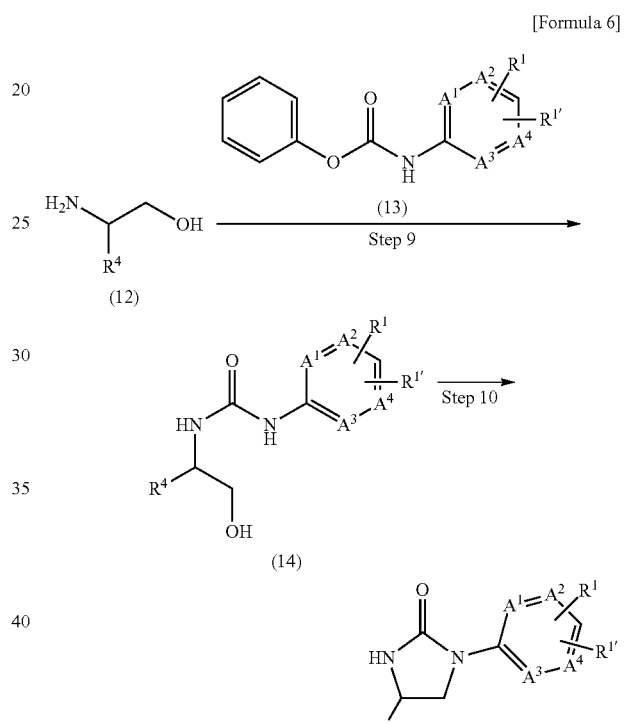

Step 9: A urea formation reaction may be performed by reacting compound (12) with, for example, compound (13) or isocyanate in an inert solvent in the presence or absence of a base, to obtain compound (14).

Step 10: Compound (14) may be subjected to an intramolecular cyclization reaction to obtain compound (1). Examples of the intramolecular cyclization reaction that occurs in this case include Mitsunobu reactions using either an organophosphorus compound and an azo compound or a phosphorus ylide reagent. The intramolecular cyclization reaction may also be performed after conversion of the hydroxyl group of compound (14) to a leaving group by mesylation, tosylation, halogenation or the like in the presence of a base.

Compound (1) mentioned above may also be produced in accordance with the process described below.

General Production Process 5

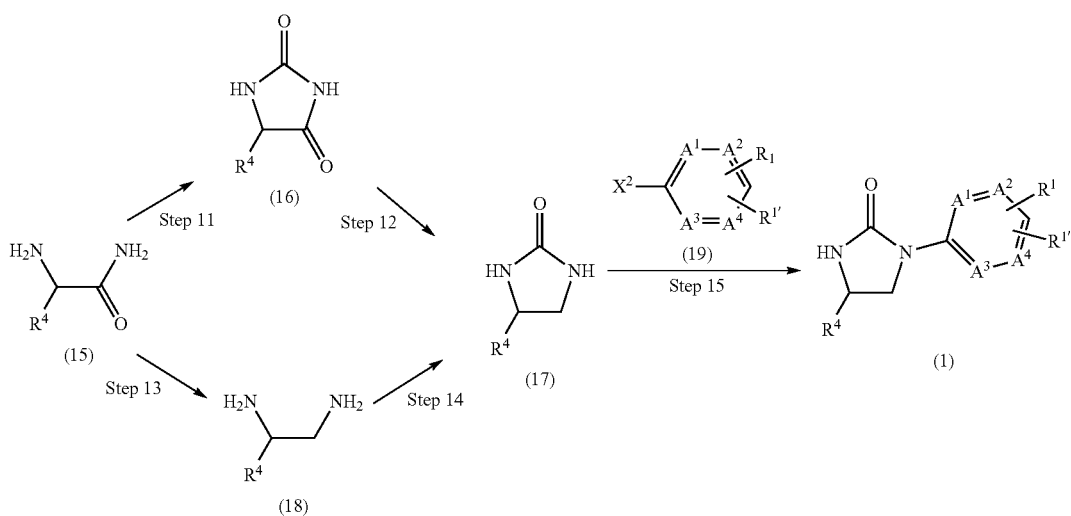

Step 11: Compound (15) may be cyclized using a reagent such as triphosgene, phosgene, carbonyldiimidazole, or 4-nitrophenyl chloroformate, in an inert solvent in the presence or absence of a base, to obtain compound (16).

Step 12: Compound (16) may be reacted with a reducing agent in an inert solvent to obtain compound (17). Examples of the reducing agent include lithium aluminum hydride, sodium bis(2-methoxyethoxy)aluminum hydride, and the like. Further, heating and stirring or use of aluminum trichloride, as needed, is preferred.

Step 13: The same process as shown in Step 12 may be performed to obtain compound (18) from compound (15).

Step 14: The same process as shown in Step 11 may be performed to obtain compound (17) from compound (18).

Step 15: Compound (17) and compound (19) may be reacted using a palladium catalyst or a copper catalyst and, if needed, a ligand of such a metal catalyst, in an inert solvent in the presence or absence of a base, to obtain compound (1). Examples of the palladium catalyst include $Pd(OAc)_2$, $Pd_2(dba)_3$, $Pd(PPh_3)_4$ and the like, and examples of the copper catalyst include CuI, CuBr and the like. Examples of the ligand of the palladium catalyst include triphenylphosphine, Xantphos, BINAP and the like, and examples of the ligand of the copper catalyst include N,N'-dimethylethylenediamine, 1,2-cyclohexanediamine, phenanthroline, proline and the like.

General Production Process 6

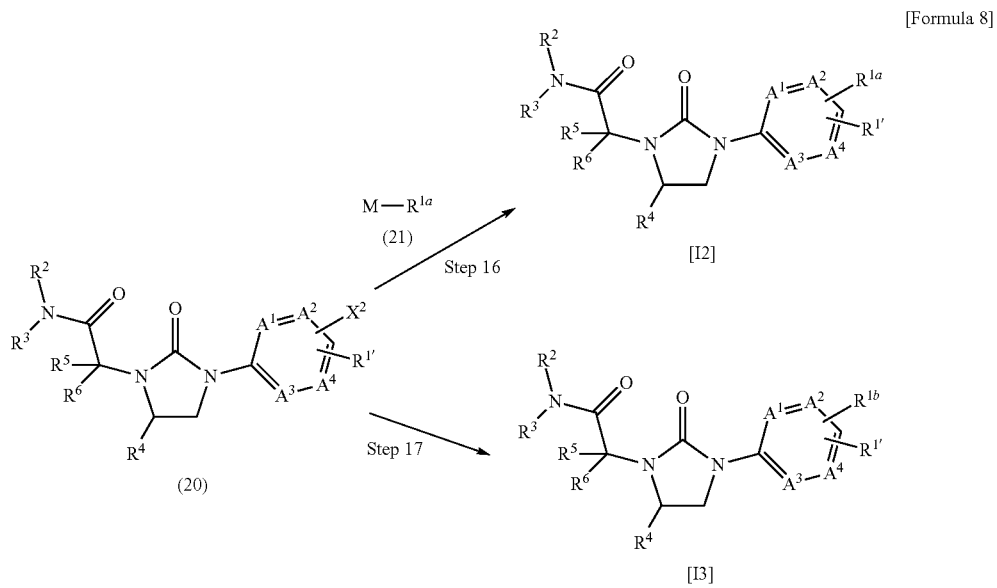

Step 16: Compound (20) may be reacted with compound (21) using a metal catalyst such as palladium, copper, iron or nickel and, if needed, a ligand, in an inert solvent in the presence or absence of a base, to obtain the inventive compound [12]. Compound (21) represents an organometallic reagent and includes, for example, Grignard reagents (e.g., $R^{1a}MgCl$), zinc reagents (e.g., $R^{1a}ZnCl$), boron reagents (e.g., those where $R^{1a}$ is attached to boric acid or a boric acid ester), and tin reagents (e.g., $R^{1a}SnBu_3$). Examples of the iron reagent include tris(2,4-pentanedionato)iron(III), and examples of the nickel reagent include 1,2-bis(diphenylphosphino)ethane nickel(II) chloride and the like.

Step 17: Compound (20) may be reacted with, for example, a $C_{1-6}$ alkylamine or a heteroaryl group having an NH group in the ring, using a metal catalyst such as palladium or copper and, if needed, a ligand, in an inert solvent in the presence or absence of a base, to obtain the inventive compound [13].

General Production Process 7

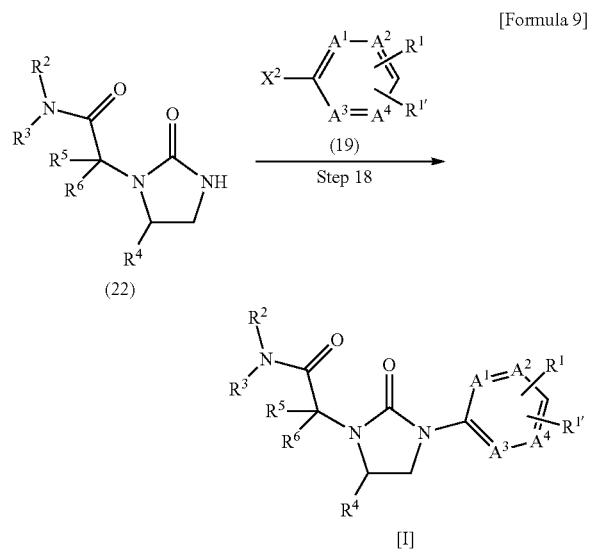

[Formula 9]

Step 18: The same process as shown in Step 15 may be performed to obtain the inventive compound [I] from compound (22).

EXAMPLES

Next, the present invention will be described in more detail by means of Production Examples, Working Examples and Test Example, but these Examples are in no way intended to limit the scope of the present invention.

The microwave reaction apparatus used in the Production Examples and Working Examples described below was Initiator from Biotage.

In the Production Examples and Working Examples below, the "NH silica gel cartridge" and "silica gel cartridge" used for purification by column chromatography were Biotage SNAP Cartridge KP-NH and Biotage SNAP Cartridge KP-Sil or HP-Sil, respectively.

In the Production Examples and Working Examples below, the "NH silica gel" and "silica gel" used for purification by preparative thin-layer chromatography (PTLC) were NH2 Silica Gel 60F254 Plate Wako (20 cm×20 cm) from Wako Pure Chemical Industries, Ltd. and Silica Gel 60F254 (20 cm×20 cm) from Merck, respectively.

In the Production Examples and Working Examples below, the purification by preparative high-performance liquid chromatography (HPLC) was performed under the conditions shown below. It should be noted that when trifluoroacetic acid was used in the main procedure for producing compounds having a basic functional group, neutralization operation or the like was conducted as appropriate for obtaining the compounds in free limn.

Apparatus: Preparative HPLC System from Gilson, Inc.
Column: Capcelpak C18 MGII 5 μm 20×150 mm from Shiseido, Co., Ltd., or Waters SunFire Prep C18 OBD 5 μm 30×50 mm
Solvent: A-liquid (0.1% trifluoroacetic acid-containing water), B-liquid (0.1% trifluoroacetic acid-containing acetonitrile)
Gradient Condition 1: 0 min (A-liquid/B-liquid=90/10), 22 min (A-liquid/B-liquid=20/80), 25 min (A-liquid/B-liquid=10/90); flow rate, 20 mL/min
Gradient Condition 2: 0 min (A-liquid/B-liquid=80/20), 20 min (A-liquid/B-liquid=5/95), 25 min (A-liquid/B-liquid=1/99); flow rate, 20 mL/min
Gradient Condition 3: 0 min (A-liquid/B-liquid=90/10), 11 min (A-liquid/B-liquid=20/80), 12 min (A-liquid/B-liquid=5/95); flow rate, 40 mL/min
Gradient Condition 4: 0 min (A-liquid/B-liquid=80/20), 10 min (A-liquid/B-liquid=5/95), 11 min (A-liquid/B-liquid=1/99); flow rate, 40 mL/min
Detection method: UV 254 nm In the Production Examples and Working Examples below, mass spectra (MS) were measured under the following conditions:
MS spectra: Shimadzu LCMS-2010EV, Micromass Platform LC, or Shimadzu LCMS-IT-TOF In the Production Examples and Working Examples below, nuclear magnetic resonance spectra (NMR) were used for structure confirmation. The nuclear magnetic resonance spectra (NMR) were measured under the following conditions:
NMR spectra: [$^1$H-NMR] 600 MHz, JNM-ECA600 (JEOL Ltd.); 500 MHz, JNM-ECA500 (JEOL Ltd.); 300 MHz, UNITYNOVA300 (Varian Inc.); 200 MHz, GEMINI2000/200 (Varian Inc.)

The RT (retention time) shown in Tables 1-9 to 1-26 are values measured with a high-performance liquid chromatography mass spectrometer (LCMS) under any one of the conditions shown below.

Condition A:
Instrument: Agilent 1290 Infinity and Agilent 6150
Column: Waters Acquity CSH C18, 1.7 μm, φ2.1×50 mm
Solvent: A-liquid (0.1% formic acid-containing water), B-liquid (0.1% formic acid-containing acetonitrile)
Gradient: 0 min (A-liquid/B-liquid=80/20), 1.2-1.4 min (A-liquid/B-liquid=1/99)
Flow rate: 0.8 mL/min, Detection method: 254 nm Condition B:
Instrument: Shimadzu LCMS-2010EV
Column: Shimpack XR-ODS, 2.2 μm, φ2.0×30 mm
Solvent: A-liquid (0.1% formic acid-containing water), B-liquid (0.1% formic acid-containing acetonitrile)
Gradient: 0 min (A-liquid/B-liquid=90/10), 3 min (A-liquid/B-liquid=0/100)
Flow rate: 0.6 mL/min, Detection method: 254 nm Condition C:
Instrument: Agilent 1100 and Micromass Platform LC
Column: Waters SunFire C18, 2.5 μm, φ4.6×50 mm Solvent: A-liquid (0.1% trifluoroacetic acid-containing water), B-liquid (0.1% trifluoroacetic acid-containing acetonitrile)

Gradient: 0 min (A-liquid/B-liquid=90/10), 0.5 min (A-liquid/B-liquid=90/10), 5.5 min (A-liquid/B-liquid=20/80), 6.0 min (A-liquid/B-liquid=1/99), 6.3 min (A-liquid/B-liquid=1/99)

Flow rate: 1 mL/min, Detection method: 254 nm

In the Production Examples and Working Examples below, compounds were named in accordance with ACD/Name (ACD/Labs 12.01, Advanced Chemistry Development Inc.)

Production Example 1

4-(2-Methylpropyl)-1-[6-(trifluoromethyl)pyridin-3-yl]imidazolidin-2-one

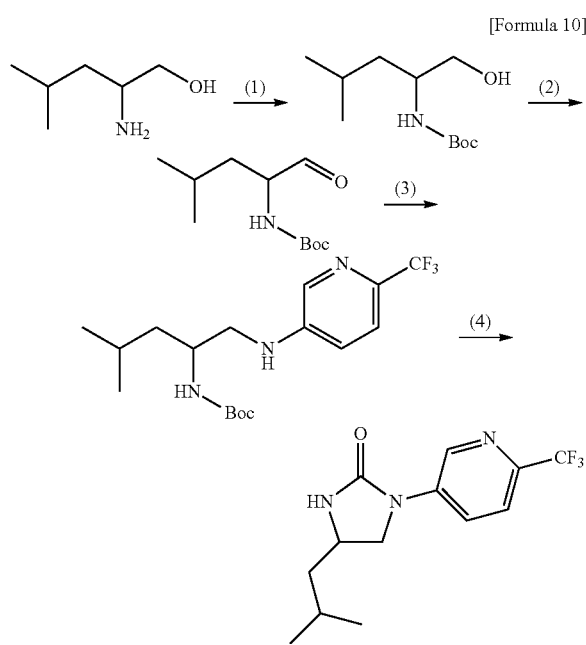

[Formula 10]

(1) Di-tert-butyl dicarbonate (4.1 g) was added to a solution of 2-amino-4-methylpentan-1-ol (2.0 g) in THF (40 mL), and the mixture was stirred at room temperature overnight. The reaction mixture was concentrated under reduced pressure, and the residue was washed with a mixed solvent of hexane/ethyl acetate (=5:1) to afford tert-butyl (1-hydroxy-4-methylpentan-2-yl)carbamate (3.7 g). (ESI pos.) m/z: 240 ([M+Na]+)

(2) To a solution of tert-butyl (1-hydroxy-4-methylpentan-2-yl)carbamate (2.7 g) in DMSO (60 mL) was added 2-iodoxybenzoic acid (3.5 g), and the mixture was stirred at room temperature for 3 hr. Water was added thereto, the resulting insoluble matter was filtered off, and the filtrate was extracted with ethyl acetate. The organic layer was washed with water and brine, and dried over anhydrous magnesium sulfate. After the dessicant was filtered off, the filtrate was concentrated under reduced pressure to afford a crude product of tert-butyl (4-methyl-1-oxopentan-2-yl)carbamate.

1H NMR (600 MHz, CHLOROFORM-d) d ppm 0.96-1.00 (m, 6H), 1.61-1.84 (m, 3H), 3.42-4.98 (m, 2H), 9.60 (s, 1H)

(3) The crude product of tert-butyl(4-methyl-1-oxopentan-2-yl)carbamate was dissolved in chloroform, 2-trifluoromethyl-5-aminopyridine (1.35 g) and sodium triacetoxyborohydride (3.52 g) were added thereto, and the mixture was stirred at room temperature overnight. Saturated aqueous sodium hydrogen carbonate solution was added to the mixture, followed by extraction with chloroform and drying over anhydrous magnesium sulfate. The dissicant was filtered off, and then the filtrate was concentrated under reduced pressure. The residue was purified by column chromatography (silica gel cartridge, hexane/ethyl acetate) to afford tert-butyl (4-methyl-1-{[6-(trifluoromethyl)pyridin-3-yl]amino}pentan-2-yl)carbamate (2.58 g).

(ESI pos.) m/z: 362 ([M+H]+)

(4) A solution of 4M hydrochloric acid in 1,4-dioxane was added to a solution of tert-butyl 4-methyl-1-{[6-(trifluoromethyl)pyridin-3-yl]amino}pentan-2-yl)carbamate (2.3 g) in ethanol (30 mL), and the mixture was stirred at room temperature overnight. After the reaction mixture was concentrated under reduced pressure, saturated aqueous sodium hydrogen carbonate solution was added thereto, followed by extraction with chloroform. After drying over anhydrous magnesium sulfate, the desiccant was filtered off and the filtrate was concentrated under reduced pressure. The residue was dissolved in THF (20 mL) and cooled in ice, triethylamine (2.0 mL) and triphosgene (0.41 g) were then added thereto, and the resulting mixture was stirred for 30 min. Saturated aqueous sodium hydrogen carbonate solution was added thereto, followed by extraction with ethyl acetate and drying over anhydrous magnesium sulfate. After the desiccant was filtered off, the filtrate was concentrated under reduced pressure, and the residue was washed with hexane/ethyl acetate (=2:1) to affore the title compound (0.58 g).

(ESI pos.) m/z: 288 ([M+H]+)

1H NMR (600 MHz, CHLOROFORM-d) d ppm 0.97-1.03 (m, 6H), 1.48-1.55 (m, 1H), 1.61-1.66 (m, 1H), 1.69-1.79 (m, 1H), 3.56 (dd, J=8.7, 6.4 Hz, 1H), 3.94-4.01 (m, 1H), 4.06-4.11 (m, 1H), 5.28 (br. s., 1H), 7.64 (d, J=8.7 Hz, 1H), 8.37 (dd, J=8.7, 2.3 Hz, 1H), 8.67 (d, J=2.8 Hz, 1H)

The following compounds were synthesized according to the similar procedure.

4-(Propan-2-yl)-1-[6-(trifluoromethyl)pyridin-3-yl]imidazolidin-2-one (ESI pos.) m/z: 274 ([M+H]+)

1-(6-Methoxypyridin-3-yl)-4-propylimidazolidin-2-one (ESI pos.) m/z: 236 ([M+H]+)

Production Example 2

(4S)-4-(Propan-2-yl)-1-[6-(trifluoromethyl)pyridin-3-yl]imidazolidin-2-one

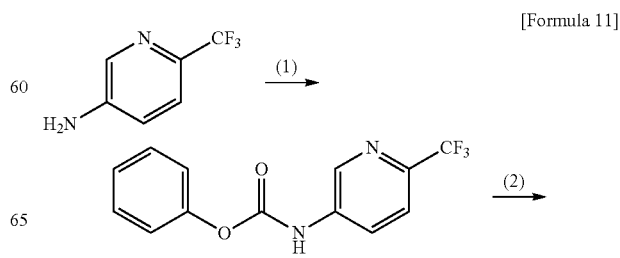

[Formula 11]

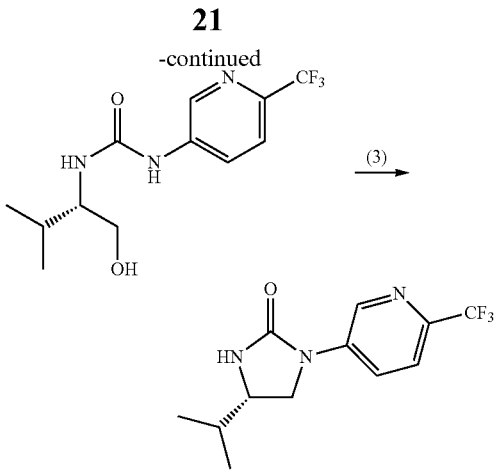

(1) Pyridine (2.9 mL) was added to a solution of 2-trifluoromethyl-5-aminopyridine (1.95 g) in chloroform (15 mL), the mixture was cooled in ice, and phenyl chloroformate (1.8 mL) was added thereto. The resulting mixture was stirred at room temperature overnight, and the reaction mixture was concentrated under reduced pressure. The residue was washed with isopropyl ether to afford phenyl[6-(trifluoromethyl)pyridin-3-yl]carbamate (2.16 g).

(ESI pos.) m/z: 283 ([M+H]+)

(2) Triethylamine (0.54 mL) and phenyl[6-(trifluoromethyl)pyridin-3-yl]carbamate (600 mg) were added to a solution of L-valinol (200 mg) in chloroform, and the mixture was stirred at 80° C. for 1 hr. The reaction mixture was concentrated under reduced pressure, and the residue was purified by column chromatography (silica gel cartridge, hexane/ethyl acetate) to afford 1-[(2S)-1-hydroxy-3-methylbutan-2-yl]-3-[6-(trifluoromethyl)pyridin-3-yl]urea (640 mg).

(ESI pos.) m/z: 292 ([M+H]+)

(3) Triphenylphosphine (770 mg) and diethyl azodicarboxylate (2.2 M solution in toluene, 1.3 mL) were added to a solution of 1-[(2S)-1-hydroxy-3-methylbutan-2-yl]-3-[6-(trifluoromethyl)pyridin-3-yl]urea (640 mg) in THF (10 mL), and the mixture was stirred at room temperature for 1 hr. The reaction mixture was concentrated under reduced pressure, the residue was purified by column chromatography (silica gel cartridge and NH silica gel cartridge, hexane/ethyl acetate), and the resulting solid was washed with isopropyl ether to afford the title compound (500 mg). This product contained by-products originating in reaction reagents.

(ESI pos.) m/z: 274 ([M+H]+)

1H NMR (600 MHz, CHLOROFORM-d) d ppm 0.96-1.05 (m, 6H), 1.76-1.86 (m, 1H), 3.59-3.66 (m, 2H), 3.99-4.08 (m, 1H), 7.64 (d, J=8.7 Hz, 1H), 8.41 (dd, J=8.7, 2.5 Hz, 1H), 8.67 (d, J=2.5 Hz, 1H)

The following compounds were synthesized according to the similar procedure.

(4R)-4-(Propan-2-yl)-1-[6-(trifluoromethyl)pyridin-3-yl]imidazolidin-2-one (4S)-4-(2-Methylpropyl)-1-[6-(trifluoromethyl)pyridin-3-yl]imidazolidin-2-one (ESI pos.) m/z: 288 ([M+H]+)

(4S)-4-(Cyclohexylmethyl)-1-[6-(trifluoromethyl)pyridin-3-yl]imidazolidin-2-one (ESI pos.) m/z: 328 ([M+H]+)

(4S)-4-(Butan-2-yl)-1-[6-(trifluoromethyl)pyridin-3-yl]imidazolidin-2-one (ESI pos.) m/z 288 ([M+H]+)

(4S)-4-Phenyl-1-[6-(trifluoromethyl)pyridin-3-yl]imidazolidin-2-one (ESI pos.) m/z: 308 ([M+H]+)

(4S)-4-tert-Butyl-1-[6-(trifluoromethyl)pyridin-3-yl]imidazolidin-2-one (ESI pos.) m/z: 288 ([M+H]+)

(4S)-4-Ethyl-1-[6-(trifluoromethyl)pyridin-3-yl]imidazolidin-2-one (ESI pos.) m/z: 260 ([M+H]+)

(4S)-1-(5-Fluoropyridin-2-yl)-4-(propan-2-yl)imidazolidin-2-one (ESI pos.) m/z: 224 ([M+H]+)

(4S)-1-(6-Bromopyridin-3-yl)-4-(propan-2-yl)imidazolidin-2-one (ESI pos.) m/z: 284 ([M+H]+)

(4S)-4-Benzyl-1-[6-(trifluoromethyl)pyridin-3-yl]imidazolidin-2-one (ESI pos.) m/z: 322 ([M+H]+)

(4S)-4-Propyl-1-[6-(trifluoromethyl)pyridin-3-yl]imidazolidin-2-one (ESI pos.) m/z: 274 ([M+H]+)

(4S)-1-(6-Bromopyridin-3-yl)-4-tert-butylimidazolidin-2-one (ESI pos.) m/z: 298 ([M+H]+)

(4S)-4-(Cyclopropylmethyl)-1-[6-(trifluoromethyl)pyridin-3-yl]imidazolidin-2-one (ESI pos.) m/z: 286 ([M+H]+)

(4S)-4-Propyl-1-[6-(trifluoromethyl)pyridin-3-yl]imidazolidin-2-one

1H NMR (200 MHz, DMSO-d₆) d ppm 0.82-0.98 (m, 3H), 1.23-1.64 (m, 4H), 3.48-3.62 (m, 1H), 3.66-3.84 (m, 1H), 3.98-4.14 (m, 1H), 7.68 (s, 1H), 7.81 (d, J=8.79 Hz, 1H), 8.17-8.28 (m, 1H), 8.86-8.93 (m, 1H)

(4R)-4-(2-Fluoropropan-2-yl)-1-[6-(trifluoromethyl)pyridin-3-yl]imidazolidin-2-one (ESI pos.) m/z: 292 ([M+H]+)

(4R)-4-(2-Methoxypropan-2-yl)-1-[6-(trifluoromethyl)pyridin-3-yl]imidazolidin-2-one (ESI pos.) m/z: 304 ([M+H]+)

(4R)-4-[(1S)-1-Fluoropropyl]-1-[6-(trifluoromethyl)pyridin-3-yl]imidazolidin-2-one 1H NMR (600 MHz, CHLOROFORM-d) d ppm 1.06-1.16 (m, 3H), 1.64-1.79 (m, 2H), 3.91 (dd, J=9.29, 5.16 Hz, 1H), 3.96-4.04 (m, 1H), 4.06-4.16 (m, 1H), 4.34-4.50 (m, 1H), 5.45 (br. s., 1H), 7.66 (d, J=8.67 Hz, 1H), 8.30-8.38 (m, 1H), 8.70-8.76 (m, 1H)

(4S)-4-Cyclopropyl-1-[6-(trifluoromethyl)pyridin-3-yl]imidazolidin-2-one (ESI pos.) m/z: 272 ([M+H]+)

(4S)-4-(2-Fluoro-2-methylpropyl)-1-[6-(trifluoromethyl)pyridin-3-yl]imidazolidin-2-one (ESI pos.) m/z: 306 ([M+H]+)

(4S)-4-[2-(Benzyloxy)ethyl]-1-[6-(trifluoromethyl)pyridin-3-yl]imidazolidin-2-one

Production Example 3

{(5S)-2-oxo-5-(propan-2-yl)-3-[6-(trifluoromethyl) pyridin-3-yl]imidazolidin-1-yl}acetic acid

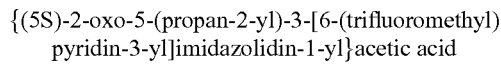

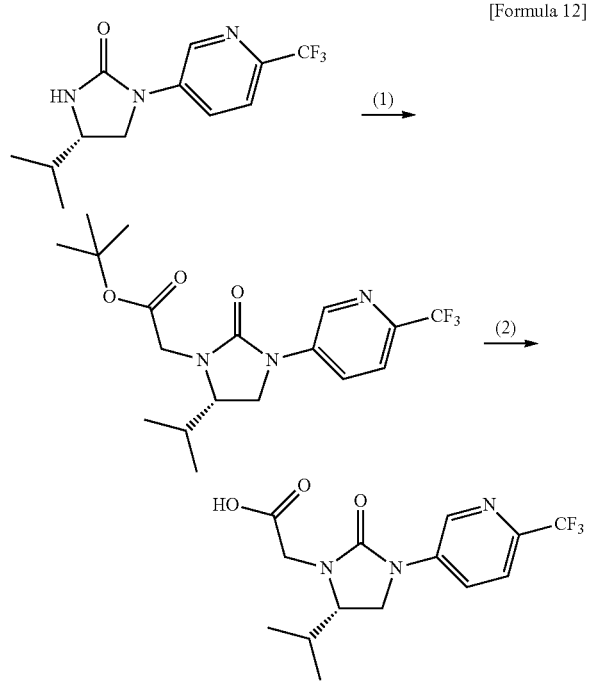

(1) Sodium hydride (0.53 g) was added to a solution of (4S)-4-(propan-2-yl)-1-[6-(trifluoromethyl)pyridin-3-yl] imidazolidin-2-one (5.6 g) in DMF (20 mL), and the mixture was stirred at room temperature for 10 min. Thereafter, tert-butyl bromoacetate (2.0 mL) was added portionwise thereto, and the mixture was stirred at room temperature for 2 hr. Water and saturated aqueous sodium hydrogen carbonate solution were added thereto, and the mixture was extracted with chloroform. The organic layer was separated out by phase-separation cartridge (Biotage, Isolute Phase Separator) and concentrated under reduced pressure. The residue was purified by column chromatography (silica gel cartridge, hexane/ethyl acetate) to afford tert-butyl {(5S)-2-oxo-5-(propan-2-yl)-3-[6-(trifluoromethyl)pyridin-3-yl]imidazolidin-1-yl}acetate (802 mg).

(ESI pos.) m/z: 388 ([M+H]+)

(2) Trifluoroacetic acid (30 mL) was added to a solution of tert-butyl {(5S)-2-oxo-5-(propan-2-yl)-3-[6-(trifluoromethyl)pyridin-3-yl]imidazolidin-1-yl}acetate (4.44 g) in chloroform (20 mL), and the mixture was stirred at room temperature for 64 hr. Additional trifluoroacetic acid (9 mL) was added thereto, the resulting mixture was further stirred for 1 hr, and the reaction mixture was then concentrated under reduced pressure. A portion (6.5 g) of the residue was dissolved in diethyl ether, followed by extraction with 6M aqueous sodium hydroxide solution and water. The water layer was washed with diethyl ether and then made acidic using 1M hydrochloric acid. After extraction with chloroform, the organic layer was separated out by phase-separation cartridge, and the solvent was distilled off under reduced pressure to afford the title compound (2.3 g).

(ESI pos.) m/z: 332 ([M+H]+)

1H NMR (600 MHz, CHLOROFORM-d) d ppm 0.90 (d, J=6.6 Hz, 3H), 1.01 (d, J=7.0 Hz, 3H), 2.06-2.16 (m, 1H), 3.59 (dd, J=8.9, 6.4 Hz, 1H), 3.78 (d, J=18.2 Hz, 1H), 3.86-3.92 (m, 1H), 3.92-3.99 (m, 1H), 4.48 (d, J=18.2 Hz, 1H), 7.64 (d, J=9.1 Hz, 1H), 8.30-8.37 (m, 1H), 8.75 (d, J=2.5 Hz, 1H)

The following compounds were synthesized according to the similar procedure.

[3-(6-Methoxypyridin-3-yl)-2-oxo-5-propylimidazolidin-1-yl]acetic acid (ESI pos.) m/z: 294 ([M+H]+)

{(5S)-2-oxo-5-(propan-2-yl)-3-[5-(trifluoromethyl)pyrimidin-2-yl]imidazolidin-1-yl}acetic acid (ESI neg.) m/z: 331 ([M−H]−)

[(5S)-3-(5-Chloropyrimidin-2-yl)-2-oxo-5-(propan-2-yl) imidazolidin-1-yl]acetic acid (ESI pos.) m/z: 299 ([M+H]+)

2-{(5S)-2-Oxo-5-(propan-2-yl)-3-[6-(trifluoromethyl)pyridin-3-yl]imidazolidin-1-yl}propanoic acid (mixture of diastereomers)

(ESI pos.) m/z: 346 ([M+H]+)

[(5S)-3-(5-Fluoropyrimidin-2-yl)-2-oxo-5-(propan-2-yl) imidazolidin-1-yl]acetic acid (ESI pos.) m/z: 283 ([M+H]+)

[(5S)-3-(6-Bromopyridin-3-yl)-5-tert-butyl-2-oxoimidazolidin-1-yl]acetic acid (ESI pos.) m/z: 356 ([M+H]+)

{(5S)-5-(Cyclopropylmethyl)-2-oxo-3-[6-(trifluoromethyl) pyridin-3-yl]imidazolidin-1-yl}acetic acid (ESI pos.) m/z: 344 ([M+H]+)

{(5S)-2-oxo-5-propyl-3-[6-(trifluoromethyl)pyridin-3-yl] imidazolidin-1-yl}acetic acid (ESI pos.) m/z: 332 ([M+H]+)

[(5S)-3-[3-Fluoro-5-(trifluoromethyl)pyridin-2-yl]-2-oxo-5-(propan-2-yl)imidazolidin-1-yl]acetic acid (ESI pos.) m/z: 350 ([M+H]+)

{(5S)-2-oxo-5-(propan-2-yl)-3-[2-(trifluoromethyl)pyrimidin-5-yl]imidazolidin-1-yl}acetic acid (ESI pos.) m/z: 333 ([M+H]+)

[(5S)-3-(5-Methoxypyrimidin-2-yl)-2-oxo-5-(propan-2-yl) imidazolidin-1-yl]acetic acid (ESI pos.) m/z: 295 ([M+H]+)

[(5S)-3-(5-Ethylpyrimidin-2-yl)-2-oxo-5-(propan-2-yl)imidazolidin-1-yl]acetic acid (ESI pos.) m/z: 293 ([M+H]+)

{(5S)-5-(2-Methylpropyl)-2-oxo-3-[6-(trifluoromethyl)pyridin-3-yl]imidazolidin-1-yl}acetic acid (ESI pos.) m/z: 346 ([M+H]+)

{(5S)-5-tert-Butyl-2-oxo-3-[6-(trifluoromethyl)pyridin-3-yl]imidazolidin-1-yl}acetic acid

[(5S)-3-[3-Fluoro-5-(trifluoromethyl)pyridin-2-yl]-5-(2-methylpropyl)-2-oxoimidazolidin-1-yl]acetic acid (ESI pos.) m/z: 364 ([M+H]+)

{(5S)-5-Cyclopropyl-2-oxo-3-[6-(trifluoromethyl)pyridin-3-yl]imidazolidin-1-yl}acetic acid (ESI pos.) m/z: 330 ([M+H]+)

{(5S)-3-[3-Fluoro-5-(trifluoromethyl)pyridin-2-yl]-2-oxo-5-propylimidazolidin-1-yl}acetic acid (ESI pos.) m/z: 372 ([M+Na]+)

{(5R)-5-[(1S)-1-Fluoropropyl]-3-[3-fluoro-5-(trifluoromethyl)pyridin-2-yl]-2-oxoimidazolidin-1-yl}acetic acid (ESI pos.) m/z: 390 ([M+Na]+)

[(5S)-3-(5-Chloropyrimidin-2-yl)-2-oxo-5-propylimidazolidin-1-yl]acetic acid (ESI pos.) m/z: 321 ([M+Na]+)

[(5S)-5-[(2S)-Butan-2-yl]-3-[3-fluoro-5-(trifluoromethyl) pyridin-2-yl]-2-oxoimidazolidin-1-yl]acetic acid (ESI pos.) m/z: 364 ([M+H]+)

[(5S)-5-[(2S)-Butan-2-yl]-3-(5-chloropyrimidin-2-yl)-2-oxoimidazolidin-1-yl]acetic acid (ESI pos.) m/z: 313 ([M+H]+)

[(5S)-5-[(2S)-Butan-2-yl]-3-(5-fluoropyrimidin-2-yl)-2-oxoimidazolidin-1-yl]acetic acid (ESI pos.) m/z: 297 ([M+H]+)

[(5S)-5-[(2S)-Butan-2-yl]-2-oxo-3-[5-(trifluoromethyl)pyrimidin-2-yl]imidazolidin-1-yl]acetic acid (ESI pos.) m/z: 247 ([M+H]+)

[(5S)-5-[(2S)-Butan-2-yl]-3-(5-chloro-3-fluoropyridin-2-yl)-2-oxoimidazolidin-1-yl]acetic acid (ESI pos.) m/z: 330 ([M+H]+)

{(5S)-5-(2-Fluoro-2-methylpropyl)-2-oxo-3-[6-(trifluoromethyl)pyridin-3-yl]imidazolidin-1-yl}acetic acid (ESI pos.) m/z: 364 ([M+H]+)

Production Example 4

(4S)-4-(Propan-2-yl)-1-[5-(trifluoromethyl)pyrimidin-2-yl]imidazolidin-2-one

[Formula 13]

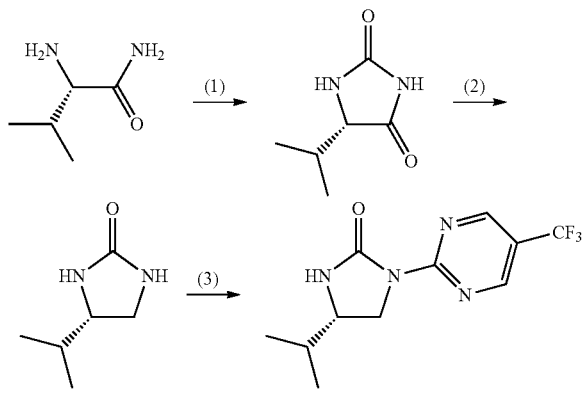

(1) To a suspension of L-valinamide hydrochloride (1.0 g) and sodium hydrogen carbonate (3.03 g) in acetonitrile (100 mL) was added p-nitrophenyl chloroformate (1.32 g), and the mixture was stirred at room temperature for 3 hr. Water was added thereto, the resulting mixture was stirred at room temperature overnight, and then acetonitrile was distilled off under reduced pressure. After extraction with ethyl acetate, the organic layer was concentrated under reduced pressure. The residue was purified by column chromatography (silica gel cartridge, chloroform/methanol) to afford (5S)-5-(propan-2-yl)imidazolidine-2,4-dione (540 mg).

(ESI pos.) m/z: 143 ([M+H]+)

(2) To a suspension of lithium aluminum hydride (290 mg) in diethyl ether (20 mL) was added (5S)-5-(propan-2-yl)imidazolidine-2,4-dione (540 mg) while cooling in ice, and the mixture was stirred at room temperature overnight. After cooling in ice, water (1 mL), 4M aqueous sodium hydroxide solution (1 mL), THF (15 mL) and ethanol (2 mL) were added thereto, and the resulting mixture was stirred at room temperature for 10 min. After filtration through Celite (registered trademark), the filtrate was concentrated under reduced pressure to afford (4S)-4-(propan-2-yl)imidazolidin-2-one (160 mg).

(ESI pos.) m/z: 129 ([M+H]+)

(3) A solution of (4S)-4-(propan-2-yl)imidazolidin-2-one (100 mg), 2-chloro-5-trifluoromethylpyrimidine (142 mg), $Pd_2(dba)_3$ (40 mg), Xantphos (45 mg) and sodium tert-butoxide (70 mg) in toluene (2 mL) was stirred at 100° C. for 1 hr. The reaction mixture was purified by column chromatography (NH silica gel cartridge and silica gel cartridge, hexane/ethyl acetate) to afford the title compound (47 mg).

1H NMR (600 MHz, CHLOROFORM-d) d ppm 0.95-1.02 (m, 6H), 1.75-1.85 (m, 1H), 3.50-3.61 (m, 1H), 3.87 (dd, J=11.1, 6.6 Hz, 1H), 4.18-4.26 (m, 1H), 5.17 (br. s., 1H), 8.84 (s, 2H)

The following compounds were synthesized according to the similar procedure.

(4S)-1-(5-Chloropyrimidin-2-yl)-4-(propan-2-yl)imidazolidin-2-one (ESI pos.) m/z: 241 ([M+H]+)

6-[(4S)-2-oxo-4-(propan-2-yeimidazolidin-1-yl]pyridine-3-carbonitrile (ESI pos.) m/z: 231 ([M+H]+)

(4S)-4-(Propan-2-yl)-1-[5-(trifluoromethyl)pyrazin-2-yl]imidazolidin-2-one (ESI pos.) m/z: 275 ([M+H]+)

(4S)-1-(5-Fluoropyrimidin-2-yl)-4-(propan-2-yl)imidazolidin-2-one (ESI pos.) m/z: 225 ([M+H]+)

(4S)-1-[3-Fluoro-5-(trifluoromethyl)pyridin-2-yl]-4-(propan-2-yl)imidazolidin-2-one (ESI pos.) m/z: 292 ([M+H]+)

(4S)-4-(Propan-2-yl)-1-[2-(trifluoromethyl)pyrimidin-5-yl]imidazolidin-2-one (ESI pos.) m/z: 275 ([M+H]+)

(4S)-1-(5-Chloropyridin-2-yl)-4-(propan-2-yl)imidazolidin-2-one (ESI pos.) m/z: 240 ([M+H]+)

(4S)-1-(5-Methoxypyrimidin-2-yl)-4-(propan-2-yl)imidazolidin-2-one (ESI pos.) m/z: 237 ([M+H]+)

(4S)-1-(5-Ethylpyrimidin-2-yl)-4-(propan-2-yl)imidazolidin-2-one (ESI pos.) m/z: 235 ([M+H]+)

(4S)-1-[3-Fluoro-5-(trifluoromethyl)pyridin-2-yl]-4-(2-methylpropyl)imidazolidin-2-one 1H NMR (600 MHz, CHLOROFORM-d) d ppm 0.95-1.01 (m, 6H), 1.47-1.56 (m, 1H), 1.61-1.77 (m, 2H), 3.76-3.85 (m, 1H), 3.93-4.03 (m, 1H), 4.07-4.19 (m, 1H), 5.12 (br. s., 1H), 7.63-7.71 (m, 1H), 8.45 (s, 1H)

(4S)-1-[3-Fluoro-5-(trifluoromethyl)pyridin-2-yl]-4-propylimidazolidin-2-one (ESI pos.) m/z: 314 ([M+Na]+)

(4S)-1-(5-Chloro-3-fluoropyridin-2-yl)-4-propylimidazolidin-2-one (ESI pos.) m/z: 258 ([M+H]+)

(4S)-4-(Cyclopropylmethyl)-1-[3-fluoro-5-(trifluoromethyl)pyridin-2-yl]imidazolidin-2-one (ESI pos.) m/z: 304 ([M+H]+)

Production Example 5

2-[(5S)-2-oxo-5-propylimidazolidin-1-yl]-N-[4-(trifluoromethyl)pyridin-2-yl]acetamide

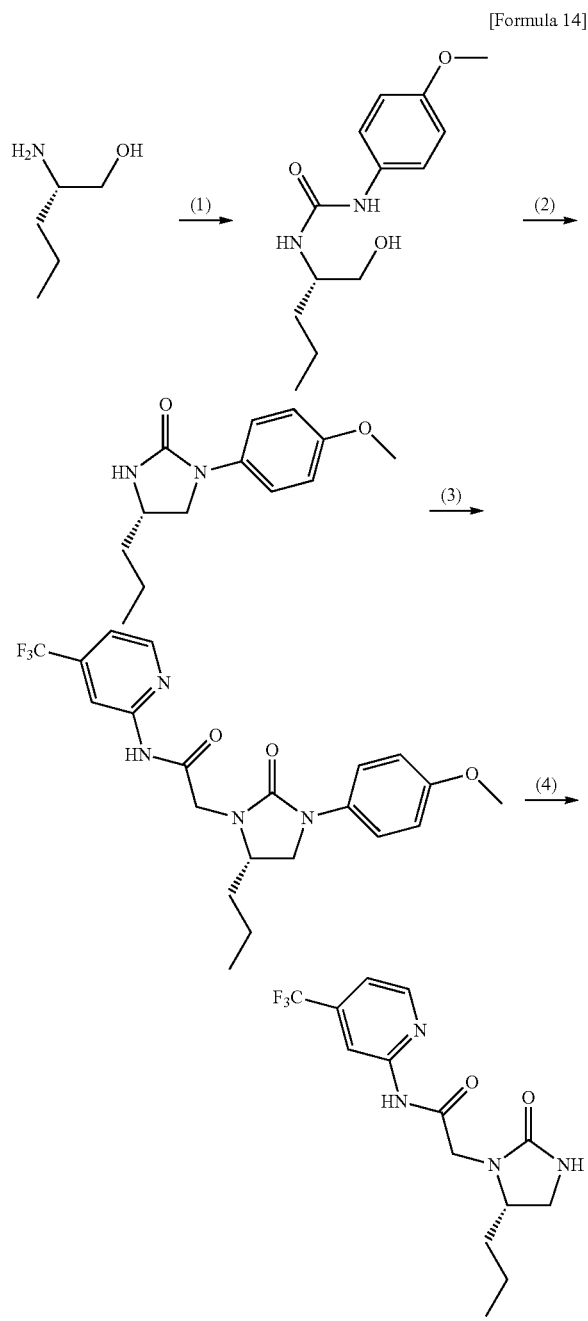

[Formula 14]

(1) A solution of (2S)-2-aminopentan-1-ol (500 mg) in THF (6 mL) was cooled in a dry ice-acetone bath under nitrogen atmosphere, and a solution of 4-methoxyphenyl isocyanate (657 mg) in THF (4 mL) was added dropwise thereto. After the mixture was stirred for 17 hr while gradually warming to room temperature, methanol was added thereto, and the solvent was distilled off under reduced pressure to afford 1-[(2S)-1-hydroxypentan-2-yl]-3-(4-methoxyphenyl)urea (1.17 g).

(ESI pos.) m/z: 253 ([M+H]+)

(2) A solution of 1-[(2S)-1-hydroxypentan-2-yl]-3-(4-methoxyphenyl)urea (550 mg) and potassium tert-butoxide (593 mg) in THF (25 mL) was cooled in ice under nitrogen atomosphere, and a solution of p-toluenesulfonylchrolide (672 mg) in THF (10 mL) was added dropwise thereto. After the mixture was stirred for 1 hr while cooling in ice, water was added thereto, and the resulting mixture was extracted with chloroform. The organic layer was separated out by phase-separation cartridge, and the solvent was distilled off under reduced pressure. The residue was purified by column chromatography (silica gel cartridge, hexane/ethyl acetate=88:12-0:100), and further recrystallized from chloroform/hexane. The solid was collected by filtration to afford (4S)-1-(4-methoxyphenyl)-4-propylimidazolidin-2-one (34 mg). In addition, the filtrate was concentrated under reduced pressure to afford (4S)-1-(4-methoxyphenyl)-4-propylimidazolidin-2-one (254 mg).

(ESI pos.) m/z: 235 ([M+H]+)

(3) Sodium hydride (60%, 27 mg) was added to a solution of (4S)-1-(4-methoxyphenyl)-4-propylimidazolidin-2-one (32 mg) in DMF (1.5 mL), and the mixture was stirred at room temperature for 15 min. To the mixture was added 2-chloro-N-[4-(trifluoromethyl)pyridin-2-yl]acetamide (39 mg), and the resulting mixture was stirred for 15 hr. Thereafter, the reaction mixture was subjected to filtration, and the filtrate was concentrated under reduced pressure. The residue was purified by preparative HPLC, and further the resulting solid was washed with isopropyl ether to afford 2-[(5S)-3-(4-methoxyphenyl)-2-oxo-5-propylimidazolidin-1-yl]-N-[4-(trifluoromethyl)pyridin-2-yl]acetamide (19 mg).

(ESI pos.) m/z: 437 ([M+H]+)

(4) A suspension of 2-[(5S)-3-(4-methoxyphenyl)-2-oxo-5-propylimidazolidin-1-yl]-N-[4-(trifluoromethyl)pyridin-2-yl]acetamide (137 mg) in acetonitrile (3 mL) was cooled in ice, and a solution of ammonium cerium nitrate (340 mg) in water (3 mL) was added dropwise thereto. After stirring the mixture at room temperature for 2 hr, an additional solution of ammonium cerium nitrate (100 mg) in water (0.5 mL) was added thereto, and the mixture was stirred at room temperature for 10 min. Saturated aqueous sodium hydrogen carbonate solution was added thereto, the resulting mixture was extracted with ethyl acetate, and then the organic layer was washed with brine, followed by drying over anhydrous magnesium sulfate. After the dissicant was filterred off, the solvent was distilled off under reduced pressure, and the residue was purified by column chromatography (silica gel cartridge, chloroform/methanol=98:2-80:20) to afford the title compound (76 mg). (ESI pos.) m/z: 331 ([M+H]+)

The following compounds were obtained according to the similar procedure.

N-(4-Chloropyridin-2-yl)-2-[(5R)-5-[(1S)-1-fluoropropyl]-2-oxoimidazolidin-1-yl]acetamide
(ESI pos.) m/z: 315 ([M+H]+)

N-(4-Cyclopropylpyridin-2-yl)-2-{(5R)-5-[(1S)-1-fluoropropyl]-2-oxoimidazolidin-1-yl}acetamide
(ESI pos.) m/z: 321 ([M+H]+)

2-{(5R)-5-[(1S)-1-Fluoropropyl]-2-oxoimidazolidin-1-yl}-N-[4-(trifluoromethyl)pyridin-2-yl]acetamide
(ESI pos.) m/z: 371 ([M+Na]+)

N-(5-Chloropyridin-2-yl)-2-[(5S)-2-oxo-5-propylimidazolidin-1-yl]acetamide
(ESI pos.) m/z: 297 ([M+H]+)

N-(5-Chloro-6-methylpyridin-2-yl)-2-[(5S)-2-oxo-5-propylimidazolidin-1-yl]acetamide
(ESI pos.) m/z: 311 ([M+H]+)

2-[(5S)-2-oxo-5-(propan-2-yl)imidazolidin-1-yl]-N-[4-(trifluoromethyl)pyridin-2-yl]acetamide
(ESI pos.) m/z: 331 ([M+H]+)
N-(4-Cyclopropylpyridin-2-yl)-2-[(5S)-2-oxo-5-(propan-2-yl)imidazolidin-1-yl]acetamide
(ESI pos.) m/z: 303 ([M+H]+)
N-(4-Chloropyridin-2-yl)-2-[(5S)-2-oxo-5-(propan-2-yl)imidazolidin-1-yl]acetamide
(ESI pos.) m/z: 297 ([M+H]+)
2-{(5S)-5-[(2S)-Butan-2-yl]-2-oxoimidazolidin-1-yl}-N-(4-chloropyridin-2-yl)acetamide
(ESI pos.) m/z: 333 ([M+Na]+)
2-{(5S)-5-[(2S)-Butan-2-yl]-2-oxoimidazolidin-1-yl}-N-(4-cyclopropylpyridin-2-yl)acetamide
(ESI pos.) m/z: 317 ([M+H]+)
2-{(5S)-5-[(2S)-Butan-2-yl]-2-oxoimidazolidin-1-yl}-N-[4-(trifluoromethyl)pyridin-2-yl]acetamide
(ESI pos.) m/z: 345 ([M+H]+)

Production Example 6

2-[(5S)-2-oxo-5-(propan-2-yl)imidazolidin-1-yl]-N-[6-(trifluoromethyl)pyridin-3-yl]acetamide

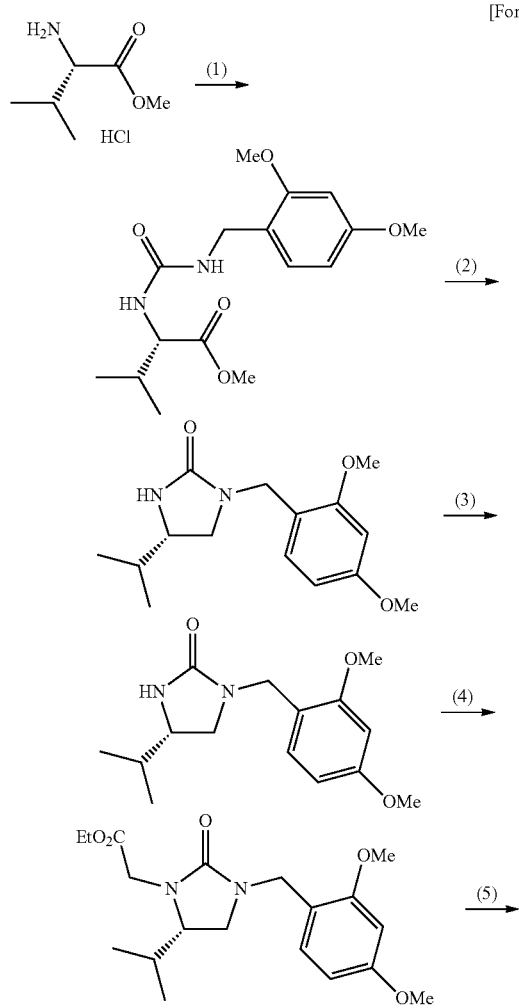

[Formula 15]

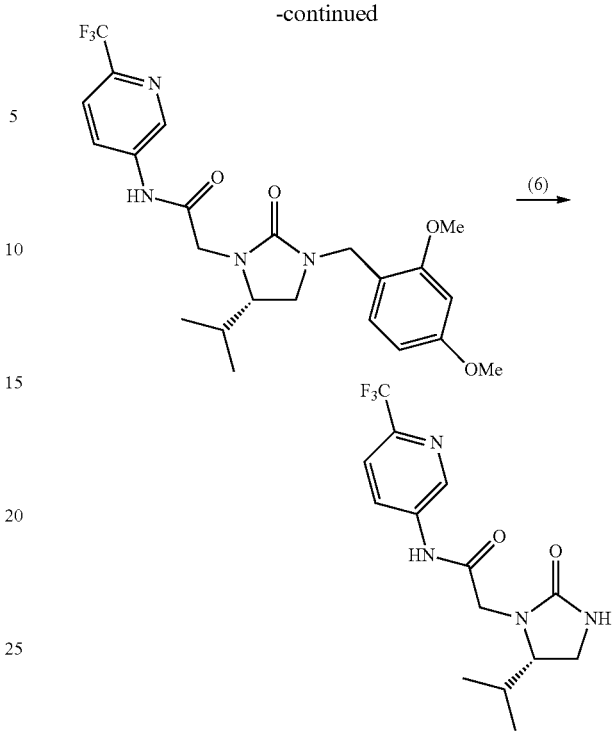

(1) To a solution of L-valine methyl ester hydrochloride (2.6 g) and triethylamine (1.6 g) in chloroform (30 mL) was added 2,4-dimethoxybenzyl isocyanate (3.0 g), and the mixture was stirred at room temperature overnight. After the solvent was distilled off under reduced pressure, the residue was purified by column chromatography (silica gel cartridge, hexane/ethyl acetate) to afford methyl N-[(2,4-dimethoxybenzyl)carbamoyl]-L-valinate (4.2 g).
(ESI pos.) m/z: 325 ([M+H]+)

(2) A solution of methyl N-[(2,4-dimethoxybenzyl)carbamoyl]-L-valinate (4.2 g) and triethylamine (1.3 g) in methanol was stirred while heating to reflux for 5 hr. After the solvent was distilled off under reduced pressure, the residue was purified by column chromatography (NH silica gel cartridge, hexane/ethyl acetate) to afford (5S)-3-(2,4-dimethoxybenzyl)-5-(propan-2-yl)imidazolidine-2,4-dione (4.3 g).
(ESI pos.) m/z: 293 ([M+H]+)

(3) Bis(2-methoxyethoxy)aluminum sodium hydride (65%, solution in toluene) was added to a solution of (5S)-3-(2,4-dimethoxybenzyl)-5-(propan-2-ypimidazolidine-2,4-dione (4.3 g) in THF (300 mL), and the mixture was stirred while heating to reflux for 3 hr. After cooling in ice, sodium sulfate decahydrate was added thereto, followed by stirring. After filtration, the solvent was distilled off under reduced pressure, and the residue was purified by column chromatography (silica gel cartridge, hexane/ethyl acetate) to afford (4S)-1-(2,4-dimethoxybenzyl)-4-(propan-2-yl)imidazolidin-2-one (2.4 g).

(4) Sodium hydride (60%, 380 mg) was added to a solution of (4S)-1-(2,4-dimethoxybenzyl)-4-(propan-2-yl)imidazolidin-2-one (2.4 g) in DMF (35 mL), and the mixture was stirred for 20 min. Ethyl bromoacetate (1.14 mL) was added thereto, and the mixture was stirred at 90° C. for 1 hr. Additional ethyl bromoacetate (1.14 g) and sodium hydride (60%, 380 mg) were added thereto, and the resulting mixture was further stirred at 90° C. for 1 hr. After the solvent was distilled off under reduced pressure, the residue was purified by column chromatography (silica gel cartridge, hexane/ethyl acetate) to afford ethyl[(55)-3-(2,4-dimethoxybenzyl)-2-oxo-5-(propan-2-yl)imidazolidin-1-yl]acetate (1.5 g).

(ESI pos.) m/z: 365 ([M+H]+)

(5) An aqueous solution of 2M sodium hydroxide (2.6 mL) was added to a solution of ethyl [(5S)-3-(2,4-dimethoxybenzyl)-2-oxo-5-(propan-2-yeimidazolidin-1-yl]acetate (850 mg) in methanol (10 mL), and the mixture was stirred at room temperature overnight. To the reaction mixture was added 2M hydrochloric acid (2.6 mL), and the reaction mixture was concentrated under reduced pressure. DMF (10 mL), 5-amino-2-trifluoromethylpyridine (380 mg), HATU (890 mg), and diisopropylethylamine (300 mg) were added thereto, and the resulting mixture was stirred at 80° C. for 3 hr. The solvent was distilled off under reduced pressure, and the residue was purified by column chromatography (silica gel cartridge, hexane/ethyl acetate) to afford 2-[(5S)-3-(2,4-dimethoxybenzyl)-2-oxo-5-(propan-2-yl)imidazolidin-1-yl]-N-[6-(trifluoromethyl)pyridin-3-yl]acetamide (900 mg).

(ESI pos.) m/z: 481 ([M+H]+)

(6) Trifluoroacetic acid (20 mL) was added to 2-[(5S)-3-(2,4-dimethoxybenzyl)-2-oxo-5-(propan-2-yl)imidazolidin-1-yl]-N-[6-(trifluoromethyl)pyridin-3-yl]acetamide (900 mg), and the mixture was stirred at room temperature for 3 hr. The solvent was distilled off under reduced pressure, and saturated sodium hydrogen carbonate was added thereto, followed by extraction with chloroform. The solvent was distilled off under reduced pressure, and the residue was purified by column chromatography (silica gel cartridge, hexane/ethyl acetate) to afford the title compound (310 mg).

(ESI pos.) m/z: 331 ([M+H]+)

Production Example 7

(2R,3S)-2-Amino-3-fluoropentan-1-ol hydrochloride

[Formula 16]

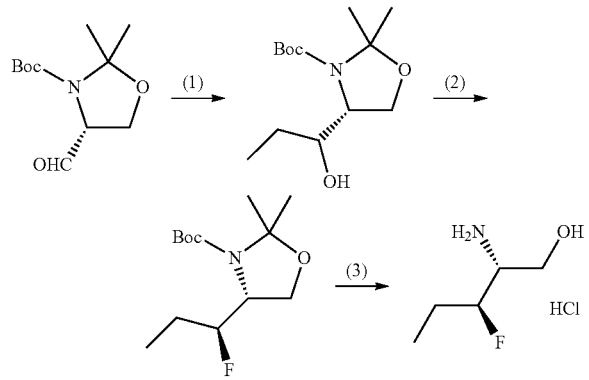

(1) A solution of tert-butyl (4R)-4-formyl-2,2-dimethyl-1,3-oxazolidine-3-carboxylate (14.0 g) in THF (250 mL) was cooled in a dry ice/acetone bath under nitrogen atmosphere, and ethyl magnesium bromide (24 mL, 3M solution in diethyl ether) was added dropwise thereto. The resulting mixture was stirred for 3 hr while elevating the temperature gradually to 0° C., and saturated aqueous ammonium chloride solution was added thereto. The mixture was separated into phases, the aqueous layer was then extracted with ethyl acetate, and the organic layer was washed with water and brine. After drying over anhydrous magnesium sulfate, the desiccant was filtered off, and the filtrate was concentrated under reduced pressure. The residue was purified by column chromatography (silica gel cartridge, hexane/ethyl acetate=92:8-37:63) to afford tert-butyl (4R)-4-(1-hydroxypropyl)-2,2-dimethyl-1,3-oxazolidine-3-carboxylate (11.14 g).

(ESI pos.) m/z: 282 ([M+Na]+)

(2) A solution of tert-butyl (4R)-4-(1-hydroxypropyl)-2,2-dimethyl-1,3-oxazolidine-3-carboxylate (10.0 g) in chloroform (200 mL) was cooled in ice under nitrogen atomosphere, diethylaminosulfur trifluoride (6.1 mL) was added dropwise thereto, and the mixutere was stirred under cooling in ice for 1 hr. Saturated aqueous sodium hydrogen carbonate solution was added thereto, and the resulting mixture was extracted with chloroform, followed by drying over anhydrous magnesium sulfate. The desiccant was filtered off, the filtrate was concentrated under reduced pressure, and then the residue was purified by column chromatography (silica gel cartridge, hexane/ethyl acetate=95:5-60:40) to afford tert-butyl ((4R)-4-[(1S)-1-fluoropropyl]-2,2-dimethyl-1,3-oxazolidine-3-carboxylate (4.74 g).

1H NMR (600 MHz, CHLOROFORM-d) d ppm 0.91 (t, J=7.22 Hz, 3H), 1.28-1.62 (m, 17H), 3.72-4.01 (m, 3H), 4.30-4.63 (m, 1H)

(3) A 5-10% HCl/methanol solution (70 mL) was added to tert-butyl((4R)-4-[(1S)-1-fluoropropyl]-2,2-dimethyl-1,3-oxazolidine-3-carboxylate (4.9 g), and the mixture was stirred at room temperature overnight. The solvent was distilled off under reduced pressure to afford the title compound (2.96 g).

(ESI pos.) m/z: 122 ([M+H]+)

Production Example 8

(4R)-4-[(1S)-1-Fluoropropyl]-1-[3-fluoro-5-(trifluoromethyl)pyridin-2-yl]imidazolidin-2-one

[Formula 17]

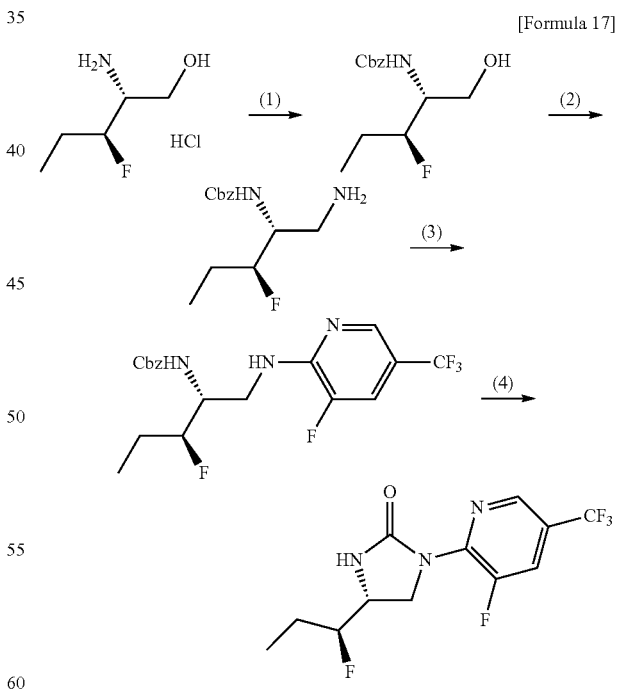

(1) A solution of (2R,3S)-2-amino-3-fluoropentan-1-ol hydrochloride (2.0 g) in THF (60 mL) was cooled in ice, a solution of potassium carbonate (4.4 g) in water (6 mL) and a solution of benzyl chloroformate (2.4 g) in THF (6 mL) were added thereto, and the mixture was stirred at room temperature overnight. Saturated aqueous sodium hydrogen carbonate solution was added thereto, followed by extraction with ethyl acetate and drying over anhydrous magnesium sulfate. After the desiccant was filtered off, the solvent was distilled off under reduced pressure, and the residue was purified by column chromatography (silica gel cartridge, hexane/ethyl acetate=88:12-0:100) to afford benzyl[(2R,3S)-3-fluoro-1-hydroxypentan-2-yl]carbamate (2.5 g).

1H NMR (600 MHz, DMSO-$d_6$) d ppm 0.88 (t, J=7.43 Hz, 3H), 1.45-1.65 (m, 2H), 3.36-3.50 (m, 2H), 3.59-3.70 (m, 1H), 4.30-4.44 (m, 1H), 4.65-4.71 (m, 1H), 4.95-5.04 (m, 2H), 7.12-7.36 (m, 5H)

(2) A solution of benzyl[(2R,3S)-3-fluoro-1-hydroxypentan-2-yl]carbamate (2.4 g) in chloroform (40 mL) was cooled in ice, triethylamine (2 mL) and methanesulfonyl chloride (0.8 mL) were added thereto, and the mixture was stirred for 30 min. Saturated sodium hydrogen carbonate was added thereto, followed by extraction with chloroform and drying over anhydrous magnesium sulfate. After the desiccant was filterred off, the solvent was distilled off under reduced pressure, and the residue was dissolved in DMF (40 mL). Sodium azide (3.06 g) was added thereto, and the mixture was stirred at 60° C. for 2 hr. Water was added thereto, the resulting mixture was extracted with ethyl acetate, and the organic layer was washed with water and brine. After drying over anhydrous magnesium sulfate, the desiccant was filtered off, and the solvent was distilled off under reduced pressure. The residue was dissolved in THF (50 mL), triphenylphosphine (3.59 g) and water (10 mL) were added thereto, and the resulting mixture was stirred at room temperature overnight. The solvent was distilled off under reduced pressure, and the residue was purified by column chromatography (silica gel cartridge, chloroform/methanol=98:2-80:20) to afford benzyl[(2R,3S)-1-amino-3-fluoropentan-2-yl]carbamate (2.34 g).

(ESI pos.) m/z: 255 ([M+H]+)

(3) Potassium carbonate was added to a solution of benzyl [(2R,3S)-1-amino-3-fluoropentan-2-yl]carbamate (2.2 g) and 2,3-difluoro-5-trifluoromethylpyridine (1.74 g) in acetonitrile (45 mL), and the mixture was stirred at 80° C. for 5 hr. The reaction mixture was diluted with ethyl acetate and washed with water and brine, and then the solvent was distilled off under reduced pressure. The residue was purified by column chromatography (silica gel cartridge, hexane/ethyl acetate=95:5-20:80) to afford benzyl[[(2R,3S)-3-fluoro-1-{[3-fluoro-5-(trifluoromethyl)pyridin-2-yl]amino}pentan-2-yl]carbamate (2.95 g).

(ESI pos.) m/z: 418 ([M+H]+)

(4) Sodium hydride (about 60%, 546 mg) was added to a solution of benzyl[(2R,3S)-3-fluoro-1-{[3-fluoro-5-(trifluoromethyl)pyridin-2-yl]amino}pentan-2-yl]carbamate (2.85 g) in THF (35 mL), and the mixture was stirred at room temperature for 6 hr. Water was added to the reaction mixture, the resulting mixture was extracted with ethyl acetate, and the organic layer was washed with brine. The solvent was distilled off under reduced pressure, and the residue was purified by column chromatography (silica gel cartridge, hexane/ethyl acetate=80:20-40:60) to afford the title compound (2.07 g).

(ESI pos.) m/z: 310 ([M+H]+)

The following compounds were obtained according to the similar procedure.

(4S)-4-[(2S)-Butan-2-yl]-1-[3-fluoro-5-(trifluoromethyl)pyridin-2-yl]imidazolidin-2-one
(ESI pos.) m/z: 306 ([M+H]+)
(4S)-4-[(2S)-Butan-2-yl]-1-(5-chloropyrimidin-2-yl)imidazolidin-2-one
(ESI pos.) m/z: 255 ([M+H]+)
(4S)-4-[(2S)-Butan-2-yl]-1-(5-fluoropyrimidin-2-yl)imidazolidin-2-one
(ESI pos.) m/z: 239 ([M+H]+)
(4S)-4-[(2S)-Butan-2-yl]-1-[5-(trifluoromethyl)pyrimidin-2-yl]imidazolidin-2-one
(ESI pos.) m/z: 289 ([M+H]+)
(4S)-4-[(2S)-Butan-2-yl]-1-(5-chloro-3-fluoropyridin-2-yl)imidazolidin-2-one
(ESI pos.) m/z: 277 ([M+H]+)

Production Example 9

(4S)-4-(2-Fluoroethyl)-1-[6-(trifluoromethyl)pyridin-3-yl]imidazolidin-2-one

[Formula 18]

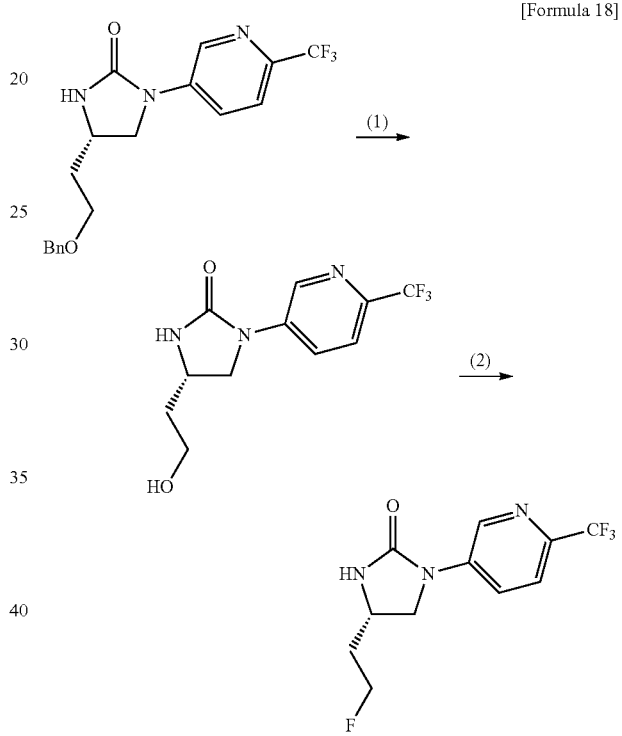

(1) Palladium hydroxide (120 mg) was added to a solution of (4S)-4-[2-(benzyloxy)ethyl]-1-[6-(trifluoromethyl)pyridin-3-yl]imidazolidin-2-one (1.12 g) in methanol (25 mL), the system was purged with hydrogen gas, and the mixture was stirred at room temperature for 3 hr. After filtration of the reaction mixture, the filtrate was concentrated under reduced pressure, and the resulting solid was washed with ethyl acetate to afford (4S)-4-(2-hydroxyethyl)-1-[6-(trifluoromethyl)pyridin-3-yl]imidazolidin-2-one (235 mg).

(2) A suspension of (4S)-4-(2-hydroxyethyl)-1-[6-(trifluoromethyl)pyridin-3-yl]imidazolidin-2-one (0.10 g) in chloroform (10 mL) was cooled in ice, diethylaminosulfur trifluoride (0.144 mL) was added thereto, and the mixture was stirred at room temperature for 3 hr. Saturated aqueous sodium hydrogen carbonate solution was added thereto, and the organic layer was washed with water and brine, followed by drying over anhydrous sodium sulfate. After the desiccant was filtered off, the filtrate was concentrated under reduced pressure, and the residue was purified by column chromatography (silica gel cartridge, hexane/ethyl acetate=4:1-0:100) to afford the title compound (0.05 g).

1H NMR (600 MHz, CHLOROFORM-d) d ppm 1.86-2.01 (m, 2H), 3.65 (dd, J=7.9, 5.2 Hz, 1H), 3.89-3.941 (m, 1H), 4.10 (d, J=7.9 Hz, 1H), 4.60 (dd, J=39.2, 4.5 Hz, 2H), 7.73 (s, 1H), 7.82 (d, J=7.2 Hz, 1H), 8.21 (d, J=7.2 Hz, 1H), 8.90 (s, 1H).

Production Example 10

(2S)-2-Amino-5-fluoropentan-1-ol hydrochloride

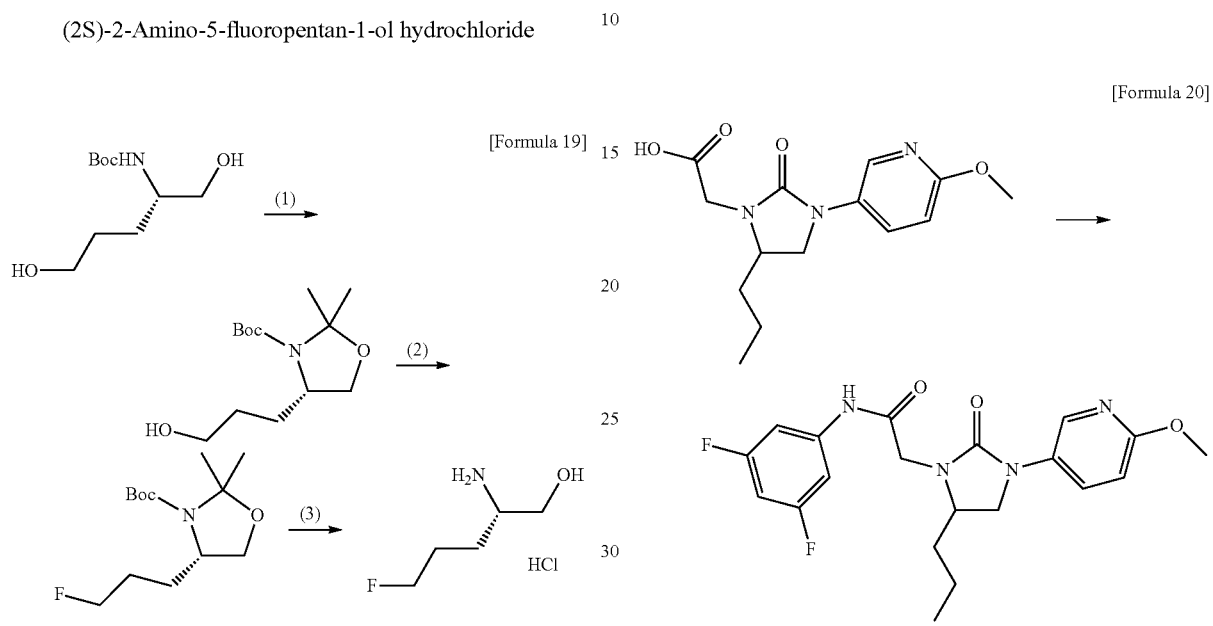

[Formula 19]

(1) A solution of tert-butyl[(2S)-1,5-dihydroxypentan-2-yl]carbamate (9.45 g), 2,2-dimethoxypropane (48 mL) and p-toluenesulfonic acid monohydrate (0.41 g) in chloroform (100 mL) was stirred at room temperature for 3 hr. Saturated aqueous sodium hydrogen carbonate solution was added thereto, and the solvent was distilled off under reduced pressure. Ethyl acetate was added thereto, and the resulting mixture was washed with water and brine, followed by drying over anhydrous sodium sulfate. After the desiccant was filtered off, the filtrate was concentrated under reduced pressure and purified by column chromatography (silica gel cartridge, hexane/ethyl acetate=10:1-0:100) to afford tert-butyl (4S)-4-(3-hydroxypropyl)-2,2-dimethyl-1,3-oxazolidine-3-carboxylate (3.05 g).

(ESI pos.) m/z: 282 ([M+Na]+)

(2) A solution of tert-butyl (4S)-4-(3-hydroxypropyl)-2,2-dimethyl-1,3-oxazolidine-3-carboxylate (3.05 g) in chloroform (40 mL) was cooled in a dry ice-acetone bath, bis(2-methoxyethyl)aminosulfur trifluoride (2.77 mL) was added thereto, and the mixture was stirred at room temperature for 3 hr. Saturated aqueous sodium hydrogen carbonate solution was added thereto, and the organic layer was washed with water and brine, followed by drying with anhydrous sodium sulfate. After the desiccant was filtered off, the filtrate was concentrated under reduced pressure, and the residue was purified by column chromatography (silica gel cartridge, hexane/ethyl acetate=10:1-2:1) to afford tert-butyl (4S)-4-(3-fluoropropyl)-2,2-dimethyl-1,3-oxazolidine-3-carboxylate (900 mg).

(3) According to the similar procedure as in Production Example 7 (3), the title compound (580 mg) was obtained from tert-butyl (4S)-4-(3-fluoropropyl)-2,2-dimethyl-1,3-oxazolidine-3-carboxylate (900 mg) as a crude product.

Working Example 1

N-(3,5-Difluorophenyl)-2-[3-(6-methoxypyridin-3-yl)-2-oxo-5-propylimidazolidin-1-yl]acetamide

[Formula 20]

N,N-diisopropylethylamine (0.06 mL), HATU (142 mg), and 3,5-difluoroaniline (48 mg) were added to a solution of [3-(6-methoxypyridin-3-yl)-2-oxo-5-propylimidazolidin-1-yl]acetic acid (100 mg) in chloroform (2 mL), and the mixture was stirred at room temperature overnight. Saturated aqueous sodium hydrogen carbonate solution was added thereto, followed by extraction with chloroform and drying over anhydrous magnesium sulfate. After the desiccant was filtered off, the filtrate was concentrated under reduced pressure. The residue was purified by column chromatography (silica gel cartridge, hexane/ethyl acetate) to afford the title compound (114 mg).

Working Example 2

2-{2-Oxo-5-(propan-2-yl)-3-[6-(trifluoromethyl)pyridin-3-yl]imidazolidin-1-yl}-N-[3-(trifluoromethyl)phenyl]acetamide

[Formula 21]

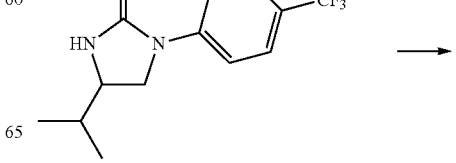

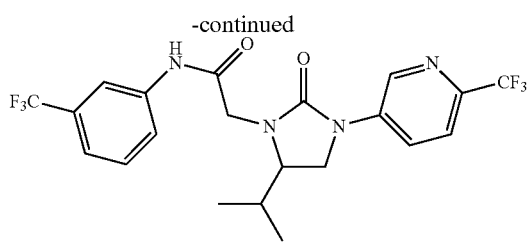

Sodium hydride (60%, 22 mg) was added to a solution of 4-(propan-2-yl)-1-[6-(trifluoromethyl)pyridin-3-yl]imidazolidin-2-one (50 mg) in DMF (1.5 mL), and the mixture was stirred at room temperature for 15 min. After 2-chloro-N-[3-(trifluoromethyl)phenyl]acetamide (52 mg) was added thereto, the resulting mixture was stirred at room temperature for 21 hr. Water and saturated aqueous sodium hydrogen carbonate solution were added to the reaction mixture, followed by extraction with chloroform. The organic layer was separated out by phase separation cartridge and concentrated under reduced pressure. The residue was purified by column chromatography (NH cartridge, and silica gel cartridge, hexane/ethyl acetate) and preparative HPLC to afford the title compound (79 mg).

Working Example 3

2-{(5S)-2-Oxo-5-(propan-2-yl)-3-[6-(trifluoromethyl)pyridin-3-yl]imidazolidin-1-yl}-N-[4-(trifluoromethyl)pyridin-2-yl]acetamide

[Formula 22]

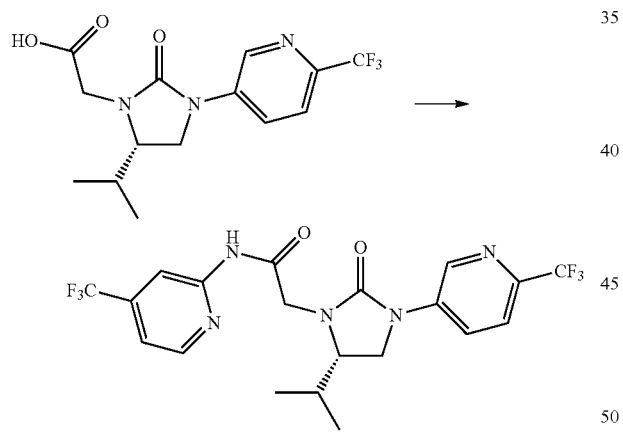

Oxalyl chloride (57 μL) and DMF (0.05 mL) were added to a solution of {(5S)-2-oxo-5-(propan-2-yl)-3-[6-(trifluoromethyl)pyridin-3-yl]imidazolidin-1-yl}acetic acid (200 mg) in chloroform (2.5 mL), and the mixture was stirred at room temperature for 1 hr. The reaction mixture was concentrated under reduced pressure to afford the residue (236 mg). Half of this residue was dissolved in chloroform (0.5 mL), and triethylamine (158 μL) was added thereto. A solution of 2-amino-4-trifluoromethylpyridine (40 mg) in chloroform (1 mL) was added thereto while cooling in ice, and the resulting mixture was stirred at room temperature for 3 hr. After the reaction mixture was concentrated under reduced pressure, the residue was purified by preparative HPLC and PTLC (hexane/ethyl acetate=1:1) to afford the title compound (20 mg).

Working Example 4

2-[(5S)-3-(6-Cyanopyridin-3-yl)-2-oxo-5-(propan-2-yl)imidazolidin-1-yl]-N-[3-(trifluoromethyl)phenyl]acetamide

[Formula 23]

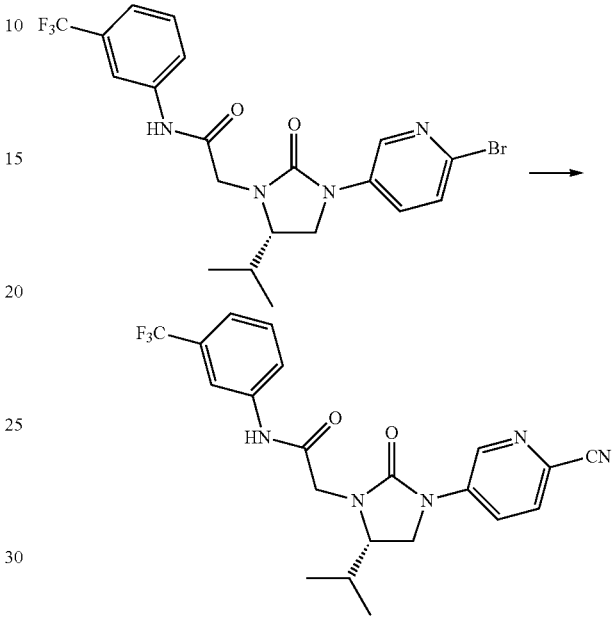

A solution of 2-[(5S)-3-(6-bromopyridin-3-yl)-2-oxo-5-(propan-2-yl)imidazolidin-1-yl]-N-[3-(trifluoromethyl)phenyl]acetamide (150 mg), zinc cyanide (91 mg), $Pd_2(dba)_3$ (8.5 mg), Xantphos (11 mg), and N,N,N',N'-tetramethylethylenediamine (14 μL) in DMF (2 mL) was stirred under irradiation with microwave at 180° C. for 30 min. Additional zinc cyanide (91 mg) was added thereto, and the resulting mixture was stirred under the same condition for 30 min. NH silica gel was added thereto, the mixture was stirred, followed by filtration, and the filtrate was concentrated under reduced pressure. The residue was purified by preparative HPLC to afford the title compound (47 mg).

Working Example 5

2-[(5S)-2-Oxo-5-(propan-2-yl)-3-[6-(1H-pyrazol-1-yl)pyridin-3-yl]imidazolidin-1-yl]-N-[3-(trifluoromethyl)phenyl]acetamide

[Formula 24]

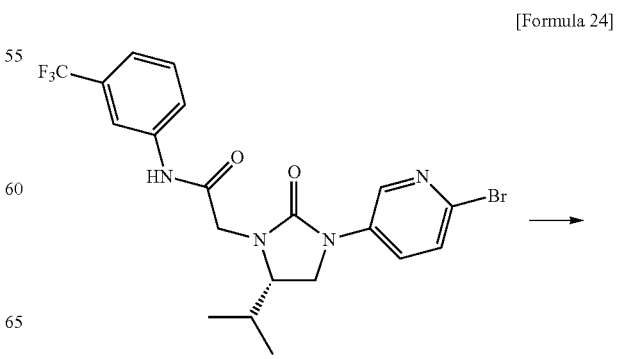

-continued

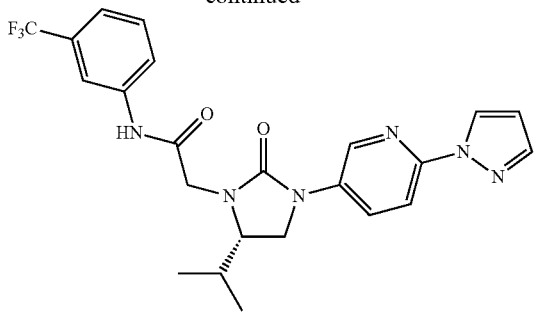

A solution of 2-[(5S)-3-(6-bromopyridin-3-yl)-2-oxo-5-(propan-2-ypimidazolidin-1-yl]-N-[3-(trifluoromethyl)phenyl]acetamide (150 mg), pyrazole (105 mg), trans-1,2-bis(methylamino)cyclohexane (18 mg), copper(I) iodide (12 mg), and cesium carbonate (302 mg) in 1,4-dioxane (2 mL) was stirred at 120° C. for 2 hr. After filtration through Celite, the filtrate was concentrated under reduced pressure. The residue was purified by preparative HPLC and PTLC (hexane/ethyl acetate=1:1) to afford the title compound (74 mg).

Working Example 6

2-[(5S)-3-[6-(Dimethylamino)pyridin-3-yl]-2-oxo-5-(propan-2-yl)imidazolidin-1-yl]-N-[3-(trifluoromethyl)phenyl]acetamide

[Formula 25]

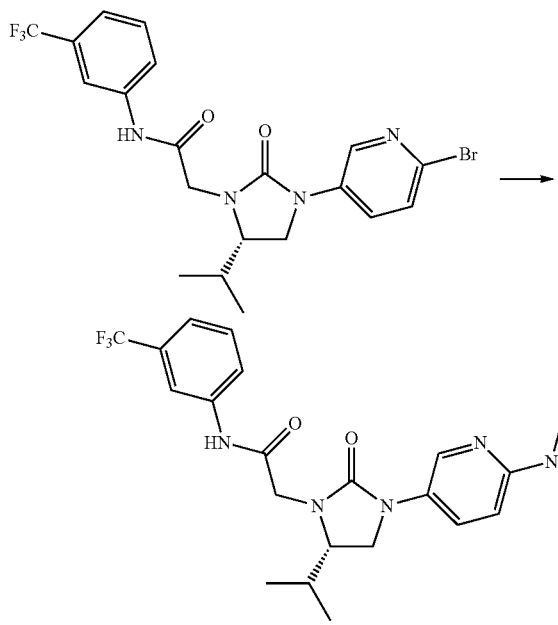

A solution of 2-[(5S)-3-(6-bromopyridin-3-yl)-2-oxo-5-(propan-2-yl)imidazolidin-1-yl]-N-[3-(trifluoromethyl)phenyl]acetamide (250 mg) and dimethyl amine (2M solution in THF, 1.3 mL), Pd$_2$(dba)$_3$ (24 mg), BINAP (32 mg), and potassium tert-butoxide (87 mg) in toluene (5 mL) was stirred at 120° C. for 2 hr. Water was added thereto, the mixture was extracted with chloroform, and the organic layer was concentrated under reduced pressure. The residue was purified by preparative HPLC and PTLC (hexane/ethyl acetate=1:1) to afford the title compound (34 mg).

Working Example 7

2-[(5S)-2-oxo-5-(propan-2-yl)-3-(6-propylpyridin-3-yl)imidazolidin-1-yl]-N-[3-(trifluoromethyl)phenyl]acetamide

[Formula 26]

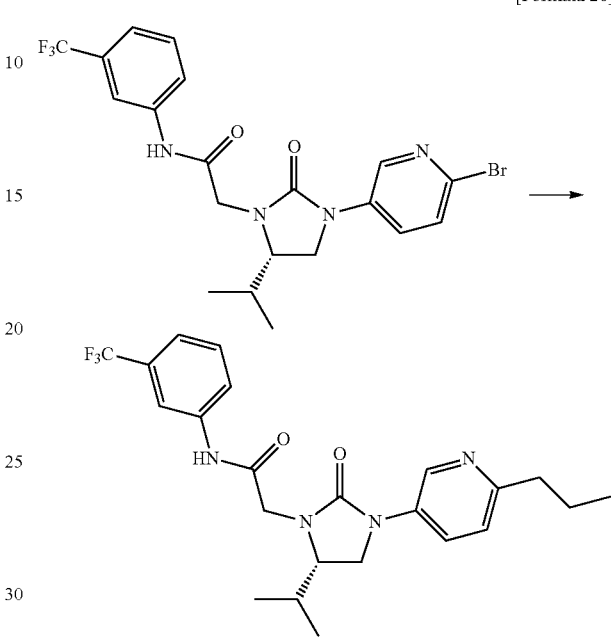

To a suspension of 2-[(5S)-3-(6-bromopyridin-3-yl)-2-oxo-5-(propan-2-yl)imidazolidin-1-yl]-N-[3-(trifluoromethyl)phenyl]acetamide (50 mg) and tris(2,4-pentanedionato)iron(III) (55 mg) in THF (1 mL) and NMP (0.1 mL) was added n-propylmagnesium bromide (2M solution in THF, 0.31 mL), and the mixture was stirred at room temperature for 1 hr. Saturated aqueous ammonium chloride solution was added thereto, the resulting mixture was extracted with acetic acid, and the organic layer was washed with water and brine. After drying over anhydrous sodium sulfate, the desiccant was filtered off, and the filtrate was concentrated under reduced pressure. The residue was purified by column chromatography (hexane/ethyl acetate) to afford the title compound (24 mg).

Working Example 8

N,N-Dimethyl-5-[(4S)-2-oxo-3-(2-oxo-2-{[3-(trifluoromethyl)phenyl]amino}ethyl)-4-(propan-2-yl)imidazolidin-1-yl]pyridine-2-carboxamide

[Formula 27]

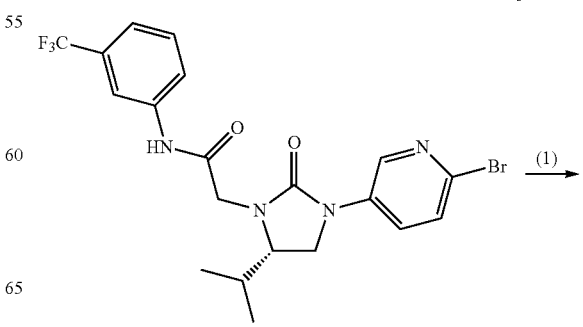

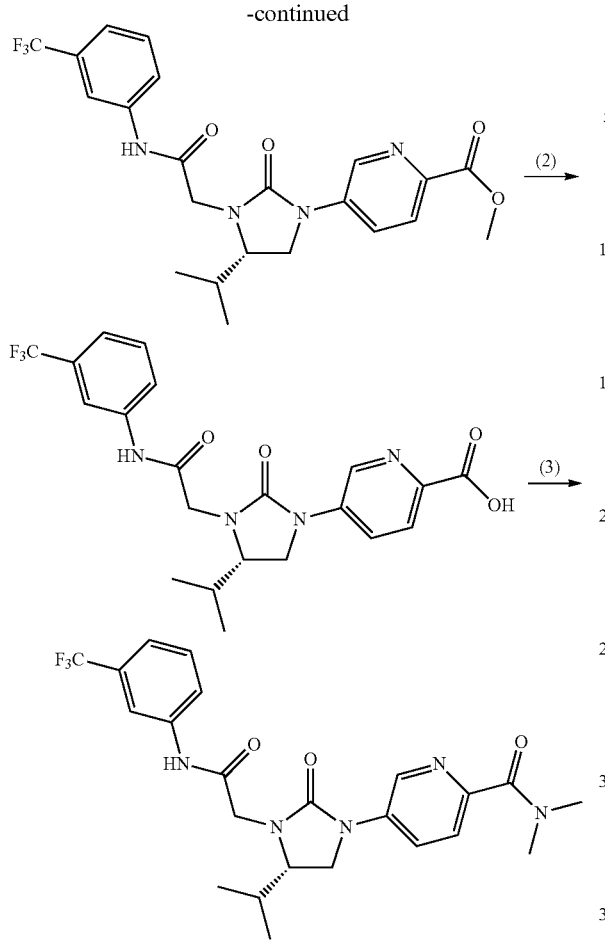

(1) A suspension of 2-[(5S)-3-(6-bromopyridin-3-yl)-2-oxo-5-(propan-2-yl)imidazolidin-1-yl]-N-[3-(trifluoromethyl)phenyl]acetamide (100 mg), potassium carbonate (43 mg), and Pd(PPh₃)₄ (24 mg) in DMF/ethanol (2:1, 2.1 mL) was stirred under atmosphere of carbon monoxide gas at 80° C. for 1.5 hr. Saturated aqueous sodium hydrogen carbonate solution was added thereto, the mixture was washed with ethyl acetate, and the organic layer was washed with water and brine. After concentration under reduced pressure, the residue was purified by preparative HPLC to afford methyl 5-[(4S)-2-oxo-3-(2-oxo-2-{[3-(trifluoromethyl)phenyl]amino]ethyl)-4-(propan-2-yl)imidazolidin-1-yl}pyridine-2-carboxylate (50 mg).

(ESI pos.) m/z: 465 ([M+H]+)

(2) To a solution of methyl 5-[(4S)-2-oxo-3-(2-oxo-2-{[3-(trifluoromethyl)phenyl]amino]ethyl)-4-(propan-2-yl)imidazolidin-1-yl}pyridine-2-carboxylate (50 mg) in methanol/water (2:1, 1.5 mL) was added 6M aqueous sodium hydroxide solution (27 µL), and the mixture was stirred at room temperature for 1 hr, followed by at 60° C. for 1 hr. After 2M hydrochloric acid was added thereto to make the mixture acidic, the resulting mixture was extracted with chloroform. The organic layer was concentrated under reduced pressure to afford 5-[(4S)-2-oxo-3-(2-oxo-2-{[3-(trifluoromethyl)phenyl]amino}ethyl)-4-(propan-2-yl)imidazo din-1-yl]pyridine-2-carboxylic acid (43 mg).

(ESI pos.) m/z: 451 ([M+H]+)

(3) According to the similar procedure as in Working Example 1, the title compound (33 mg) was obtained from 5-[(4S)-2-oxo-3-(2-oxo-2-{[3-(trifluoromethyl)phenyl]amino}ethyl)-4-(propan-2-yeimidazolidin-1-yl]pyridine-2-carboxylic acid (43 mg) and dimethylamine (solution in THF).

Working Example 9

2-[(5S)-3-(5-Fluoropyrimidin-2-yl)-2-oxo-5-propylimidazolidin-1-yl]-N-[4-(trifluoromethyl)pyridin-2-yl]acetamide

[Formula 28]

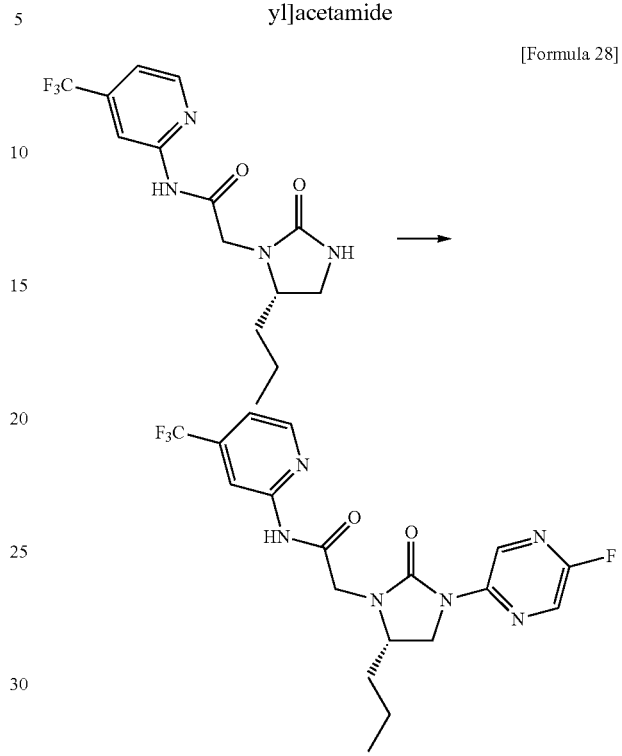

A solution of 2-[(5S)-2-oxo-5-propylimidazolidin-1-yl]-N-[4-(trifluoromethyl)pyridin-2-yl]acetamide (70 mg), 2-chloro-5-fluoropyrimidine (33 mg), Pd₂(dba)₃ (22 mg), Xantphos (24 mg), and sodium tert-butoxide (30 mg) in toluene was stirred at 80° C. for 2 hr. Saturated aqueous sodium hydrogen carbonate solution was added thereto, followed by extraction with ethyl acetate and drying over anhydrous magnesium sulfate. The desiccant was filtered off, the solvent was distilled off under reduced pressure, and the residue was purified by preparative HPLC to afford the title compound (27 mg).

Working Example 10

N-[6-(Difluoromethyl)pyridin-3-yl]-2-{(5S)-5-(2-methylpropyl)-2-oxo-3-[6-(trifluoromethyl)pyridin-3-yl]imidazolidin-1-yl}acetamide

[Formula 29]

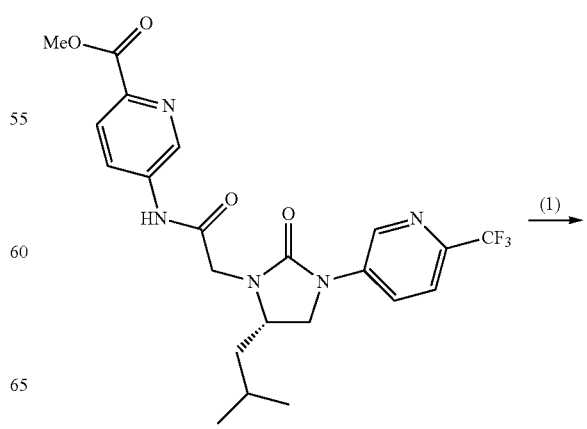

43

-continued

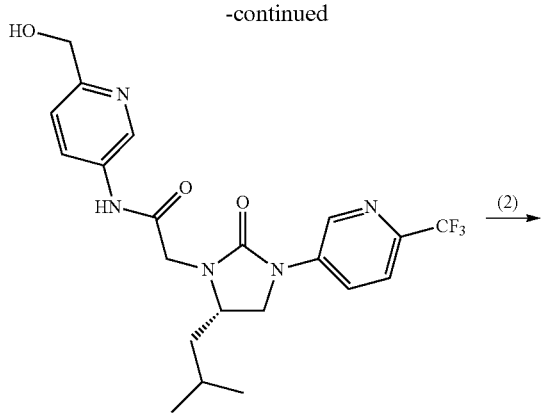

(1) Lithium borohydride (27 mg) was added to a solution of methyl 5-[({(5S)-5-(2-methylpropyl)-2-oxo-3-[6-(trifluoromethyl)pyridin-3-yl]imidazolidin-1-yl}acethyl)amino]pyridine-2-carboxylate (160 mg) in THF (2 mL), and the mixture was stirred at room temperature for 18 hr. Saturated aqueous ammonium chloride solution was added thereto, followed by extraction with chloroform. The solvent was distilled off under reduced pressure, and the residue was purified by preparative HPLC to afford N-[6-(hydroxymethyl)pyridin-3-yl]-2-{(5S)-5-(2-methylpropyl)-2-oxo-3-[6-(trifluoromethyl)pyridin-3-yl]imidazolidin-1-yl}acetamide (43 mg).

(ESI pos.) m/z: 452 ([M+H]+)

(2) To a solution of N-[6-(hydroxymethyl)pyridin-3-yl]-2-[(5S)-5-(2-methylpropyl)-2-oxo-3-[6-(trifluoromethyl)pyridin-3-yl]imidazolidin-1-yl]acetamide (35 mg) in DMSO (1 mL) was added 2-iodoxybenzoic acid (26 mg), and the mixture was stirred at room temperature for 2 hr. Water and ethyl acetate were added thereto, the resulting mixture was subjected to filtration, and then the filtrate was extracted with ethyl acetate. The organic layer was washed with water and brine and then dried over anhydrous magnesium sulfate. After the desiccant was filtered off, the solvent was distilled off under reduced pressure. The residue was dissolved in chloroform (1 mL) and cooled in ice, and then diethylaminosulfur trifluoride (0.08 mL) was added thereto. After the resulting mixture was stirred at room temperature for 3 days, water was added thereto, followed by extraction with chloroform. After the solvent was distilled off under reduced pressure, the residue was purified by PTLC (silica gel, hexane/ethyl acetate=1: 1, and NH silica gel, hexane/ethyl acetate=1:1), and the solid was washed with isopropyl ether to afford the title compound (3.8 mg).

Working Example 11

N-(6-Acetylpyridin-3-yl)-2-{(5S)-5-(2-methylpropyl)-2-oxo-3-[6-(trifluoromethyl)pyridin-3-yl]imidazolidin-1-yl}acetamide

[Formula 30]

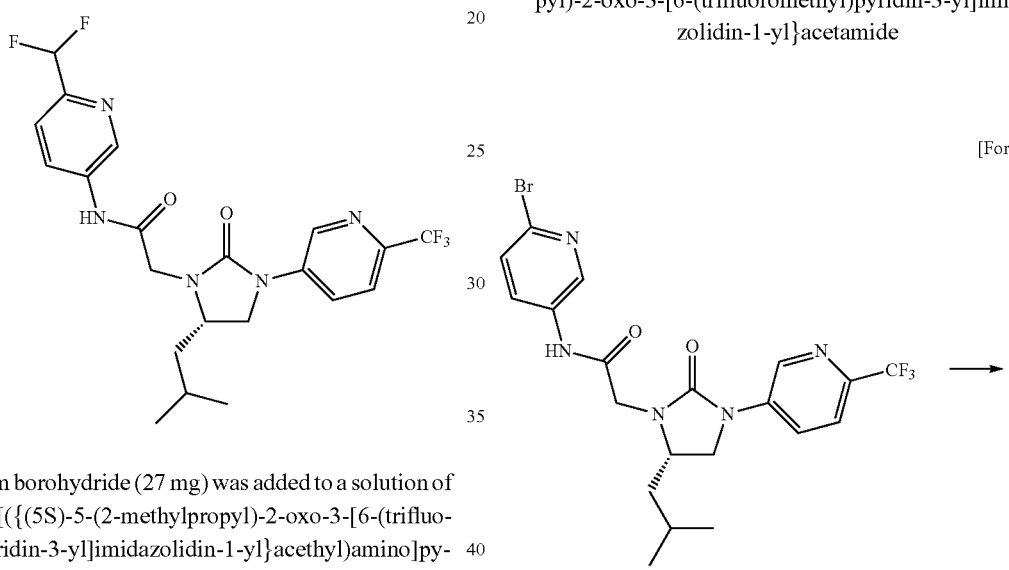

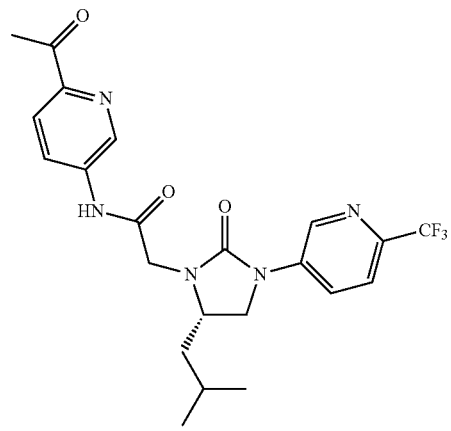

A suspension of N-(6-bromopyridin-3-yl)-2-{(5S)-5-(2-methylpropyl)-2-oxo-3-[6-(trifluoromethyl)pyridin-3-yl]imidazolidin-1-yl}acetamide (78 mg), tributyl(1-ethoxyvinyl)tin (145 mg), bis(triphenylphosphine)palladium(II) dichloride (22 mg), and copper(I) iodide (6.3 mg) in acetonitrile (1.5 mL) was stirred under irradiation with microwave at 150° C. for 2 hr. Saturated aqueous sodium hydrogen carbonate solution was added thereto, followed by extraction with chloroform. The organic layer was separated by phase separation cartridge, and the solvent was distilled off under reduced pressure. The residue was purified by preparative HPLC, 1M HCl (1.5 mL) was added to the resulting product, and the mixture was stirred at room temperature for 10 min. The mixture was made basic with saturated sodium hydrogen carbonate, followed by extraction with chloroform, and the solvent was distilled off under reduced pressure to afford the title compound (60 mg).

Working Example 12

N-(6-Cyclopropylpyridin-3-yl)-2-{(5S)-5-(2-methylpropyl)-2-oxo-3-[6-(trifluoromethyl)pyridin-3-yl]imidazolidin-1-yl}acetamide

[Formula 31]

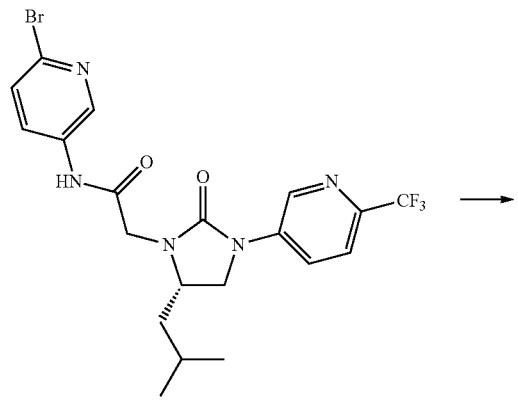

→

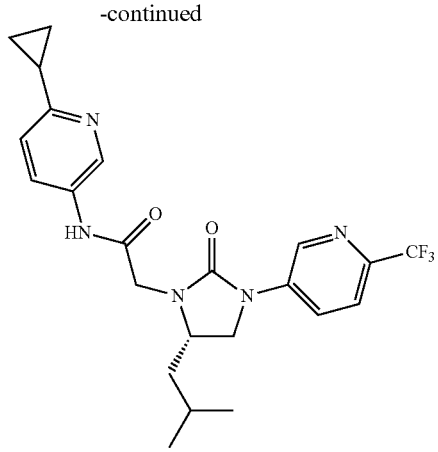

A solution of N-(6-bromopyridin-3-yl)-2-{(5S)-5-(2-methylpropyl)-2-oxo-3-[6-(trifluoromethyl)pyridin-3-yl]imidazolidin-1-yl}acetamide (50 mg), cyclopropyl boronic acid (17 mg), palladium acetate (1.1 mg), triphenylphosphine (2.6 mg), and potassium carbonate (41 mg) in toluene/water (=20:1, 1.5 mL) was stirred at 110° C. for 9 hr. Additional cyclopropyl boronic acid (35 mg) was added thereto, and the mixture was further stirred at 110° C. for 6 hr, followed by at 80° C. for 2 hr. The solvent was distilled off under reduced pressure, and the residue was purified by preparative HPLC. After further purification by PTLC(NH silica gel, hexane/ethyl acetate=1:1), the resulting solid was washed with isopropyl ether to afford the title compound (2.5 mg).

Tables 1-1 to 1-26 show the structural formulae and instrumental data of the compounds shown in Working Examples 1 to 12 and compounds synthesized in manners similar to those of the exemplified compounds. Each number shown in the column of "Example" in the tables indicates which one of the above Working Examples 1 to 12 the synthesis of each intended compound was based on. The column of "Configuration" shows the configuration of the carbon atom to which $R^4$ is attached in the inventive compound as represented by formula [I], and the term "racemate" refers to a racemic mixture.

TABLE 1-1

| Compound | Example | Structure | Configuration | (ESI pos.) m/z (ESI neg.) m/z | 1H-NMR |
|---|---|---|---|---|---|
| 1 | 1 | 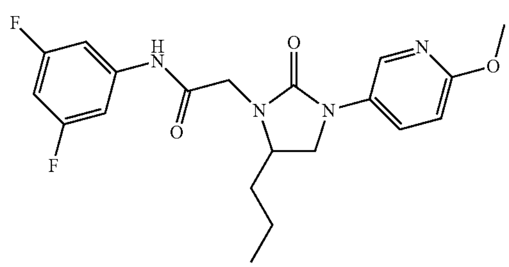 [SMILES: CCCC1CN(c2ccc(OC)nc2)C(=O)N1CC(=O)Nc1cc(F)cc(F)c1] | racemate | 405 ([M + H]+) | 1H NMR (600 MHz, CHLOROFORM-d) d ppm 0.98 (t, J = 7.3 Hz, 3 H), 1.33-1.42 (m, 2 H), 1.51-1.57 (m, 1 H), 1.81-1.89 (m, 1 H), 3.52 (dd, J = 8.7, 7.3 Hz, 1 H), 3.77-3.86 (m, 2 H), 3.92 (s, 3 H), 3.96 (t, J = 8.9 Hz, 1 H), 4.13 (d, J = 15.6 Hz, 1 H), 6.53 (tt, J = 8.7, 2.3 Hz, 1 H), 6.77 (d, J = 9.2 Hz, 1 H), 7.09-7.15 (m, 2 H), 8.03 (dd, J = 9.2, 2.8 Hz, 1 H), 8.10 (d, J = 2.8 Hz, 1 H), 8.94 (br. s., 1 H) |

TABLE 1-1-continued

| Compound | Example | Structure | Configuration | (ESI pos.) m/z (ESI neg.) m/z | 1H-NMR |
|---|---|---|---|---|---|
| 2 | 2 | 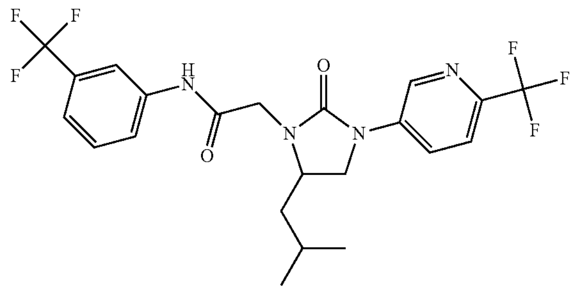 [SMILES: CC(C)CC1CN(c2ccc(C(F)(F)F)nc2)C(=O)N1CC(=O)Nc1cccc(C(F)(F)F)c1] | racemate | 489 ([M + H]+) | |
| 3 | 2 | 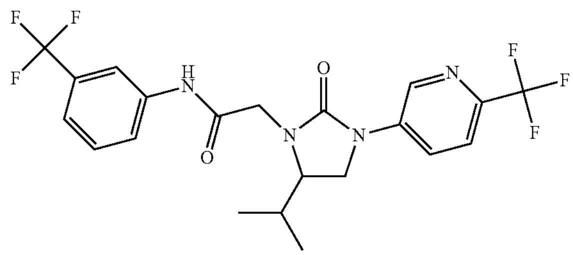 [SMILES: CC(C)C1CN(c2ccc(C(F)(F)F)nc2)C(=O)N1CC(=O)Nc1cccc(C(F)(F)F)c1] | racemate | 475 ([M + H]+) | |
| 4 | 2 | 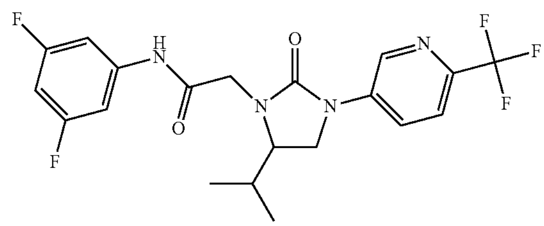 [SMILES: CC(C)C1CN(c2ccc(C(F)(F)F)nc2)C(=O)N1CC(=O)Nc1cc(F)cc(F)c1] | racemate | 443 ([M + H]+) | |
| 5 | 2 | 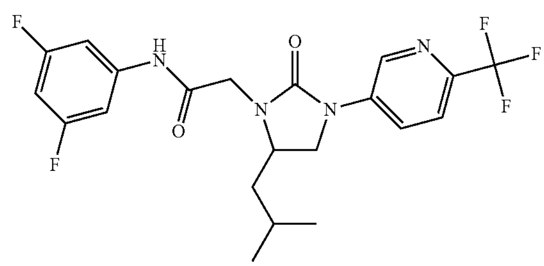 [SMILES: CC(C)CC1CN(c2ccc(C(F)(F)F)nc2)C(=O)N1CC(=O)Nc1cc(F)cc(F)c1] | racemate | 457 ([M + H]+) | |
| 6 | 2 | 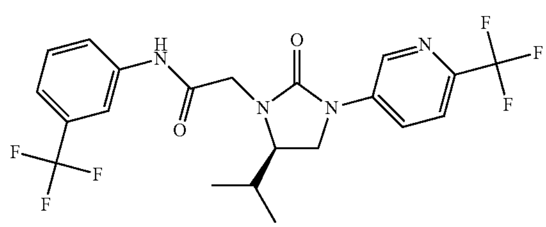 [SMILES: CC(C)[C@@H]1CN(c2ccc(C(F)(F)F)nc2)C(=O)N1CC(=O)Nc1cccc(C(F)(F)F)c1] | R | 475 ([M + H]+) | |
| 7 | 2 | 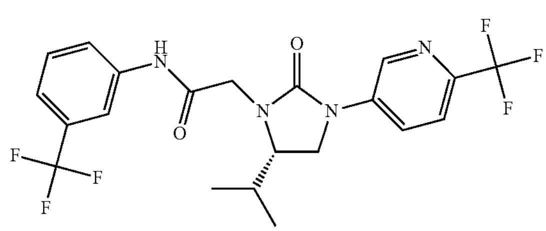 [SMILES: CC(C)[C@H]1CN(c2ccc(C(F)(F)F)nc2)C(=O)N1CC(=O)Nc1cccc(C(F)(F)F)c1] | S | 475 ([M + H]+) | 1H NMR (600 MHz, CHLOROFORM-d) d ppm 0.89 (d, J = 6.6 Hz, 3 H), 1.03 (d, J = 7.0 Hz, 3 H), 1.21-1.35 (m, 2 H), 2.22-2.32 (m, 1 H), 3.60-3.71 (m, 1 H), 3.90-3.97 (m, 2 H), 3.99-4.06 (m, 1 H), 4.08-4.15 (m, 1 H), 7.34-7.39 (m, 1 H), 7.40-7.47 (m, 1 H), 7.63-7.70 (m, 2 H), 7.85 (s, 1 H), 8.28-8.37 (m, 1 H), 8.71 (br. s., 1 H), 8.80 (d, J = 2.9 Hz, 1 H) |

TABLE 1-1-continued

| Compound | Example | Structure | Configuration | (ESI pos.) m/z (ESI neg.) m/z | 1H-NMR |
|---|---|---|---|---|---|
| 8 | 2 | 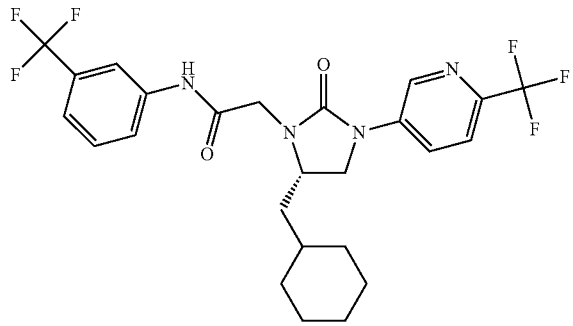 [SMILES: O=C(CN1C(=O)N(c2ccc(C(F)(F)F)nc2)C[C@@H]1CC1CCCCC1)Nc1cccc(C(F)(F)F)c1] | S | 529 ([M + H]+) | 1H NMR (600 MHz, CHLOROFORM-d) d ppm 0.93-1.89 (m, 13 H), 3.56-3.63 (m, 1 H), 3.94-4.04 (m, 2 H), 4.07-4.16 (m, 2 H), 7.33-7.38 (m, 1 H), 7.38-7.44 (m, 1 H), 7.63-7.69 (m, 2 H), 7.83 (s, 1 H), 8.27 (dd, J = 8.7, 2.5 Hz, 1 H), 8.57 (s, 1 H), 8.81 (d, J = 2.5 Hz, 1 H) |
| 9 | 2 | 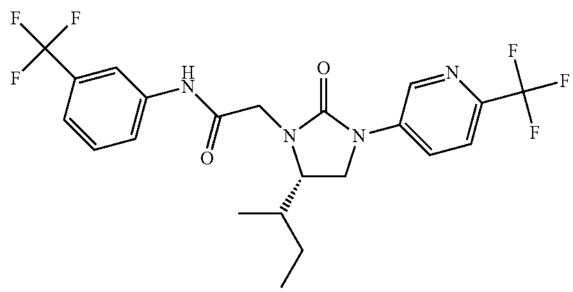 [SMILES: CCC(C)[C@H]1CN(c2ccc(C(F)(F)F)nc2)C(=O)N1CC(=O)Nc1cccc(C(F)(F)F)c1] | S | 489 ([M + H]+) | 1H NMR (600 MHz, CHLOROFORM-d) d ppm 0.86 (d, J = 6.6 Hz, 3 H), 1.03 (t, J = 7.4 Hz, 3 H), 1.23-1.35 (m, 1 H), 1.37-1.47 (m, 1 H), 1.97-2.06 (m, 1 H), 3.65 (dd, J = 9.5, 6.6 Hz, 1 H), 3.91 (t, J = 9.5 Hz, 1 H), 4.01-4.06 (m, 2 H), 4.07-4.12 (m, 1 H), 7.35-7.40 (m, 1 H), 7.41-7.47 (m, 1 H), 7.64-7.72 (m, 2 H), 7.86 (s, 1 H), 8.29-8.37 (m, 1 H), 8.70 (br. s., 1 H), 8.79 (d, J = 2.5 Hz, 1 H) |

TABLE 1-2

| Compound | Example | Structure | Configuration | (ESI pos.) m/z (ESI neg.) m/z | 1H-NMR |
|---|---|---|---|---|---|
| 10 | 2 | 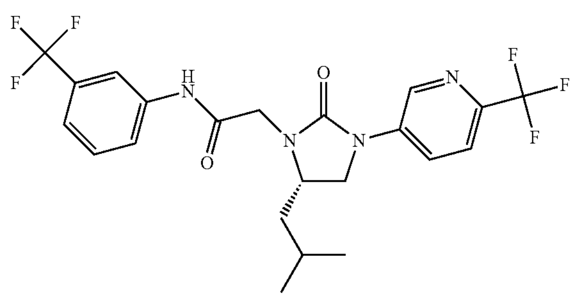 [SMILES: CC(C)C[C@H]1CN(c2ccc(C(F)(F)F)nc2)C(=O)N1CC(=O)Nc1cccc(C(F)(F)F)c1] | S | 489 ([M + H]+) | 1H NMR (600 MHz, CHLOROFORM-d) d ppm 1.01 (d, J = 6.2 Hz, 3 H), 1.03 (d, J = 6.2 Hz, 3 H), 1.46-1.88 (m, 3 H), 3.61 (dd, J = 8.9, 7.6 Hz, 1 H), 3.93-4.02 (m, 2 H), 4.08-4.13 (m, 1 H), 4.16 (d, J = 15.7 Hz, 1 H), 7.35-7.40 (m, 1 H), 7.41-7.47 (m, 1 H), 7.64-7.71 (m, 2 H), 7.84 (s, 1 H), 8.26-8.34 (m, 1 H), 8.53 (br. s., 1 H), 8.78 (d, J = 2.9 Hz, 1 H) |
| 11 | 2 | 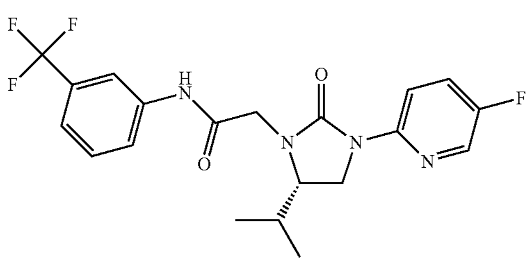 [SMILES: CC(C)[C@H]1CN(c2ccc(F)cn2)C(=O)N1CC(=O)Nc1cccc(C(F)(F)F)c1] | S | 447 ([M + Na]+) | 1H NMR (600 MHz, CHLOROFORM-d) d ppm 0.87 (d, J = 7.0 Hz, 3 H), 1.01 (d, J = 7.0 Hz, 3 H), 2.14-2.25 (m, 1 H), 3.79-3.92 (m, 2 H), 3.99-4.14 (m, 3 H), 7.28-7.49 (m, 3 H), 7.58-7.69 (m, 1 H), 7.83 (br. s., 1 H), 8.15 (d, J = 2.9 Hz, 1 H), 8.22-8.35 (m, 1 H), 9.05 (br. s., 1 H) |

TABLE 1-2-continued

| Compound | Example | Structure | Configuration | (ESI pos.) m/z (ESI neg.) m/z | 1H-NMR |
|---|---|---|---|---|---|
| 12 | 2 | 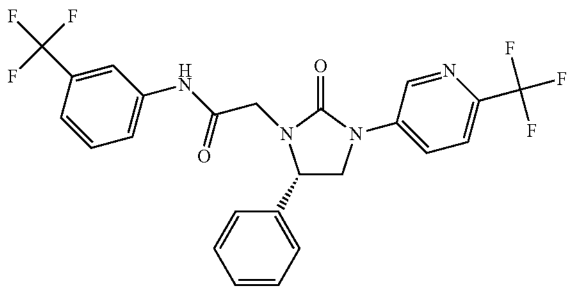 [SMILES: O=C(CN1C(=O)N(c2ccc(C(F)(F)F)nc2)C[C@@H]1c1ccccc1)Nc1cccc(C(F)(F)F)c1] | S | 509 ([M + H]+) | 1H NMR (600 MHz, CHLOROFORM-d) d ppm 3.53 (d, J = 16.1 Hz, 1 H), 3.77 (dd, J = 9.3, 7.6 Hz, 1 H), 4.16 (d, J = 16.5 Hz, 1 H), 4.26 (t, J = 9.3 Hz, 1 H), 4.98 (dd, J = 9.3, 7.6 Hz, 1 H), 7.22-7.40 (m, 7 H), 7.46-7.52 (m, 1 H), 7.59 (d, J = 9.1 Hz, 1 H), 7.70 (s, 1 H), 7.99 (br. s., 1 H), 8.27 (dd, J = 8.7, 2.5 Hz, 1 H), 8.68 (d, J = 2.5 Hz, 1 H) |
| 13 | 2 | 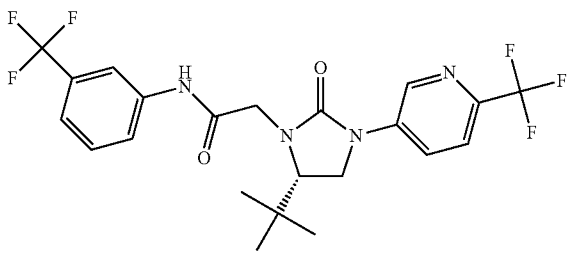 [SMILES: CC(C)(C)[C@H]1CN(c2ccc(C(F)(F)F)nc2)C(=O)N1CC(=O)Nc1cccc(C(F)(F)F)c1] | S | 489 ([M + H]+) | 1H NMR (600 MHz, CHLOROFORM-d) d ppm 1.05 (s, 9 H), 3.63 (dd, J = 9.5, 5.4 Hz, 1 H), 3.72 (dd, J = 9.5, 5.0 Hz, 1 H), 4.00 (d, J = 16.1 Hz, 1 H), 4.06 (t, J = 9.5 Hz, 1 H), 4.34 (d, J = 16.1 Hz, 1 H), 7.35-7.40 (m, 1 H), 7.41-7.46 (m, 1 H), 7.66-7.71 (m, 2 H), 7.85 (s, 1 H), 8.33 (dd, J = 8.7, 2.5 Hz, 1 H), 8.76-8.82 (m, 2 H) |
| 14 | 2 | 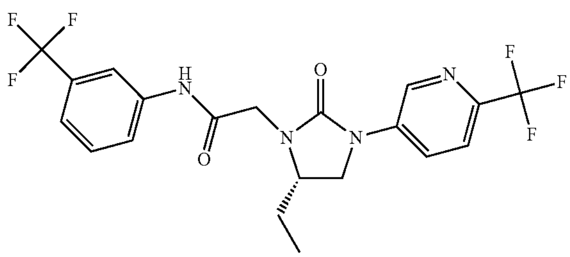 [SMILES: CC[C@H]1CN(c2ccc(C(F)(F)F)nc2)C(=O)N1CC(=O)Nc1cccc(C(F)(F)F)c1] | S | 461 ([M + H]+) | 1H NMR (600 MHz, CHLOROFORM-d) d ppm 1.00 (t, J = 7.4 Hz, 3 H), 1.64-1.73 (m, 1 H), 1.92-2.00 (m, 1 H), 3.59-3.64 (m, 1 H), 3.90-3.96 (m, 1 H), 4.01 (d, J = 15.7 Hz, 1 H), 4.06-4.16 (m, 2 H), 7.33-7.38 (m, 1 H), 7.40-7.46 (m, 1 H), 7.63-7.70 (m, 2 H), 7.85 (s, 1 H), 8.32 (dd, J = 8.7, 2.5 Hz, 1 H), 8.56 (br. s., 1 H), 8.79 (d, J = 2.5 Hz, 1 H) |
| 15 | 2 | 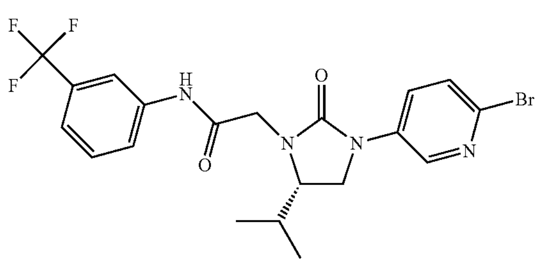 [SMILES: CC(C)[C@H]1CN(c2ccc(Br)nc2)C(=O)N1CC(=O)Nc1cccc(C(F)(F)F)c1] | S | 485 ([M + H]+) | 1H NMR (600 MHz, CHLOROFORM-d) d ppm 0.88 (d, J = 6.6 Hz, 3 H), 1.01 (d, J = 6.6 Hz, 3 H), 2.19-2.30 (m, 1 H), 3.58 (dd, J = 8.9, 6.4 Hz, 1 H), 3.83-3.89 (m, 1 H), 3.90-3.95 (m, 1 H), 4.00-4.11 (m, 2 H), 7.31-7.48 (m, 3 H), 7.64 (d, J = 8.3 Hz, 1 H), 7.85 (s, 1 H), 8.06-8.15 (m, 1 H), 8.40 (d, J = 2.9 Hz, 1 H), 8.84 (br. s., 1 H) |
| 16 | 2 | 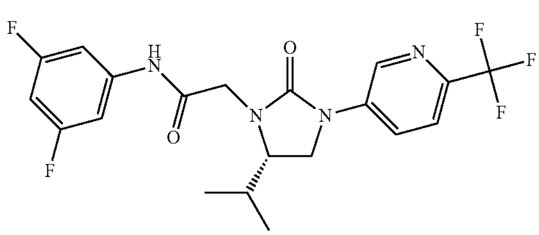 [SMILES: CC(C)[C@H]1CN(c2ccc(C(F)(F)F)nc2)C(=O)N1CC(=O)Nc1cc(F)cc(F)c1] | S | 443 ([M + H]+) | 1H NMR (600 MHz, CHLOROFORM-d) d ppm 0.88 (d, J = 7.0 Hz, 3 H), 1.03 (d, J = 6.6 Hz, 3 H), 2.20-2.31 (m, 1 H), 3.66 (dd, J = 7.8, 5.0 Hz, 1 H), 3.86-3.99 (m, 3 H), 4.13 (d, J = 15.7 Hz, 1 H), 6.52-6.60 (m, 1 H), 7.10-7.18 (m, 2 H), 7.69 (d, J = 8.7 Hz, 1 H), 8.33 (dd, J = 8.7, 2.5 Hz, 1 H), 8.75-8.83 (m, 2 H) |

TABLE 1-2-continued

| Compound | Example | Structure | Configuration | (ESI pos.) m/z (ESI neg.) m/z | 1H-NMR |
|---|---|---|---|---|---|
| 17 | 1 | 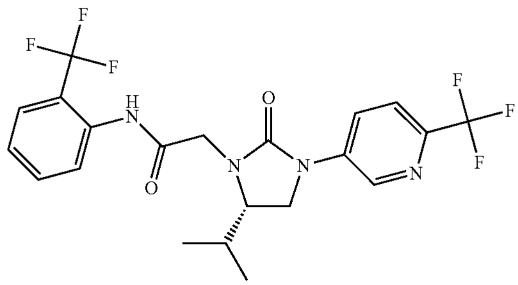 [SMILES: CC(C)[C@H]1CN(c2ccc(C(F)(F)F)nc2)C(=O)N1CC(=O)Nc1ccccc1C(F)(F)F] | S | 475 ([M + H]+) | 1H NMR (600 MHz, CHLOROFORM-d) d ppm 0.90 (d, J = 7.0 Hz, 3 H), 1.03 (d, J = 7.0 Hz, 3 H), 2.20-2.29 (m, 1 H), 3.66 (dd, J = 8.5, 5.6 Hz, 1 H), 3.87-4.05 (m, 3 H), 4.28 (d, J = 16.1 Hz, 1 H), 7.26-7.30 (m, 1 H), 7.55-7.59 (m, 1 H), 7.61-7.64 (m, 1 H), 7.68 (d, J = 8.7 Hz, 1 H), 8.12-8.21 (m, 1 H), 8.36-8.45 (m, 2 H), 8.76 (d, J = 2.5 Hz, 1 H) |
| 18 | 3 | 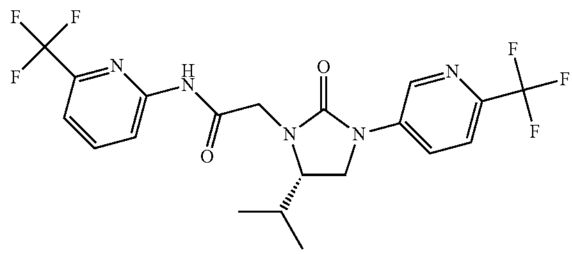 [SMILES: CC(C)[C@H]1CN(c2ccc(C(F)(F)F)nc2)C(=O)N1CC(=O)Nc1cccc(C(F)(F)F)n1] | S | 476 ([M + H]+) | 1H NMR (600 MHz, CHLOROFORM-d) d ppm 0.92 (d, J = 6.6 Hz, 3 H), 1.04 (d, J = 6.6 Hz, 3 H), 2.20 (t, J = 1.0 Hz, 1 H), 3.61-3.70 (m, 1 H), 3.91-4.03 (m, 3 H), 4.32 (d, J = 16.5 Hz, 1 H), 7.44 (d, J = 7.8 Hz, 1 H), 7.67 (d, J = 9.1 Hz, 1 H), 7.88 (t, J = 8.1 Hz, 1 H), 8.37 (d, J = 8.7 Hz, 1 H), 8.40-8.46 (m, 1 H), 8.55 (br. s., 1 H), 8.74 (d, J = 2.5 Hz, 1 H) |

TABLE 1-3

| Compound | Example | Structure | Configuration | (ESI pos.) m/z (ESI neg.) m/z | 1H-NMR |
|---|---|---|---|---|---|
| 19 | 3 | 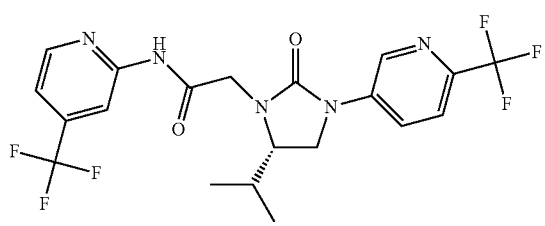 [SMILES: CC(C)[C@H]1CN(c2ccc(C(F)(F)F)nc2)C(=O)N1CC(=O)Nc1cc(C(F)(F)F)ccn1] | S | 476 ([M + H]+) | 1H NMR (600 MHz, CHLOROFORM-d) d ppm 0.91 (d, J = 7.0 Hz, 3 H), 1.04 (d, J = 7.0 Hz, 3 H), 2.19-2.25 (m, 1 H), 3.61-3.68 (m, 1 H), 3.92-3.98 (m, 2 H), 4.06 (d, J = 16.5 Hz, 1 H), 4.23 (d, J = 16.5 Hz, 1 H), 7.26-7.30 (m, 1 H), 7.66 (d, J = 8.7 Hz, 1 H), 8.40-8.43 (m, 1 H), 8.44-8.48 (m, 2 H), 8.74 (d, J = 2.9 Hz, 1 H), 8.85 (br. s., 1 H) |
| 20 | 4 | 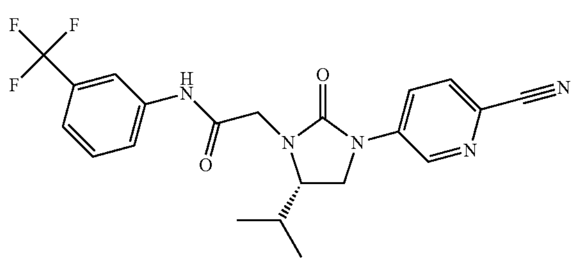 [SMILES: CC(C)[C@H]1CN(c2ccc(C#N)nc2)C(=O)N1CC(=O)Nc1cccc(C(F)(F)F)c1] | S | 432 ([M + H]+) | 1H NMR (600 MHz, CHLOROFORM-d) d ppm 0.89 (d, J = 7.0 Hz, 3 H), 1.04 (d, J = 7.0 Hz, 3 H), 2.23-2.31 (m, 1 H), 3.60-3.69 (m, 1 H), 3.89-4.01 (m, 2 H), 4.04-4.14 (m, 2 H), 7.34-7.41 (m, 1 H), 7.41-7.47 (m, 1 H), 7.62-7.73 (m, 2 H), 7.85 (s, 1 H), 8.30 (dd, J = 8.7, 2.5 Hz, 1 H), 8.59 (br. s., 1 H), 8.81 (d, J = 2.5 Hz, 1 H) |

TABLE 1-3-continued

| Compound | Example | Structure | Configuration | (ESI pos.) m/z (ESI neg.) m/z | 1H-NMR |
|---|---|---|---|---|---|
| 21 | 5 | 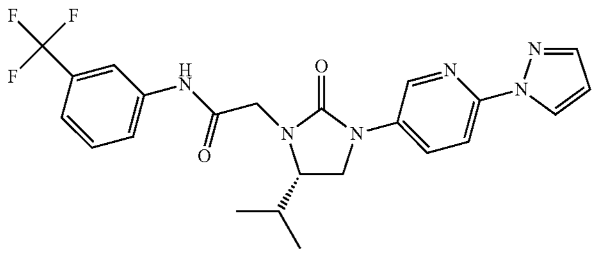 [SMILES: CC(C)[C@H]1CN(c2ccc(-n3cccn3)nc2)C(=O)N1CC(=O)Nc1cccc(C(F)(F)F)c1] | S | 473 ([M + H]+) | 1H NMR (600 MHz, CHLOROFORM-d) d ppm 0.91 (d, J = 6.6 Hz, 3 H), 1.03 (d, J = 6.6 Hz, 3 H), 2.26 (td, J = 6.9, 3.1 Hz, 1 H), 3.66 (dd, J = 7.6, 5.2 Hz, 1 H), 3.87-3.94 (m, 2 H), 3.97 (d, J = 15.7 Hz, 1 H), 4.16 (d, J = 15.3 Hz, 1 H), 6.45-6.49 (m, 1 H), 7.33-7.47 (m, 2 H), 7.65-7.70 (m, 1 H), 7.71-7.75 (m, 1 H), 7.88 (s, 1 H), 7.99 (d, J = 9.1 Hz, 1 H), 8.19-8.25 (m, 1 H), 8.52 (d, J = 2.5 Hz, 1 H), 8.55 (d, J = 2.5 Hz, 1 H), 8.91 (br. s., 1 H) |
| 22 | 6 | 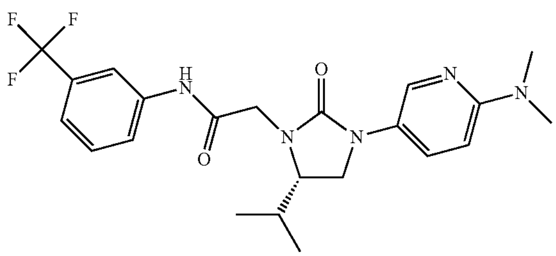 [SMILES: CC(C)[C@H]1CN(c2ccc(N(C)C)nc2)C(=O)N1CC(=O)Nc1cccc(C(F)(F)F)c1] | S | 450 ([M + H]+) | 1H NMR (600 MHz, CHLOROFORM-d) d ppm 0.89 (d, J = 6.6 Hz, 3 H), 0.97 (d, J = 7.0 Hz, 3 H), 2.14-2.25 (m, 1 H), 3.07 (s, 6 H), 3.55 (dd, J = 8.5, 6.0 Hz, 1 H), 3.72-3.88 (m, 3 H), 4.15 (d, J = 15.3 Hz, 1 H), 6.55 (d, J = 9.5 Hz, 1 H), 7.30-7.45 (m, 2 H), 7.64-7.72 (m, 1 H), 7.80-7.88 (m, 2 H), 8.12 (d, J = 2.5 Hz, 1 H), 9.19 (br. s., 1 H) |
| 23 | 7 | 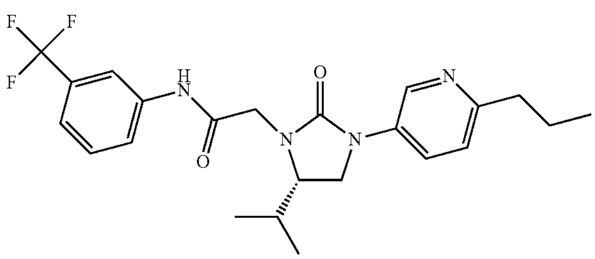 [SMILES: CCCc1ccc(N2C[C@H](C(C)C)N(CC(=O)Nc3cccc(C(F)(F)F)c3)C2=O)cn1] | S | 449 ([M + H]+) | 1H NMR (600 MHz, CHLOROFORM-d) d ppm 0.88 (d, J = 6.6 Hz, 3 H), 0.96 (t, J = 7.2 Hz, 3 H), 1.00 (d, J = 7.0 Hz, 3 H), 1.65-1.81 (m, 2 H), 2.15-2.28 (m, 1 H), 2.69-2.80 (m, 2 H), 3.55-3.65 (m, 1 H), 3.83-3.93 (m, 2 H), 3.96-4.14 (m, 2 H), 7.05-7.18 (m, 1 H), 7.28-7.42 (m, 2 H), 7.57-7.67 (m, 1 H), 7.85 (s, 1 H), 8.01-8.09 (m, 1 H), 8.57 (d, J = 2.5 Hz, 1 H), 9.10 (br. s., 1 H) |
| 24 | 3 | 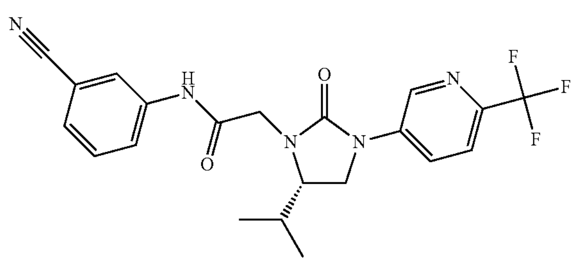 [SMILES: CC(C)[C@H]1CN(c2ccc(C(F)(F)F)nc2)C(=O)N1CC(=O)Nc1cccc(C#N)c1] | S | 432 ([M + H]+) | 1H NMR (600 MHz, CHLOROFORM-d) d ppm 0.88 (d, J = 7.0 Hz, 3 H), 1.04 (d, J = 7.0 Hz, 3 H), 2.22-2.30 (m, 1 H), 3.66 (dd, J = 7.4, 4.5 Hz, 1 H), 3.89-4.00 (m, 3 H), 4.16 (d, J = 15.7 Hz, 1 H), 7.38-7.45 (m, 2 H), 7.62-7.66 (m, 1 H), 7.69 (d, J = 8.7 Hz, 1 H), 7.99 (s, 1 H), 8.32 (dd, J = 8.7, 2.5 Hz, 1 H), 8.81 (d, J = 2.5 Hz, 1 H), 8.87 (br. s., 1 H) |

TABLE 1-3-continued

| Compound | Example | Structure | Configuration | (ESI pos.) m/z (ESI neg.) m/z | 1H-NMR |
|---|---|---|---|---|---|
| 25 | 3 | 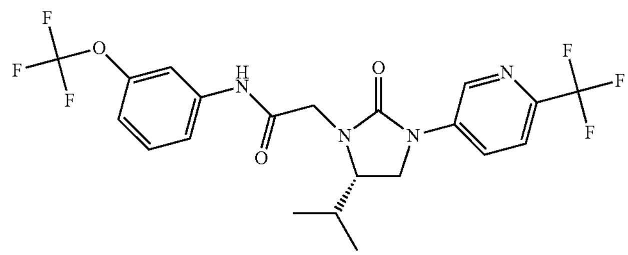 [SMILES: CC(C)[C@H]1CN(c2ccc(C(F)(F)F)nc2)C(=O)N1CC(=O)Nc1cccc(OC(F)(F)F)c1] | S | 491 ([M + H]+) | 1H NMR (600 MHz, CHLOROFORM-d) d ppm 0.89 (d, J = 7.0 Hz, 3 H), 1.03 (d, J = 7.0 Hz, 3 H), 2.22-2.31 (m, 1 H), 3.62-3.68 (m, 1 H), 3.90-3.97 (m, 2 H), 3.99-4.04 (m, 1 H), 4.08-4.14 (m, 1 H), 6.96-7.01 (m, 1 H), 7.31-7.36 (m, 2 H), 7.59 (s, 1 H), 7.68 (d, J = 8.7 Hz, 1 H), 8.33 (dd, J = 8.7, 2.5 Hz, 1 H), 8.63 (br. s., 1 H), 8.80 (d, J = 2.5 Hz, 1 H) |
| 26 | 3 | 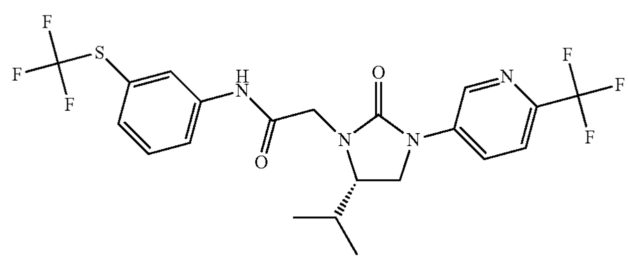 [SMILES: CC(C)[C@H]1CN(c2ccc(C(F)(F)F)nc2)C(=O)N1CC(=O)Nc1cccc(SC(F)(F)F)c1] | S | 507 ([M + H]+) | 1H NMR (600 MHz, CHLOROFORM-d) d ppm 0.89 (d, J = 6.6 Hz, 3 H), 1.04 (d, J = 7.0 Hz, 3 H), 2.23-2.31 (m, 1 H), 3.63-3.68 (m, 1 H), 3.91-3.97 (m, 2 H), 4.00-4.05 (m, 1 H), 4.10-4.14 (m, 1 H), 7.36-7.43 (m, 2 H), 7.62-7.66 (m, 1 H), 7.68 (d, J = 8.7 Hz, 1 H), 7.87 (s, 1 H), 8.34 (dd, J = 8.7, 2.5 Hz, 1 H), 8.62 (br. s., 1 H), 8.80 (d, J = 2.5 Hz, 1 H) |
| 27 | 3 | 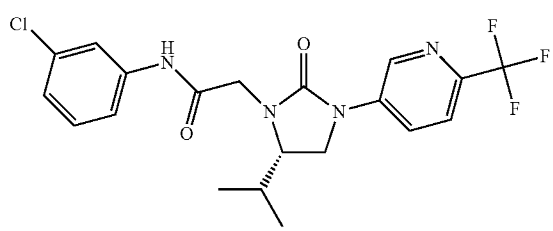 [SMILES: CC(C)[C@H]1CN(c2ccc(C(F)(F)F)nc2)C(=O)N1CC(=O)Nc1cccc(Cl)c1] | S | 441 ([M + H]+) | 1H NMR (600 MHz, CHLOROFORM-d) d ppm 0.88 (d, J = 6.6 Hz, 3 H), 1.03 (d, J = 7.0 Hz, 3 H), 2.21-2.31 (m, 1 H), 3.60-3.69 (m, 1 H), 3.89-3.96 (m, 2 H), 3.98-4.05 (m, 1 H), 4.07-4.14 (m, 1 H), 7.06-7.14 (m, 1 H), 7.24 (t, J = 8.3 Hz, 1 H), 7.31-7.36 (m, 1 H), 7.61-7.73 (m, 2 H), 8.33 (dd, J = 8.7, 2.5 Hz, 1 H), 8.57 (br. s., 1 H), 8.80 (d, J = 2.5 Hz, 1 H) |

TABLE 1-4

| Compound | Example | Structure | Configuration | (ESI pos.) m/z (ESI neg.) m/z | 1H-NMR |
|---|---|---|---|---|---|
| 28 | 3 | 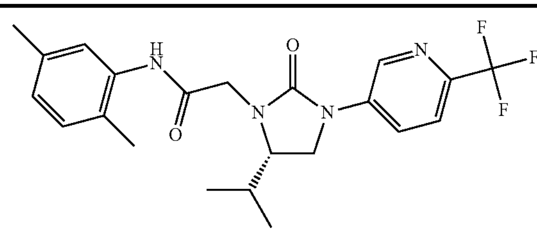 | S | 435 ([M + H]+) | 1H NMR (600 MHz, CHLOROFORM-d) d ppm 0.90 (d, J = 6.6 Hz, 3 H), 1.03 (d, J = 7.0 Hz, 3 H), 2.23 (s, 3 H), 2.27-2.31 (m, 1 H), 2.31 (s, 3 H), 3.63 (dd, J = 6.8, 4.3 Hz, 1 H), 3.86-3.97 (m, 2 H), 4.01-4.14 (m, 2 H), 6.88 (d, J = 7.8 Hz, 1 H), 7.05 (d, J = 7.4 Hz, 1 H), 7.66 (d, J = 8.7 Hz, 1 H), 7.76 (s, 1 H), 8.24 (br. s., 1 H), 8.27-8.34 (m, 1 H), 8.82 (d, J = 2.5 Hz, 1 H) |

TABLE 1-4-continued

| Compound | Example | Structure | Configuration | (ESI pos.) m/z (ESI neg.) m/z | 1H-NMR |
|---|---|---|---|---|---|
| 29 | 3 | 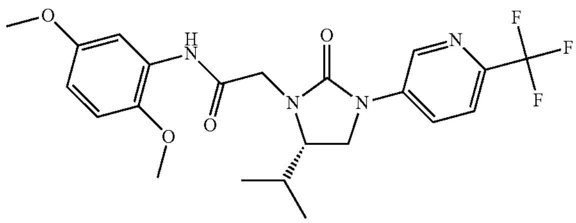 [SMILES: COc1ccc(OC)c(NC(=O)CN2C(=O)N(c3ccc(C(F)(F)F)nc3)C[C@@H]2C(C)C)c1] | S | 467 ([M + H]+) | 1H NMR (600 MHz, CHLOROFORM-d) δ ppm 0.90 (d, J = 6.6 Hz, 3 H), 1.02 (d, J = 7.0 Hz, 3 H), 2.19-2.27 (m, 1 H), 3.63 (dd, J = 9.1, 6.2 Hz, 1 H), 3.78 (s, 3 H), 3.82 (s, 3 H), 3.87-4.03 (m, 3 H), 4.31 (d, J = 16.1 Hz, 1 H), 6.59 (dd, J = 8.9, 3.1 Hz, 1 H), 6.79 (d, J = 9.1 Hz, 1 H), 7.66 (d, J = 9.1 Hz, 1 H), 8.04 (d, J = 3.3 Hz, 1 H), 8.36 (dd, J = 8.7, 2.5 Hz, 1 H), 8.45 (br.s., 1 H), 8.81 (d, J = 2.5 Hz, 1 H) |
| 30 | 3 | 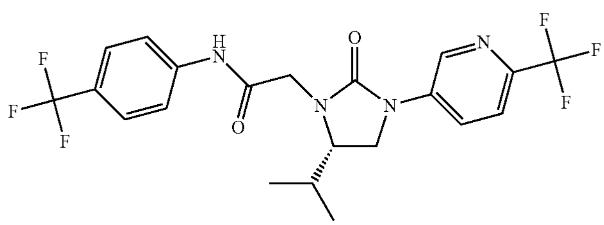 [SMILES: CC(C)[C@H]1CN(c2ccc(C(F)(F)F)nc2)C(=O)N1CC(=O)Nc1ccc(C(F)(F)F)cc1] | S | 475 ([M + H]+) | 1H NMR (600 MHz, CHLOROFORM-d) δ ppm 0.88 (d, J = 7.0 Hz, 3 H), 1.03 (d, J = 7.0 Hz, 3 H), 2.22-2.31 (m, 1 H), 3.60-3.71 (m, 1 H), 3.89-3.98 (m, 2 H), 3.99-4.06 (m, 1 H), 4.10-4.18 (m, 1 H), 7.53-7.60 (m, 2 H), 7.63 (d, J = 8.3 Hz, 2 H), 7.68 (d, J = 8.7 Hz, 1 H), 8.30 (dd, J = 8.7, 2.5 Hz, 1 H), 8.77-8.85 (m, 2 H) |
| 31 | 3 | 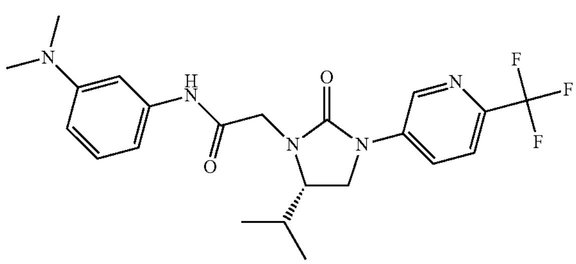 [SMILES: CC(C)[C@H]1CN(c2ccc(C(F)(F)F)nc2)C(=O)N1CC(=O)Nc1cccc(N(C)C)c1] | S | 450 ([M + H]+) | 1H NMR (600 MHz, CHLOROFORM-d) δ ppm 0.89 (d, J = 6.6 Hz, 3 H), 1.02 (d, J = 7.0 Hz, 3 H), 2.23-2.32 (m, 1 H), 2.95 (s, 6 H), 3.63 (dd, J = 8.7, 5.8 Hz, 1 H), (m, 3.88-3.98 (m, 2 H), 3.98-4.05 (m, 1 H), 4.07-4.13 (m, 1 H), 6.46-6.52 (m, 1 H), 6.73-6.78 (m, 1 H), 7.03 (s, 1 H), 7.16 (t, J = 8.3 Hz, 1 H), 7.66 (d, J = 8.7 Hz, 1 H), 8.16 (br.s., 1 H), 8.34 (dd, J = 8.7, 2.5 Hz, 1 H), 8.80 (d, J = 2.5 Hz, 1 H) |
| 32 | 3 | 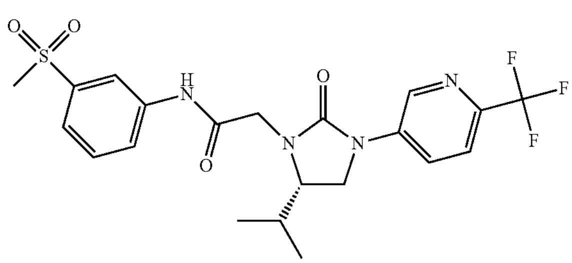 [SMILES: CC(C)[C@H]1CN(c2ccc(C(F)(F)F)nc2)C(=O)N1CC(=O)Nc1cccc(S(C)(=O)=O)c1] | S | 485 ([M + H]+) | 1H NMR (600 MHz, CHLOROFORM-d) δ ppm 0.89 (d, J = 6.6 Hz, 3 H), 1.04 (d, J = 7.0 Hz, 3 H), 2.22-2.31 (m, 1 H), 3.06 (s, 3 H), 3.63-3.71 (m, 1 H), 3.89-3.98 (m, 2 H), 4.00-4.07 (m, 1 H), 4.10-4.18 (m, 1 H), 7.52 (t, J = 8.1 Hz, 1 H), 7.65-7.73 (m, 2 H), 7.83-7.90 (m, 1 H), 8.05-8.10 (m, 1 H), 8.31-8.37 (m, 1 H), 8.78-8.82 (m, 1 H), 8.84 (s, 1 H) |

TABLE 1-4-continued

| Compound | Example | Structure | Configuration | (ESI pos.) m/z (ESI neg.) m/z | 1H-NMR |
|---|---|---|---|---|---|
| 33 | 2 | 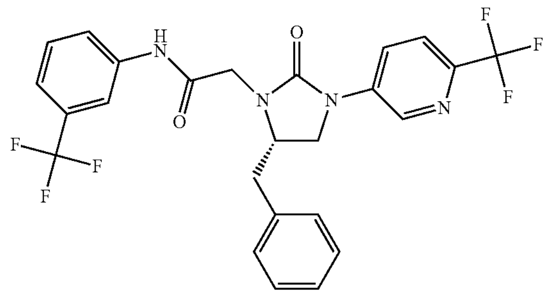 [SMILES: O=C(CN1C(=O)N(c2ccc(C(F)(F)F)nc2)C[C@@H]1Cc1ccccc1)Nc1cccc(C(F)(F)F)c1] | S | 523 ([M + H]+) | 1H NMR (600 MHz, CHLOROFORM-d) d ppm 2.84 (dd, J = 13.6, 8.7 Hz, 1 H), 3.29 (dd, J = 13.6, 5.0 Hz, 1 H), 3.65 (dd, J = 9.3, 6.4 Hz, 1 H), 3.93 (t, J = 9.1 Hz, 1 H), 4.04-4.09 (m, 1 H), 4.15-4.19 (m, 1 H), 4.23-4.31 (m, 1 H), 7.18-7.24 (m, 2 H), 7.27-7.39 (m, 4 H), 7.41-7.48 (m, 1 H), 7.59-7.70 (m, 2 H), 7.84 (s, 1 H), 8.15-8.23 (m, 1 H), 8.36 (br.s., 1 H), 8.74 (d, J = 2.5 Hz, 1 H) |
| 34 | 2 | 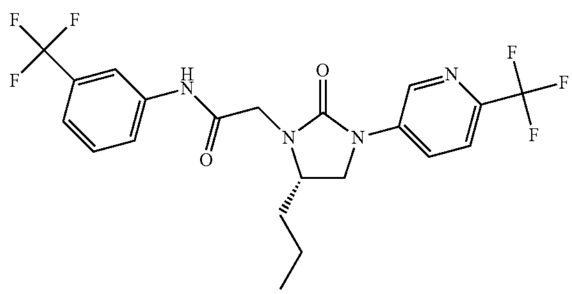 [SMILES: CCC[C@H]1CN(c2ccc(C(F)(F)F)nc2)C(=O)N1CC(=O)Nc1cccc(C(F)(F)F)c1] | S | 475 ([M + H]+) | 1H NMR (600 MHz, CHLOROFORM-d) d ppm 1.02 (t, J = 7.2 Hz, 3 H), 1.36-1.48 (m, 2 H), 1.58-1.68 (m, 1 H), 1.86-1.96 (m, 1 H), 3.62 (dd, J = 9.1, 7.0 Hz, 1 H), 3.92-3.98 (m, 1 H), 4.01 (d, J = 16.1 Hz, 1 H), 4.06-4.18 (m, 2 H), 7.34-7.40 (m, 1 H), 7.40-7.47 (m, 1 H), 7.63-7.71 (m, 2 H), 7.85 (s, 1 H), 8.31 (dd, J = 8.7, 2.5 Hz, 1 H), 8.57 (br.s., 1 H), 8.78 (d, J = 2.5 Hz, 1 H) |
| 35 | 5 | 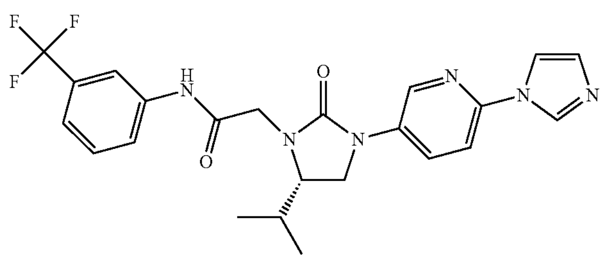 [SMILES: CC(C)[C@H]1CN(c2ccc(-n3ccnc3)nc2)C(=O)N1CC(=O)Nc1cccc(C(F)(F)F)c1] | S | 507 ([M + H]+) | 1H NMR (600 MHz, CHLOROFORM-d) d ppm 0.91 (d, J = 6.6 Hz, 3 H), 1.04 (d, J = 7.0 Hz, 3 H), 2.24-2.30 (m, 1 H), 3.62-3.69 (m, 1 H), 3.89-3.96 (m, 2 H), 4.01 (d, J = 15.7 Hz, 1 H), 4.14 (d, J = 15.7 Hz, 1 H), 7.21 (s, 1 H), 7.34-7.40 (m, 2 H), 7.42-7.47 (m, 1 H), 7.60-7.63 (m, 1 H), 7.68-7.73 (m, 1 H), 7.86 (s, 1 H), 8.29 (s, 1 H), 8.35-8.40 (m, 1 H), 8.49 (d, J = 2.5 Hz, 1 H), 8.86 (br.s., 1 H) |
| 36 | 3 | 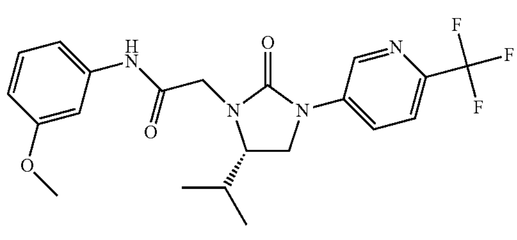 | S | 437 ([M + H]+) | 1H NMR (600 MHz, CHLOROFORM-d) d ppm 0.84 (d, J = 6.6 Hz, 3 H), 0.98 (d, J = 7.0 Hz, 3 H), 2.17-2.27 (m, 1 H), 3.57-3.63 (m, 1 H), 3.75 (s, 3 H), 3.83-3.92 (m, 2 H), 3.96-4.05 (m, 2 H), 6.61-6.65 (m, 1 H), 6.91-6.96 (m, 1 H), 7.17 (t, J = 8.3 Hz, 1 H), 7.20-7.23 (m, 1 H), 7.62 (d, J = 8.7 Hz, 1 H), 8.25-8.32 (m, 2 H), 8.74 (d, J = 2.5 Hz, 1 H) |

TABLE 1-5

| Compound | Example | Structure | Configuration | (ESI pos.) m/z (ESI neg.) m/z | 1H-NMR |
|---|---|---|---|---|---|
| 37 | 3 | 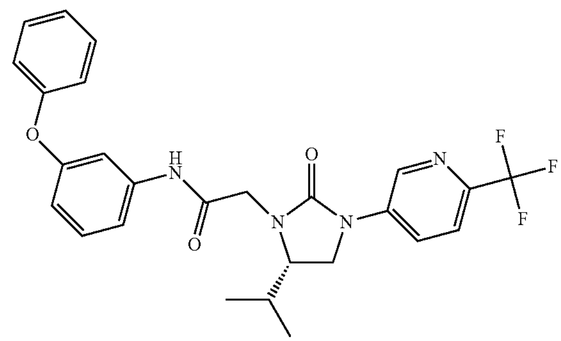 [SMILES: CC(C)[C@H]1CN(c2ccc(C(F)(F)F)nc2)C(=O)N1CC(=O)Nc1cccc(Oc2ccccc2)c1] | S | 499 ([M + H]+) | 1H NMR (600 MHz, CHLOROFORM-d) d ppm 0.87 (d, J = 6.6 Hz, 3 H), 1.01 (d, J = 7.0 Hz, 3 H), 2.17-2.30 (m, 1 H), 3.59-3.67 (m, 1 H), 3.86-3.95 (m, 2 H), 3.99-4.11 (m, 2 H), 6.71-6.78 (m, 1 H), 7.00 (d, J = 7.8 Hz, 2 H), 7.07-7.14 (m, 1 H), 7.17-7.37 (m, 5 H), 7.66 (d, J = 8.7 Hz, 1 H), 8.33 (dd, J = 8.7, 2.5 Hz, 1 H), 8.39 (br. s., 1 H), 8.72-8.80 (m, 1 H) |
| 38 | 3 | 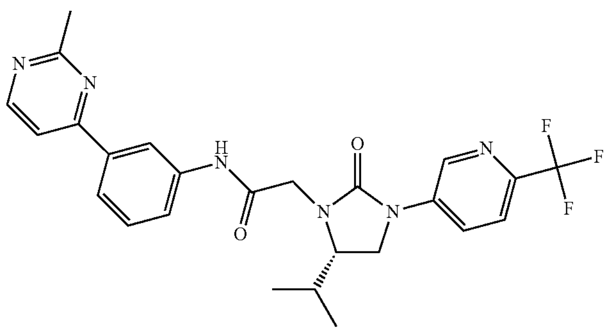 [SMILES: Cc1nccc(-c2cccc(NC(=O)CN3C(=O)N(c4ccc(C(F)(F)F)nc4)C[C@@H]3C(C)C)c2)n1] | S | 499 ([M + H]+) | 1H NMR (600 MHz, CHLOROFORM-d) d ppm 0.90(d, J = 7.0 Hz, 3 H), 1.03 (d, J = 7.0 Hz, 3 H), 2.23-2.34 (m, 1 H), 2.79 (s, 3 H), 3.62-3.67 (m, 1 H), 3.90-3.99 (m, 2 H), 4.10 (s, 2 H), 7.43-7.53 (m, 2 H), 7.64-7.73 (m, 2 H), 7.81 (d, J = 7.4 Hz, 1 H), 8.19-8.25 (m, 1 H), 8.34 (dd, J = 8.7, 2.5 Hz, 1 H), 8.53 (s, 1 H), 8.67 (d, J = 5.0 Hz, 1 H), 8.82 (d, J = 2.5 Hz, 1 H) |
| 39 | 3 | 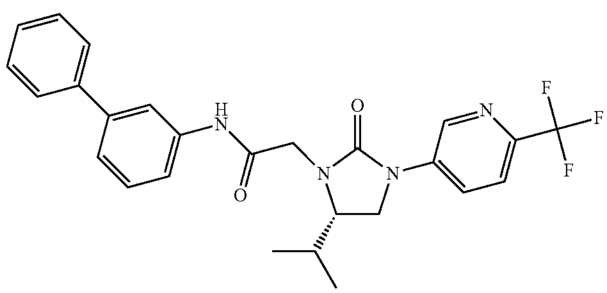 [SMILES: CC(C)[C@H]1CN(c2ccc(C(F)(F)F)nc2)C(=O)N1CC(=O)Nc1cccc(-c2ccccc2)c1] | S | 483 ([M + H]+) | 1H NMR (600 MHz, CHLOROFORM-d) d ppm 0.90 (d, J = 7.0 Hz, 3 H), 1.03 (d, J = 7.0 Hz, 3 H), 2.24-2.34 (m, 1 H), 3.65 (dd, J = 8.1, 5.2 Hz, 1 H), 3.89-3.99 (m, 2 H), 4.04-4.14 (m, 2 H), 7.32-7.47 (m, 5 H), 7.52 (s, 1 H), 7.56-7.60 (m, 2 H), 7.67 (d, J = 8.7 Hz, 1 H), 7.75 (s, 1 H), 8.35 (dd, J = 8.7, 2.5 Hz, 1 H), 8.46 (br. s., 1 H), 8.77-8.84 (m, 1 H) |
| 40 | 3 | 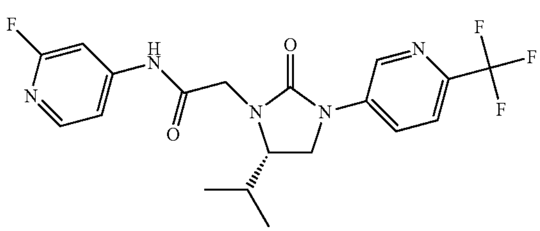 [SMILES: CC(C)[C@H]1CN(c2ccc(C(F)(F)F)nc2)C(=O)N1CC(=O)Nc1ccnc(F)c1] | S | 426 ([M + H]+) | 1H NMR (600 MHz, CHLOROFORM-d) d ppm 0.88 (d, J = 7.0 Hz, 3 H), 1.04 (d, J = 7.0 Hz, 3 H), 2.20-2.29 (m, 1 H), 3.67 (dd, J = 8.7, 5.8 Hz, 1 H), 3.87-4.00 (m, 3 H), 4.17 (d, J = 15.7 Hz, 1 H), 7.16 (d, J = 5.4 Hz, 1 H), 7.29-7.34 (m, 1 H), 7.69 (d, J = 9.1 Hz, 1 H), 8.10 (d, J = 5.8 Hz, 1 H), 8.26-8.32 (m, 1 H), 8.82 (d, J = 2.9 Hz, 1 H), 9.17 (br. s., 1 H) |
| 41 | 3 | 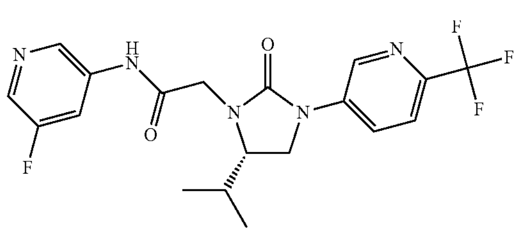 [SMILES: CC(C)[C@H]1CN(c2ccc(C(F)(F)F)nc2)C(=O)N1CC(=O)Nc1cncc(F)c1] | S | 426 ([M + H]+) | 1H NMR (600 MHz, CHLOROFORM-d) d ppm 0.89 (d, J = 7.0 Hz, 3 H), 1.04 (d, J = 7.0 Hz, 3 H), 2.22-2.31 (m, 1 H), 3.67 (dd, J = 7.6, 4.3 Hz, 1 H), 3.91-3.97 (m, 2 H), 4.00 (d, J = 15.7 Hz, 1 H), 4.16 (d, J = 15.7 Hz, 1 H), 6.92 (dd, J = 8.7, 3.3 Hz, 1 H), 7.68 (d, J = 8.7 Hz, 1 H), 8.09-8.16 (m, 1 H), 8.23-8.28 (m, 1 H), 8.30-8.35 (m, 1 H), 8.74 (br. s., 1 H), 8.80 (d, J = 2.5 Hz, 1 H) |

TABLE 1-5-continued

| Compound | Example | Structure | Configuration | (ESI pos.) m/z (ESI neg.) m/z | 1H-NMR |
|---|---|---|---|---|---|
| 42 | 3 | 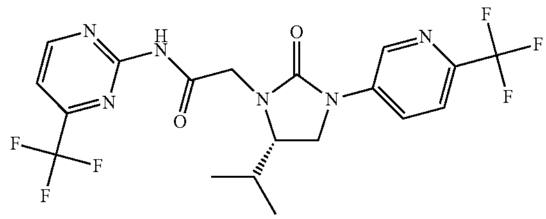 [SMILES: CC(C)[C@H]1CN(c2ccc(C(F)(F)F)nc2)C(=O)N1CC(=O)Nc1nccc(C(F)(F)F)n1] | S | 477 ([M + H]+) | 1H NMR (600 MHz, CHLOROFORM-d) d ppm 0.94 (d, J = 7.0 Hz, 3 H), 1.02 (d, J = 7.0 Hz, 3 H), 2.06-2.22 (m, 1 H), 3.62 (dd, J = 8.9, 6.4 Hz, 1 H), 3.91-3.98 (m, 1 H), 4.00-4.06 (m, 1 H), 4.34 (d, J = 17.8 Hz, 1 H), 4.86 (d, J = 17.8 Hz, 1 H), 7.36 (d, J = 5.0 Hz, 1 H), 7.64 (d, J = 9.1 Hz, 1 H), 8.33-8.41 (m, 1 H), 8.51 (br. s., 1 H), 8.76 (d, J = 2.9 Hz, 1 H), 8.86 (d, J = 5.0 Hz, 1 H) |
| 43 | 3 | 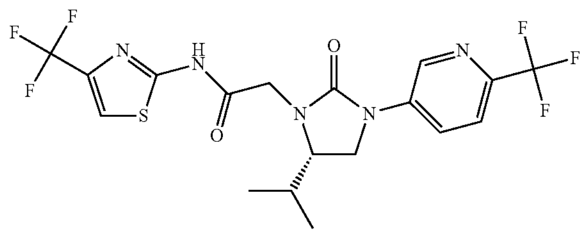 [SMILES: CC(C)[C@H]1CN(c2ccc(C(F)(F)F)nc2)C(=O)N1CC(=O)Nc1nc(C(F)(F)F)cs1] | S | 482 ([M + H]+) | 1H NMR (600 MHz, CHLOROFORM-d) d ppm 0.88 (d, J = 6.6 Hz, 3 H), 1.03 (d, J = 6.6 Hz, 3 H), 2.13-2.26 (m, 1 H), 3.66 (dd, J = 9.1, 5.8 Hz, 1 H), 3.84-4.01 (m, 2 H), 4.11-4.24 (m, 2 H), 7.37-7.46 (m, 1 H), 7.68 (d, J = 8.7 Hz, 1 H), 8.37-8.47 (m, 1 H), 8.71 (d, J = 2.5 Hz, 1 H), 9.95 (br. s., 1 H) |
| 44 | 5 | 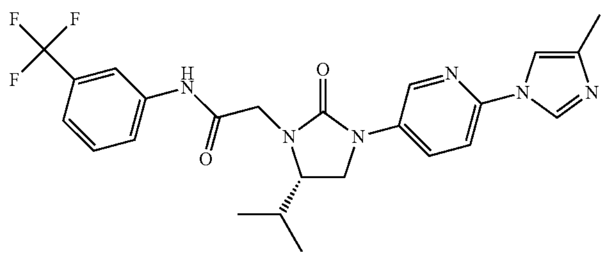 [SMILES: Cc1cn(-c2ccc(N3C[C@H](C(C)C)N(CC(=O)Nc4cccc(C(F)(F)F)c4)C3=O)cn2)cn1] | S | 487 ([M + H]+) | 1H NMR (600 MHz, CHLOROFORM-d) d ppm 0.91 (d, J = 7.0 Hz, 3 H), 1.03 (d, J = 7.0 Hz, 3 H), 2.23-2.28 (m, 1 H), 2.31 (s, 3 H), 3.59-3.70 (m, 1 H), 3.85-3.95 (m, 2 H), 4.02 (d, J = 15.7 Hz, 1 H), 4.09-4.18 (m, 1 H), 7.29-7.33 (m, 2 H), 7.34-7.40 (m, 1 H), 7.40-7.46 (m, 1 H), 7.66-7.75 (m, 1 H), 7.86 (s, 1 H), 8.20 (s, 1 H), 8.34 (dd, J = 9.1, 2.9 Hz, 1 H), 8.46 (d, J = 2.9 Hz, 1 H), 8.92 (br. s., 1 H) |
| 45 | 5 | 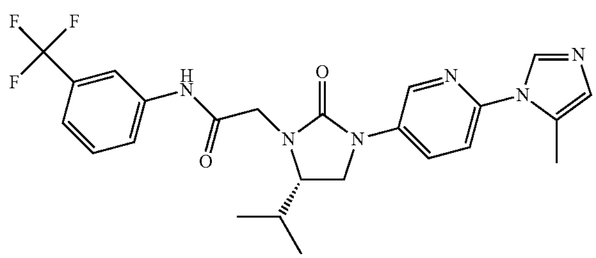 [SMILES: Cc1cncn1-c1ccc(N2C[C@H](C(C)C)N(CC(=O)Nc3cccc(C(F)(F)F)c3)C2=O)cn1] | S | 487 ([M + H]+) | 1H NMR (600 MHz, CHLOROFORM-d) d ppm 0.91 (d, J = 7.0 Hz, 3 H), 1.04 (d, J = 6.6 Hz, 3 H), 2.23-2.31 (m, 1 H), 2.36 (s, 3 H), 3.62-3.71 (m, 1 H), 3.90-3.97 (m, H), (d, 2 H), 4.01 (d, J = 15.7 Hz, 1 H), 4.14 (d, J = 15.7 Hz, 1 H), 6.90 (s, 1 H), 7.31-7.40 (m, 2 H), 7.41-7.47 (m, 1 H), 7.66-7.73 (m, 1 H), 7.81-7.89 (m, 2 H), 8.39 (dd, J = 8.7, 2.9 Hz, 1 H), 8.59 (d, J = 2.9 Hz, 1 H), 8.81 (br. s., 1 H) |

TABLE 1-6

| Compound | Example | Structure | Configuration | (ESI pos.) m/z (ESI neg.) m/z | 1H-NMR |
|---|---|---|---|---|---|
| 46 | 7 | 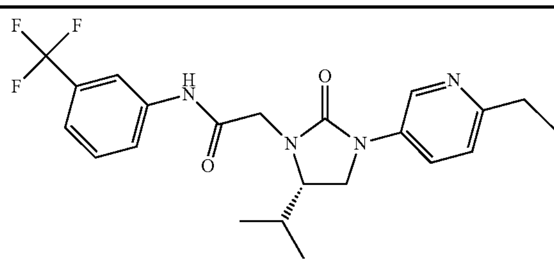 | S | 435 ([M + H]+) | 1H NMR (600 MHz, CHLOROFORM-d) d ppm 0.89 (d, J = 7.0 Hz, 3 H), 1.01 (d, J = 7.0 Hz, 3 H), 1.30 (t, J = 7.6 Hz, 3 H), 2.19-2.30 (m, 1 H), 2.82 (q, J = 7.4 Hz, 2 H), 3.62 (dd, J = 8.5, 6.0 Hz, 1 H), 3.81-3.96 (m, 3 H), 4.16 (d, J = 15.3 Hz, 1 H), 7.18 (d, J = 8.3 Hz, 1 H), 7.32-7.38 (m, 1 H), 7.40-7.46 (m, 1 H), 7.65-7.71 (m, 1 H), 7.86 (s, 1 H), 8.04-8.12 (m, 1 H), 8.56 (d, J = 2.5 Hz, 1 H), 8.99 (br. s., 1 H) |

TABLE 1-6-continued

| Compound | Example | Structure | Configuration | (ESI pos.) m/z (ESI neg.) m/z | 1H-NMR |
|---|---|---|---|---|---|
| 47 | 7 | 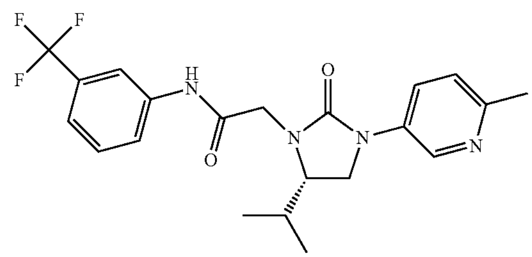 [SMILES: Cc1ccc(N2C[C@H](C(C)C)N(CC(=O)Nc3cccc(C(F)(F)F)c3)C2=O)cn1] | S | 421 ([M + H]+) | 1H NMR (600 MHz, CHLOROFORM-d) d ppm 0.88 (d, J = 7.0 Hz, 3 H), 1.01 (d, J = 7.0 Hz, 3 H), 2.18-2.27 (m, 1 H), 2.54 (s, 3 H), 3.61 (dd, J = 8.3, 5.8 Hz, 1 H), 3.80-3.96 (m, 3 H), 4.15 (d, J = 15.7 Hz, 1 H), 7.16 (d, J = 8.7 Hz, 1 H), 7.33-7.38 (m, 1 H), 7.39-7.46 (m, 1 H), 7.64-7.71 (m, 1 H), 7.85 (s, 1 H), 8.02-8.09 (m, 1 H), 8.52 (d, J = 2.5 Hz, 1 H), 8.96 (br. s., 1 H) |
| 48 | 8 | 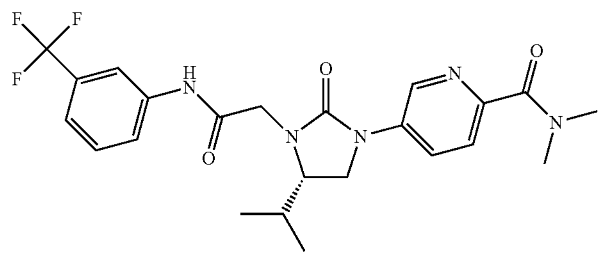 [SMILES: CC(C)[C@H]1CN(c2ccc(C(=O)N(C)C)nc2)C(=O)N1CC(=O)Nc1cccc(C(F)(F)F)c1] | S | 478 ([M + H]+) | 1H NMR (600 MHz, CHLOROFORM-d) d ppm 0.89 (d, J = 7.0 Hz, 3 H), 1.02 (d, J = 7.0 Hz, 3 H), 2.21-2.29 (m, 1 H), 3.14 (s, 3 H), 3.15 (s, 3 H), 3.61-3.67 (m, 1 H), 3.86-3.96 (m, 2 H), 3.98 (d, J = 15.7 Hz, 1 H), 4.14 (d, J = 15.7 Hz, 1 H), 7.34-7.39 (m, 1 H), 7.40-7.46 (m, 1 H), 7.64-7.69 (m, 1 H), 7.73 (d, J = 8.7 Hz, 1 H), 7.86 (s, 1 H), 8.09-8.17 (m, 1 H), 8.75 (d, J = 2.5 Hz, 1 H), 8.83 (br. s., 1 H) |
| 49 | 1 | 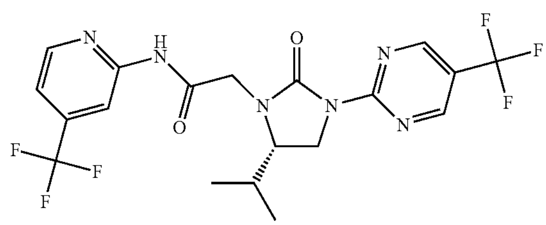 [SMILES: CC(C)[C@H]1CN(c2ncc(C(F)(F)F)cn2)C(=O)N1CC(=O)Nc1cc(C(F)(F)F)ccn1] | S | 477 ([M + H]+) | 1H NMR (600 MHz, CHLOROFORM-d) d ppm 0.90 (d, J = 6.6 Hz, 3 H), 1.03 (d, J = 7.0 Hz, 3 H), 2.17-2.28 (m, 1 H), 3.85-3.94 (m, 2 H), 4.03-4.17 (m, 2 H), 4.27 (d, J = 16.1 Hz, 1 H), 8.40-8.47 (m, 2 H), 8.82-8.87 (m, 3 H) |
| 50 | 3 | 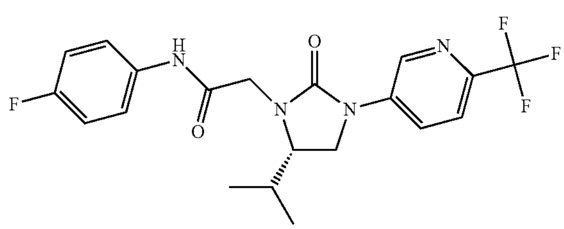 [SMILES: CC(C)[C@H]1CN(c2ccc(C(F)(F)F)nc2)C(=O)N1CC(=O)Nc1ccc(F)cc1] | S | 425 ([M + H]+) | 1H NMR (600 MHz, CHLOROFORM-d) d ppm 0.88 (d, J = 7.0 Hz, 1.02 (d, J = 6.6 Hz, 3 H), 2.20-2.32 (m, 1 H), 3.56-3.67 (m, 1 H), 3.87-3.95 (m, 2 H), 3.97-4.04 (m, 1 H), 4.05-4.12 (m, 1 H), 6.96-7.06 (m, 2 H), 7.42-7.54 (m, 2 H), 7.66 (d, J = 8.7 Hz, 1 H), 8.31 (dd, J = 8.7, 2.5 Hz, 1 H), 8.44 (br. s., 1 H), 8.80 (d, J = 2.5 Hz, 1 H) |
| 51 | 3 | 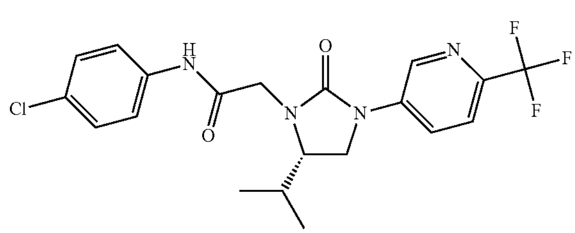 [SMILES: CC(C)[C@H]1CN(c2ccc(C(F)(F)F)nc2)C(=O)N1CC(=O)Nc1ccc(Cl)cc1] | S | 441 ([M + H]+) | 1H NMR (600 MHz, CHLOROFORM-d) d ppm 0.88 (d, J = 7.0 Hz, 3 H), 1.03 (d, J = 7.0 Hz, 3 H), 2.19-2.33 (m, 1 H), 3.60-3.69 (m, 1 H), 3.89-3.96 (m, 2 H), 3.97-4.04 (m, 1 H), 4.06-4.14 (m, 1 H), 7.28 (d, J = 9.1 Hz, 2 H), 7.47 (d, J = 9.1 Hz, 2 H), 7.67 (d, J = 8.7 Hz, 1 H), 8.32 (dd, J = 8.7, 2.5 Hz, 1 H), 8.53 (br. s., 1 H), 8.81 (d, J = 2.5 Hz, 1 H) |
| 52 | 3 | 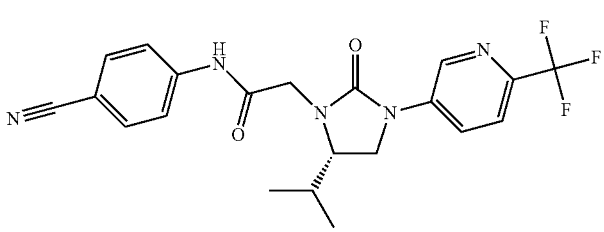 [SMILES: CC(C)[C@H]1CN(c2ccc(C(F)(F)F)nc2)C(=O)N1CC(=O)Nc1ccc(C#N)cc1] | S | 432 ([M + H]+) | 1H NMR (600 MHz, CHLOROFORM-d) d ppm 0.88 (d, J = 7.0 Hz, 3 H), 1.03 (d, J = 7.0 Hz, 3 H), 2.21-2.31 (m, 1 H), 3.66 (dd, J = 7.8, 5.0 Hz, 1 H), 3.86-4.02 (m, 3 H), 4.16 (d, J = 15.7 Hz, 1 H), 7.56-7.72 (m, 5 H), 8.26-8.33 (m, 1 H), 8.83 (d, J = 2.5 Hz, 1 H), 8.99 (br. s., 1 H) |

TABLE 1-6-continued

| Compound | Example | Structure | Configuration | (ESI pos.) m/z (ESI neg.) m/z | 1H-NMR |
|---|---|---|---|---|---|
| 53 | 3 | 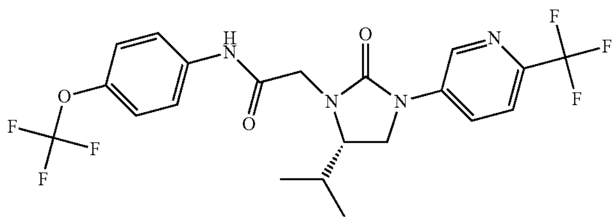 [SMILES: CC(C)[C@H]1CN(c2ccc(C(F)(F)F)nc2)C(=O)N1CC(=O)Nc1ccc(OC(F)(F)F)cc1] | S | 491 ([M + H]+) | 1H NMR (600 MHz, CHLOROFORM-d) d ppm 0.89 (d, J = 6.6 Hz, 3 H), 1.03 (d, J = 7.0 Hz, 3 H), 2.21-2.34 (m, 1 H), 3.61-3.69 (m, 1 H), 3.89-3.97 (m, 2 H), 4.02 (s, 1 H), 4.08-4.15 (m, 1 H), 7.18 (d, J = 8.7 Hz, 2 H), 7.55 (d, J = 9.1 Hz, 2 H), 7.68 (d, J = 8.7 Hz, 1 H), 8.31 (dd, J = 8.7, 2.5 Hz, 1 H), 8.62 (br. s., 1 H), 8.81 (d, J = 2.5 Hz, 1 H) |
| 54 | 3 | 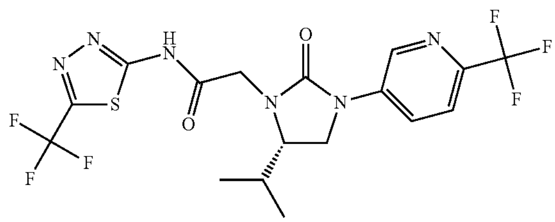 [SMILES: CC(C)[C@H]1CN(c2ccc(C(F)(F)F)nc2)C(=O)N1CC(=O)Nc1nnc(C(F)(F)F)s1] | S | 483 ([M + H]+) | 1H NMR (600 MHz, CHLOROFORM-d) d ppm 0.91 (d, J = 6.6 Hz, 3 H), 1.04 (d, J = 7.0 Hz, 3 H), 2.12-2.24 (m, 1 H), 3.69 (dd, J = 8.9, 6.0 Hz, 1 H), 3.88-4.03 (m, 2 H), 4.27-4.39 (m, 2 H), 7.68 (d, J = 9.1 Hz, 1 H), 8.37-8.45 (m, 1 H), 8.73 (d, J = 2.5 Hz, 1 H) |

TABLE 1-7

| Compound | Example | Structure | Configuration | (ESI pos.) m/z (ESI neg.) m/z | 1H-NMR |
|---|---|---|---|---|---|
| 55 | 3 | 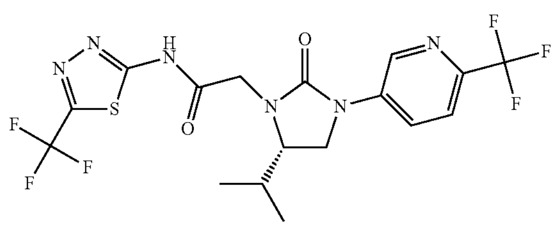 | S | 438 ([M + H]+) | 1H NMR (600 MHz, CHLOROFORM-d) d ppm 0.87 (d, J = 6.6 Hz, 3 H), 1.02 (d, J = 7.0 Hz, 3 H), 2.20-2.29 (m, 1 H), 3.65 (dd, J = 8.1, 5.2 Hz, 1 H), 3.87-4.01 (m, 6 H), 4.12 (d, J = 15.7 Hz, 1 H), 6.94-6.99 (m, 1 H), 7.00-7.05 (m, 1 H), 7.68 (d, J = 8.7 Hz, 1 H), 8.06 (d, J = 5.8 Hz, 1 H), 8.30-8.37 (m, 1 H), 8.71 (br. s., 1 H), 8.79 (d, J = 2.5 Hz, 1 H) |
| 56 | 3 | 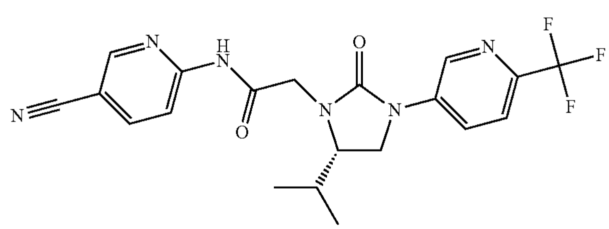 [SMILES: CC(C)[C@H]1CN(c2ccc(C(F)(F)F)nc2)C(=O)N1CC(=O)Nc1ccc(C#N)cn1] | S | 433 ([M + H]+) | 1H NMR (600 MHz, CHLOROFORM-d) d ppm 0.90 (d, J = 7.0 Hz, 3 H), 1.04 (d, J = 7.0 Hz, 3 H), 2.14-2.28 (m, 1 H), 3.67 (dd, J = 8.3, 5.8 Hz, 1 H), 3.87-4.00 (m, 2 H), 4.07-4.21 (m, 2 H), 7.67 (d, J = 9.1 Hz, 1 H), 7.95 (dd, J = 8.7, 2.5 Hz, 1 H), 8.30 (d, J = 8.7 Hz, 1 H), 8.37-8.45 (m, 1 H), 8.55-8.61 (m, 1 H), 8.75 (d, J = 2.9 Hz, 1 H), 9.03 (s, 1 H) |
| 57 | 3 | 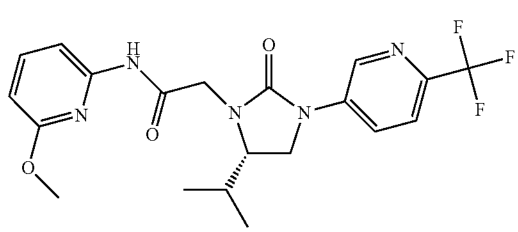 [SMILES: COc1cccc(NC(=O)CN2C(=O)N(c3ccc(C(F)(F)F)nc3)C[C@@H]2C(C)C)n1] | S | 438 ([M + H]+) | 1H NMR (600 MHz, CHLOROFORM-d) d ppm 0.90 (d, J = 7.0 Hz, 3 H), 1.02 (d, J = 6.6 Hz, 3 H), 2.18-2.27 (m, 1 H), 3.63 (dd, J = 8.5, 5.6 Hz, 1 H), 3.85 (s, 3 H), 3.89-4.03 (m, 3 H), 4.20-4.31 (m, 1 H), 6.50 (d, J = 8.3 Hz, 1 H), 7.54-7.60 (m, 1 H), 7.62-7.73 (m, 2 H), 8.24 (br. s., 1 H), 8.37 (dd, J = 8.7, 2.5 Hz, 1 H), 8.78 (d, J = 2.5 Hz, 1 H) |

TABLE 1-7-continued

| Compound | Example | Structure | Configuration | (ESI pos.) m/z (ESI neg.) m/z | 1H-NMR |
|---|---|---|---|---|---|
| 58 | 3 | 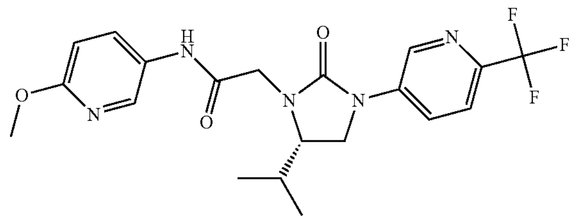 [SMILES: COc1ccc(NC(=O)CN2C(=O)N(c3ccc(C(F)(F)F)nc3)C[C@@H]2C(C)C)cn1] | S | 438 ([M + H]+) | 1H NMR (600 MHz, CHLOROFORM-d) d ppm 0.89 (d, J = 7.0 Hz, 3 H), 1.03 (d, J = 7.0 Hz, 3 H), 2.22-2.32 (m, 1 H), 3.60-3.69 (m, 1 H), 3.88-3.97 (m, 5 H), 3.99-4.06 (m, 1 H), 4.08-4.15 (m, 1 H), 6.73 (d, J = 8.7 Hz, 1 H), 7.67 (d, J = 9.1 Hz, 1 H), 7.84 (dd, J = 8.9, 2.7 Hz, 1 H), 8.22 (d, J = 2.5 Hz, 1 H), 8.31-8.39 (m, 2 H), 8.79 (d, J = 2.5 Hz, 1 H) |
| 59 | 3 | 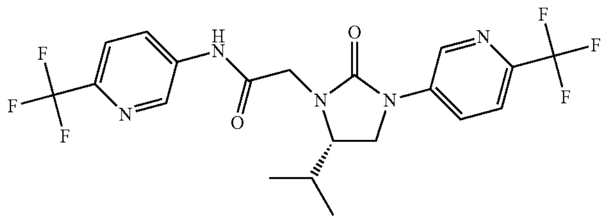 [SMILES: CC(C)[C@H]1CN(c2ccc(C(F)(F)F)nc2)C(=O)N1CC(=O)Nc1ccc(C(F)(F)F)nc1] | S | 476 ([M + H]+) | 1H NMR (600 MHz, CHLOROFORM-d) d ppm 0.89 (d, J = 6.6 Hz, 3 H), 1.04 (d, J = 7.0 Hz, 3 H), 2.21-2.33 (m, 1 H), 3.68 (dd, J = 7.8, 5.0 Hz, 1 H), 3.88-4.05 (m, 3 H), 4.20 (d, J = 15.7 Hz, 1 H), 7.64 (d, J = 8.7 Hz, 1 H), 7.69 (d, J = 8.7 Hz, 1 H), 8.25-8.35 (m, 2 H), 8.70 (d, J = 2.5 Hz, 1 H), 8.80 (d, J = 2.5 Hz, 1 H), 9.10 (s, 1 H) |
| 60 | 3 | 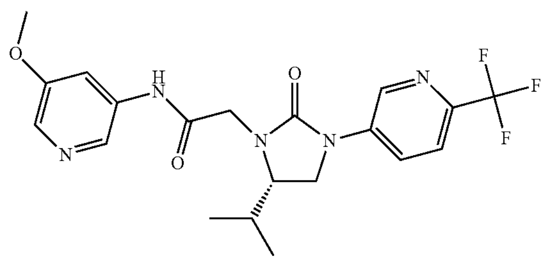 [SMILES: COc1cncc(NC(=O)CN2C(=O)N(c3ccc(C(F)(F)F)nc3)C[C@@H]2C(C)C)c1] | S | 438 ([M + H]+) | 1H NMR (600 MHz, CHLOROFORM-d) d ppm 0.89 (d, J = 6.6 Hz, 3 H), 1.04 (d, J = 7.0 Hz, 3 H), 2.22-2.31 (m, 1 H), 3.61-3.69 (m, 1 H), 3.86 (s, 3 H), 3.90-3.98 (m, 2 H), 4.00-4.06 (m, 1 H), 4.10-4.16 (m, 1 H), 7.68 (d, J = 8.7 Hz, 1 H), 7.77-7.84 (m, 1 H), 8.08 (d, J = 2.5 Hz, 1 H), 8.15 (d, J = 2.1 Hz, 1 H), 8.32-8.39 (m, 1 H), 8.63 (s, 1 H), 8.78 (d, J = 2.9 Hz, 1 H) |
| 61 | 3 | 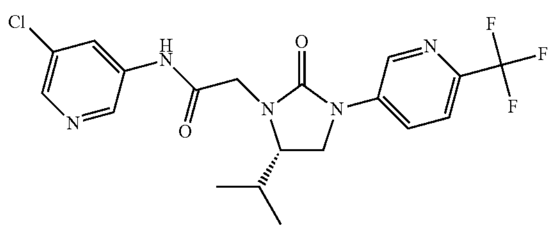 [SMILES: CC(C)[C@H]1CN(c2ccc(C(F)(F)F)nc2)C(=O)N1CC(=O)Nc1cncc(Cl)c1] | S | 442 ([M + H]+) | 1H NMR (600 MHz, CHLOROFORM-d) d ppm 0.90 (d, J = 7.0 Hz, 3 H), 1.03 (d, J = 7.0 Hz, 3 H), 2.14-2.24 (m, 1 H), 3.60-3.69 (m, 1 H), 3.89-3.99 (m, 2 H), 4.04 (d, J = 16.5 Hz, 1 H), 4.21 (d, J = 16.5 Hz, 1 H), 7.04-7.10 (m, 1 H), 7.66 (d, J = 8.7 Hz, 1 H), 8.18 (d, J = 5.4 Hz, 1 H), 8.24 (s, 1 H), 8.39-8.45 (m, 1 H), 8.67 (br. s., 1 H), 8.73 (d, J = 2.5 Hz, 1 H) |
| 62 | 3 | 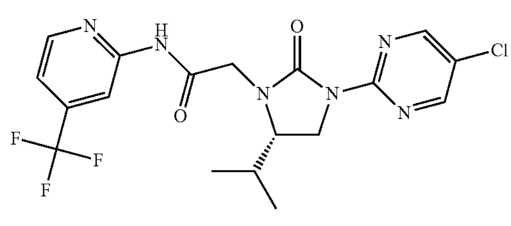 [SMILES: CC(C)[C@H]1CN(c2ncc(Cl)cn2)C(=O)N1CC(=O)Nc1cc(C(F)(F)F)ccn1] | S | 443 ([M + H]+) | 1H NMR (600 MHz, CHLOROFORM-d) d ppm 0.90 (d, J = 7.0 Hz, 3 H), 1.02 (d, J = 7.0 Hz, 3 H), 2.13-2.26 (m, 1 H), 3.80-3.91 (m, 2 H), 4.00-4.14 (m, 2 H), 4.18-4.28 (m, 1 H), 7.24-7.26 (m, 1 H), 8.40-8.46 (m, 2 H), 8.58 (s, 2 H), 8.97 (br. s., 1 H) |
| 63 | 3 | 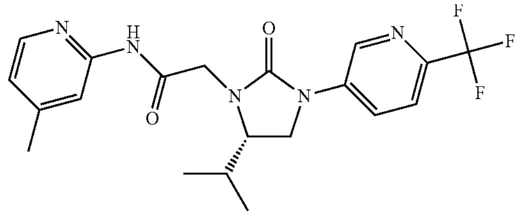 | S | 422 ([M + H]+) | 1H NMR (600 MHz, CHLOROFORM-d) d ppm 0.90 (d, J = 7.0 Hz, 3 H), 1.02 (d, J = 7.0 Hz, 3 H), 2.15-2.26 (m, 1 H), 2.36 (s, 3 H), 3.59-3.67 (m, 1 H), 3.89-4.03 (m, 3 H), 4.25-4.32 (m, 1 H), 6.86-6.91 (m, 1 H), 7.65 (d, J = 8.7 Hz, 1 H), 8.00 (br. s., 1 H), 8.13 (d, J = 5.0 Hz, 1 H), 8.40-8.49 (m, 2 H), 8.72 (d, J = 2.9 Hz, 1 H) |

TABLE 1-8

| Compound | Example | Structure | Configuration | (ESI pos.) m/z (ESI neg.) m/z | 1H-NMR |
|---|---|---|---|---|---|
| 64 | 3 | 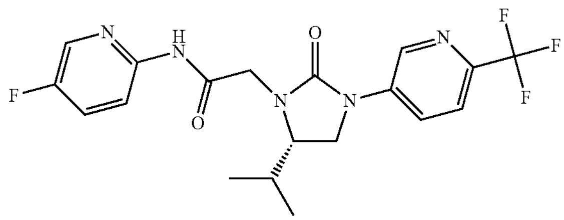 [SMILES: CC(C)[C@H]1CN(c2ccc(C(F)(F)F)nc2)C(=O)N1CC(=O)Nc1ccc(F)cn1] | S | 426 ([M + H]+) | 1H NMR (600 MHz, CHLOROFORM-d) d ppm 0.90 (d, J = 6.6 Hz, 3 H), 1.03 (d, J = 7.0 Hz, 3 H), 2.17-2.27 (m, 1 H), 3.59-3.68 (m, 1 H), 3.89-3.98 (m, 2 H), 4.03 (d, J = 16.5 Hz, 1 H), 4.22 (d, J = 16.1 Hz, 1 H), 7.37-7.49 (m, 1 H), 7.66 (d, J = 9.1 Hz, 1 H), 8.11-8.22 (m, 2 H), 8.43 (dd, J = 8.7, 2.5 Hz, 1 H), 8.63 (br. s., 1 H), 8.74 (d, J = 2.5 Hz, 1 H) |
| 65 | 3 | 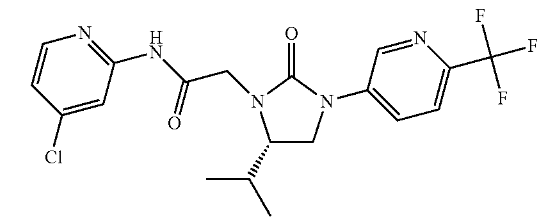 [SMILES: CC(C)[C@H]1CN(c2ccc(C(F)(F)F)nc2)C(=O)N1CC(=O)Nc1cc(Cl)ccn1] | S | 442 ([M + H]+) | 1H NMR (600 MHz, CHLOROFORM-d) d ppm 0.91 (d, J = 6.6 Hz, 3 H), 1.03 (d, J = 7.0 Hz, 3 H), 2.14-2.26 (m, 1 H), 3.61-3.69 (m, 1 H), 3.89-3.98 (m, 2 H), 4.04 (d, J = 16.5 Hz, 1 H), 4.22 (d, J = 16.5 Hz, 1 H), 7.02-7.10 (m, 1 H), 7.66 (d, J = 8.7 Hz, 1 H), 8.18 (d, J = 5.4 Hz, 1 H), 8.25 (s, 1 H), 8.40-8.45 (m, 1 H), 8.69 (br. s., 1 H), 8.74 (d, J = 2.5 Hz, 1 H) |
| 66 | 3 | 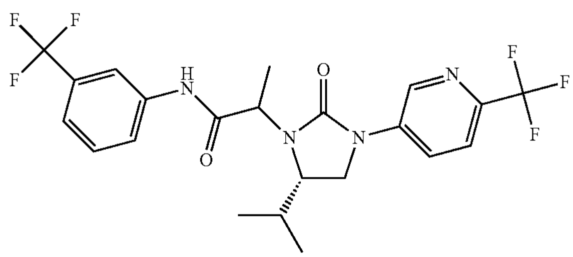 [SMILES: CC(C)[C@H]1CN(c2ccc(C(F)(F)F)nc2)C(=O)N1C(C)C(=O)Nc1cccc(C(F)(F)F)c1] | S | 489 ([M + H]+) | |
| 67 | 3 | 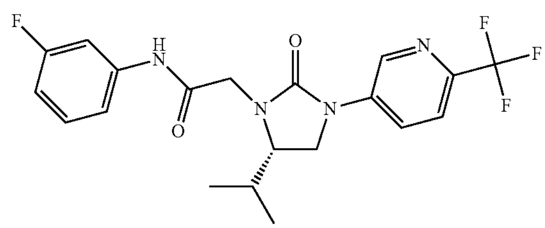 [SMILES: CC(C)[C@H]1CN(c2ccc(C(F)(F)F)nc2)C(=O)N1CC(=O)Nc1cccc(F)c1] | S | 425 ([M + H]+) | 1H NMR (600 MHz, CHLOROFORM-d) d ppm 0.88 (d, J = 7.0 Hz, 3 H), 1.03 (d, J = 7.0 Hz, 3 H), 2.21-2.32 (m, 1 H), 3.61-3.68 (m, 1 H), 3.89-3.96 (m, 2 H), 3.98-4.04 (m, 1 H), 4.07-4.14 (m, 1 H), 6.77-6.85 (m, 1 H), 7.10- 7.16 (m, 1 H), 7.21-7.30 (m, 1 H), 7.46-7.53 (m, 1 H), 7.68 (d, J = 8.7 Hz, 1 H), 8.27-8.35 (m, 1 H), 8.60 (br. s., 1 H), 8.80 (d, J = 2.5 Hz, 1 H) |
| 68 | 3 | 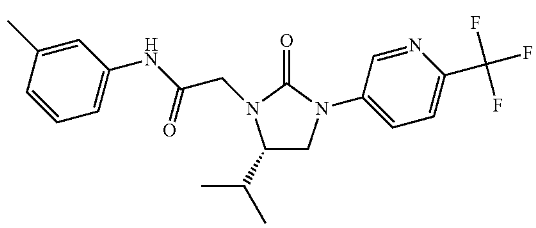 [SMILES: Cc1cccc(NC(=O)CN2C(=O)N(c3ccc(C(F)(F)F)nc3)C[C@@H]2C(C)C)c1] | S | 421 ([M + H]+) | 1H NMR (600 MHz, CHLOROFORM-d) d ppm 0.89 (d, J = 6.6 Hz, 3 H), 1.02 (d, J = 7.0 Hz, 3 H), 2.22-2.30 (m, 1 H), 2.34 (s, 3 H), 3.64 (dd, J = 7.6, 4.7 Hz, 1 H), 3.87-3.98 (m, 2 H), 4.06 (s, 2 H), 6.91-6.97 (m, 1 H), 7.20 (t, J = 7.8 Hz, 1 H), 7.27-7.32 (m, 1 H), 7.35 (s, 1 H), 7.67 (d, J = 8.7 Hz, 1 H), 8.25-8.38 (m, 2 H), 8.80 (d, J = 2.5 Hz, 1 H) |
| 69 | 3 | 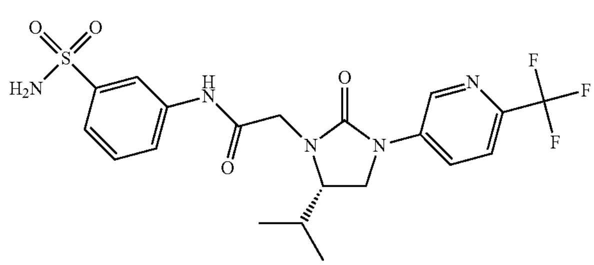 [SMILES: CC(C)[C@H]1CN(c2ccc(C(F)(F)F)nc2)C(=O)N1CC(=O)Nc1cccc(S(N)(=O)=O)c1] | S | 486 ([M + H]+) | 1H NMR (600 MHz, CHLOROFORM-d) d ppm 0.89 (d, J = 7.0 Hz, 3 H), 1.03 (d, J = 6.6 Hz, 3 H), 2.19-2.29 (m, 1 H), 3.64 (dd, J = 8.7, 5.8 Hz, 1 H), 3.94-4.08 (m, 3 H), 4.18 (d, J = 16.1 Hz, 1 H), 5.04 (s, 2 H), 7.34 (t, J = 7.8 Hz, 1 H), 7.54-7.60 (m, 1 H), 7.66 (d, J = 8.7 Hz, 2 H), 7.93 (s, 1 H), 8.15-8.21 (m, 1 H), 8.86-8.91 (m, 1 H), 8.98 (s, 1 H) |

TABLE 1-8-continued

| Compound | Example | Structure | Configuration | (ESI pos.) m/z (ESI neg.) m/z | 1H-NMR |
|---|---|---|---|---|---|
| 70 | 3 | 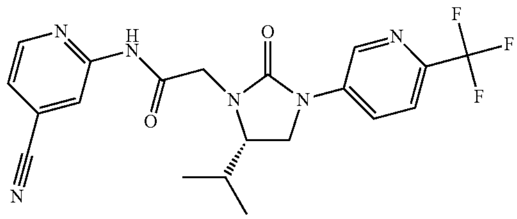 [SMILES: CC(C)[C@H]1CN(c2ccc(C(F)(F)F)nc2)C(=O)N1CC(=O)Nc1cc(C#N)ccn1] | S | 433 ([M + H]+) | 1H NMR (600 MHz, CHLOROFORM-d) d ppm 0.90 (d, J = 7.0 Hz, 3 H), 1.04 (d, J = 7.0 Hz, 3 H), 2.17-2.26 (m, 1 H), 3.61-3.70 (m, 1 H), 3.88-3.99 (m, 2 H), 4.07-4.13 (m, 1 H), 4.14-4.21 (m, 1 H), 7.26-7.28 (m, 1 H), 7.66 (d, J = 8.7 Hz, 1 H), 8.39 (dd, J = 8.9, 2.7 Hz, 1 H), 8.43-8.49 (m, 2 H), 8.76 (d, J = 2.5 Hz, 1 H), 9.00 (br. s., 1 H) |
| 71 | 3 | 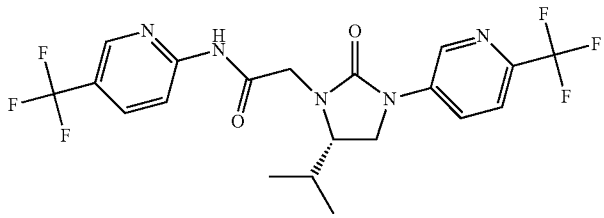 [SMILES: CC(C)[C@H]1CN(c2ccc(C(F)(F)F)nc2)C(=O)N1CC(=O)Nc1ccc(C(F)(F)F)cn1] | S | 476 ([M + H]+) | 1H NMR (600 MHz, CHLOROFORM-d) d ppm 0.90 (d, J = 7.0 Hz, 3 H), 1.03 (d, J = 7.0 Hz, 3 H), 2.15-2.26 (m, 1 H), 3.58-3.69 (m, 1 H), 3.86-3.99 (m, 2 H), 4.08 (d, J = 16.5 Hz, 1 H), 4.17-4.25 (m, 1 H), 7.66 (d, J = 9.1 Hz, 1 H), 7.92 (dd, J = 8.7, 2.1 Hz, 1 H), 8.25-8.33 (m, 1 H), 8.41 (dd, J = 8.7, 2.5 Hz, 1 H), 8.51-8.57 (m, 1 H), 8.74 (d, J = 2.5 Hz, 1 H), 8.90 (br. s., 1 H) |
| 72 | 3 | 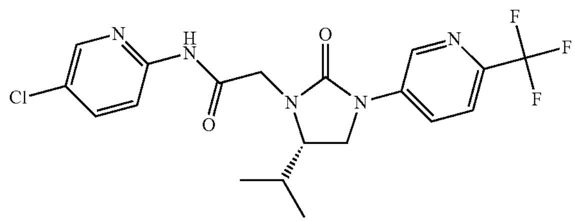 [SMILES: CC(C)[C@H]1CN(c2ccc(C(F)(F)F)nc2)C(=O)N1CC(=O)Nc1ccc(Cl)cn1] | S | 442 ([M + H]+) | 1H NMR (600 MHz, CHLOROFORM-d) d ppm 0.90 (d, J = 6.6 Hz, 3 H), 1.03 (d, J = 7.0 Hz, 3 H), 2.14-2.27 (m, 1 H), 3.58-3.68 (m, 1 H), 3.88-3.99 (m, 2 H), 4.04 (d, J = 16.1 Hz, 1 H), 4.21 (d, J = 16.5 Hz, 1 H), 7.64-7.71 (m, 2 H), 8.10-8.19 (m, 1 H), 8.24 (d, J = 2.5 Hz, 1 H), 8.43 (dd, J = 8.7, 2.5 Hz, 1 H), 8.64 (br. s., 1 H), 8.74 (d, J = 2.9 Hz, 1 H) |

TABLE 1-9

| Compound | Example | Structure | Configuration | (ESI pos.) m/z | RT (min) condition |
|---|---|---|---|---|---|
| 73 | 3 | 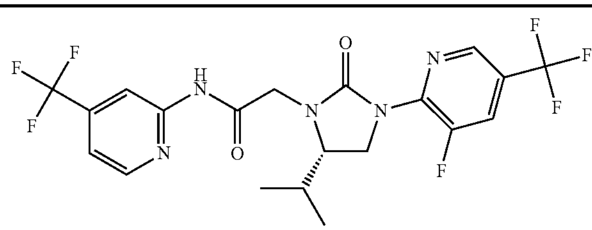 | S | 494 ([M + H]+) | 1.164 condition A |
| 74 | 3 | 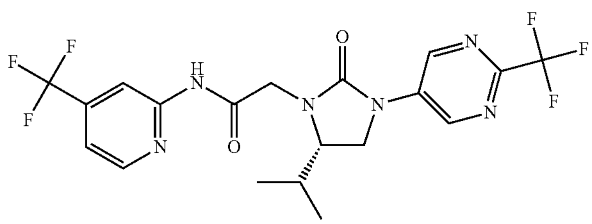 [SMILES: CC(C)[C@H]1CN(c2cnc(C(F)(F)F)nc2)C(=O)N1CC(=O)Nc1cc(C(F)(F)F)ccn1] | S | 477 ([M + H]+) | 1.079 condition A |
| 75 | 2 | 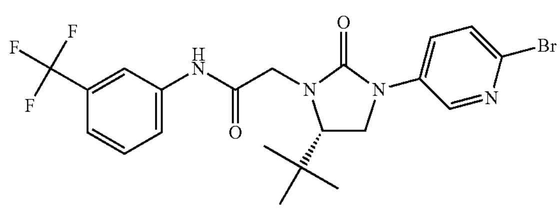 [SMILES: CC(C)(C)[C@H]1CN(c2ccc(Br)nc2)C(=O)N1CC(=O)Nc1cccc(C(F)(F)F)c1] | S | 499 ([M + H]+) | 1.155 condition A |

TABLE 1-9-continued

| Compound | Example | Structure | Configuration | (ESI pos.) m/z | RT (min) condition |
|---|---|---|---|---|---|
| 76 | 2 | 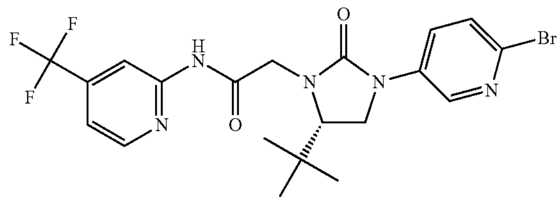 [SMILES: CC(C)(C)[C@H]1CN(c2ccc(Br)nc2)C(=O)N1CC(=O)Nc1cc(C(F)(F)F)ccn1] | S | 500 ([M + H]+) | 1.126 condition A |
| 77 | 3 | 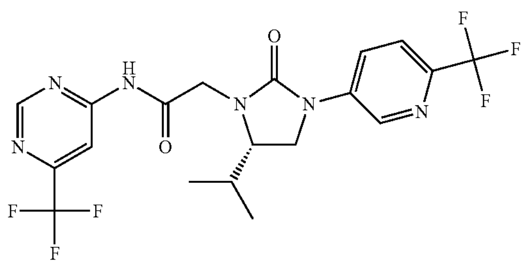 [SMILES: CC(C)[C@H]1CN(c2ccc(C(F)(F)F)nc2)C(=O)N1CC(=O)Nc1cc(C(F)(F)F)ncn1] | S | 477 ([M + H]+) | 1.066 condition A |
| 78 | 2 | 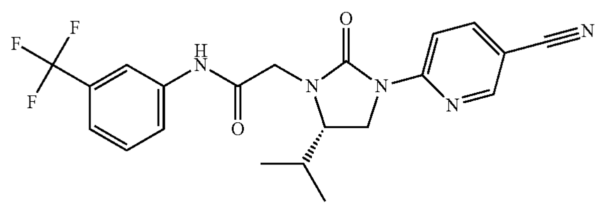 [SMILES: CC(C)[C@H]1CN(c2ccc(C#N)cn2)C(=O)N1CC(=O)Nc1cccc(C(F)(F)F)c1] | S | 432 ([M + H]+) | 2.63 condition C |
| 79 | 2 | 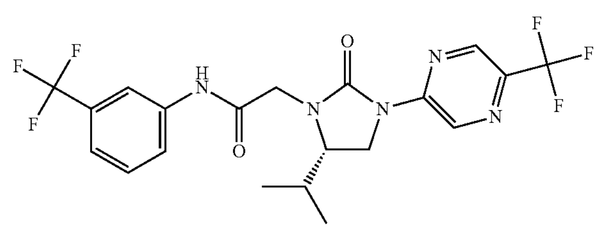 [SMILES: CC(C)[C@H]1CN(c2cnc(C(F)(F)F)cn2)C(=O)N1CC(=O)Nc1cccc(C(F)(F)F)c1] | S | 476 ([M + H]+) | 2.80 condition C |
| 80 | 4 | 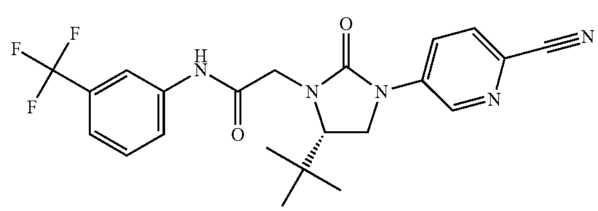 [SMILES: CC(C)(C)[C@H]1CN(c2ccc(C#N)nc2)C(=O)N1CC(=O)Nc1cccc(C(F)(F)F)c1] | S | 446 ([M + H]+) | 1.081 condition A |
| 81 | 7 | 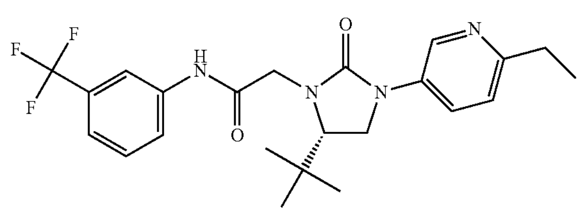 [SMILES: CCc1ccc(N2C[C@H](C(C)(C)C)N(CC(=O)Nc3cccc(C(F)(F)F)c3)C2=O)cn1] | S | 449 ([M + H]+) | 0.750 condition A |
| 82 | 3 | 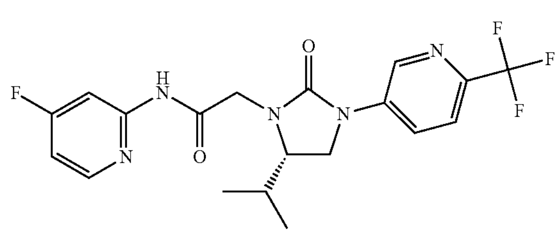 [SMILES: CC(C)[C@H]1CN(c2ccc(C(F)(F)F)nc2)C(=O)N1CC(=O)Nc1cc(F)ccn1] | S | 426 ([M + H]+) | 1.001 condition A |

TABLE 1-10

| Compound | Example | Structure | Configuration | (ESI pos.) m/z | RT (min) condition |
|---|---|---|---|---|---|
| 83 | 3 | 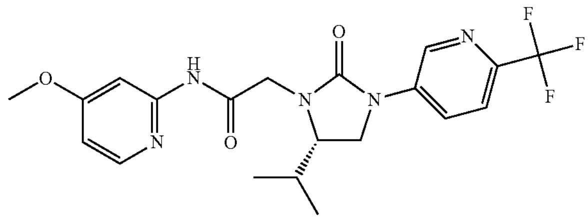 [SMILES: COc1ccnc(NC(=O)CN2C(=O)N(c3ccc(C(F)(F)F)nc3)C[C@@H]2C(C)C)c1] | S | 438 ([M + H]+) | 0.740 condition A |
| 84 | 2 | 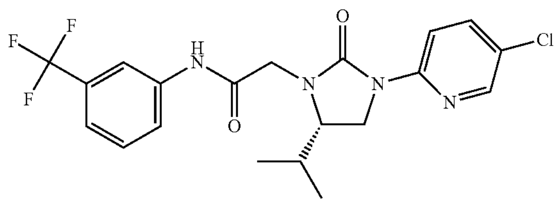 [SMILES: CC(C)[C@H]1CN(c2ccc(Cl)cn2)C(=O)N1CC(=O)Nc1cccc(C(F)(F)F)c1] | S | 441 ([M + H]+) | 1.121 condition A |
| 85 | 2 | 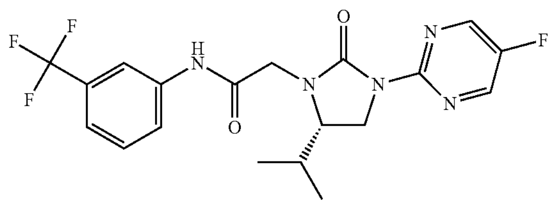 [SMILES: CC(C)[C@H]1CN(c2ncc(F)cn2)C(=O)N1CC(=O)Nc1cccc(C(F)(F)F)c1] | S | 426 ([M + H]+) | 0.985 condition A |
| 86 | 3 | 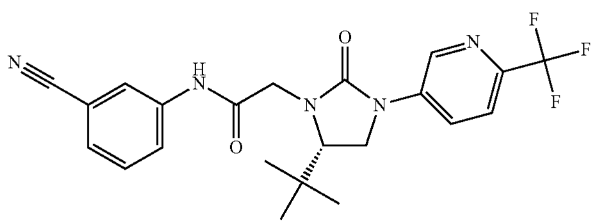 [SMILES: CC(C)(C)[C@H]1CN(c2ccc(C(F)(F)F)nc2)C(=O)N1CC(=O)Nc1cccc(C#N)c1] | S | 446 ([M + H]+) | 1.052 condition A |
| 87 | 3 | 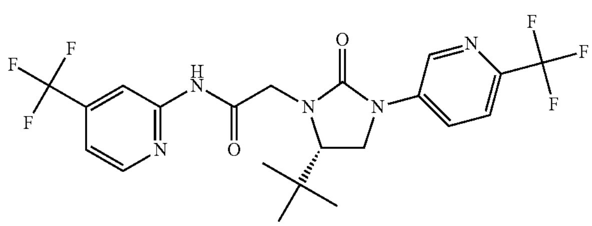 [SMILES: CC(C)(C)[C@H]1CN(c2ccc(C(F)(F)F)nc2)C(=O)N1CC(=O)Nc1cc(C(F)(F)F)ccn1] | S | 490 ([M + H]+) | 1.146 condition A |
| 88 | 3 | 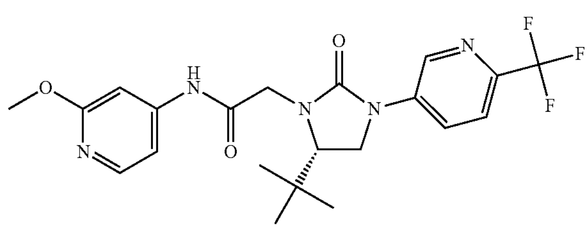 [SMILES: COc1cc(NC(=O)CN2C(=O)N(c3ccc(C(F)(F)F)nc3)C[C@@H]2C(C)(C)C)ccn1] | S | 452 ([M + H]+) | 0.933 condition A |
| 89 | 3 | 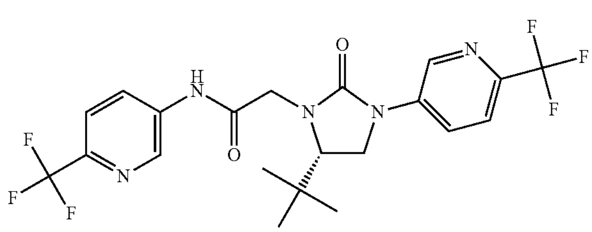 [SMILES: CC(C)(C)[C@H]1CN(c2ccc(C(F)(F)F)nc2)C(=O)N1CC(=O)Nc1ccc(C(F)(F)F)nc1] | S | 490 ([M + H]+) | 1.096 condition A |

TABLE 1-10-continued

| Compound | Example | Structure | Configuration | (ESI pos.) m/z | RT (min) condition |
|---|---|---|---|---|---|
| 90 | 4 | 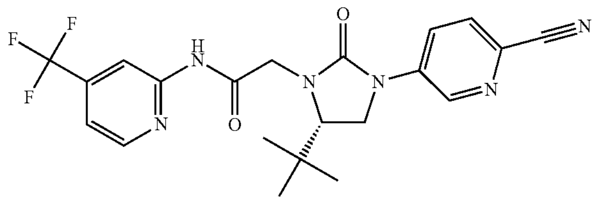 [SMILES: CC(C)(C)[C@H]1CN(c2ccc(C#N)nc2)C(=O)N1CC(=O)Nc1cc(C(F)(F)F)ccn1] | S | 447 ([M + H]+) | 1.044 condition A |
| 91 | 3 | 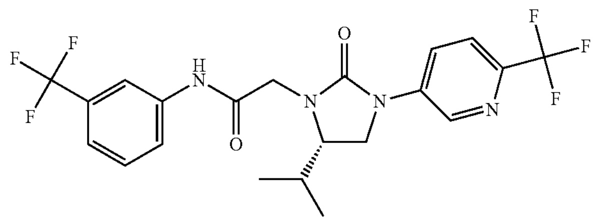 [SMILES: CC(C)[C@H]1CN(c2ccc(C(F)(F)F)nc2)C(=O)N1CC(=O)Nc1cccc(C(F)(F)F)c1] | S | 476 ([M + H]+) | 1.037 condition A |
| 92 | 3 | 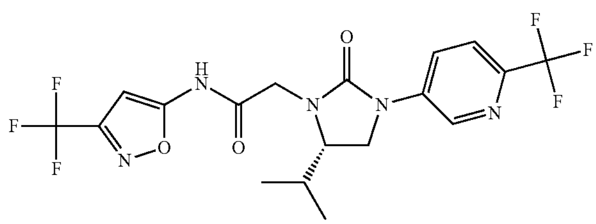 [SMILES: CC(C)[C@H]1CN(c2ccc(C(F)(F)F)nc2)C(=O)N1CC(=O)Nc1cc(C(F)(F)F)no1] | S | 466 ([M + H]+) | 1.098 condition A |

TABLE 1-11

| Compound | Example | Structure | Configuration | (ESI pos.) m/z | RT (min) condition |
|---|---|---|---|---|---|
| 93 | 1 | 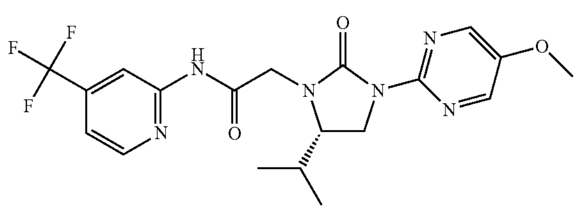 | S | 439 ([M + H]+) | 0.922 condition A |
| 94 | 1 | 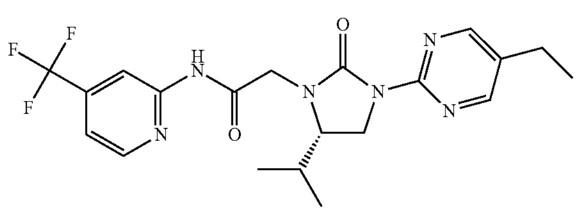 | S | 437 ([M + H]+) | 0.977 condition A |
| 95 | 7 | 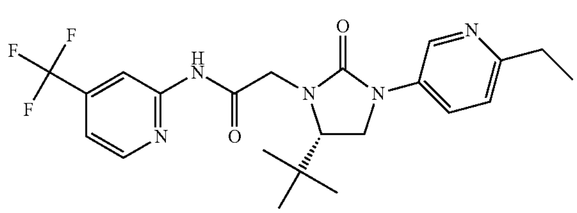 [SMILES: CCc1ccc(N2C[C@H](C(C)(C)C)N(CC(=O)Nc3cc(C(F)(F)F)ccn3)C2=O)cn1] | S | 450 ([M + H]+) | 0.702 condition A |

TABLE 1-11-continued

| Compound | Example | Structure | Configuration | (ESI pos.) m/z | RT (min) condition |
|---|---|---|---|---|---|
| 96 | 3 | 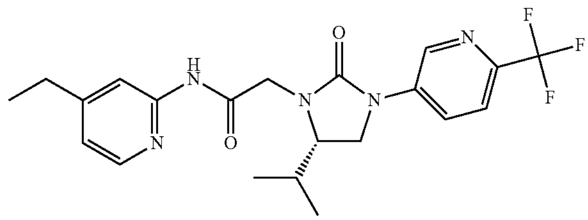 | S | 436 ([M + H]+) | 0.994 condition A |
| 97 | 3 | 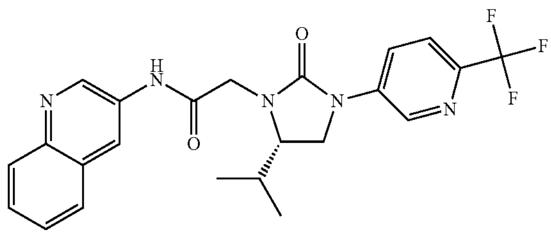 [SMILES: CC(C)[C@H]1CN(c2ccc(C(F)(F)F)nc2)C(=O)N1CC(=O)Nc1cnc2ccccc2c1] | S | 458 ([M + H]+) | 0.947 condition A |
| 98 | 3 | 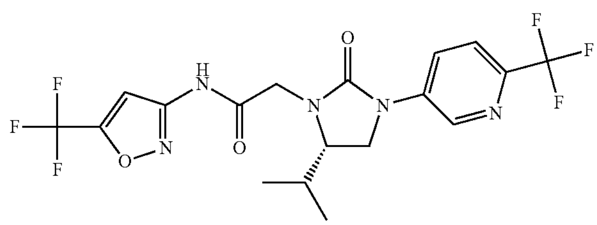 | S | 454 ([M + H]+) | 1.109 condition A |
| 99 | 3 | 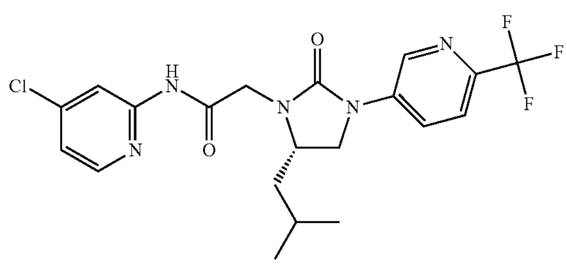 [SMILES: CC(C)C[C@H]1CN(c2ccc(C(F)(F)F)nc2)C(=O)N1CC(=O)Nc1cc(Cl)ccn1] | S | 456 ([M + H]+) | 1.135 condition A |
| 100 | 3 | 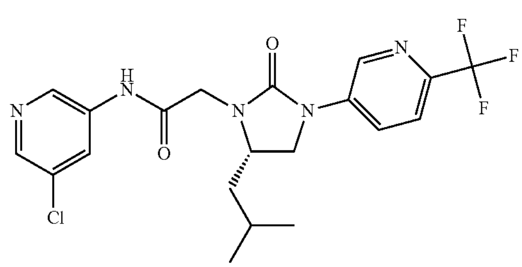 [SMILES: CC(C)C[C@H]1CN(c2ccc(C(F)(F)F)nc2)C(=O)N1CC(=O)Nc1cncc(Cl)c1] | S | 456 ([M + H]+) | 1.061 condition A |
| 101 | 3 | 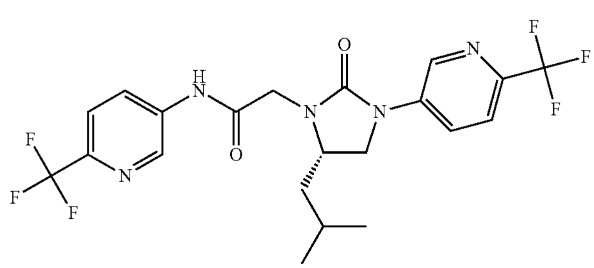 [SMILES: CC(C)C[C@H]1CN(c2ccc(C(F)(F)F)nc2)C(=O)N1CC(=O)Nc1ccc(C(F)(F)F)nc1] | S | 490 ([M + H]+) | 1.061 condition A |

TABLE 1-11-continued

| Compound | Example | Structure | Configuration | (ESI pos.) m/z | RT (min) condition |
|---|---|---|---|---|---|
| 102 | 1 | 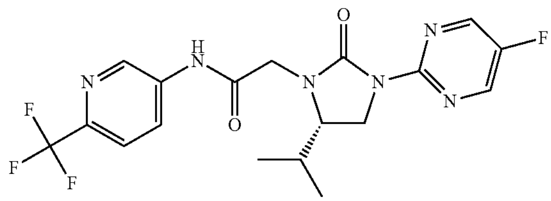 [SMILES: CC(C)[C@H]1CN(c2ncc(F)cn2)C(=O)N1CC(=O)Nc1ccc(C(F)(F)F)nc1] | S | 426 ([M + H]+) | 1.87 condition C |

TABLE 1-12

| Compound | Example | Structure | Configuration | (ESI pos.) m/z | RT (min) condition |
|---|---|---|---|---|---|
| 103 | 3 | 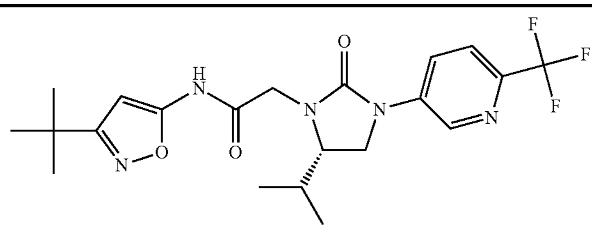 | S | 454 ([M + H]+) | 1.098 condition A |
| 104 | 1 | 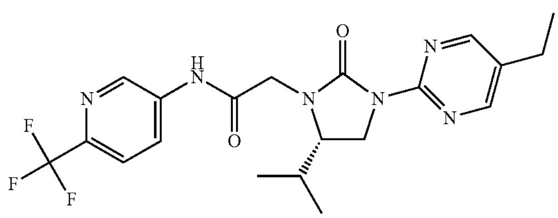 [SMILES: CCc1cnc(N2C[C@H](C(C)C)N(CC(=O)Nc3ccc(C(F)(F)F)nc3)C2=O)nc1] | S | 437 ([M + H]+) | 0.918 condition A |
| 105 | 3 | 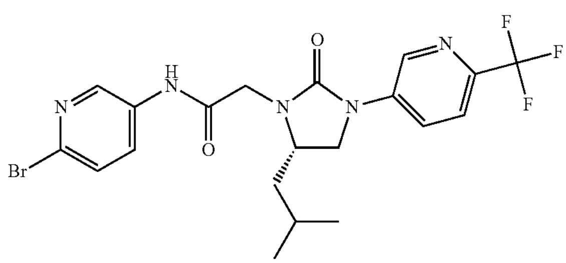 [SMILES: CC(C)C[C@H]1CN(c2ccc(C(F)(F)F)nc2)C(=O)N1CC(=O)Nc1ccc(Br)nc1] | S | 500 ([M + H]+) | 1.076 condition A |
| 106 | 3 | 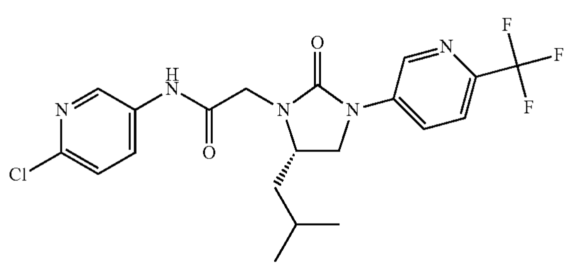 [SMILES: CC(C)C[C@H]1CN(c2ccc(C(F)(F)F)nc2)C(=O)N1CC(=O)Nc1ccc(Cl)nc1] | S | 456 ([M + H]+) | 1.90 condition B |
| 107 | 7 | 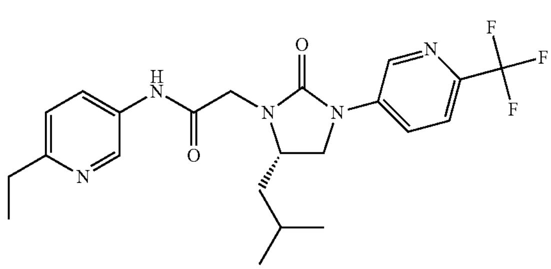 [SMILES: CCc1ccc(NC(=O)CN2C(=O)N(c3ccc(C(F)(F)F)nc3)C[C@@H]2CC(C)C)cn1] | S | 450 ([M + H]+) | 1.48 condition B |

TABLE 1-12-continued

| Compound | Example | Structure | Configuration | (ESI pos.) m/z | RT (min) condition |
|---|---|---|---|---|---|
| 108 | 11 | 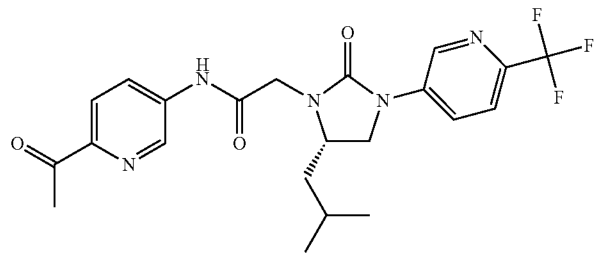 [SMILES: CC(=O)c1ccc(NC(=O)CN2C(=O)N(c3ccc(C(F)(F)F)nc3)C[C@@H]2CC(C)C)cn1] | S | 464 ([M + H]+) | 1.84 condition B |
| 109 | 3 | 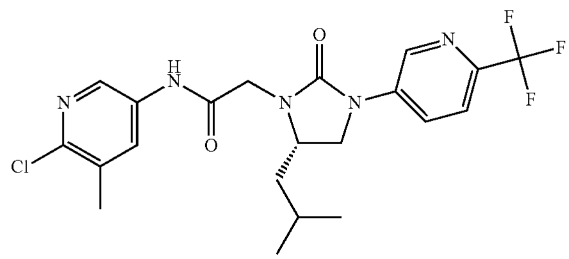 [SMILES: Cc1cc(NC(=O)CN2C(=O)N(c3ccc(C(F)(F)F)nc3)C[C@@H]2CC(C)C)cnc1Cl] | S | 470 ([M + H]+) | 1.96 condition B |
| 110 | 3 | 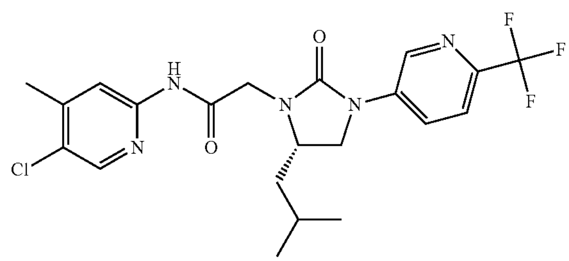 [SMILES: Cc1cc(NC(=O)CN2C(=O)N(c3ccc(C(F)(F)F)nc3)C[C@@H]2CC(C)C)ncc1Cl] | S | 470 ([M + H]+) | 2.06 condition B |
| 111 | 10 | 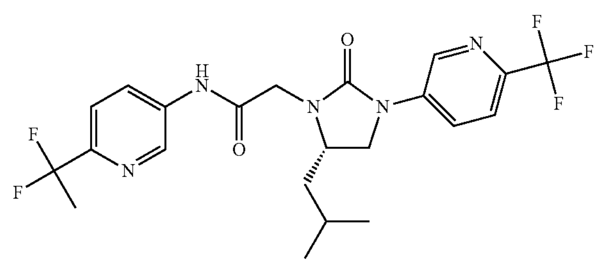 [SMILES: CC(C)C[C@H]1CN(c2ccc(C(F)(F)F)nc2)C(=O)N1CC(=O)Nc1ccc(C(C)(F)F)nc1] | S | 486 ([M + H]+) | 1.95 condition B |
| 112 | 10 | 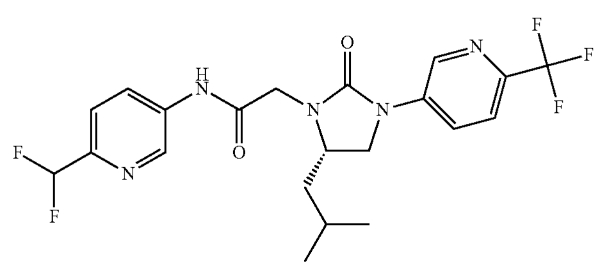 [SMILES: CC(C)C[C@H]1CN(c2ccc(C(F)(F)F)nc2)C(=O)N1CC(=O)Nc1ccc(C(F)F)nc1] | S | 472 ([M + H]+) | 1.88 condition B |

TABLE 1-13

| Compound | Example | Structure | Configuration | (ESI pos.) m/z | RT (min) condition |
|---|---|---|---|---|---|
| 113 | 2 | 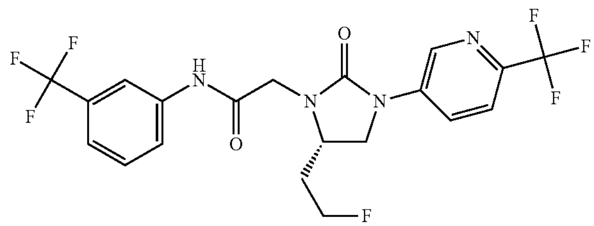 [SMILES: O=C(CN1C(=O)N(c2ccc(C(F)(F)F)nc2)C[C@@H]1CCF)Nc1cccc(C(F)(F)F)c1] | S | 479 ([M + H]+) | 1.92 condition B |
| 114 | 12 | 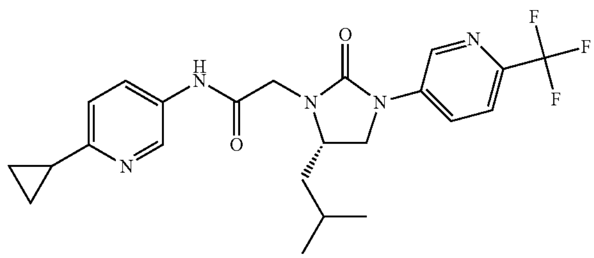 | S | 462 ([M + H]+) | 0.813 condition A |
| 115 | 3 | 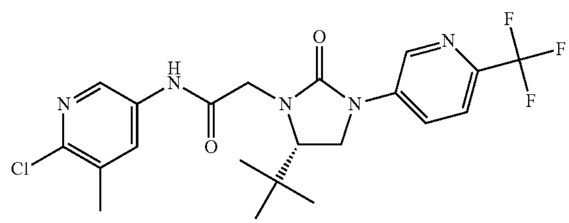 [SMILES: Cc1cc(NC(=O)CN2C(=O)N(c3ccc(C(F)(F)F)nc3)C[C@@H]2C(C)(C)C)cnc1Cl] | S | 470 ([M + H]+) | 1.081 condition A |
| 116 | 3 | 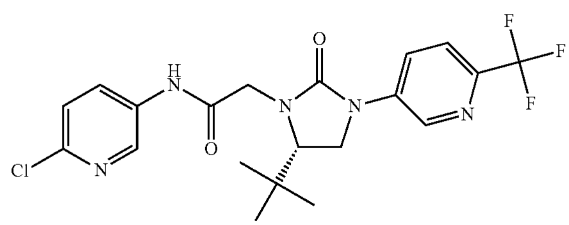 [SMILES: CC(C)(C)[C@H]1CN(c2ccc(C(F)(F)F)nc2)C(=O)N1CC(=O)Nc1ccc(Cl)nc1] | S | 456 ([M + H]+) | 1.037 condition A |
| 117 | 3 | 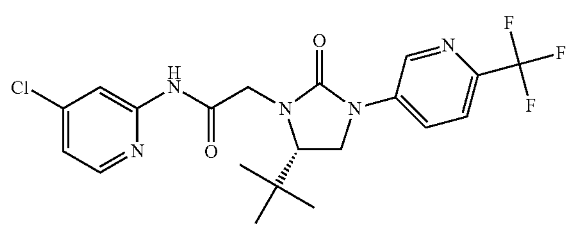 [SMILES: CC(C)(C)[C@H]1CN(c2ccc(C(F)(F)F)nc2)C(=O)N1CC(=O)Nc1cc(Cl)ccn1] | S | 456 ([M + H]+) | 1.121 condition A |
| 118 | 3 | 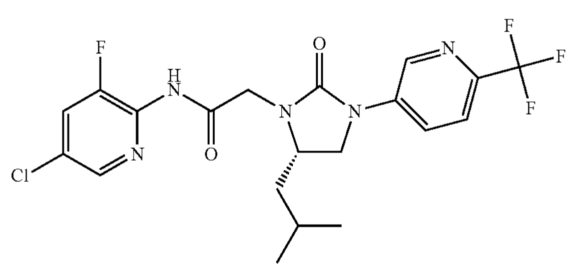 [SMILES: CC(C)C[C@H]1CN(c2ccc(C(F)(F)F)nc2)C(=O)N1CC(=O)Nc1ncc(Cl)cc1F] | S | 474 ([M + H]+) | 1.063 condition A |

TABLE 1-13-continued

| Compound | Example | Structure | Configuration | (ESI pos.) m/z | RT (min) condition |
|---|---|---|---|---|---|
| 119 | 3 | 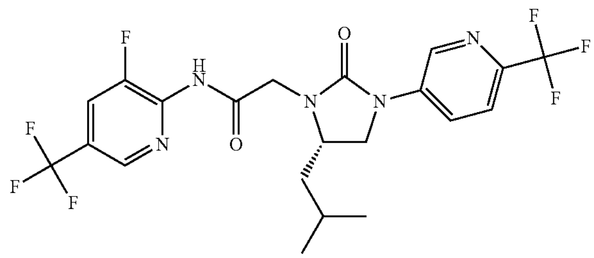 [SMILES: CC(C)C[C@H]1CN(c2ccc(C(F)(F)F)nc2)C(=O)N1CC(=O)Nc1ncc(C(F)(F)F)cc1F] | S | 508 ([M + H]+) | 1.113 condition A |
| 120 | 3 | 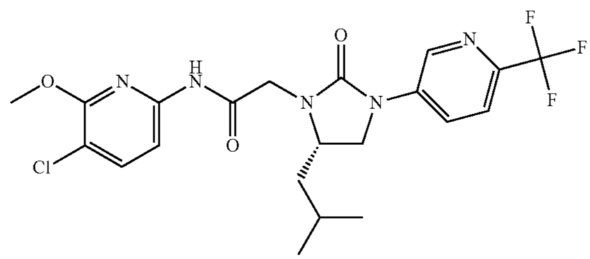 [SMILES: COc1nc(NC(=O)CN2C(=O)N(c3ccc(C(F)(F)F)nc3)C[C@@H]2CC(C)C)ccc1Cl] | S | 486 ([M + H]+) | 1.195 condition A |
| 121 | 3 | 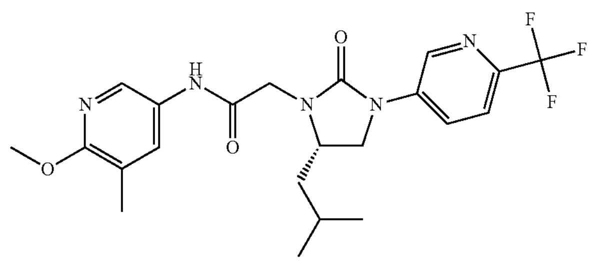 [SMILES: COc1ncc(NC(=O)CN2C(=O)N(c3ccc(C(F)(F)F)nc3)C[C@@H]2CC(C)C)cc1C] | S | 466 ([M + H]+) | 1.078 condition A |
| 122 | 1 | 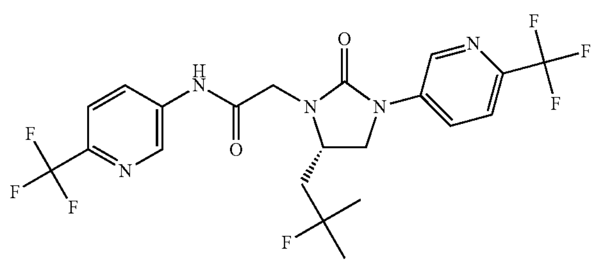 [SMILES: CC(C)(F)C[C@H]1CN(c2ccc(C(F)(F)F)nc2)C(=O)N1CC(=O)Nc1ccc(C(F)(F)F)nc1] | S | 508 ([M + H]+) | 1.92 condition B |

TABLE 1-14

| Compound | Example | Structure | Configuration | (ESI pos.) m/z | RT (min) condition |
|---|---|---|---|---|---|
| 123 | 9 | 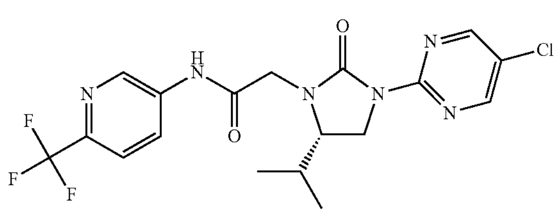 [SMILES: CC(C)[C@H]1CN(c2ncc(Cl)cn2)C(=O)N1CC(=O)Nc1ccc(C(F)(F)F)nc1] | S | 443 ([M + H]+) | 1.74 condition B |

TABLE 1-14-continued

| Compound | Example | Structure | Configuration | (ESI pos.) m/z | RT (min) condition |
|---|---|---|---|---|---|
| 124 | 1 | 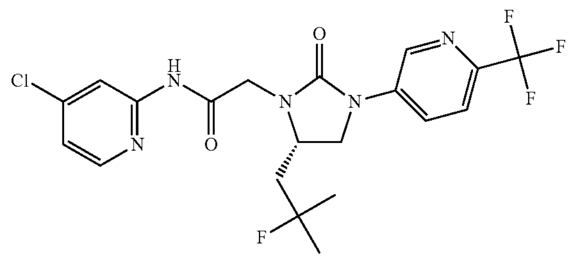 [SMILES: CC(C)(F)C[C@H]1CN(c2ccc(C(F)(F)F)nc2)C(=O)N1CC(=O)Nc1cc(Cl)ccn1] | S | 474 ([M + H]+) | 1.92 condition B |
| 125 | 3 | 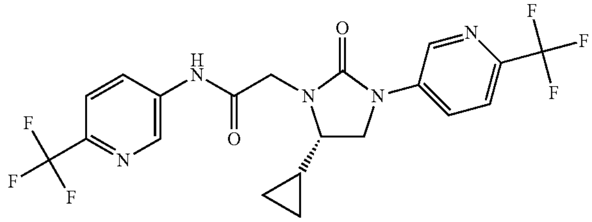 [SMILES: O=C(CN1C(=O)N(c2ccc(C(F)(F)F)nc2)C[C@@H]1C1CC1)Nc1ccc(C(F)(F)F)nc1] | S | 474 ([M + H]+) | 1.024 condition A |
| 126 | 3 | 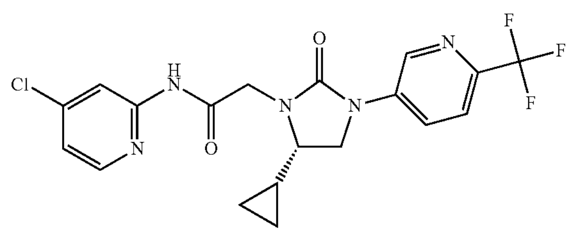 [SMILES: O=C(CN1C(=O)N(c2ccc(C(F)(F)F)nc2)C[C@@H]1C1CC1)Nc1cc(Cl)ccn1] | S | 440 ([M + H]+) | 1.034 condition A |
| 127 | 9 | 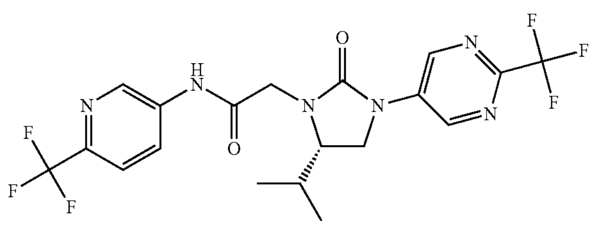 [SMILES: CC(C)[C@H]1CN(c2cnc(C(F)(F)F)nc2)C(=O)N1CC(=O)Nc1ccc(C(F)(F)F)nc1] | S | 477 ([M + H]+) | 1.87 condition B |
| 128 | 9 | 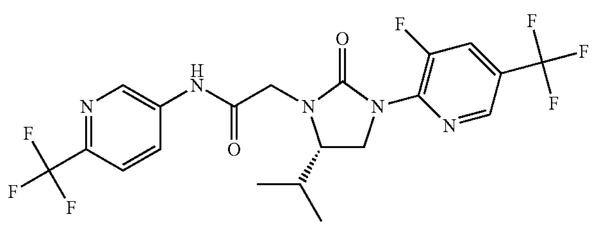 [SMILES: CC(C)[C@H]1CN(c2ncc(C(F)(F)F)cc2F)C(=O)N1CC(=O)Nc1ccc(C(F)(F)F)nc1] | S | 494 ([M + H]+) | 1.97 condition B |
| 129 | 9 | 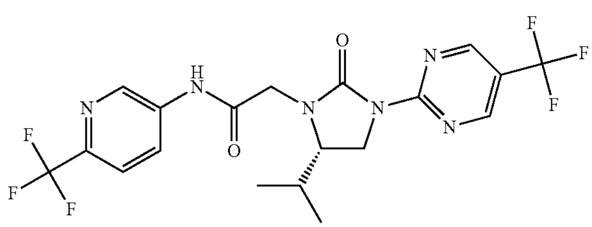 [SMILES: CC(C)[C@H]1CN(c2ncc(C(F)(F)F)cn2)C(=O)N1CC(=O)Nc1ccc(C(F)(F)F)nc1] | S | 477 ([M + H]+) | 1.82 condition B |

TABLE 1-14-continued

| Compound | Example | Structure | Configuration | (ESI pos.) m/z | RT (min) condition |
|---|---|---|---|---|---|
| 130 | 3 | 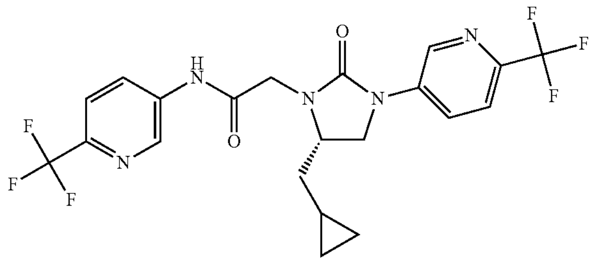 [SMILES: O=C(CN1C(=O)N(c2ccc(C(F)(F)F)nc2)C[C@@H]1CC1CC1)Nc1ccc(C(F)(F)F)nc1] | S | 488 ([M + H]+) | 1.073 condition A |
| 131 | 3 | 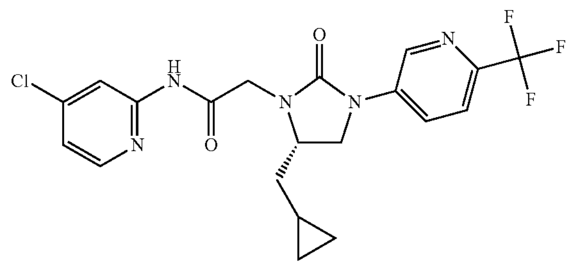 [SMILES: O=C(CN1C(=O)N(c2ccc(C(F)(F)F)nc2)C[C@@H]1CC1CC1)Nc1cc(Cl)ccn1] | S | 454 ([M + H]+) | 1.088 condition A |
| 132 | 3 | 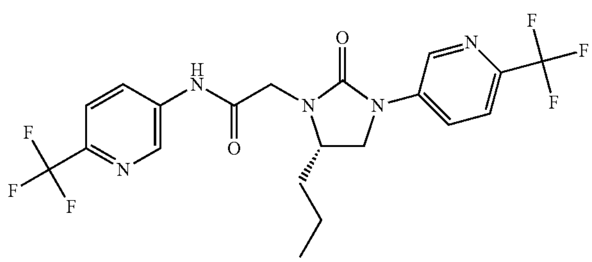 [SMILES: CCC[C@H]1CN(c2ccc(C(F)(F)F)nc2)C(=O)N1CC(=O)Nc1ccc(C(F)(F)F)nc1] | S | 476 ([M + H]+) | 1.068 condition A |

TABLE 1-15

| Compound | Example | Structure | Configuration | (ESI pos.) m/z | RT (min) condition |
|---|---|---|---|---|---|
| 133 | 3 | 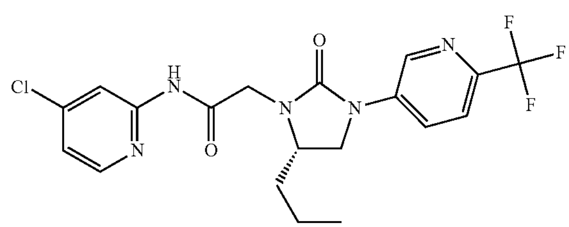 [SMILES: CCC[C@H]1CN(c2ccc(C(F)(F)F)nc2)C(=O)N1CC(=O)Nc1cc(Cl)ccn1] | S | 442 ([M + H]+) | 1.084 condition A |
| 134 | 3 | 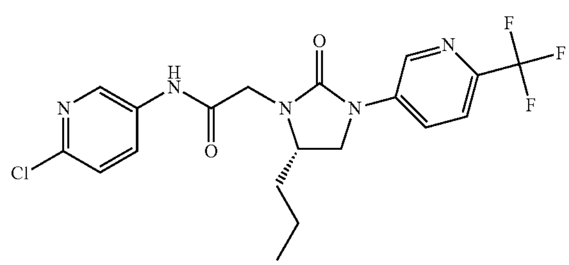 [SMILES: CCC[C@H]1CN(c2ccc(C(F)(F)F)nc2)C(=O)N1CC(=O)Nc1ccc(Cl)nc1] | S | 442 ([M + H]+) | 1.003 condition A |

TABLE 1-15-continued

| Compound | Example | Structure | Configuration | (ESI pos.) m/z | RT (min) condition |
|---|---|---|---|---|---|
| 135 | 3 | 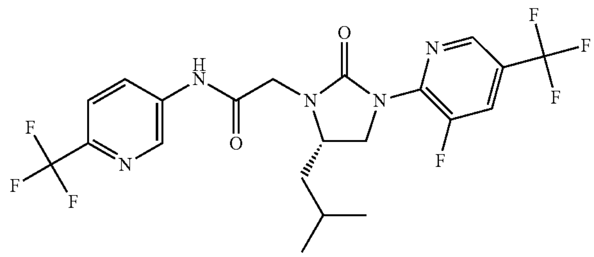 [SMILES: CC(C)C[C@H]1CN(c2ncc(C(F)(F)F)cc2F)C(=O)N1CC(=O)Nc1ccc(C(F)(F)F)nc1] | S | 508 ([M + H]+) | 1.162 condition A |
| 136 | 3 | 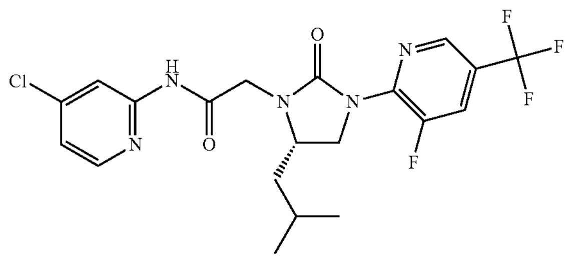 [SMILES: CC(C)C[C@H]1CN(c2ncc(C(F)(F)F)cc2F)C(=O)N1CC(=O)Nc1cc(Cl)ccn1] | S | 474 ([M + H]+) | 1.188 condition A |
| 137 | 2 | 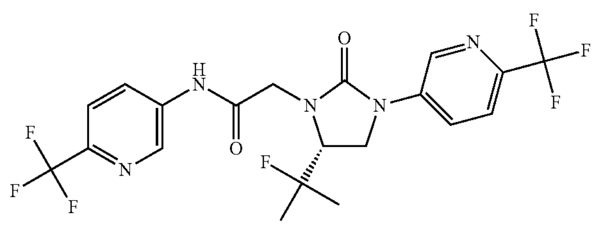 [SMILES: CC(C)(F)[C@H]1CN(c2ccc(C(F)(F)F)nc2)C(=O)N1CC(=O)Nc1ccc(C(F)(F)F)nc1] | R | 494 ([M + H]+) | 1.016 condition A |
| 138 | 3 | 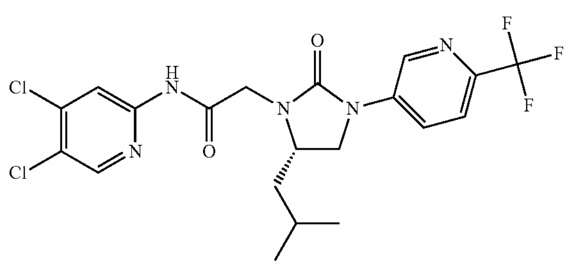 | S | 490 ([M + H]+) | 1.230 condition A |
| 139 | 2 | 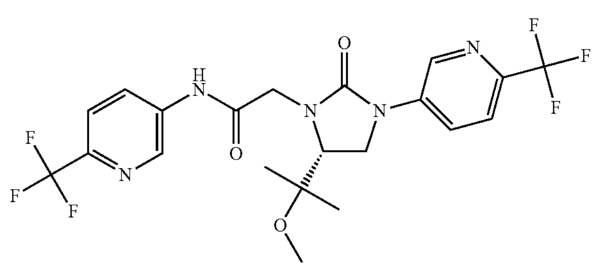 [SMILES: COC(C)(C)[C@H]1CN(c2ccc(C(F)(F)F)nc2)C(=O)N1CC(=O)Nc1ccc(C(F)(F)F)nc1] | R | 506 ([M + H]+) | 1.021 condition A |
| 140 | 3 | 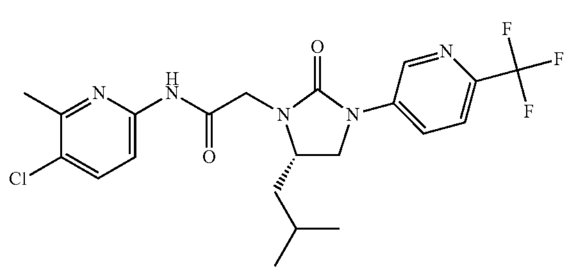 [SMILES: Cc1nc(NC(=O)CN2C(=O)N(c3ccc(C(F)(F)F)nc3)C[C@@H]2CC(C)C)ccc1Cl] | S | 470 ([M + H]+) | 1.193 condition A |

TABLE 1-15-continued

| Compound | Example | Structure | Configuration | (ESI pos.) m/z | RT (min) condition |
|---|---|---|---|---|---|
| 141 | 2 | 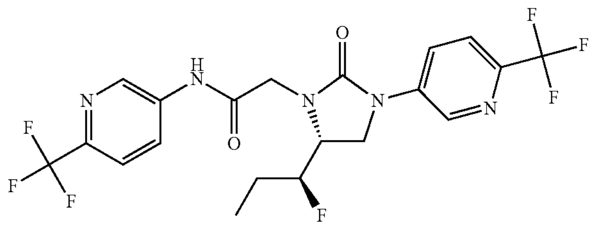 [SMILES: CC[C@H](F)[C@H]1CN(c2ccc(C(F)(F)F)nc2)C(=O)N1CC(=O)Nc1ccc(C(F)(F)F)nc1] | R | 494 ([M + H]+) | 1.026 condition A |
| 142 | 3 | 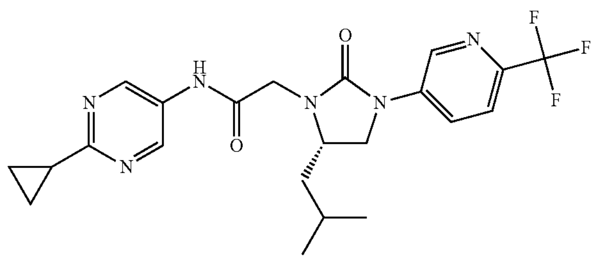 [SMILES: CC(C)C[C@H]1CN(c2ccc(C(F)(F)F)nc2)C(=O)N1CC(=O)Nc1cnc(C2CC2)nc1] | S | 463 ([M + H]+) | 1.010 condition A |

TABLE 1-16

| Compound | Example | Structure | Configuration | (ESI pos.) m/z | RT (min) condition |
|---|---|---|---|---|---|
| 143 | 3 | 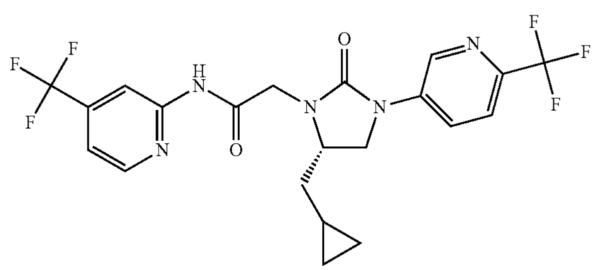 [SMILES: O=C(CN1C(=O)N(c2ccc(C(F)(F)F)nc2)C[C@@H]1CC1CC1)Nc1cc(C(F)(F)F)ccn1] | S | 488 ([M + H]+) | 1.114 condition A |
| 144 | 2 | 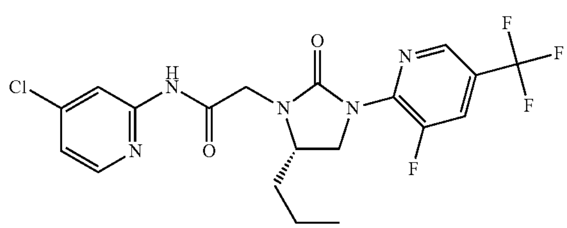 [SMILES: CCC[C@H]1CN(c2ncc(C(F)(F)F)cc2F)C(=O)N1CC(=O)Nc1cc(Cl)ccn1] | S | 460 ([M + H]+) | 1.131 condition A |
| 145 | 2 | 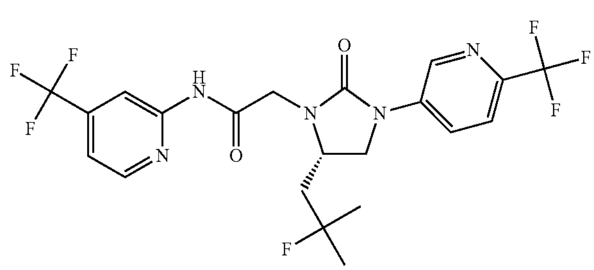 [SMILES: CC(C)(F)C[C@H]1CN(c2ccc(C(F)(F)F)nc2)C(=O)N1CC(=O)Nc1cc(C(F)(F)F)ccn1] | S | 508 ([M + H]+) | 1.100 condition A |

TABLE 1-16-continued

| Compound | Example | Structure | Configuration | (ESI pos.) m/z | RT (min) condition |
|---|---|---|---|---|---|
| 146 | 1 | 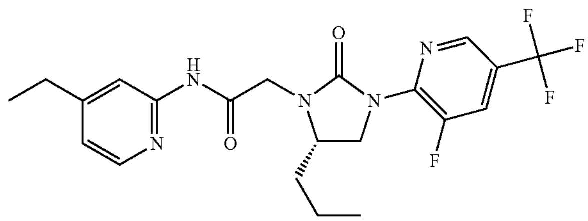 [SMILES: CCC[C@H]1CN(c2ncc(C(F)(F)F)cc2F)C(=O)N1CC(=O)Nc1cc(CC)ccn1] | S | 454 ([M + H]+) | 1.009 condition A |
| 147 | 1 | 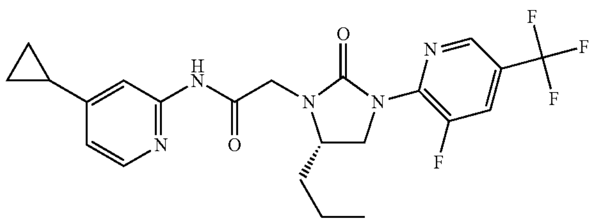 [SMILES: CCC[C@H]1CN(c2ncc(C(F)(F)F)cc2F)C(=O)N1CC(=O)Nc1cc(C2CC2)ccn1] | S | 466 ([M + H]+) | 0.965 condition A |
| 148 | 2 | 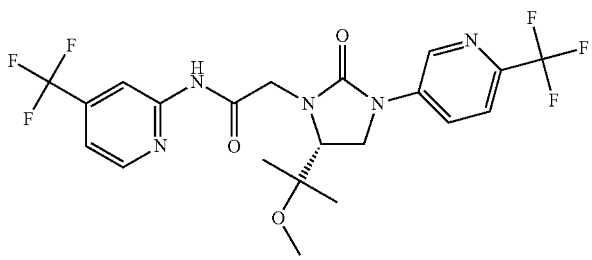 [SMILES: COC(C)(C)[C@H]1CN(c2ccc(C(F)(F)F)nc2)C(=O)N1CC(=O)Nc1cc(C(F)(F)F)ccn1] | R | 506 ([M + H]+) | 1.076 condition A |
| 149 | 2 | 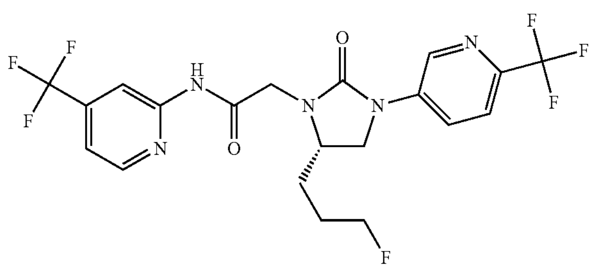 [SMILES: O=C(CN1C(=O)N(c2ccc(C(F)(F)F)nc2)C[C@@H]1CCCF)Nc1cc(C(F)(F)F)ccn1] | S | 494 ([M + H]+) | 12.16 condition A |
| 150 | 2 | 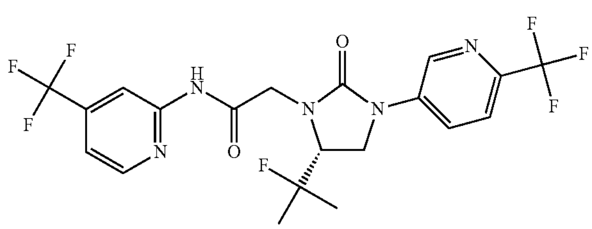 [SMILES: CC(C)(F)[C@H]1CN(c2ccc(C(F)(F)F)nc2)C(=O)N1CC(=O)Nc1cc(C(F)(F)F)ccn1] | R | 494 ([M + H]+) | 1.068 condition A |
| 151 | 2 | 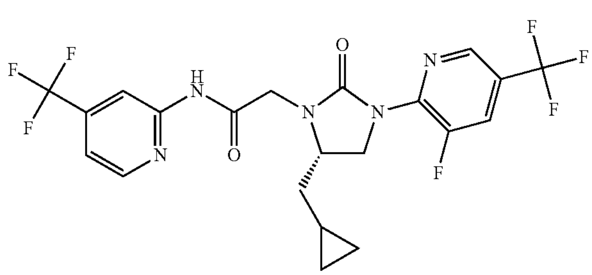 [SMILES: O=C(CN1C(=O)N(c2ncc(C(F)(F)F)cc2F)C[C@@H]1CC1CC1)Nc1cc(C(F)(F)F)ccn1] | S | 506 ([M + H]+) | 1.168 condition A |

TABLE 1-16-continued

| Compound | Example | Structure | Configuration | (ESI pos.) m/z | RT (min) condition |
|---|---|---|---|---|---|
| 152 | 2 | 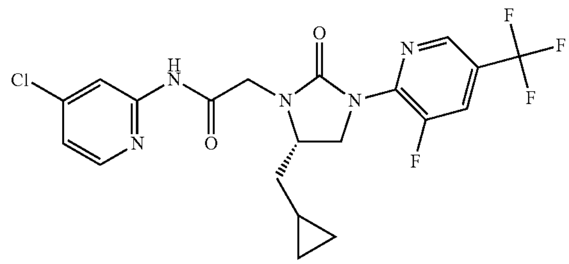 [SMILES: O=C(CN1C(=O)N(c2ncc(C(F)(F)F)cc2F)C[C@@H]1CC1CC1)Nc1cc(Cl)ccn1] | S | 472 ([M + H]+) | 1.133 condition A |

TABLE 1-17

| Compound | Example | Structure | Configuration | (ESI pos.) m/z | RT (min) condition |
|---|---|---|---|---|---|
| 153 | 2 | 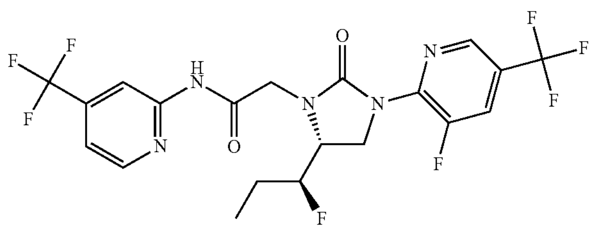 [SMILES: CC[C@H](F)[C@H]1CN(c2ncc(C(F)(F)F)cc2F)C(=O)N1CC(=O)Nc1cc(C(F)(F)F)ccn1] | R | 512 ([M + H]+) | 1.123 condition A |
| 154 | 2 | 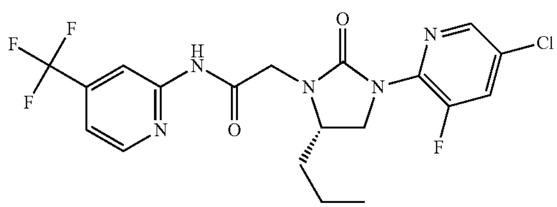 [SMILES: CCC[C@H]1CN(c2ncc(Cl)cc2F)C(=O)N1CC(=O)Nc1cc(C(F)(F)F)ccn1] | S | 460 ([M + H]+) | 2.27 condition B |
| 155 | 2 | 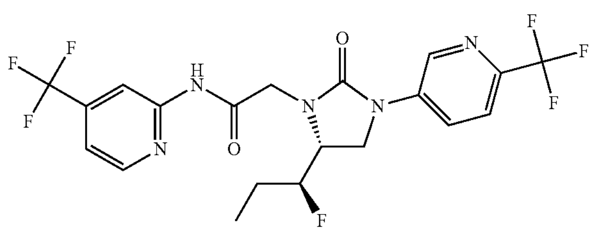 [SMILES: CC[C@H](F)[C@H]1CN(c2ccc(C(F)(F)F)nc2)C(=O)N1CC(=O)Nc1cc(C(F)(F)F)ccn1] | R | 494 ([M + H]+) | 1.075 condition A |
| 156 | 1 | 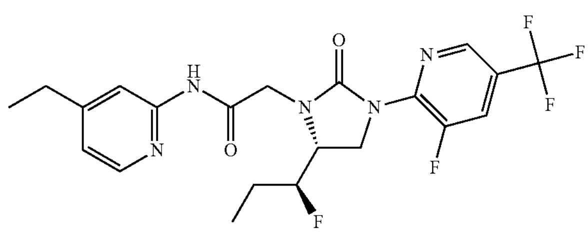 [SMILES: CCc1ccnc(NC(=O)CN2C(=O)N(c3ncc(C(F)(F)F)cc3F)C[C@@H]2[C@@H](F)CC)c1] | R | 472 ([M + H]+) | 0.969 condition A |
| 157 | 1 | 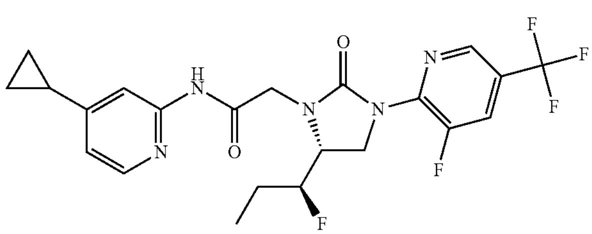 [SMILES: CC[C@H](F)[C@H]1CN(c2ncc(C(F)(F)F)cc2F)C(=O)N1CC(=O)Nc1cc(C2CC2)ccn1] | R | 484 ([M + H]+) | 0.924 condition A |

TABLE 1-17-continued

| Compound | Example | Structure | Configuration | (ESI pos.) m/z | RT (min) condition |
|---|---|---|---|---|---|
| 158 | 3 | 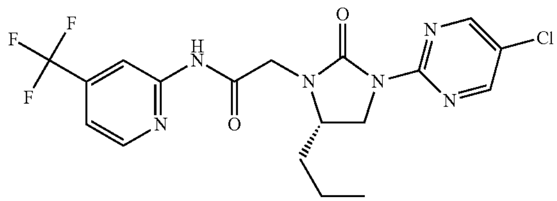 [SMILES: CCC[C@H]1CN(c2ncc(Cl)cn2)C(=O)N1CC(=O)Nc1cc(C(F)(F)F)ccn1] | S | 443 ([M + H]+) | 1.015 condition A |
| 159 | 3 | 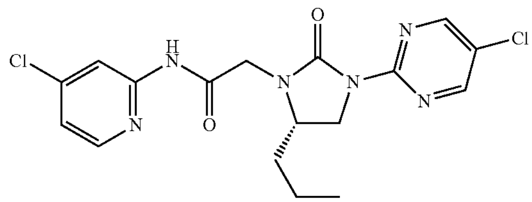 [SMILES: CCC[C@H]1CN(c2ncc(Cl)cn2)C(=O)N1CC(=O)Nc1cc(Cl)ccn1] | S | 409 ([M + H]+) | 0.958 condition A |
| 160 | 3 | 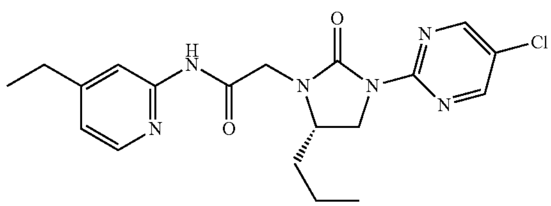 [SMILES: CCC[C@H]1CN(c2ncc(Cl)cn2)C(=O)N1CC(=O)Nc1cc(CC)ccn1] | S | 403 ([M + H]+) | 0.788 condition A |
| 161 | 9 | 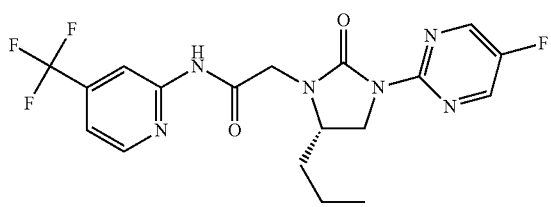 [SMILES: CCC[C@H]1CN(c2ncc(F)cn2)C(=O)N1CC(=O)Nc1cc(C(F)(F)F)ccn1] | S | 427 ([M + H]+) | 0.943 condition A |
| 162 | 3 | 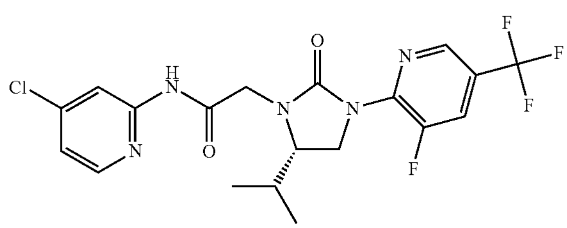 [SMILES: CC(C)[C@H]1CN(c2ncc(C(F)(F)F)cc2F)C(=O)N1CC(=O)Nc1cc(Cl)ccn1] | S | 460 ([M + H]+) | 1.114 condition A |

TABLE 1-18

| Compound | Example | Structure | Configuration | (ESI pos.) m/z | RT (min) condition |
|---|---|---|---|---|---|
| 163 | 3 | 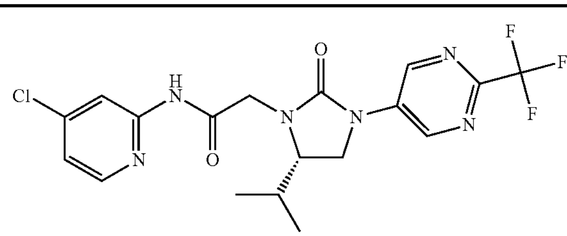 | S | 443 ([M + H]+) | 1.029 condition A |

TABLE 1-18-continued

| Compound | Example | Structure | Configuration | (ESI pos.) m/z | RT (min) condition |
|---|---|---|---|---|---|
| 164 | 3 | 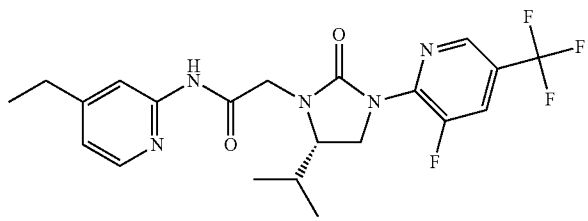 [SMILES: CCc1ccnc(NC(=O)CN2C(=O)N(c3ncc(C(F)(F)F)cc3F)C[C@@H]2C(C)C)c1] | S | 454 ([M + H]+) | 0.986 condition A |
| 165 | 3 | 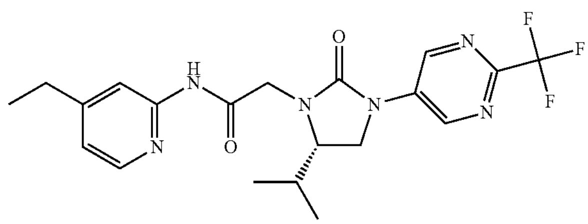 | S | 437 ([M + H]+) | 0.906 condition A |
| 166 | 3 | 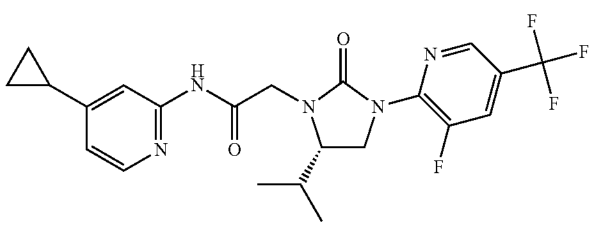 [SMILES: CC(C)[C@H]1CN(c2ncc(C(F)(F)F)cc2F)C(=O)N1CC(=O)Nc1cc(C2CC2)ccn1] | S | 466 ([M + H]+) | 0.943 condition A |
| 167 | 3 | 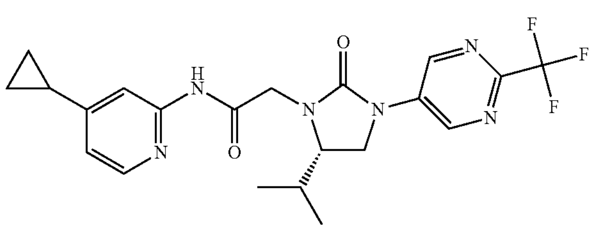 [SMILES: CC(C)[C@H]1CN(c2cnc(C(F)(F)F)nc2)C(=O)N1CC(=O)Nc1cc(C2CC2)ccn1] | S | 449 ([M + H]+) | 0.866 condition A |
| 168 | 3 | 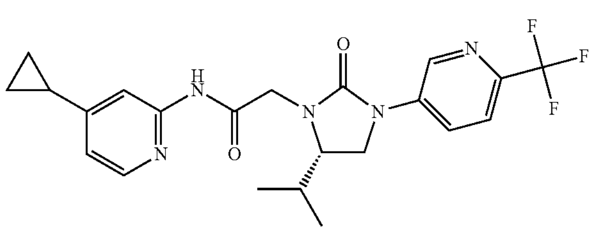 [SMILES: CC(C)[C@H]1CN(c2ccc(C(F)(F)F)nc2)C(=O)N1CC(=O)Nc1cc(C2CC2)ccn1] | S | 448 ([M + H]+) | 0.890 condition A |
| 169 | 9 | 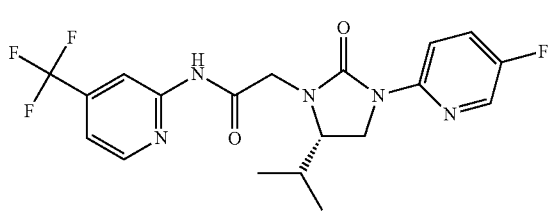 [SMILES: CC(C)[C@H]1CN(c2ccc(F)cn2)C(=O)N1CC(=O)Nc1cc(C(F)(F)F)ccn1] | S | 426 ([M + H]+) | 1.109 condition A |
| 170 | 9 | 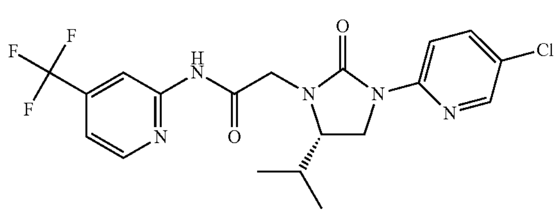 [SMILES: CC(C)[C@H]1CN(c2ccc(Cl)cn2)C(=O)N1CC(=O)Nc1cc(C(F)(F)F)ccn1] | S | 442 ([M + H]+) | 1.194 condition A |

TABLE 1-18-continued

| Compound | Example | Structure | Configuration | (ESI pos.) m/z | RT (min) condition |
|---|---|---|---|---|---|
| 171 | 9 | 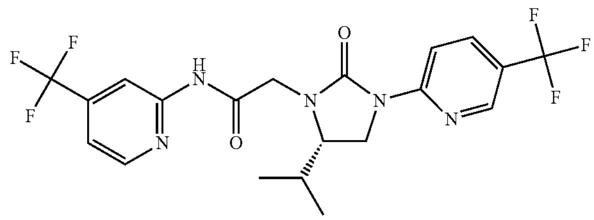 [SMILES: CC(C)[C@H]1CN(c2ccc(C(F)(F)F)cn2)C(=O)N1CC(=O)Nc1cc(C(F)(F)F)ccn1] | S | 476 ([M + H]+) | 1.218 condition A |
| 172 | 9 | 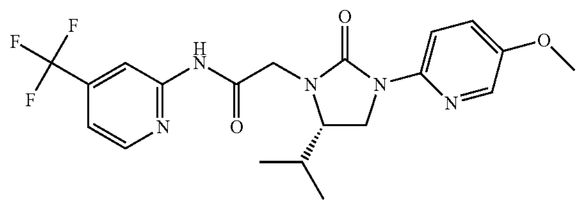 [SMILES: COc1ccc(N2C[C@H](C(C)C)N(CC(=O)Nc3cc(C(F)(F)F)ccn3)C2=O)nc1] | S | 438 ([M + H]+) | 1.038 condition A |

TABLE 1-19

| Compound | Example | Structure | Configuration | (ESI pos.) m/z | RT (min) condition |
|---|---|---|---|---|---|
| 173 | 9 | 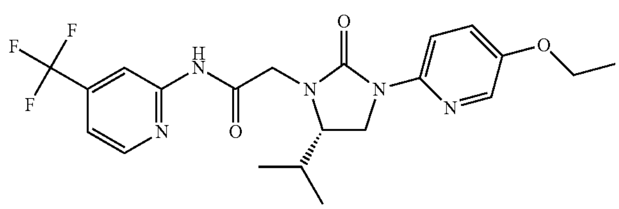 [SMILES: CCOc1ccc(N2C[C@H](C(C)C)N(CC(=O)Nc3cc(C(F)(F)F)ccn3)C2=O)nc1] | S | 452 ([M + H]+) | 1.107 condition A |
| 174 | 9 | 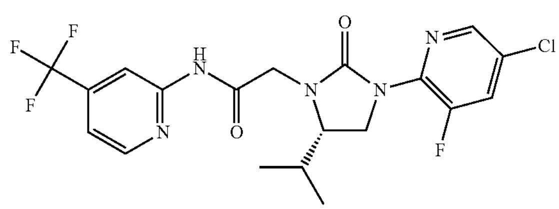 [SMILES: CC(C)[C@H]1CN(c2ncc(Cl)cc2F)C(=O)N1CC(=O)Nc1cc(C(F)(F)F)ccn1] | S | 460 ([M + H]+) | 1.109 condition A |
| 175 | 9 | 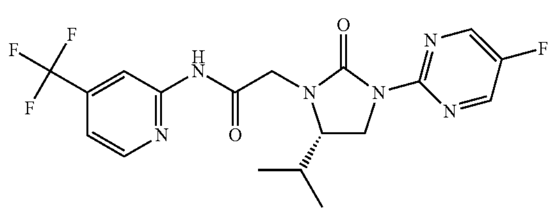 [SMILES: CC(C)[C@H]1CN(c2ncc(F)cn2)C(=O)N1CC(=O)Nc1cc(C(F)(F)F)ccn1] | S | 427 ([M + H]+) | 0.927 condition A |
| 176 | 9 | 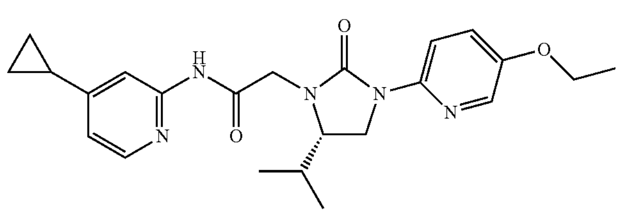 [SMILES: CCOc1ccc(N2C[C@H](C(C)C)N(CC(=O)Nc3cc(C4CC4)ccn3)C2=O)nc1] | S | 424 ([M + H]+) | 0.861 condition A |

TABLE 1-19-continued

| Compound | Example | Structure | Configuration | (ESI pos.) m/z | RT (min) condition |
|---|---|---|---|---|---|
| 177 | 9 | 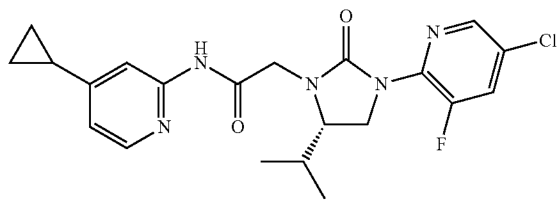 [SMILES: CC(C)[C@H]1CN(c2ncc(Cl)cc2F)C(=O)N1CC(=O)Nc1cc(C2CC2)ccn1] | S | 432 ([M + H]+) | 0.861 condition A |
| 178 | 9 | 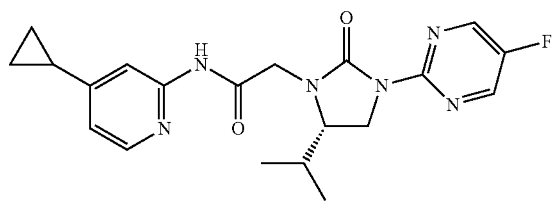 [SMILES: CC(C)[C@H]1CN(c2ncc(F)cn2)C(=O)N1CC(=O)Nc1cc(C2CC2)ccn1] | S | 399 ([M + H]+) | 0.643 condition A |
| 179 | 9 | 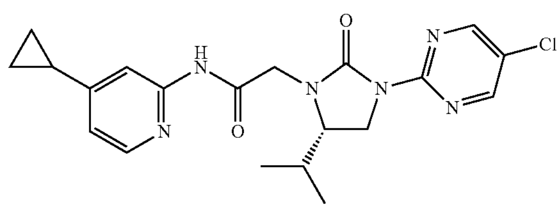 [SMILES: CC(C)[C@H]1CN(c2ncc(Cl)cn2)C(=O)N1CC(=O)Nc1cc(C2CC2)ccn1] | S | 415 ([M + H]+) | 0.727 condition A |
| 180 | 9 | 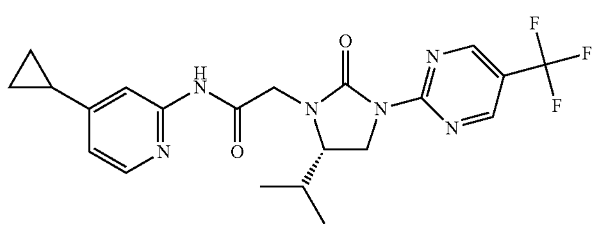 [SMILES: CC(C)[C@H]1CN(c2ncc(C(F)(F)F)cn2)C(=O)N1CC(=O)Nc1cc(C2CC2)ccn1] | S | 449 ([M + H]+) | 0.812 condition A |
| 181 | 9 | 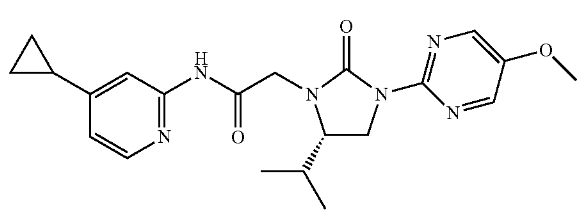 [SMILES: COc1cnc(N2C[C@H](C(C)C)N(CC(=O)Nc3cc(C4CC4)ccn3)C2=O)nc1] | S | 411 ([M + H]+) | 0.637 condition A |
| 182 | 9 | 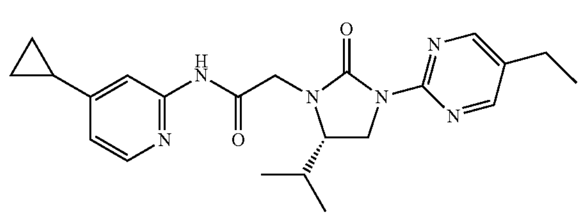 [SMILES: CCc1cnc(N2C[C@H](C(C)C)N(CC(=O)Nc3cc(C4CC4)ccn3)C2=O)nc1] | S | 409 ([M + H]+) | 0.707 condition A |

TABLE 1-20

| Compound | Example | Structure | Configuration | (ESI pos.) m/z | RT (min) condition |
|---|---|---|---|---|---|
| 183 | 2 | 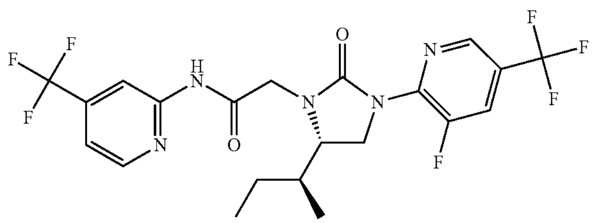 [SMILES: CC[C@H](C)[C@H]1CN(c2ncc(C(F)(F)F)cc2F)C(=O)N1CC(=O)Nc1cc(C(F)(F)F)ccn1] | S | 508 ([M + H]+) | 2.39 condition B |
| 184 | 2 | 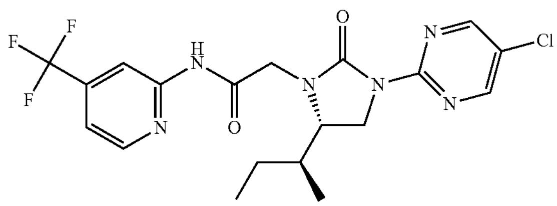 [SMILES: CC[C@H](C)[C@H]1CN(c2ncc(Cl)cn2)C(=O)N1CC(=O)Nc1cc(C(F)(F)F)ccn1] | S | 457 ([M + H]+) | 2.18 condition B |
| 185 | 9 | 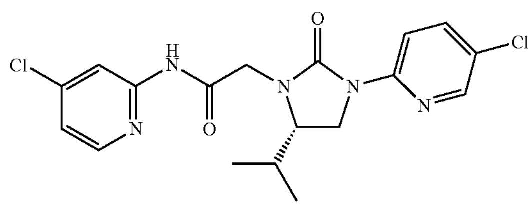 [SMILES: CC(C)[C@H]1CN(c2ccc(Cl)cn2)C(=O)N1CC(=O)Nc1cc(Cl)ccn1] | S | 408 ([M + H]+) | 1.162 condition A |
| 186 | 9 | 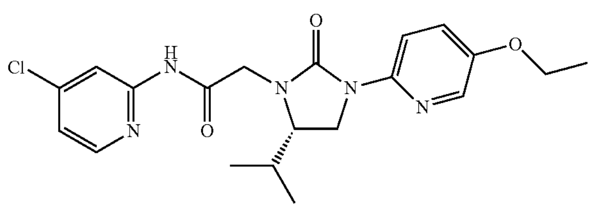 [SMILES: CCOc1ccc(N2C[C@H](C(C)C)N(CC(=O)Nc3cc(Cl)ccn3)C2=O)nc1] | S | 418 ([M + H]+) | 1.059 condition A |
| 187 | 9 | 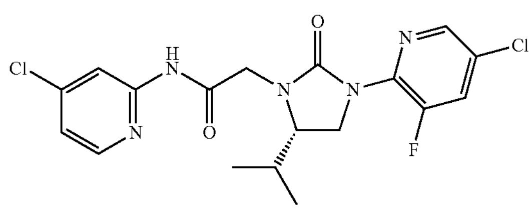 [SMILES: CC(C)[C@H]1CN(c2ncc(Cl)cc2F)C(=O)N1CC(=O)Nc1cc(Cl)ccn1] | S | 426 ([M + H]+) | 1.063 condition A |
| 188 | 9 | 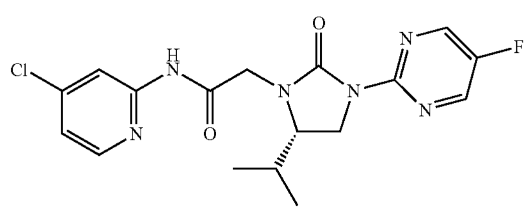 [SMILES: CC(C)[C@H]1CN(c2ncc(F)cn2)C(=O)N1CC(=O)Nc1cc(Cl)ccn1] | S | 393 ([M + H]+) | 0.864 condition A |
| 189 | 9 | 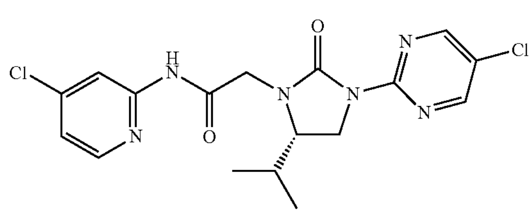 [SMILES: CC(C)[C@H]1CN(c2ncc(Cl)cn2)C(=O)N1CC(=O)Nc1cc(Cl)ccn1] | S | 409 ([M + H]+) | 0.937 condition A |

TABLE 1-20-continued

| Compound | Example | Structure | Configuration | (ESI pos.) m/z | RT (min) condition |
|---|---|---|---|---|---|
| 190 | 9 | 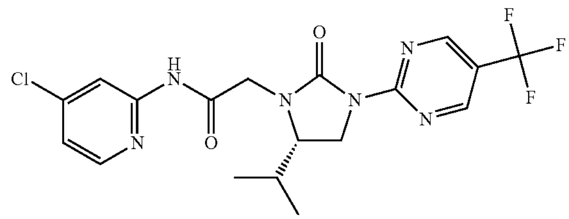 [SMILES: CC(C)[C@H]1CN(c2ncc(C(F)(F)F)cn2)C(=O)N1CC(=O)Nc1cc(Cl)ccn1] | S | 443 ([M + H]+) | 0.995 condition A |
| 191 | 9 | 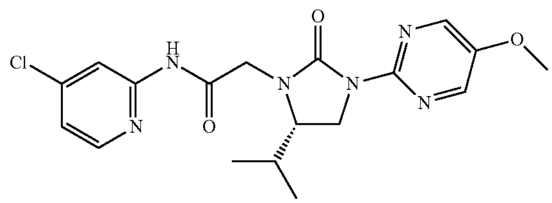 [SMILES: COc1cnc(N2C[C@H](C(C)C)N(CC(=O)Nc3cc(Cl)ccn3)C2=O)nc1] | S | 405 ([M + H]+) | 0.852 condition A |
| 192 | 9 | 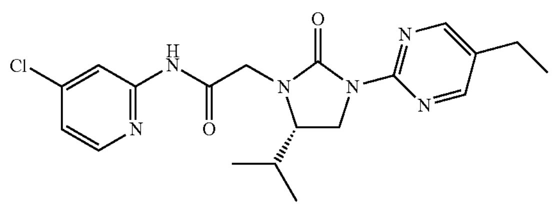 [SMILES: CCc1cnc(N2C[C@H](C(C)C)N(CC(=O)Nc3cc(Cl)ccn3)C2=O)nc1] | S | 403 ([M + H]+) | 0.907 condition A |

TABLE 1-21

| Compound | Example | Structure | Configuration | (ESI pos.) m/z | RT (min) condition |
|---|---|---|---|---|---|
| 193 | 9 | 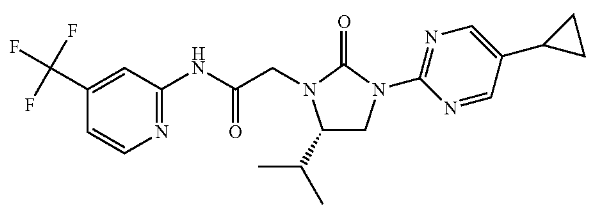 [SMILES: CC(C)[C@H]1CN(c2ncc(C3CC3)cn2)C(=O)N1CC(=O)Nc1cc(C(F)(F)F)ccn1] | S | 449 ([M + H]+) | 0.991 condition A |
| 194 | 9 | 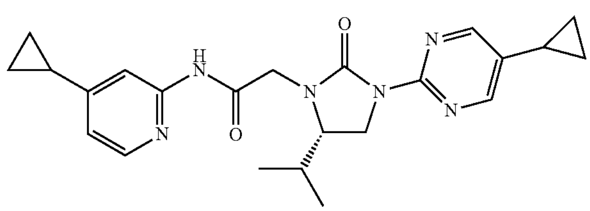 [SMILES: CC(C)[C@H]1CN(c2ncc(C3CC3)cn2)C(=O)N1CC(=O)Nc1cc(C2CC2)ccn1] | S | 421 ([M + H]+) | 0.737 condition A |
| 195 | 9 | 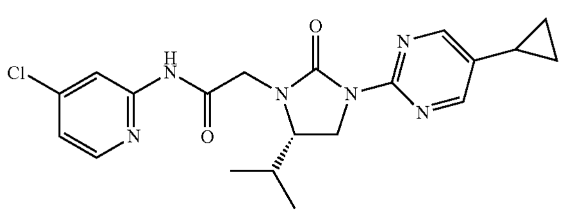 [SMILES: CC(C)[C@H]1CN(c2ncc(C3CC3)cn2)C(=O)N1CC(=O)Nc1cc(Cl)ccn1] | S | 415 ([M + H]+) | 0.934 condition A |

TABLE 1-21-continued

| Compound | Example | Structure | Configuration | (ESI pos.) m/z | RT (min) condition |
|---|---|---|---|---|---|
| 196 | 3 | 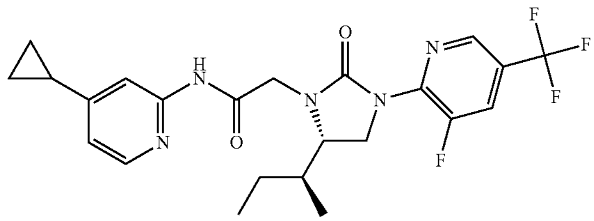 [SMILES: CC[C@H](C)[C@H]1CN(c2ncc(C(F)(F)F)cc2F)C(=O)N1CC(=O)Nc1cc(C2CC2)ccn1] | S | 480 ([M + H]+) | 2.10 condition B |
| 197 | 3 | 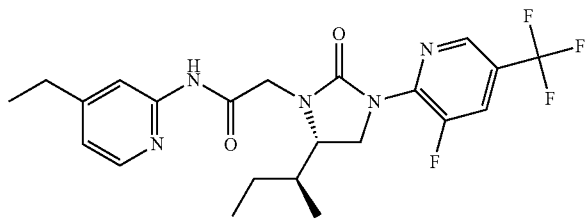 [SMILES: CCc1ccnc(NC(=O)CN2C(=O)N(c3ncc(C(F)(F)F)cc3F)C[C@@H]2[C@@H](C)CC)c1] | S | 468 ([M + H]+) | 2.18 condition B |
| 198 | 3 | 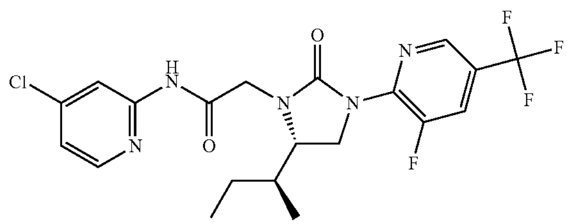 [SMILES: CC[C@H](C)[C@H]1CN(c2ncc(C(F)(F)F)cc2F)C(=O)N1CC(=O)Nc1cc(Cl)ccn1] | S | 474 ([M + H]+) | 2.35 condition B |
| 199 | 3 | 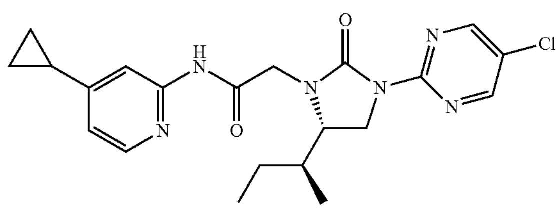 [SMILES: CC[C@H](C)[C@H]1CN(c2ncc(Cl)cn2)C(=O)N1CC(=O)Nc1cc(C2CC2)ccn1] | S | 429 ([M + H]+) | 1.79 condition B |
| 200 | 3 | 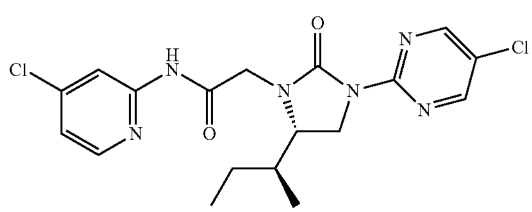 [SMILES: CC[C@H](C)[C@H]1CN(c2ncc(Cl)cn2)C(=O)N1CC(=O)Nc1cc(Cl)ccn1] | S | 423 ([M + H]+) | 2.10 condition B |
| 201 | 3 | 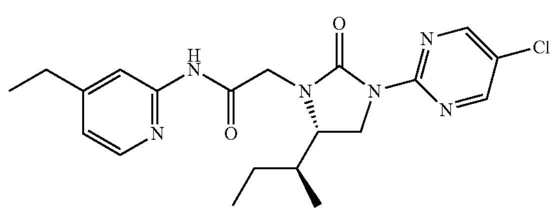 [SMILES: CCc1ccnc(NC(=O)CN2C(=O)N(c3ncc(Cl)cn3)C[C@@H]2[C@@H](C)CC)c1] | S | 417 ([M + H]+) | 1.86 condition B |
| 202 | 9 | 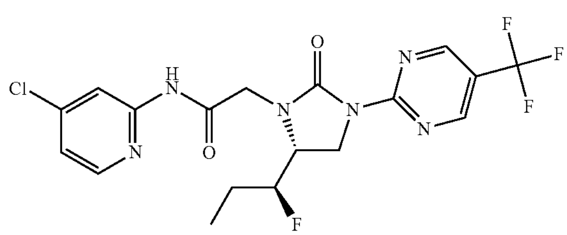 [SMILES: CC[C@H](F)[C@H]1CN(c2ncc(C(F)(F)F)cn2)C(=O)N1CC(=O)Nc1cc(Cl)ccn1] | R | 461 ([M + H]+) | 0.968 condition A |

TABLE 1-22

| Compound | Example | Structure | Configuration | (ESI pos.) m/z | RT (min) condition |
|---|---|---|---|---|---|
| 203 | 9 | 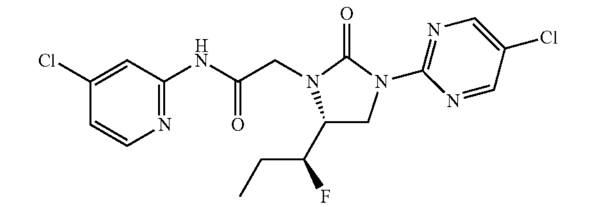 [SMILES: CC[C@H](F)[C@H]1CN(c2ncc(Cl)cn2)C(=O)N1CC(=O)Nc1cc(Cl)ccn1] | R | 427 ([M + H]+) | 0.908 condition A |
| 204 | 9 | 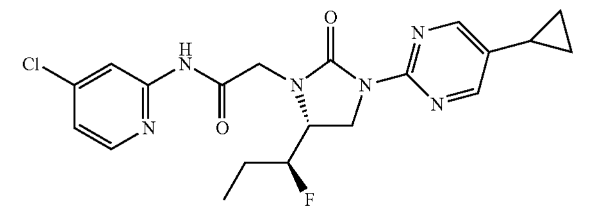 [SMILES: CC[C@H](F)[C@H]1CN(c2ncc(C3CC3)cn2)C(=O)N1CC(=O)Nc1cc(Cl)ccn1] | R | 433 ([M + H]+) | 0.914 condition A |
| 205 | 9 | 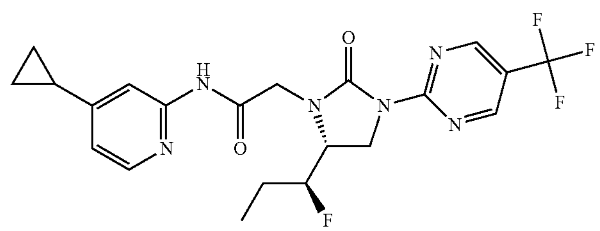 [SMILES: CC[C@H](F)[C@H]1CN(c2ncc(C(F)(F)F)cn2)C(=O)N1CC(=O)Nc1cc(C2CC2)ccn1] | R | 467 ([M + H]+) | 0.802 condition A |
| 206 | 9 | 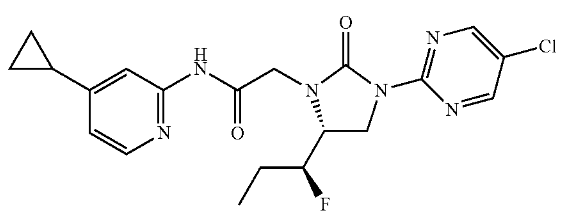 [SMILES: CC[C@H](F)[C@H]1CN(c2ncc(Cl)cn2)C(=O)N1CC(=O)Nc1cc(C2CC2)ccn1] | R | 433 ([M + H]+) | 0.716 condition A |
| 207 | 9 | 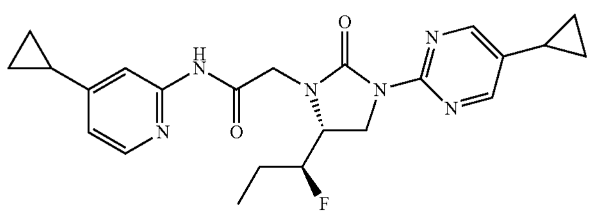 [SMILES: CC[C@H](F)[C@H]1CN(c2ncc(C3CC3)cn2)C(=O)N1CC(=O)Nc1cc(C2CC2)ccn1] | R | 439 ([M + H]+) | 0.729 condition A |
| 208 | 9 | 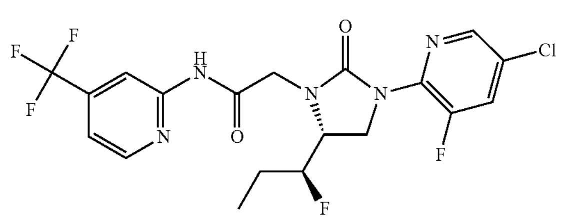 [SMILES: CC[C@H](F)[C@H]1CN(c2ncc(Cl)cc2F)C(=O)N1CC(=O)Nc1cc(C(F)(F)F)ccn1] | R | 478 ([M + H]+) | 1.082 condition A |
| 209 | 9 | 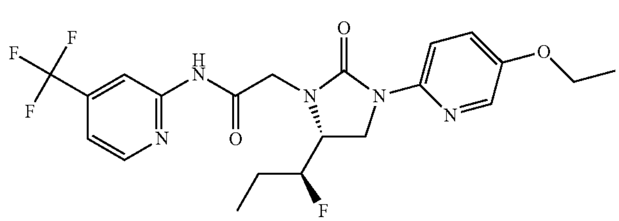 [SMILES: CCOc1ccc(N2C[C@H]([C@@H](F)CC)N(CC(=O)Nc3cc(C(F)(F)F)ccn3)C2=O)nc1] | R | 470 ([M + H]+) | 1.087 condition A |

TABLE 1-22-continued

| Compound | Example | Structure | Configuration | (ESI pos.) m/z | RT (min) condition |
|---|---|---|---|---|---|
| 210 | 9 | 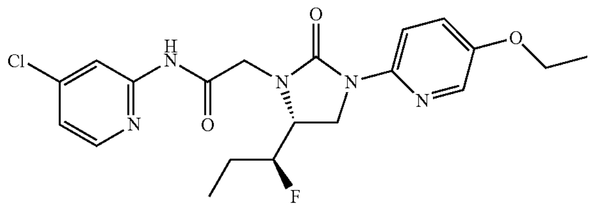 [SMILES: CCOc1ccc(N2C[C@H]([C@@H](F)CC)N(CC(=O)Nc3cc(Cl)ccn3)C2=O)nc1] | R | 436 ([M + H]+) | 1.039 condition A |
| 211 | 9 | 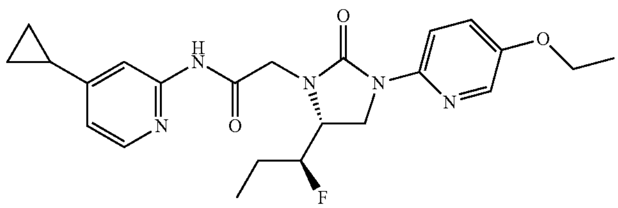 | R | 442 ([M + H]+) | 0.860 condition A |
| 212 | 9 | 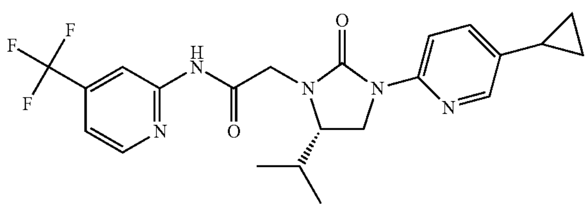 [SMILES: CC(C)[C@H]1CN(c2ccc(C3CC3)cn2)C(=O)N1CC(=O)Nc1cc(C(F)(F)F)ccn1] | S | 448 ([M + H]+) | 1.085 condition A |

TABLE 1-23

| Compound | Example | Structure | Configuration | (ESI pos.) m/z | RT (min) condition |
|---|---|---|---|---|---|
| 213 | 9 | 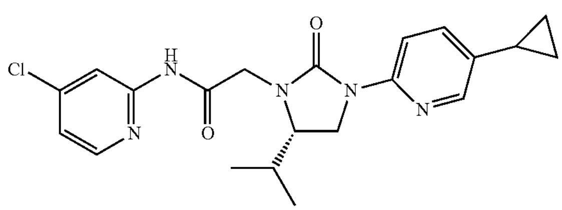 [SMILES: CC(C)[C@H]1CN(c2ccc(C3CC3)cn2)C(=O)N1CC(=O)Nc1cc(Cl)ccn1] | S | 414 ([M + H]+) | 1.028 condition A |
| 214 | 9 | 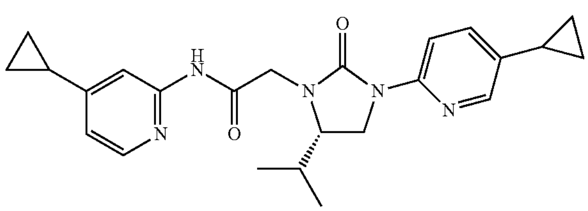 [SMILES: CC(C)[C@H]1CN(c2ccc(C3CC3)cn2)C(=O)N1CC(=O)Nc1cc(C2CC2)ccn1] | S | 420 ([M + H]+) | 0.857 condition A |
| 215 | 9 | 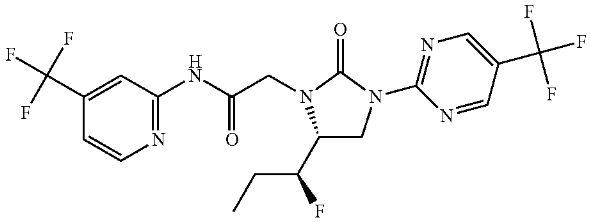 [SMILES: CC[C@H](F)[C@H]1CN(c2ncc(C(F)(F)F)cn2)C(=O)N1CC(=O)Nc1cc(C(F)(F)F)ccn1] | R | 495 ([M + H]+) | 1.024 condition A |

TABLE 1-23-continued

| Compound | Example | Structure | Configuration | (ESI pos.) m/z | RT (min) condition |
|---|---|---|---|---|---|
| 216 | 9 | 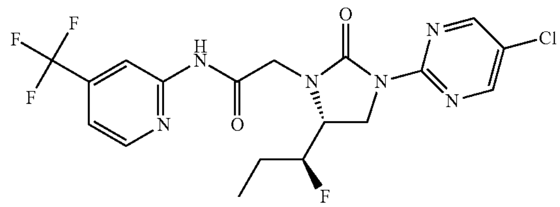 [SMILES: CC[C@H](F)[C@H]1CN(c2ncc(Cl)cn2)C(=O)N1CC(=O)Nc1cc(C(F)(F)F)ccn1] | R | 461 ([M + H]+) | 0.968 condition A |
| 217 | 9 | 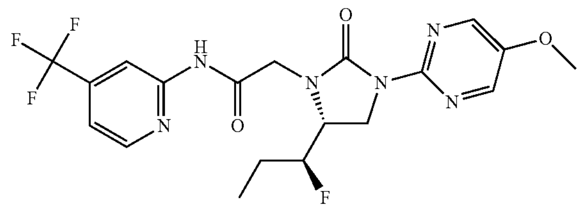 [SMILES: CC[C@H](F)[C@H]1CN(c2ncc(OC)cn2)C(=O)N1CC(=O)Nc1cc(C(F)(F)F)ccn1] | R | 457 ([M + H]+) | 0.893 condition A |
| 218 | 9 | 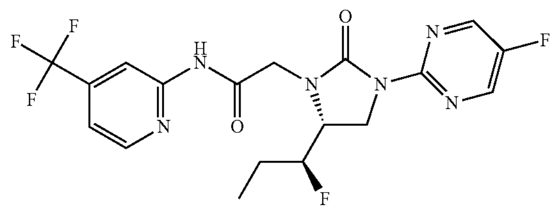 [SMILES: CC[C@H](F)[C@H]1CN(c2ncc(F)cn2)C(=O)N1CC(=O)Nc1cc(C(F)(F)F)ccn1] | R | 445 ([M + H]+) | 0.903 condition A |
| 219 | 9 | 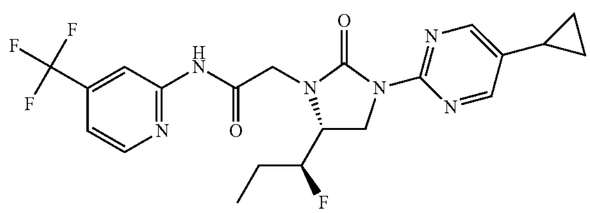 [SMILES: CC[C@H](F)[C@H]1CN(c2ncc(C3CC3)cn2)C(=O)N1CC(=O)Nc1cc(C(F)(F)F)ccn1] | R | 467 ([M + H]+) | 0.971 condition A |
| 220 | 9 | 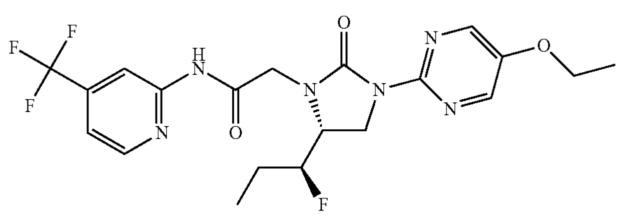 [SMILES: CCOc1cnc(N2C[C@H]([C@@H](F)CC)N(CC(=O)Nc3cc(C(F)(F)F)ccn3)C2=O)nc1] | R | 471 ([M + H]+) | 0.955 condition A |
| 221 | 9 | 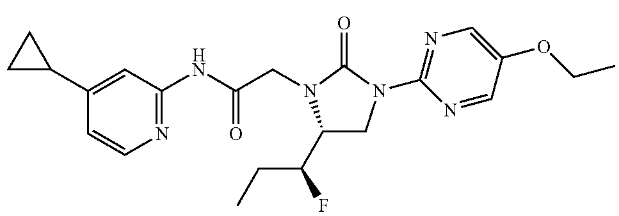 | R | 443 ([M + H]+) | 0.704 condition A |
| 222 | 9 | 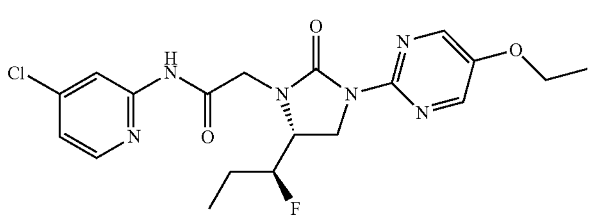 [SMILES: CCOc1cnc(N2C[C@H]([C@@H](F)CC)N(CC(=O)Nc3cc(Cl)ccn3)C2=O)nc1] | R | 437 ([M + H]+) | 0.897 condtion A |

TABLE 1-24

| Compound | Example | Structure | Configuration | (ESI pos.) m/z | RT (min) condition |
|---|---|---|---|---|---|
| 223 | 9 | 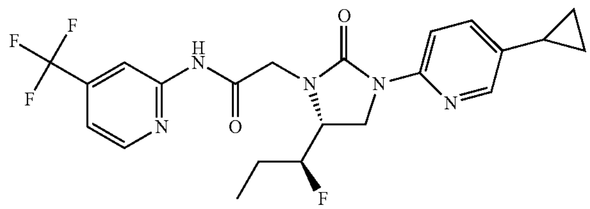 [SMILES: CC[C@H](F)[C@H]1CN(c2ccc(C3CC3)cn2)C(=O)N1CC(=O)Nc1cc(C(F)(F)F)ccn1] | R | 466 ([M + H]+) | 1.095 condition A |
| 224 | 9 | 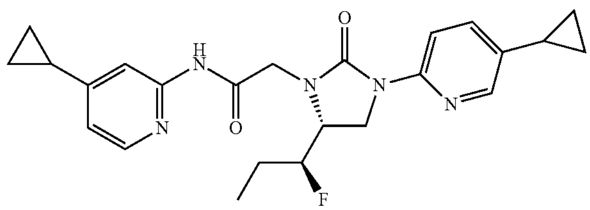 [SMILES: CC[C@H](F)[C@H]1CN(c2ccc(C3CC3)cn2)C(=O)N1CC(=O)Nc1cc(C2CC2)ccn1] | R | 438 ([M + H]+) | 0.882 condition A |
| 225 | 9 | 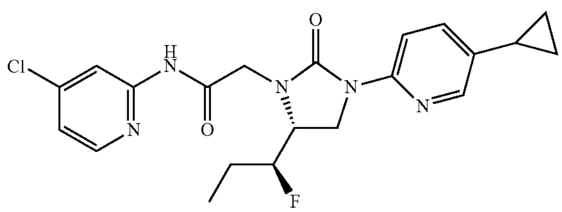 [SMILES: CC[C@H](F)[C@H]1CN(c2ccc(C3CC3)cn2)C(=O)N1CC(=O)Nc1cc(Cl)ccn1] | R | 432 ([M + H]+) | 1.044 condition A |
| 226 | 3 | 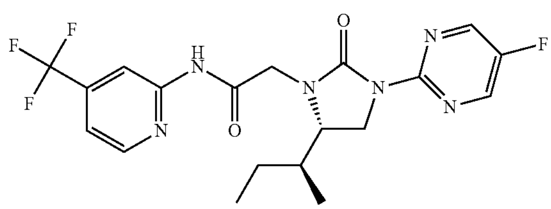 [SMILES: CC[C@H](C)[C@H]1CN(c2ncc(F)cn2)C(=O)N1CC(=O)Nc1cc(C(F)(F)F)ccn1] | S | 441 ([M + H]+) | 2.08 condition B |
| 227 | 3 | 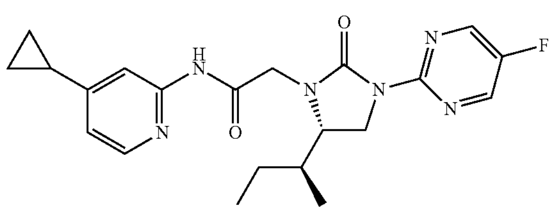 [SMILES: CC[C@H](C)[C@H]1CN(c2ncc(F)cn2)C(=O)N1CC(=O)Nc1cc(C2CC2)ccn1] | S | 413 ([M + H]+) | 1.66 condition B |
| 228 | 3 | 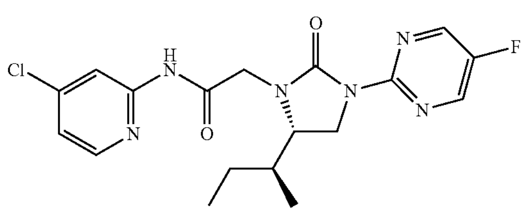 [SMILES: CC[C@H](C)[C@H]1CN(c2ncc(F)cn2)C(=O)N1CC(=O)Nc1cc(Cl)ccn1] | S | 407 ([M + H]+) | 1.99 condition B |
| 229 | 3 | 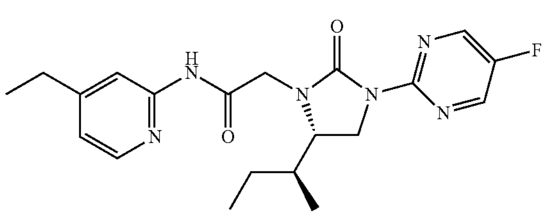 [SMILES: CCc1ccnc(NC(=O)CN2C(=O)N(c3ncc(F)cn3)C[C@@H]2[C@@H](C)CC)c1] | S | 401 ([M + H]+) | 1.72 condition B |

TABLE 1-24-continued

| Compound | Example | Structure | Configuration | (ESI pos.) m/z | RT (min) condition |
|---|---|---|---|---|---|
| 230 | 9 | 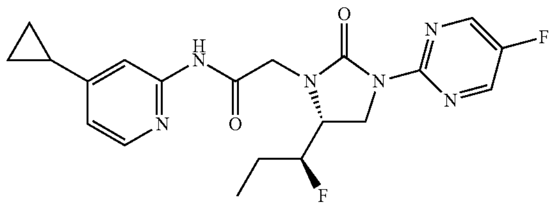 [SMILES: CC[C@H](F)[C@H]1CN(c2ncc(F)cn2)C(=O)N1CC(=O)Nc1cc(C2CC2)ccn1] | R | 417 ([M + H]+) | 0.636 condition A |
| 231 | 9 | 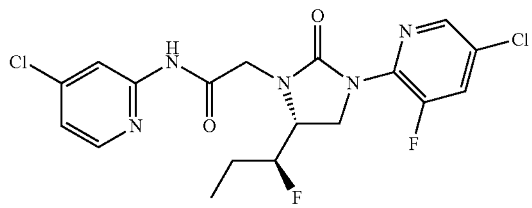 [SMILES: CC[C@H](F)[C@H]1CN(c2ncc(Cl)cc2F)C(=O)N1CC(=O)Nc1cc(Cl)ccn1] | R | 444 ([M + H]+) | 1.030 condition A |
| 232 | 3 | 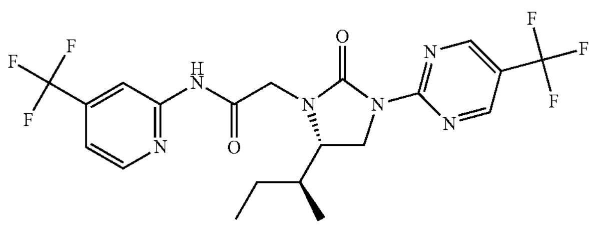 [SMILES: CC[C@H](C)[C@H]1CN(c2ncc(C(F)(F)F)cn2)C(=O)N1CC(=O)Nc1cc(C(F)(F)F)ccn1] | S | 491 ([M + H]+) | 2.24 condition B |

TABLE 1-25

| Compound | Example | Structure | Configuration | (ESI pos.) m/z | RT (min) condition |
|---|---|---|---|---|---|
| 233 | 3 | 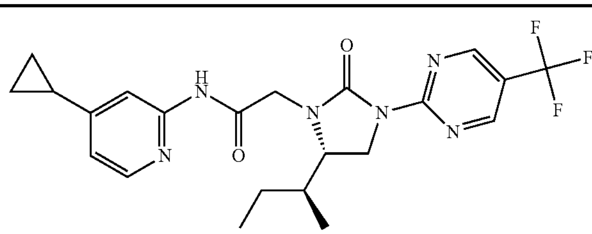 | S | 463 ([M + H]+) | 1.92 condition B |
| 234 | 3 | 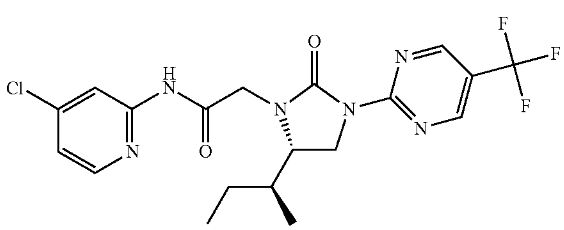 [SMILES: CC[C@H](C)[C@H]1CN(c2ncc(C(F)(F)F)cn2)C(=O)N1CC(=O)Nc1cc(Cl)ccn1] | S | 457 ([M + H]+) | 2.18 condition B |
| 235 | 3 | 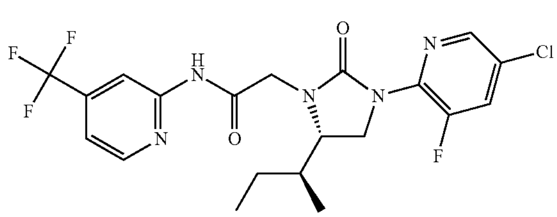 [SMILES: CC[C@H](C)[C@H]1CN(c2ncc(Cl)cc2F)C(=O)N1CC(=O)Nc1cc(C(F)(F)F)ccn1] | S | 474 ([M + H]+) | 2.34 condition B |

TABLE 1-25-continued

| Compound | Example | Structure | Configuration | (ESI pos.) m/z | RT (min) condition |
|---|---|---|---|---|---|
| 236 | 9 | 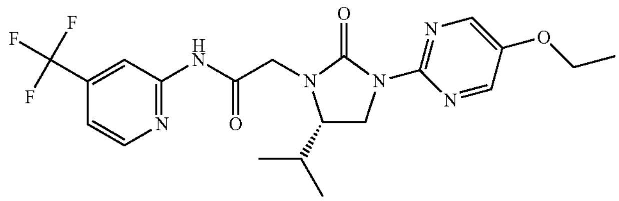 [SMILES: CCOc1cnc(N2C[C@H](C(C)C)N(CC(=O)Nc3cc(C(F)(F)F)ccn3)C2=O)nc1] | S | 453 ([M + H]+) | 0.982 condition A |
| 237 | 9 | 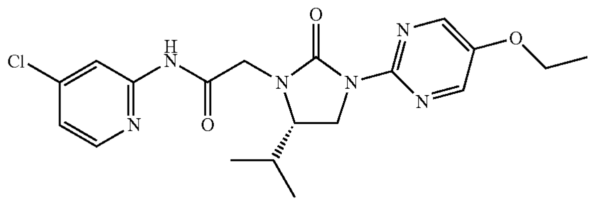 [SMILES: CCOc1cnc(N2C[C@H](C(C)C)N(CC(=O)Nc3cc(Cl)ccn3)C2=O)nc1] | S | 419 ([M + H]+) | 0.923 condition A |
| 238 | 9 | 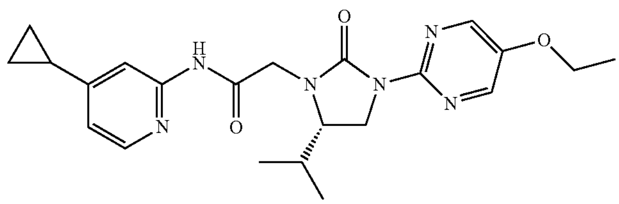 [SMILES: CCOc1cnc(N2C[C@H](C(C)C)N(CC(=O)Nc3cc(C4CC4)ccn3)C2=O)nc1] | S | 425 ([M + H]+) | 0.716 condition A |
| 239 | 3 | 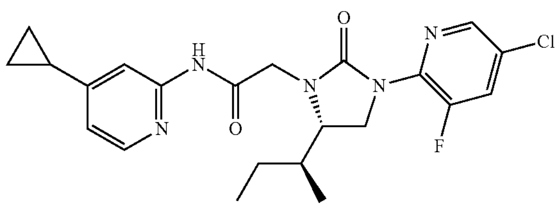 [SMILES: CC[C@H](C)[C@H]1CN(c2ncc(Cl)cc2F)C(=O)N1CC(=O)Nc1cc(C2CC2)ccn1] | S | 446 ([M + H]+) | 2.02 condition B |
| 240 | 9 | 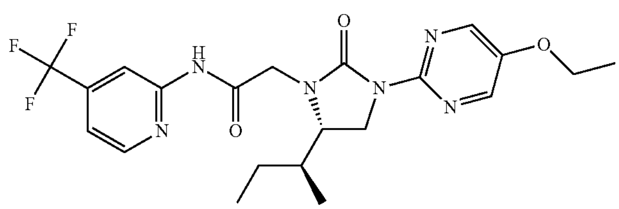 [SMILES: CCOc1cnc(N2C[C@H]([C@@H](C)CC)N(CC(=O)Nc3cc(C(F)(F)F)ccn3)C2=O)nc1] | S | 467 ([M + H]+) | 1.048 condition A |
| 241 | 9 | 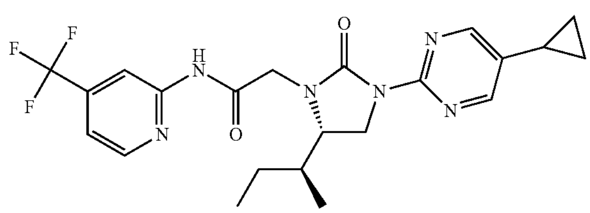 [SMILES: CC[C@H](C)[C@H]1CN(c2ncc(C3CC3)cn2)C(=O)N1CC(=O)Nc1cc(C(F)(F)F)ccn1] | S | 463 ([M + H]+) | 1.069 condition A |
| 242 | 9 | 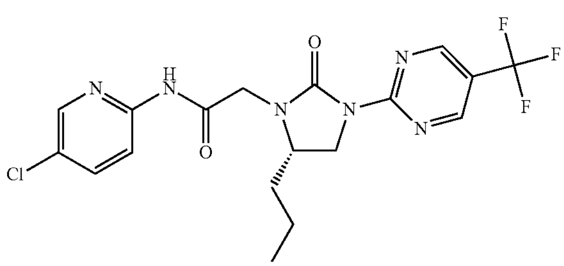 [SMILES: CCC[C@H]1CN(c2ncc(C(F)(F)F)cn2)C(=O)N1CC(=O)Nc1ccc(Cl)cn1] | S | 443 ([M + H]+) | 1.008 condition A |

TABLE 1-26
| Compound | Example | Structure | Configuration | (ESI pos.) m/z | RT (min) condition |
|---|---|---|---|---|---|
| 243 | 9 | 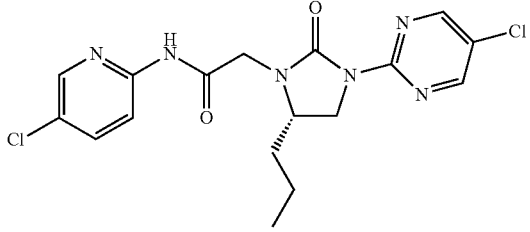 [SMILES: CCC[C@H]1CN(c2ncc(Cl)cn2)C(=O)N1CC(=O)Nc1ccc(Cl)cn1] | S | 409 ([M + H]+) | 0.951 condition A |
| 244 | 9 | 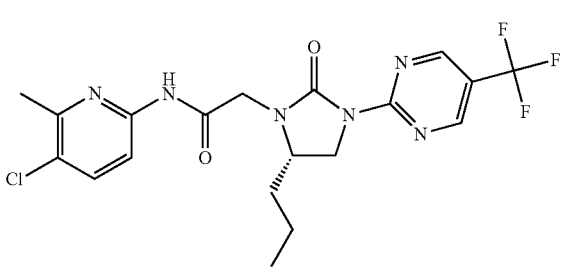 [SMILES: CCC[C@H]1CN(c2ncc(C(F)(F)F)cn2)C(=O)N1CC(=O)Nc1ccc(Cl)c(C)n1] | S | 457 ([M + H]+) | 1.073 condition A |
| 245 | 9 | 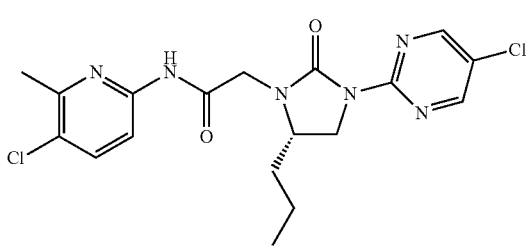 [SMILES: CCC[C@H]1CN(c2ncc(Cl)cn2)C(=O)N1CC(=O)Nc1ccc(Cl)c(C)n1] | S | 423 ([M + H]+) | 1.025 condition A |
| 246 | 9 | 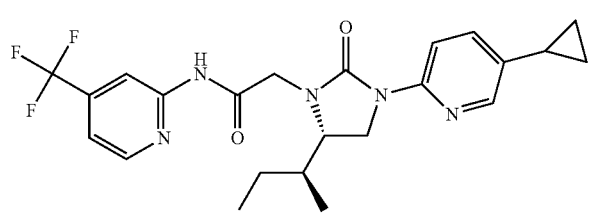 [SMILES: CC[C@H](C)[C@H]1CN(c2ccc(C3CC3)cn2)C(=O)N1CC(=O)Nc1cc(C(F)(F)F)ccn1] | S | 462 ([M + H]+) | 1.159 condition A |
| 247 | 9 | 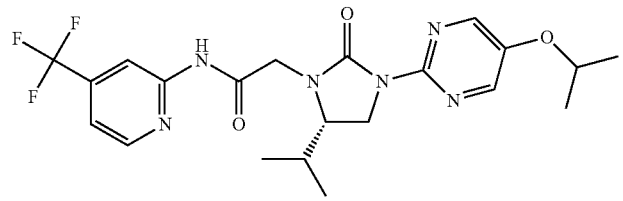 [SMILES: CC(C)Oc1cnc(N2C[C@H](C(C)C)N(CC(=O)Nc3cc(C(F)(F)F)ccn3)C2=O)nc1] | S | 467 ([M + H]+) | 1.039 condition A |
| 248 | 9 | 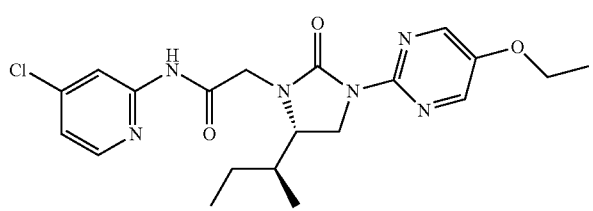 [SMILES: CCOc1cnc(N2C[C@H]([C@@H](C)CC)N(CC(=O)Nc3cc(Cl)ccn3)C2=O)nc1] | S | 433 ([M + H]+) | 0.995 condition A |
| 249 | 9 | 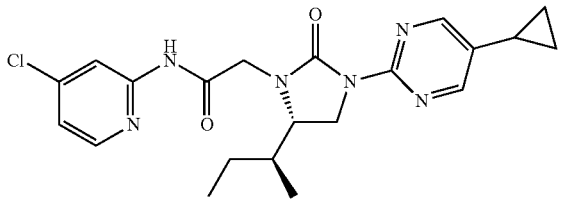 [SMILES: CC[C@H](C)[C@H]1CN(c2ncc(C3CC3)cn2)C(=O)N1CC(=O)Nc1cc(Cl)ccn1] | S | 429 ([M + H]+) | 1.008 condition A |

TABLE 1-26-continued

| Compound | Example | Structure | Configuration | (ESI pos.) m/z | RT (min) condition |
|---|---|---|---|---|---|
| 250 | 9 | 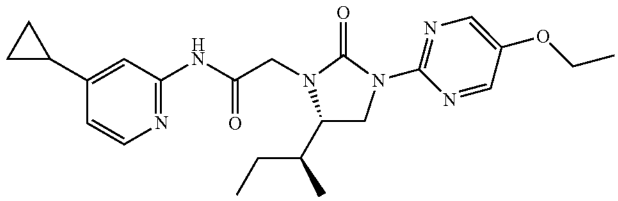 [SMILES: CCOc1cnc(N2C[C@H]([C@@H](C)CC)N(CC(=O)Nc3cc(C4CC4)ccn3)C2=O)nc1] | S | 439 ([M + H]+) | 0.800 condition A |
| 251 | 9 | 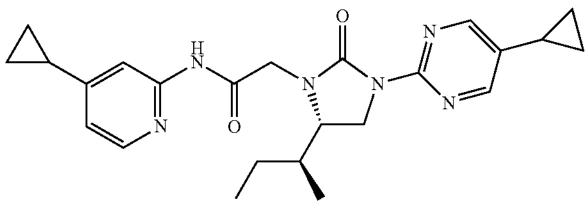 [SMILES: CC[C@H](C)[C@H]1CN(c2ncc(C3CC3)cn2)C(=O)N1CC(=O)Nc1cc(C2CC2)ccn1] | S | 435 ([M + H]+) | 0.822 condition A |

The $^1$H-NMR data of the following compounds listed below among those shown in Tables 1-9 and 1-26 are shown below:

Compound 73

1H NMR (600 MHz, CHLOROFORM-d) d ppm 0.96 (d, J=7.02 Hz, 3H), 1.02 (d, J=6.61 Hz, 3H), 2.12-2.30 (m, 1H), 3.84-3.97 (m, 2H), 4.02-4.15 (m, 2H), 4.17-4.28 (m, 1H), 7.20-7.27 (m, 1H), 7.64-7.74 (m, 1H), 8.41-8.50 (m, 3H), 8.97 (br. s., 1H)

Compound 74

1H NMR (600 MHz, CHLOROFORM-d) d ppm 0.92 (d, J=6.61 Hz, 3H), 1.05 (d, J=7.02 Hz, 3H), 2.19-2.28 (m, 1H), 3.63 (dd, J=9.08, 6.19 Hz, 1H), 3.90-4.07 (m, 3H), 4.32 (d, J=16.51 Hz, 1H), 7.28-7.31 (m, 1H), 8.41-8.48 (m, 2H), 8.68 (br. s., 1H), 9.18 (s, 2H)

Compound 93

1H NMR (600 MHz, CHLOROFORM-d) d ppm 0.90 (d, J=7.02 Hz, 3H), 1.01 (d, J=7.02 Hz, 3H), 2.12-2.23 (m, 1H), 3.78-3.83 (m, 1H), 3.84-3.88 (m, 1H), 3.90 (s, 3H), 4.03-4.08 (m, 1H), 4.10-4.18 (m, 2H), 7.24-7.26 (m, 1H), 8.34 (s, 2H), 8.41-8.47 (m, 2H), 9.09 (br. s., 1H)

Compound 94

1H NMR (600 MHz, CHLOROFORM-d) d ppm 0.90 (d, J=6.61 Hz, 3H), 1.01 (d, J=7.02 Hz, 3H), 1.25 (t, J=7.64 Hz, 3H), 2.15-2.24 (m, 1H), 2.61 (q, J=7.84 Hz, 2H), 3.77-3.84 (m, 1H), 3.87 (dd, J=10.94, 6.40 Hz, 1H), 4.07 (dd, J=10.73, 9.50 Hz, 1H), 4.10-4.17 (m, 2H), 7.23-7.25 (m, 1H), 8.41-8.45 (m, 2H), 8.48 (s, 2H), 9.05 (br. s., 1H)

Compound 103

1H NMR (600 MHz, CHLOROFORM-d) d ppm 0.89 (d, J=7.0 Hz, 3H), 1.03 (d, J=7.0 Hz, 3H), 1.32 (s, 9H), 2.13-2.26 (m, 1H), 3.66 (dd, J=8.9, 6.0 Hz, 1H), 3.83-4.01 (m, 2H), 4.05-4.17 (m, 2H), 6.27 (s, 1H), 7.68 (d, J=8.7 Hz, 1H), 8.40 (dd, J=8.7, 2.5 Hz, 1H), 8.72 (d, J=2.5 Hz, 1H), 9.32 (br. s., 1H)

Compound 107

1H NMR (600 MHz, CHLOROFORM-d) d ppm 0.98-1.04 (m, 2H), 1.29 (t, J=7.6 Hz, 1H), 1.72-1.85 (m, 1H), 2.76-2.86 (m, 1H), 3.57-3.65 (m, 1H), 3.91-4.04 (m, 1H), 4.11 (t, J=8.9 Hz, 1H), 4.18 (d, J=16.1 Hz, 1H), 7.15-7.29 (m, 2H), 7.64-7.71 (m, 1H), 8.32-8.38 (m, 1H), 8.52-8.59 (m, 1H), 8.73-8.77 (m, 1H)

Compound 108

1H NMR (600 MHz, CHLOROFORM-d) d ppm 1.02 (s, 6H), 1.57-1.67 (m, 2H), 1.75-1.84 (m, 1H), 2.69 (s, 3H), 3.58-3.68 (m, 1H), 3.91-4.00 (m, 2H), 4.08-4.16 (m, 1H), 4.21 (d, J=16.1 Hz, 1H), 7.69 (d, J=9.1 Hz, 1H), 8.05 (d, J=8.7 Hz, 1H), 8.15-8.22 (m, 1H), 8.29-8.35 (m, 1H), 8.68-8.72 (m, 1H), 8.76-8.80 (m, 1H), 8.83-8.87 (m, 1H)

Compound 112

1H NMR (600 MHz, CHLOROFORM-d) d ppm 0.85-0.98 (m, 6H), 1.41-1.48 (m, 2H), 1.62-1.76 (m, 1H), 3.49-3.58 (m, 1H), 3.80-3.91 (m, 2H), 3.98-4.05 (m, 1H), 4.11 (d, J=15.7 Hz, 1H), 6.36-6.64 (m, 1H), 7.52 (d, J=8.3 Hz, 1H), 7.59 (d, J=9.1 Hz, 1H), 8.09-8.24 (m, 2H), 8.53-8.58 (m, 1H), 8.61 (s, 1H), 8.65-8.69 (m, 1H)

Compound 114

1H NMR (600 MHz, CHLOROFORM-d) d ppm 0.94-0.97 (m, 4H), 0.97-1.03 (m, 6H), 1.46-1.53 (m, 1H), 1.69-1.83 (m, 2H), 1.96-2.03 (m, 1H), 3.54-3.61 (m, 1H), 3.90-4.00 (m, 2H), 4.04-4.18 (m, 2H), 7.08 (d, J=8.3 Hz, 1H), 7.66 (d, J=8.7 Hz, 1H), 7.86-7.93 (m, 1H), 8.21 (br. s., 1H), 8.29-8.36 (m, 1H), 8.39-8.43 (m, 1H), 8.71-8.76 (m, 1H)

Compound 148

1H NMR (600 MHz, CHLOROFORM-d) d ppm 1.22 (s, 3H), 1.24 (s, 3H), 3.24 (s, 3H), 3.60 (dd, J=9.1, 6.2 Hz, 1H), 3.96 (dd, J=9.9, 6.2 Hz, 1H), 4.02-4.10 (m, 1H), 4.26 (d, J=16.5 Hz, 1H), 4.45 (d, J=16.5 Hz, 1H), 7.66 (d, J=9.1 Hz, 1H), 8.41-8.47 (m, 2H), 8.50 (s, 1H), 8.69 (br. s., 1H), 8.70-8.73 (m, 1H)

Compound 152

1H NMR (600 MHz, CHLOROFORM-d) d ppm 0.11-0.24 (m, 2H), 0.49-0.61 (m, 2H), 0.65-0.76 (m, 1H), 1.63-1.75 (m, 2H), 3.94-4.04 (m, 2H), 4.04-4.10 (m, 2H), 4.14-4.20 (m, 1H), 4.21-4.29 (m, 1H), 7.06 (dd, J=5.4, 1.7 Hz, 1H), 7.71 (dd, J=9.5, 1.7 Hz, 1H), 8.17 (d, J=5.4 Hz, 1H), 8.27 (s, 1H), 8.48 (s, 1H), 8.74 (br. s., 1H)

Compound 155

1H NMR (600 MHz, CHLOROFORM-d) d ppm 1.12 (t, J=7.4 Hz, 3H), 1.59-1.72 (m, 1H), 1.74-1.88 (m, 1H), 3.90 (dd, J=8.5, 6.8 Hz, 1H), 4.01-4.17 (m, 2H), 4.18-4.24 (m, 1H), 4.25-4.32 (m, 1H), 4.62-4.78 (m, 1H), 7.28 (d, J=5.8 Hz, 1H), 7.67 (d, J=8.7 Hz, 1H), 8.36-8.42 (m, 1H), 8.44-8.50 (m, 2H), 8.72-8.80 (m, 2H)

Compound 161

1H NMR (600 MHz, CHLOROFORM-d) d ppm 0.98 (t, J=7.4 Hz, 3H), 1.32-1.48 (m, 2H), 1.54-1.63 (m, 1H), 1.80-1.89 (m, 1H), 3.73-3.84 (m, 2H), 4.04 (d, J=16.5 Hz, 1H), 4.20-4.28 (m, 2H), 7.23-7.25 (m, 1H), 8.40-8.44 (m, 1H), 8.46 (s, 1H), 8.51 (s, 2H), 8.86 (br. s., 1H)

Compound 193

1H NMR (600 MHz, CHLOROFORM-d) d ppm 0.68-0.72 (m, 2H), 0.88 (d, J=6.6 Hz, 3H), 1.00 (d, J=7.0 Hz, 3H), 1.01-1.05 (m, 2H), 1.79-1.86 (m, 1H), 2.14-2.22 (m, 1H), 3.61-3.67 (m, 1H), 3.77-3.88 (m, 2H), 4.05 (dd, J=10.7, 9.5 Hz, 1H), 4.13 (s, 2H), 7.22-7.25 (m, 1H), 8.38 (s, 2H), 8.40-8.45 (m, 2H), 9.10 (br. s., 1H)

Compound 195

1H NMR (600 MHz, CHLOROFORM-d) d ppm 0.66-0.74 (m, 2H), 0.88 (d, J=7.0 Hz, 3H), 0.95-1.08 (m, 5H), 1.76-1.88 (m, 1H), 2.10-2.23 (m, 1H), 3.74-3.92 (m, 2H), 3.99-4.19 (m, 3H), 6.98-7.06 (m, 1H), 8.15 (d, J=5.4 Hz, 1H), 8.21-8.28 (m, 1H), 8.38 (s, 2H), 8.94 (br. s., 1H)

Compound 248

1H NMR (600 MHz, CHLOROFORM-d) d ppm 0.87 (d, J=6.6 Hz, 3H), 0.99 (t, J=7.4 Hz, 3H), 1.25-1.32 (m, 1H), 1.36-1.42 (m, 1H), 1.45 (t, J=7.0 Hz, 3H), 1.90-1.96 (m, 1H), 3.81-3.86 (m, 1H), 3.87-3.92 (m, 1H), 4.00-4.17 (m, 5H), 7.05 (dd, J=5.4, 2.1 Hz, 1H), 8.16 (d, J=5.4 Hz, 1H), 8.25-8.28 (m, 1H), 8.32 (s, 2H), 8.95-8.99 (m, 1H)

Compound 249

1H NMR (600 MHz, CHLOROFORM-d) d ppm 0.68-0.73 (m, 2H), 0.86 (d, J=6.6 Hz, 3H), 0.99 (t, J=7.4 Hz, 3H), 1.01-1.05 (m, 2H), 1.22-1.33 (m, 1H), 1.35-1.45 (m, 1H), 1.76-1.87 (m, 1H), 1.89-1.98 (m, 1H), 3.80-3.87 (m, 1H), 3.88-3.93 (m, 1H), 3.99-4.18 (m, 3H), 7.01-7.06 (m, 1H), 8.16 (d, J=5.4 Hz, 1H), 8.23-8.29 (m, 1H), 8.38 (s, 2H), 8.95 (br. s., 1H)

Compound 250

1H NMR (600 MHz, CHLOROFORM-d) d ppm 0.84-0.91 (m, 5H), 0.98 (t, J=7.4 Hz, 3H), 1.09-1.14 (m, 2H), 1.25-1.33 (m, 1H), 1.36-1.42 (m, 1H), 1.44 (t, J=7.0 Hz, 3H), 1.88-1.94 (m, 2H), 3.83 (dd, J=10.5, 6.4 Hz, 1H), 3.91-3.96 (m, 1H), 3.96-4.00 (m, 1H), 4.03-4.07 (m, 1H), 4.10 (q, J=6.7 Hz, 2H), 4.23-4.30 (m, 1H), 6.71-6.75 (m, 1H), 7.93-7.98 (m, 1H), 8.03-8.06 (m, 1H), 8.31 (s, 2H)

Compound 251

1H NMR (600 MHz, CHLOROFORM-d) d ppm 0.57-0.63 (m, 2H), 0.69-0.74 (m, 2H), 0.76 (d, J=6.6 Hz, 3H), 0.87 (t, J=7.4 Hz, 3H), 0.90-0.95 (m, 2H), 0.95-1.00 (m, 2H), 1.14-1.23 (m, 1H), 1.25-1.34 (m, 1H), 1.69-1.76 (m, 1H), 1.76-1.85 (m, 2H), 3.72 (dd, J=10.7, 6.6 Hz, 1H), 3.79-3.85 (m, 1H), 3.87 (d, J=16.5 Hz, 1H), 3.90-3.96 (m, 1H), 4.14 (d, J=16.5 Hz, 1H), 6.60 (dd, J=5.4, 1.2 Hz, 1H), 7.74-7.80 (m, 1H), 7.97 (d, J=5.4 Hz, 1H), 8.28 (s, 2H), 8.53 (br. s., 1H)

Test Example 1

Glycine Uptake Inhibition Experiment

A glycine uptake experiment was conducted in accordance with the method published in Neuron, 8, 927-935, 1992. In the experiment, T98G cells (glioma cells) expressing human type 1 glycine transporter (GlyT1) were used. The T98G cells were seeded in a 96-well plate at $2.0 \times 10^4$ cells/well and cultured overnight in a $CO_2$ incubator. The test substance was dissolved in a 100% DMSO solution and then dissolved in a 10 mM HEPES buffer solution (pH 7.4) containing 150 mM sodium chloride, 1 mM calcium chloride, 5 mM potassium chloride, 1 mM magnesium chloride, 10 mM glucose and 0.2% bovine serum albumin. After removing the cell culture medium, the test substance was subjected to a 10-min pretreatment. Subsequently, the test substance and [$^3$H] glycine (final concentration: 250 nM) were added to the cells and reaction was performed at room temperature for 15 minutes. After the end of the reaction, the extracellular fluid was aspirated with a manifold to remove excess labeled glycine present outside the cells, and then the cells were lysed with a 0.5 M aqueous sodium hydroxide solution. The glycine content in the cells was determined by measuring the radioactivity in the cell lysate with a liquid scintillation counter. Glycine uptake in the presence of 10 μM ALX$^{5407}$ was defined as non-specific uptake, and the value calculated by subtracting the amount of the non-specific uptake from the total uptake in the absence of 10 μM ALX5407 was defined as specific uptake. In addition, glycine uptake inhibitory activity (IC$_{50}$ value) was calculated from an inhibition curve at the concentrations of each test substance ranging from $10^{-9}$ to $10^{-5}$ M.

It should be noted that ALX$^{5407}$ is an HCl salt of N-[(3R)-3-([1,1'-biphenyl]-4-yloxy)-3-(4-fluorophenyl)propyl]-N-methylglycine.

All the compounds of the Working Examples in the present invention were found to have IC$_{50}$ values of less than 10 μM. Specific examples of their IC$_{50}$ values are as follows:

Compound 8, 0.66 μM; Compound 11, 0.089 μM; Compound 12, 0.071 μM; Compound 13, 0.074 μM; Compound 54, 0.80 μM; Compound 61, 0.053 μM; Compound 62, 0.033 μM; Compound 93, 0.054 μM; Compound 98, 0.26 μM; Compound 103, 0.23 μM; Compound 104, 0.24 μM; Compound 148, 0.075 μM; Compound 152, 0.043 μM; Compound 165, 0.15 μM; Compound 186, 0.045 μM; Compound 188, 0.60 μM; Compound 193, 0.022 μM; Compound 220, 0.017 μM; Compound 248, 0.016 μM; Compound 249, 0.018 μM; and Compound 250, 0.024 μM.

INDUSTRIAL APPLICABILITY

The inventive compounds have glycine transporter (GlyT1)-inhibiting activity, and thus, are effective in the prevention or treatment of diseases associated with the glycine transporter which are, specifically, schizophrenia, Alzheimer's disease, cognitive impairment, dementia, anxiety disorders (e.g., generalized anxiety disorder, panic disorder, obsessive-compulsive disorder, social anxiety disorder, post-traumatic stress disorder, specific phobias, acute stress disorder), depression, drug dependence, spasm, tremor, pain, Parkinson's disease, attention deficit hyperactivity disorder, bipolar disorder, eating disorder, sleep disorders or the like.

The invention claimed is:

1. A compound of formula [I] or a pharmaceutically acceptable salt thereof:

[Formula 1]

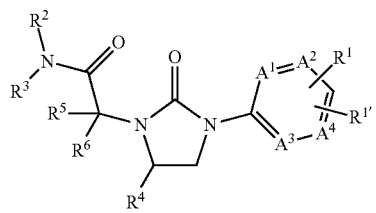

wherein $R^1$ and $R^{1'}$ are the same or different, and each represent a hydrogen atom, a halogen atom, a $C_{1-6}$ alkoxy group, a haloC$_{1-6}$ alkyl group, a cyano group, a heteroaryl group (which may be substituted by a $C_{1-6}$ alkyl group), a $C_{1-6}$ alkyl group, a $C_{3-6}$ cycloalkyl group, a $C_{1-6}$ alkylamino group, or the formula $CONR^7R^8$ ($R^7$ and $R^8$ are the same or different, and each represent a hydrogen atom or a $C_{1-6}$ alkyl group), $R^2$ represents a hydrogen atom or a $C_{1-6}$ alkyl group, $R^3$ represents a phenyl group (which may be substituted by 1 to 3 substituents selected from halogen atoms, cyano groups, $C_{1-6}$ alkyl groups, $C_{1-6}$ alkoxy groups, $C_{1-6}$ alkylamino groups, $C_{1-6}$ alkylsulfonyl groups, $haloC_{1-6}$ alkyl groups, $haloC_{1-6}$ alkoxy groups, $haloC_{1-6}$ alkylsulfanyl groups, phenyl groups, phenoxy groups, heteroaryl groups (which may be substituted by a $C_{1-6}$ alkyl group), and the formula $—SO_2NR^9R^{10}$ ($R^9$ and $R^{10}$ are the same or different, and each represent a hydrogen atom or a $C_{1-6}$ alkyl group)) or a heteroaryl group or a bicyclic heteroaryl group (the each heteroaryl group may be substituted by 1 to 3 substituents selected from halogen atoms, $C_{1-6}$ alkyl groups, $C_{3-6}$ cycloalkyl groups, $C_{1-6}$ alkoxy groups, cyano groups, $C_{1-6}$ alkanoyl groups, and $haloC_{1-6}$ alkyl groups), $R^4$ represents a $C_{1-6}$ alkyl group (which may be substituted by 1 to 3 halogen atoms, a $C_{1-6}$ alkoxy group, a $C_{3-6}$ cycloalkyl group, or a phenyl group), a $C_{3-6}$ cycloalkyl group, or a phenyl group, $R^5$ and $R^6$ are the same or different, and each represent a hydrogen atom or a $C_{1-6}$ alkyl group, and $A^1$, $A^2$, $A^3$, and $A^4$ are the same or different, and each represent the formula CH or a nitrogen atom, provided that one or two of $A^1$, $A^2$, $A^3$, and $A^4$ represent a nitrogen atom.

2. The compound or pharmaceutically acceptable salt thereof according to claim 1, wherein $R^1$ is a hydrogen atom, a halogen atom, a $C_{1-6}$ alkoxy group, a $haloC_{1-6}$ alkyl group, a cyano group, a heteroaryl group (which may be substituted by a $C_{1-6}$ alkyl group), a $C_{1-6}$ alkyl group, a $C_{1-6}$ alkylamino group, or the formula $CONR^7R^8$ ($R^7$ and $R^8$ are the same or different, and each represent a hydrogen atom or a $C_{1-6}$ alkyl group), $R^{1'}$ is a hydrogen atom, $R^3$ is a phenyl group (which may be substituted by 1 to 3 substituents selected from halogen atoms, cyano groups, $C_{1-6}$ alkyl groups, $C_{1-6}$ alkoxy groups, $C_{1-6}$ alkylamino groups, $C_{1-6}$ alkylsulfonyl groups, $haloC_{1-6}$ alkyl groups, $haloC_{1-6}$ alkoxy groups, $haloC_{1-6}$ alkylsulfanyl groups, phenyl groups, phenoxy groups, heteroaryl groups (which may be substituted by a $C_{1-6}$ alkyl group), and the formula $—SO_2NR^9R^{10}$ ($R^9$ and $R^{10}$ are the same or different, and each represent a hydrogen atom or a $C_{1-6}$ alkyl group)) or a heteroaryl group (which may be substituted by 1 to 3 substituents selected from halogen atoms, $C_{1-6}$ alkyl groups, $C_{1-6}$ alkoxy groups, cyano groups, and $haloC_{1-6}$ alkyl groups), and $R^4$ is a $C_{1-6}$ alkyl group (which may be substituted by a $C_{3-6}$ cycloalkyl group or a phenyl group) or a phenyl group.

3. The compound or pharmaceutically acceptable salt thereof according to claim 1, wherein $R^4$ is a $C_{1-6}$ alkyl group which may be substituted by 1 to 3 halogen atoms.

4. The compound or pharmaceutically acceptable salt thereof according to claim 1, wherein $R^4$ is a $C_{1-6}$ alkyl group.

5. The compound or pharmaceutically acceptable salt thereof according to claim 1, wherein $R^2$ is a hydrogen atom, and $R^5$ and $R^6$ are both a hydrogen atom.

6. The compound or pharmaceutically acceptable salt thereof according to claim 5, wherein $R^1$ is a halogen atom, a $C_{1-6}$ alkoxy group, a $haloC_{1-6}$ alkyl group, a cyano group, a heteroaryl group (which may be substituted by a $C_{1-6}$ alkyl group), a $C_{1-6}$ alkyl group, a $C_{1-6}$ alkylamino group, or the formula $CONR^7R^8$ ($R^7$ and $R^8$ are the same or different, and each represent a hydrogen atom or a $C_{1-6}$ alkyl group), and $R^{1'}$ is a hydrogen atom.

7. The compound or pharmaceutically acceptable salt thereof according to claim 1, wherein $R^1$ is a halogen atom, a $C_{1-6}$ alkoxy group, a $haloC_{1-6}$ alkyl group, a $C_{1-6}$ alkyl group, or a $C_{3-6}$ cycloalkyl group, and $R^{1'}$ is a hydrogen atom, a halogen atom, a $C_{1-6}$ alkoxy group, a $haloC_{1-6}$ alkyl group, a $C_{1-6}$ alkyl group, or a $C_{3-6}$ cycloalkyl group.

8. The compound or pharmaceutically acceptable salt thereof according to claim 1, wherein $R^1$ is attached in the para position.

9. The compound or pharmaceutically acceptable salt thereof according to claim 1, wherein any one of $A^1$, $A^2$, $A^3$ and $A^4$ is a nitrogen atom or $A^1$ and $A^3$ are both a nitrogen atom.

10. The compound or pharmaceutically acceptable salt thereof according to claim 1, wherein $A^1$ is a nitrogen atom, $A^2$ and $A^4$ are both the formula CH, and $A^3$ is the formula CH or a nitrogen atom.

11. The compound or pharmaceutically acceptable salt thereof according to claim 1, wherein $R^3$ is a heteroaryl group (which may be substituted by 1 to 3 substituents selected from halogen atoms, $C_{1-6}$ alkyl groups, $C_{3-6}$ cycloalkyl groups, $C_{1-6}$ alkoxy groups, cyano groups, $C_{1-6}$ alkanoyl groups, and $haloC_{1-6}$ alkyl groups).

12. The compound or pharmaceutically acceptable salt thereof according to claim 1, wherein $R^3$ is a pyridyl group (which may be substituted by 1 to 3 substituents selected from halogen atoms, $C_{1-6}$ alkyl groups, $C_{3-6}$ cycloalkyl groups, $C_{1-6}$ alkoxy groups, cyano groups, $C_{1-6}$ alkanoyl groups, and $haloC_{1-6}$ alkyl groups).

13. The compound or pharmaceutically acceptable salt thereof according to claim 1, wherein $R^3$ is a pyridyl group (which may be substituted by 1 to 3 substituents selected from halogen atoms, $C_{1-6}$ alkyl groups, $C_{3-6}$ cycloalkyl groups, and $haloC_{1-6}$ alkyl groups).

14. The compound or pharmaceutically acceptable salt thereof according to claim 1, wherein the compound is selected from the group consisting of:

2-[(5S)-3-(5-methoxypyrimidin-2-yl)-2-oxo-5-(propan-2-yl)imidazolidin-1-yl]-N-[4-(trifluoromethyl)pyridin-2-yl]acetamide, 2-[(5S)-3-(5-ethylpyrimidin-2-yl)-2-oxo-5-(propan-2-yl)imidazolidin-1-yl]-N-[4-(trifluoromethyl)pyridin-2-yl]acetamide, 2-[(5S)-3-(5-chloropyrimidin-2-yl)-2-oxo-5-propylimidazolidin-1-yl]-N-[4-(trifluoromethyl)pyridin-2-yl]acetamide, N-(4-chloropyridin-2-yl)-2-[(5S)-3-(5-chloropyrimidin-2-yl)-2-oxo-5-propylimidazolidin-1-yl]acetamide, 2-[(5S)-3-(5-chloropyrimidin-2-yl)-2-oxo-5-propylimidazolidin-1-yl]-N-(4-ethylpyridin-2-yl)acetamide, 2-[(5S)-3-(5-fluoropyrimidin-2-yl)-2-oxo-5-propylimidazolidin-1-yl]-N-[4-(trifluoromethyl)pyridin-2-yl]acetamide, 2-[(5S)-3-(5-fluoropyrimidin-2-yl)-2-oxo-5-(propan-2-yl)imidazolidin-1-yl]-N-[4-(trifluoromethyl)pyridin-2-yl]acetamide, N-(4-cyclopropylpyridin-2-yl)-2-{(5S)-2-oxo-5-(propan-2-yl)-3-[5-(trifluoromethyl)pyrimidin-2-yl]imidazolidin-1-yl}acetamide, 2-[(5S)-5-[(2S)-butan-2-yl]-3-(5-chloropyrimidin-2-yl)-2-oxoimidazolidin-1-yl]-N-[4-(trifluoromethyl)pyridin-2-yl]acetamide, N-(4-chloropyridin-2-yl)-2-[(5S)-3-(5-chloropyrimidin-2-yl)-2-oxo-5-(propan-2-yl)imidazolidin-1-yl]acetamide, N-(4-chloropyridin-2-yl)-2-{(5S)-2-oxo-5-(propan-2-yl)-3-[5-(trifluoromethyl)pyrimidin-2-yl]imidazolidin-1-yl}acetamide, 2-[(5S)-3-(5-cyclopropylpyrimidin-2-yl)-2-oxo-5-(propan-2-yl)imidazolidin-1-yl]-N-[4-(trifluoromethyl)pyridin-2-yl]acetamide, N-(4-chloropyridin-2-yl)-2-[(5S)-3-(5-cyclopropylpyrimidin-2-yl)-2-oxo-5-(propan-2-yl)imidazolidin-1-yl]acetamide, 2-[(5S)-5-[(2S)-butan-2-yl]-3-(5-chloropyrimidin-2-yl)-2-oxoimidazolidin-1-yl]-N-(4-cyclopropylpyridin-2-yl)acetamide, 2-[(5S)-5-[(2S)-butan-2-yl]-3-(5-chloropyrimidin-2-yl)-2-oxoimidazolidin-1-yl]-N-(4-chloropyridin-2-yl)acetamide, 2-[(5S)-5-[(2S)-butan-2-yl]-3-(5-chloropyrimidin-2-yl)-2-oxoimidazolidin-1-yl]-N-(4-ethylpyridin-2-yl)acetamide, N-(4-chloropyridin-2-yl)-2-{(5R)-5-[(1S)-1-fluoropropyl]-2-oxo-3-[5-(trifluoromethyl)pyrimidin-2-yl]imidazolidin-1-yl}acetamide, N-(4-chloropyridin-2-yl)-2-{(5R)-3-(5-chloropyrimidin-2-yl)-5-[(1S)-1-fluoropropyl]-2-oxoimidazolidin-1-yl}acetamide, N-(4-cyclopropylpyridin-2-yl)-2-{(5R)-5-[(1S)-1-fluoropropyl]-2-oxo-3-[5-(trifluoromethyl)pyrimidin-2-yl]imidazolidin-1-yl}acetamide, 2-{(5R)-5-[(1S)-1-fluoropropyl]-2-oxo-3-[5-(trifluoromethyl)pyrimidin-2-yl]imidazolidin-1-yl}-N-[4-(trifluoromethyl)pyridin-2-yl]acetamide, 2-{(5R)-3-(5-chloropyrimidin-2-yl)-5-[(1S)-1-fluoropropyl]-2-oxoimidazolidin-1-yl}-N-[4-(trifluoromethyl)pyridin-2-yl]acetamide, 2-[(5R)-5-[(1S)-1-fluoropropyl]-3-(5-fluoropyrimidin-2-yl)-2-oxoimidazolidin-1-yl]-N-[4-(trifluoromethyl)pyridin-2-yl]acetamide, 2-{(5R)-3-(5-cyclopropylpyrimidin-2-yl)-5-[(1S)-1-fluoropropyl]-2-oxoimidazolidin-1-yl}-N-[4-(trifluoromethyl)pyridin-2-yl]acetamide, 2-{(5R)-3-(5-ethoxypyrimidin-2-yl)-5-[(1S)-1-fluoropropyl]-2-oxoimidazolidin-1-yl}-N-[4-(trifluoromethyl)pyridin-2-yl]acetamide, N-(4-cyclopropylpyridin-2-yl)-2-{(5R)-3-(5-ethoxypyrimidin-2-yl)-5-[(1S)-1-fluoropropyl]-2-oxoimidazolidin-1-yl}acetamide, N-(4-chloropyridin-2-yl)-2-{(5R)-3-(5-ethoxypyrimidin-2-yl)-5-[(1S)-1-fluoropropyl]-2-oxoimidazolidin-1-yl}acetamide, 2-[(5S)-5-[(2S)-butan-2-yl]-3-(5-fluoropyrimidin-2-yl)-2-oxoimidazolidin-1-yl]-N-[4-(trifluoromethyl)pyridin-2-yl]acetamide, 2-{(5S)-5-[(2S)-butan-2-yl]-2-oxo-3-[5-(trifluoromethyl)pyrimidin-2-yl]imidazolidin-1-yl}-N-(4-cyclopropylpyridin-2-yl)acetamide, 2-{(5S)-5-[(2S)-butan-2-yl]-2-oxo-3-[5-(trifluoromethyl)pyrimidin-2-yl]imidazolidin-1-yl}-N-(4-chloropyridin-2-yl)acetamide, 2-[(5S)-3-(5-ethoxypyrimidin-2-yl)-2-oxo-5-(propan-2-yl)imidazolidin-1-yl]-N-[4-(trifluoromethyl)pyridin-2-yl]acetamide, N-(4-chloropyridin-2-yl)-2-[(5S)-3-(5-ethoxypyrimidin-2-yl)-2-oxo-5-(propan-2-yl)imidazolidin-1-yl]acetamide, N-(4-cyclopropylpyridin-2-yl)-2-[(5S)-3-(5-ethoxypyrimidin-2-yl)-2-oxo-5-(propan-2-yl)imidazolidin-1-yl]acetamide, 2-[(5S)-5-[(2S)-butan-2-yl]-3-(5-ethoxypyrimidin-2-yl)-2-oxoimidazolidin-1-yl]-N-[4-(trifluoromethyl)pyridin-2-yl]acetamide, 2-[(5S)-5-[(2S)-butan-2-yl]-3-(5-cyclopropylpyrimidin-2-yl)-2-oxoimidazolidin-1-yl]-N-[4-(trifluoromethyl)pyridin-2-yl]acetamide, N-(5-chloropyridin-2-yl)-2-{(5S)-2-oxo-5-propyl-3-[5-(trifluoromethyl)pyrimidin-2-yl]imidazolidin-1-yl}acetamide, N-(5-chloro-6-methylpyridin-2-yl)-2-{(5S)-2-oxo-5-propyl-3-[5-(trifluoromethyl)pyrimidin-2-yl]imidazolidin-1-yl}acetamide, N-(5-chloro-6-methylpyridin-2-yl)-2-[(5S)-3-(5-chloropyrimidin-2-yl)-2-oxo-5-propylimidazolidin-1-yl]acetamide, 2-{(5S)-2-oxo-5-(propan-2-yl)-3-[5-(propan-2-yloxy)pyrimidin-2-yl]imidazolidin-1-yl}-N-[4-(trifluoromethyl)pyridin-2-yl]acetamide, 2-[(5S)-5-[(2S)-butan-2-yl]-3-(5-ethoxypyrimidin-2-yl)-2-oxoimidazolidin-1-yl]-N-(4-chloropyridin-2-yl)acetamide, 2-[(5S)-5-[(2S)-butan-2-yl]-3-(5-cyclopropylpyrimidin-2-yl)-2-oxoimidazolidin-1-yl]-N-(4-chloropyridin-2-yl)acetamide, 2-[(5S)-5-[(2S)-butan-2-yl]-3-(5-ethoxypyrimidin-2-yl)-2-oxoimidazolidin-1-yl]-N-(4-cyclopropylpyridin-2-yl)acetamide, and 2-[(5S)-5-[(2S)-butan-2-yl]-3-(5-cyclopropylpyrimidin-2-yl)-2-oxoimidazolidin-1-yl]-N-(4-cyclopropylpyridin-2-yl)acetamide.

15. A pharmaceutical composition comprising, as an active ingredient, the compound or pharmaceutically acceptable salt thereof according to claim 1.

16. An agent for treating schizophrenia, which comprises, as an active ingredient, the compound or pharmaceutically acceptable salt thereof according to claim 1.

* * * * *